United States Patent
Bender et al.

(10) Patent No.: US 6,306,892 B1
(45) Date of Patent: Oct. 23, 2001

(54) METALLOPROTEINASE INHIBITORS, PHARMACEUTICAL COMPOSITIONS CONTAINING THEM, AND THEIR USE

(75) Inventors: Steven L. Bender, Oceanside, CA (US); Arlindo L. Castelhano, New City, NY (US); Wesley K. M. Chong, Encinitas, CA (US); Melwyn A. Abreo, Imperial Beach, CA (US); Roland J. Billedeau; Jian Jeffrey Chen, both of Santa Clara, CA (US); Judith G. Deal, Temecula, CA (US)

(73) Assignees: Agouron Pharmaceuticals, Inc., La Jolla; Syntex Inc., Palo Alto, both of CA (US)

( * ) Notice: Subject to any disclaimer, the term of this patent is extended or adjusted under 35 U.S.C. 154(b) by 0 days.

(21) Appl. No.: 09/598,208

(22) Filed: Jun. 21, 2000

Related U.S. Application Data

(62) Division of application No. 09/309,602, filed on May 11, 1999, now Pat. No. 6,174,915, which is a division of application No. 08/823,962, filed on Mar. 25, 1997, now Pat. No. 6,008,243.

(51) Int. Cl.[7] ........................ A61K 31/381; C07D 333/04
(52) U.S. Cl. .................. 514/438; 549/77; 548/315.1; 548/230; 548/225; 546/281.4; 435/184; 514/397; 514/376; 514/336; 514/439; 514/440
(58) Field of Search ........................ 514/438, 376, 514/336, 439, 440; 549/77; 548/230, 225, 315.1; 546/281.4; 435/184

(56) References Cited

U.S. PATENT DOCUMENTS

| | | |
|---|---|---|
| 4,032,639 | 6/1977 | Freed et al. . |
| 5,183,900 | 2/1993 | Galardy et al. . |
| 5,189,178 | 2/1993 | Galardy et al. . |
| 5,256,657 | 10/1993 | Singh et al. . |
| 5,455,258 | 10/1995 | MacPherson et al. . |
| 5,506,242 | 4/1996 | MacPherson et al. . |
| 5,552,419 | 9/1996 | MacPherson et al. . |
| 5,569,665 | 10/1996 | Porter et al. . |
| 5,672,598 | 9/1997 | De et al. .............................. 514/212 |

FOREIGN PATENT DOCUMENTS

| | | |
|---|---|---|
| 195 42 189 | 5/1997 | (DE) . |
| 276436 | 8/1988 | (EP) . |
| 438223 | 7/1991 | (EP) . |
| 0489577 | 6/1992 | (EP) . |
| 0489579 | 6/1992 | (EP) . |
| 606046 | 7/1994 | (EP) . |
| 757037 | 2/1997 | (EP) . |
| 757984 | 2/1997 | (EP) . |
| WO 92/06966 | 4/1992 | (WO) . |
| WO 92/09563 | 6/1992 | (WO) . |
| WO 92/21360 | 12/1992 | (WO) . |
| WO 93/24449 | 12/1993 | (WO) . |
| WO 93/24475 | 12/1993 | (WO) . |
| WO 94/02466 | 2/1994 | (WO) . |
| WO 94/12169 | 6/1994 | (WO) . |
| WO 94/24140 | 10/1994 | (WO) . |
| WO 94/25434 | 11/1994 | (WO) . |
| WO 95/04735 | 2/1995 | (WO) . |
| WO 95/12603 | 5/1995 | (WO) . |
| WO 95/19961 | 7/1995 | (WO) . |
| WO 95/22966 | 8/1995 | (WO) . |
| WO 95/32944 | 12/1995 | (WO) . |
| WO 95/35275 | 12/1995 | (WO) . |
| WO 95/35276 | 12/1995 | (WO) . |
| WO 96/00214 | 1/1996 | (WO) . |
| WO 96/06074 | 2/1996 | (WO) . |
| WO 96/16027 | 5/1996 | (WO) . |
| WO 96/16931 | 6/1996 | (WO) . |
| WO 96/23791 | 8/1996 | (WO) . |
| WO 96/27583 | 9/1996 | (WO) . |
| WO 96/29313 | 9/1996 | (WO) . |
| WO 96/33172 | 10/1996 | (WO) . |
| WO 97/18194 | 5/1997 | (WO) . |
| WO 97/19068 | 5/1997 | (WO) . |

(List continued on next page.)

OTHER PUBLICATIONS

Bender et al., "Metalloprotease of Matrix Inhibitors (CASE RAN 4070/106)," *Industrial Property Gazette*, pp. 241.

Tamura et al., "Highly Selective and Orally Active Inhibitors of Type IV Collagenase (MMP–9 and MMP–2): N–Sulfonylamino Acid Derivatives", J. Med. Chem. (1998), 41(4), pp. 640–649.

(List continued on next page.)

*Primary Examiner*—Charanjit S. Aulakh

(57) ABSTRACT

The present invention is directed to compound of the formula I:

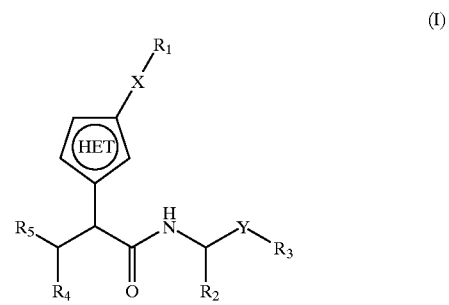

(I)

wherein $R_1$, $R_2$, $R_3$, $R_4$, $R_5$, X, Y, and

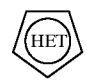

are as defined herein.

These compounds are useful for inhibiting the activity of a metalloproteinase by contacting the metalloproteinase with an effective amount of the inventive compounds.

20 Claims, No Drawings

FOREIGN PATENT DOCUMENTS

| | | |
|---|---|---|
| WO 97/20824 | 6/1997 | (WO) . |
| WO 97/22587 | 6/1997 | (WO) . |
| WO 97/23459 | 7/1997 | (WO) . |
| WO 97/25969 | 7/1997 | (WO) . |
| WO 97/27174 | 7/1997 | (WO) . |
| WO 98/07697 | 2/1998 | (WO) . |
| WO 98/08815 | 3/1998 | (WO) . |
| WO 98/08825 | 3/1998 | (WO) . |

OTHER PUBLICATIONS

Fisher et al., "Molecular basis of sun–induced premature skin ageing and retinoid antagonism", Nature, vol. 379, No. 6563 (1996), pp. 335–339.

Saarialho–Kere et al., "Distinct Populations of Basal Keratinocytes Express Stromelysin–1 and Stromelysin–2 in Chronic Wounds", The Journal of Clinical Investigation, vol. 94, p. 79–88.

Newby et al., "Extracellular matrix degrading metalloproteinases in the pathogenesis of arteriosclerosis", Arteriosclerosis, Supplement to Basic Research in Cardiology, vol. 89, Supl. 1 (1994), pp. 59–70.

McMillan et al., "Characterization of a Glomerular Epithelial Cell Metalloproteinase as Matrix Metalloproteinase–9 with Enhanced Expression in a Model of Membranous Nephropathy", The Journal of Clinical Investigation, vol. 97, No. 4 (1996), pp. 1094–1101.

Balaaouaj et al., "Human Macrophage Metalloelastase", The Journal of Biological Chemistry, vol. 270, No. 24 (1995), pp. 14568–14575.

Martin, "Synthesis of Aldehydes, Ketones, and Carboxylic Acids from Lower Carbonyl Compounds by C–C Coupling Reactions", Synthesis, No. 9 (1979), pp. 633–655.

Yabroff et al., "The Relative Strengths of Some Hydrocarbon Derivatives of Boric Acid", The Journal of the American Chemical Society, vol. 56 (1934), pp. 1850–1857.

Malon et al., "Chiroptical Properties and Conformation of N–Acetyl–L–Amino Acids N'–Methylamides with Aliphatic Side Chains", Collection Czechoslovak Chem. Commun., vol. 48 (1983), pp. 2844–2861.

Pridgen et al., "Regiospecific Synthesis of Arylfurans Employing a Nickel(II)–Phosphine Complex as a Catalyst in the Homolytic Cross–Coupling of Grignard Reagents to Halofurans", J. Org. Chem., vol. 47, No. 8 (1982), pp. 1590–1592.

Yang et al., "Regiospecific Synthesis of 3,4–Disubstituted Furans and 3–Substituted Furans Using 3,4–Bis(tri–n–butylstannyl)furan and 3–(Tri–n–butylstannyl)furan as Building Blocks", Tetrahedron, vol. 50, No. 32 (1994), pp. 9583–9608.

Ribereau et al., "Synthesis and physical properties of the six furylpyridines", Canadian Journal of Chemistry, vol. 61, No. 2 (1983), pp. 334–342.

Ishikura et al., "A Novel Synthesis of 4–Aryl– and 4–Heteroarylpyridines via Diethyl(4–pyridyl)borane", Chem. Pharm. Bull., vol. 33, No. 11 (1985), pp. 4755–4763.

Delacotte et al., "Synthesis of Tritiated Threonine with a High Specific Activity", Journal of Labelled Compounds and Radiopharmaceuticals, vol. 29, No. 10 (1991), pp. 1141–1146.

Robinson, et al., "Inhibitors of MMP–1: An Examination of P1' Cα Gem–Disubstitution in the Succinamide Hydroxamate Series," Bioorganic & Medicinal Chemistry Letters, vol. 6, No. 14 (1996), pp. 1719–1724.

Firestone et al., "Total Synthesis of β–Lactam Antibiotics. IV. Epimerization of 6(7)–Aminopenicillins and– cephalosporins from α to β1," Journal of Organic Chemistry, vol. 39, No. 4 (1974), pp. 437–440.

Walker, "Vinylogous Amides of 2–Methylaminoethanol and Their Behavior with Lithium Aluminum Hydride. Vinylogous Urethanes of Ethanolamides and Their Acetylation," Journal of Organic Chemistry, vol. 27, (1962), pp. 4227–4231.

Cumberbatch, et al., "The Synthesis and Conformational Analysis of a Pair of Diastereoisomeric Cyclic Peptides with cis and trans Amide Bonds, Respectively," Journal of the Chemical Society, Chemical Communications, No. 7 (1993), pp. 641–642.

Capps, et al., "Novel Catalytic Rearrangements of 2–Vinyl–1,3–Thiazetidines," Tetrahedron Letters, vol. 25, No. 37 (1984), pp. 4157–4160.

Sakai, et al., "Convenient Synthesis of 1,4–Thiazane–3–Carboxylic Acid Derivatives," Chemical and Pharmaceutical Bulletin, vol. 29, No. 6 (1981), pp. 1554–1560.

Woessner, Jr., "Matrix metalloproteinases and their inhibitors in connective tissue remodeling", The FASEB Journal, vol. 5, No. 8 (1991), pp. 2145–2154.

Freije et al., "Molecular Cloning and Expression of Collagenase–3, a Novel Human Matrix Metalloproteinase Produced by Breast Carcinomas", The Journal of Biological Chemistry, vol. 269, No. 24 (1994), pp. 16766–16773.

Mitchell et al., "Cloning, Expression, and Type II Collagenolytic Activity of Matrix Metalloproteinase–13 from Human Osteoarthritic Cartilage", The Journal of Clinical Investigation, vol. 97, No. 3 (1996), pp. 761–768.

Ray et al., "Matrix metalloproteinases and malignant disease: recent developments", Expert Opinions on Investigational Drugs, vol. 5, No. 3 (1996), pp. 323–335.

Birkedal–Hansen, "Host–Mediated Extracellular Matrix Destruction by Metalloproteinases", Molecular Pathogenesis or Periodontal Disease (1994), pp. 191–202.

Gijbels et al., "Gelatinase in the cerebrospinal fluid of patients with multiple sclerosis and other inflammatory neurological disorders", Journal of Neuroimmunology, 41 (1992), pp. 29–34.

O'Day et al., "Differences in Response in Vivo to Amphotericin B Among Candida albicans Strains", Investigative Ophthalmology & Visual Science, vol. 32, No. 5 (1991), pp. 1569–1572.

Rosenberg et al., "Tumor necrosis factor–α–induced gelatinase B causes delayed opening of the blood–brain barrier: an expanded therapeutic window", Brain Research, vol. 703, Nos. 1–2 (1995), pp. 151–155.

Rosenberg et al., "Proteolytic Cascade Enzymes Increase in Focal Cerebral Ischemia in Rat", Journal of Cerebral Blood Flow and Metabolism, vol. 16, No. 3 (1996), pp. 360–366.

Friedrich–Bochnitschek et al., "Allyl Esters as Carboxy Protecting Groups in the Synthesis of O–Glycopeptides", J. Org. Chem. (1989), pp. 751–756.

Belshaw et al., "Chlorotrimethylsilane Mediates Formation of ω–Allyl Esters of Aspartic and Glutamic Acids", Synthetic Communications, vol. 20, No. 20 (1990), pp. 3157–3160.

McNamara et al., "Synthesis of 4–Cyano–4'halobiphenyls", J. Org. Chem., vol. 41, No. 6 (1976), p. 1071.

Amatore et al., "Efficient palladium–catalyzed synthesis of unsymmetrical donor–acceptor biaryls and polyaryls", *Journal of Organometallic Chemistry*, vol. 390, No. 3 (1990), pp. 389–398.

Boy et al., "Electrosynthesis of Unsymmetrical Donor–Acceptor Polyaryls", *Tetrahedron Letters*, vol. 33, No. 4 (1992), pp. 491–494.

Pospišek et al., "Tert–Leucine and Its Simple Peptides", *Collection Czechoslov. Chem. Commun.,* vol. 42 (1977), pp. 1069–1076.

Carpino et al., "Tetramethylfluoroformamidinium Hexafluorophosphate: A Rapid–Acting Peptide Coupling Reagent for Solution and Solid Phase Peptide Synthesis", *J. Am. Chem. Soc.,* vol. 117, No. 19 (1995), pp. 5401–5402.

Freskos, "Use of R–Pantolactone in the Synthesis of L–Tert Leucine Derivatives", *Synthetic Communications,* vol. 24, No. 4 (1994), pp. 557–563.

Abdel–Meguid et al., "An Orally Bioavailable HIV–1 Protease Inhibitor Containing an Imidazole–Derived Peptide Bond Replacement: Crystallographic and Pharmacokinetic Analysis", *Biochemistry*, vol. 33, No. 39 (1994), pp. 11671–11677.

Mathias, "Esterification and Alkylation Reactions Employing Isoureas", *International Journal of Methods in Synthetic Organic Chemistry,* No. 8 (1979), pp. 561–576.

Boger et al., "Total Synthesis of Azafluoranthene Alkaloids: Rufescine and Imelutine", *J. Org. Chem.* (1984), vol. 49, No. 21, pp. 4050–4055.

Ellis et al., "Antifungal activity of some imidazole derivatives", *J. Pharm. Pharmacol.* (1964), vol. 16, pp. 400–407.

Von E. Felder et al., Helv. Chim. Acta, vol. 43, No. 117 (1960), p. 888–894.

Aebischer et al., "Synthesis and NMDA Antagonistic Properties of the Enantiomers of 4–(3–Phosphonopropyl)piperazine–2–carboxylic Acid (CPP) and of the Unsaturated Analogue (E)–4(3–Phosphonoprop–2–enyl)piperazine–2–carboxylic Acid (CPP–end)," Helvetica Chimica Acta, vol. 72 (1989), p. 1043–1051.

Brunwin et al., "Total Synthesis of Nuclear Analogues of 7–Methylcephalosporin," J.C.S. Perkin I (1973), p. 1321–1328.

Knight et al., "A novel coumarin–labelled peptide for sensitive continous assays of the matrix metalloproteinases," FEBS, vol. 296, No. 3 (1992), p. 263–266.

Menegatti et al., "Inhibition of Serine Proteinases by Tetra-–p–Amidinophenoxy–neo–Pentane: Thermodynamic and Molecular Modeling Study," J. Enzyme Inhibition, vol. 2 (1987), p. 23–30.

Johnson, "Collagenase Inhibitors," DN&P, vol. 3, No. 8 (1990), p. 453–458.

Henderson et al., "Design of Inhibitors of Articular Cartilage Destruction," Drugs of the Future, vol. 15, No. 5 (1990), p. 495–508.

Harrison et al., "A Semicontinuous, High–Performance Liquid Chromatography–Based Assay for Stromelysin," Analytical Biochemistry, vol. 180 (1989), p. 110–113.

Shinmei et al., "The Mechanism of Cartilage Degradation in Osteoarthritic Joints," Seminars in Arthritis and Rheumatism, vol. 19, No. 4, Suppl. 1 (1990), p. 16–20.

Weingarten et al., "Spectrophotometric Assay for Vertebrate Collegenase," Analytical Biochemistry, vol. 147 (1985) p. 437–440.

Davies et al., "A Synthetic Matrix Metalloproteinase Inhibitor Decreases Tumor Burden and Prolongs Survival of Mice Bearing Human Ovarian Carcinoma Xenografts," Cancer Research, vol. 53 (1993), p. 2087–2091.

Brinckerhoff, "Joint Destruction in Arthritis: Metalloproteinases in the Spotlight," Arthritis & Rheumatism, vol. 34, No. 9 (1991), p. 1073–1075.

Morrison, "Kinetics of the Reversible Inhibition of Enzyme-–Catalyzed Reactions by Tight–Binding Inhibitors," Biochem. Biophys. Acta, vol. 185 (1969), p. 269–286.

Lohmander et al., "Metalloproteinases, Tissue Inhibitor, and Proteoglycan Fragments in Knee Synovial Fluid in Human Osteoarthritis," Arthritis & Rheumatism, vol. 36, No. 2 (1993), p. 181–187.

Schwartz et al., "Synthetic Inhibitors of Bacterial and Mammalian Interstitial Collagenases," Progress in Medicinal Chemistry, vol. 29 (1992), p. 271–334.

Johnson et al., "Collagenase Inhibitors: Their Design and Potential Therapeutic Use", *J. Enzyme Inhibition*, vol. 2, (1987), p. 1–22.

Morphy et al., "Matrix Metalloproteinase Inhibitors: Current Status," *Current Medicinal Chemistry*, (1995), 2, pp. 743–762.

Porter et al., "Recent developments in matrix metalloproteinase inhibitors," *Exp. Opin. Ther. Patents* (1995) 5(12), pp. 1287–1296.

Beckett et al., "Recent advances in matrix metalloproteinase inhibitor research," *DDT,* vol. 1, No. 1 (Jan. 1996), pp. 16–26.

Greenstein, *Chemistry of the Amino Acids,* (1984), p. 886–889.

Smith et al., "A Superior Synthesis of Diaryl Ethers by the Use of Ultrasound in the Ullman Reaction," *J. Chem. Soc. Perkin Trans. I,* (1992), p. 407–408.

Sammes et al., "A Novel, Simple Method for the Preparation of Hindered Diphenyl Ethers," *J. Chem. Soc. Perkin Trans. I,* (1988), p. 3229–3231.

Hassner et al., "Aminopyridines a Acylation Catalysts for Tertiary Alcohols," *Tetrahedron,* vol. 34 (1978), pp. 2069–2076.

Sprague et al., "Studies in the Cyanine Dye Series. IX. 4,4'–Pyridocyanines and 4–Pyrido–4'–cyanines," *Journal of the American Chemical Society,* Vo. 59, No. 12 (1937), p. 2697–2699.

Shao et al., "An Enantiometric Synthesis of allo–Threonines and β–Hydroxyvalines," *J. Org. Chem.,* vol. 61, No. 8 (1996), pp. 2582–2583.

Thompson et al., "A General Synthesis of 5–Arylnicotinates," *J. Org. Chem.,* vol. 49, No. 26 (1984), pp. 5237–5243.

Gehring et al., "Characterization of the Phe–81 and Val–82 Human Fibroblast Collagenase Catalytic Domain Purified from *Escherichia coli,*" *The Journal of Biological Chemistry,* vol. 270, No. 38 (1995), pp. 22507–22513.

Marcy et al., "Human Fibroblast Stromelysin Catalytic Domain: Expression, Purification, and Characterization of a C–Terminally Truncated Form," *Biochemistry,* vol. 30, No. 26 (1991), p. 6476–6483.

METALLOPROTEINASE INHIBITORS, PHARMACEUTICAL COMPOSITIONS CONTAINING THEM, AND THEIR USE

CROSS-REFERENCE TO RELATED APPLICATION

This application is a division of U.S. patent application Ser. No. 09/309,602, filed May 11, 1999, now U.S. Pat. No. 6,174,915, which is a division of U.S. patent application Ser. No. 08/823,962, filed Mar. 25, 1997, now issued as U.S. Pat. No. 6,008,243, and claims benefit under 35 U.S.C. §119(e) of U.S. Provisional Patent Application No. 60/029,115, filed Oct. 24, 1996.

Matrix metalloproteases ("MMPs") are a family of proteases (enzymes) involved in the degradation and remodeling of connective tissues. Members of this family of endopeptidase enzymes are secreted as proenzymes from various cell types that reside in or are associated with connective tissue, such as fibroblasts, monocytes, macrophages, endothelial cells, and invasive or metastatic tumor cells. MMP expression is stimulated by growth factors and cytokines in the local tissue environment, where these enzymes act to specifically degrade protein components of the extracellular matrix, such as collagen, proteoglycans (protein core), fibronectin and laminin. These ubiquitous extracellular matrix components are present in the linings of joints, interstitial connective tissues, basement membranes and cartilage.

The MMPs share a number of properties, including zinc and calcium dependence, secretion as zymogens, and 40–50% amino acid sequence homology. Eleven metalloenzymes have been well-characterized as MMP's in humans, including three collagenases, three stromelysins, two gelatinases, matrilysin, metalloelastase, and membrane-type MMP, as discussed in greater detail below.

Interstitial collagenases catalyze the initial and rate-limiting cleavage of native collagen types I, II and III. Collagen, the major structural protein of mammals, is an essential component of the matrix of many tissues, for example, cartilage, bone, tendon and skin. Interstitial collagenases are very specific matrix metalloproteases which cleave these collagens to give two fragments which spontaneously denature at physiological temperatures and therefore become susceptible to cleavage by less specific enzymes. Cleavage by the collagenases results in the loss of structural integrity of the target tissue, essentially an irreversible process. There are currently three known human collagenases, the first two of which are relatively well-characterized (*FASEB J.*, 5, 2145–54 (1991)). Human fibroblast-type collagenase (HFC, MMP-1, or collagenase-1) is produced by a wide variety of cells including fibroblasts and macrophages. Human neutrophil-type collagenase (HNC, MMP-8, or collagenase-2) has so far only been demonstrated to be produced by neutrophils. The most recently discovered member of this group of MMPs is human collagenase-3 (MMP-13), which was originally found in breast carcinomas (*J. Biol. Chem.*, 269, 16,766–16,773) (1994)), but has since shown to be produced by chondrocytes (*J Clin. Invest.* 97, 761–768, 1996).

The gelatinases include two distinct, but highly related, enzymes: a 72-kD enzyme (gelatinase A, HFG, MMP-2) secreted by fibroblasts and a wide variety of other cell types, and a 92-kD enzyme (gelatinase B, HNG, MMP-9) released by mononuclear phagocytes, neutrophils, corneal epithelial cells, tumor cells, cytotrophoblasts and keratinocytes. These gelatinases have been shown to degrade gelatins (denatured collagens), collagen types IV (basement membrane) and V, fibronectin and insoluble elastin.

Stromelysins 1 and 2 have been shown to cleave a broad range of matrix substrates, including laminin, fibronectin, proteoglycans, and collagen types IV and IX in their non-helical domains.

Matrilysin (MMP-7, PUMP-1) has been shown to degrade a wide range of matrix substrates including proteoglycans, gelatins, fibronectin, elastin and laminin. Its expression has been documented in mononuclear phagocytes, rate uterine explants and sporadically in tumors. Other less characterized MMPs include macrophage metalloelastase (MME, MMP-12), membrane type MMP (MMP-14), and stromelysin-3 (MMP-11).

Excessive degradation of extracellular matrix by MMPs is implicated in the pathogenesis of many diseases of both chronic and acute nature. For example, numerous studies, as reviewed in *Exp. Opin. Invest. Drugs*, 5, 323–335, (1996), have established that expression and activation of MMPs are critical events in tumor growth, invasion and metastasis. In addition, MMP activity has been found to be required for angiogenesis, which is necessary for tumor growth as well for other pathological conditions such as macular degeneration.

MMPs, especially stromelysin-1, collagenases-1, and collagenase-3, have been strongly implicated in the destruction of articular cartilage that is the hallmark of rheumatoid arthritis and osteoarthritis. See, for example, *J. Clin. Invest.*, 97, 761–768 (1996). In addition, the tissue destruction associated with gingivitis and periodontal disease is believed to be mediated by overexpression of MMPs in response to proinflammatory cytokines. See *Molecular Pathogenesis of Periodontal Disease*, Ch. 17, 191–202 (1994). Other diseases in which critical roles for MMPs have been identified include multiple sclerosis (*J. Neuroimmunol.*, 41, 29–34 (1992)), corneal ulceration (*Invest. Opthalmol and Visual Sci.*, 32, 1569–1575 (1989)), stroke (*Brain Research*, 703, 151–155 (1995) and *J Cereb. Blood Flow Metab.*, 16, 360–366 (1996)), sun-induced skin ageing (*Nature*, 379, 335–339 (1996)), chronic obstructive pulmonary disease, such as emphysema (*Am. J Respir. Cell. Mol. Biol.* 7, 5160–5165 (1994)), chronic ulceration (*J. Clin. Invest.*, 94, 79–88 (1994)), cardiac arrhythmia, and endometriosis. Finally, roles for MMP-mediated degradation of basement membranes have been proposed in the rupture of atherosclerotic plaques (*Basic Res. Cardiol.*, 89(SUPPL.1), 59–70, (1994)) and in the development of glomerular disease (*J. Clin. Invest.*, 97, 1094–1101 (1996)).

Inhibitors of MMPs are expected to provide useful treatments for the diseases described above in which degradation of the extracellular matrix by MMPs contributes to the pathogenesis of the disease. In general, selective MMP inhibitors of particular subsets of MMPs may offer therapeutic advantages, as it has been typically observed that a limited number of members of the MMP family are involved in any one of the disease states listed above. For example, the involvement of individual collagenases in the degradation of tissue collagens probably depends markedly on the tissue. The tissue distribution of human collagenases suggests that collagenase-3 is the major participant in the degradation of the collagen matrix of cartilage, while collagenase-1 is more likely to be involved in tissue remodeling of skin and other soft tissues. In addition, stromelysin-1 appears to be largely responsible for excessive loss of proteoglycan from cartilage. Thus, the inventive compounds disclosed herein that are selective inhibitors for collagenase-3 and stromelysin over collagenase-1 are preferred for treatment of diseases associated with cartilage erosion, such as rheumatoid and osteoarthritis. Similarly, among the MMPs, metalloelastase has been specifically implicated in the pathology of pulmonary emphysema. See *J. Biol. Chem.* 270, 14568–14575 (1995).

The design and uses of MMP inhibitors are reviewed, for example, in *J Enzyme Inhibition,* 2, 1–22 (1987); *Progress in Medicinal Chemistry* 29, 271–334 (1992); *Current Medicinal Chemistry,* 2, 743–762 (1995); *Exp. Opin. Ther. Patents,* 5, 1287–1296 (1995); and *Drug Discovery Today,* 1, 16–26 (1996). MMP inhibitors are also the subject of numerous patents and patent applications. In the majority of these publications, the preferred inventive compounds are hydroxamic acids, as it has been well-established that the hydroxamate function is the optimal zinc-coordinating functionality for binding to the active site of MMPs. For example, the hydroxamate inhibitors described in the literature are generally 100 to 1000-fold more potent than the correponding inhibitors wherein the hydroxamic acid functionality is replaced by a carboxylic acid functionality. Nevertheless, hydroxamic acids tend to exhibit relatively poor bioavailability. The preferred compounds disclosed herein are carboxylic acid inhibitors that possess inhibitory potency against certain of the MMPs that is comparable to the potency of the hydroxamic acid inhibitors that have been reported in the literature. The following patents and patent applications disclose carboxylic acid inhibitiors that are, as are the inventive carboxylic acid inhibitors disclosed herein, monoamine derivatives of substituted succinic acids: Celltech Ltd.: EP-A-0489577 (WO 92/099565), EP-A-0489579, WO 93/24475, WO 93/244449; British Biotech Pharameuticals Ltd.: WO 95/32944, WO 95/19961; Sterling Winthrop, Inc.: U.S. Pat. No. 5,256,657; Sanofi Winthrop, Inc.: WO 95/22966; and Syntex (U.S.A.) Inc. WO 94/04735, WO 95/12603, and WO 96/16027.

SUMMARY OF THE INVENTION

The present invention is directed to compounds of the formula I:

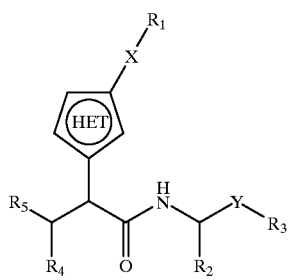

(I)

wherein

X is a single bond or a straight or branched, saturated or unsaturated chain containing 1 to 6 carbon atoms, wherein on e or more of the carbon atoms are optionally independently replaced with O or S, and wherein one or more of the hydrogen atoms are optionally replaced with F;

Y is a single bond, —CH(OH)—, or —C(O)—;

$R_1$ is H, an alkyl group, an aryl group, a heteroaryl group, a cycloalkyl group, or a heterocycloalkyl group;

$R_2$ is H, an alkyl group, an aryl group, a heteroaryl group, a cycloalkyl group, a heterocycloalkyl group, or $C(O)R_{10}$ wherein $R_{10}$ is H, an O-alkyl group, an alkyl group, an aryl group, a heteroaryl group, a cycloalkyl group, a heterocycloalkyl group, an O-aryl group, an O-alkyl group, or $NR_{11}R_{12}$;

wherein $R_{11}$ is H, an alkyl group, an O-alkyl group, an aryl group, a heteroaryl group, a cycloalkyl group, or a heterocycloalkyl group, and wherein $R_{12}$ is H, an alkyl group, an aryl group, a heteroaryl group, a cycloalkyl group, or a heterocycloalkyl group, or wherein $R_{11}$ and $R_{12}$ form, together with the nitrogen to which they are attached, a heteroaryl group or a heterocycloalkyl group; and $R_3$ is H, an alkyl group, an aryl group, a heteroaryl group, a cycloalkyl group, a heterocycloalkyl group, $NR_{11}R_{12}$, or $OR_{11}$, wherein $R_{11}$ and $R_{12}$ are as defined above, or $R_2$ and $R_3$, together with the atom(s) to which they are attached, form a cycloalkyl group or a heterocycloalkyl group;

$R_4$ is H or any suitable organic moiety;

$R_5$ is C(O)NHOH, C(O)$OR_{13}$, SH, N(OH)CHO, SC(O)$R_{14}$, P(O)(OH)$R_{15}$, or P(O)(OH)$OR_{13}$;

$R_{13}$ is H, an alkyl group, or an aryl group, $R_{14}$ is an alkyl group or an aryl group, and $R_{15}$ is an alkyl group; and

is a heteroaryl group having five ring atoms, including 1, 2 or 3 heteroatoms selected from O, S, and N;

and pharmaceutically acceptable salts and solvates thereof, and pharmaceutically acceptable prodrugs thereof, said prodrugs being different from compounds of the formula (I); with the proviso that if the compound of formula (I) is:

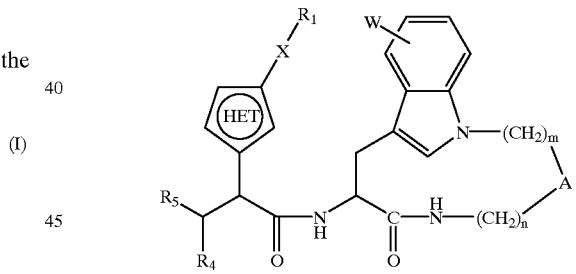

wherein $R_1$, $R_4$, and $R_5$ are as defined above, W is H, OH, a halo group, an alkyl group, or an O-alkyl group, and further wherein when m is 2, 3, or 4, n is 1, 2, 3, or 4, and A is $CH_2$, O, NH, or N-alkyl; and when m is 4, 5, or 6, n is 0, and A is —CHJ—, wherein J is carboxy, alkoxycarbonyl, or carbamoyl;

or a pharmaceutically acceptable salt or solvate thereof, or a pharmaceutically acceptable prodrug thereof, said prodrug being different from a compound of the formula (I); then

is pyrrolyl.

The present invention is further directed to pharmaceutical compositions comprising a therapeutically effective amount of a compound of formula 1, or a pharmaceutically acceptable salt or solvate thereof, or a pharmaceutically acceptable prodrug thereof, said prodrug being different from a compound of the formula (I).

The present invention is even further directed to methods of using the compounds of formula (I), and pharmaceutically acceptable salts and solvates thereof, and pharmaceutically acceptable prodrugs thereof, said prodrug being different from a compound of the formula (I).

DETAILED DESCRIPTION OF THE INVENTION

The present invention is directed to compounds of the formula I:

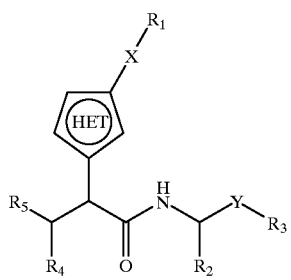

(I)

wherein

X is a single bond or a straight or branched, saturated or unsaturated chain containing 1 to 6 carbon atoms, wherein one or more of the carbon atoms are optionally independently replaced with O or S, and wherein one or more of the hydrogen atoms are optionally replaced with F;

Y is a single bond, —CH(OH)—, or —C(O)—;

$R_1$ is H, an alkyl group, an aryl group, a heteroaryl group, a cycloalkyl group, or a heterocycloalkyl group;

$R_2$ is H, an alkyl group, an aryl group, a heteroaryl group, a cycloalkyl group, a heterocycloalkyl group, or $C(O)R_{10}$,
 wherein $R_{10}$ is H, an alkyl group, an aryl group, a heteroaryl group, a cycloalkyl group, a heterocycloalkyl group, an O-aryl group, an O-alkyl group, or $NR_{11}R_{12}$;
  wherein $R_{11}$ is H, an alkyl group, an O-alkyl group, an aryl group, a heteroaryl group, a cycloalkyl group, or a heterocycloalkyl group, and
  wherein $R_{12}$ is H, an alkyl group, an aryl group, a heteroaryl group, a cycloalkyl group, or a heterocycloalkyl group,
  or wherein $R_{11}$ and $R_{12}$ form, together with the nitrogen to which they are attached, a heteroaryl group or a heterocycloalkyl group; and $R_3$ is H, an alkyl group, an aryl group, a heteroaryl group, a cycloalkyl group, a heterocycloalkyl group, $NR_{11}R_{12}$, or $OR_{11}$, wherein $R_{11}$ and $R_{12}$ are as defined above, or $R_2$ and $R_3$, together with the atom(s) to which they are attached, form a cycloalkyl group or a heterocycloalkyl group;

$R_4$ is H or any suitable organic moiety;

$R_5$ is C(O)NHOH, $C(O)OR_{13}$, SH, N(OH)CHO, $SC(O)R_{14}$, $P(O)(OH)R_{15}$, or $P(O)(OH)OR_{13}$,
  wherein $R_{13}$ is H, an alkyl group, or an aryl group;
  $R_{14}$ is an alkyl group or an aryl group; and $R_{15}$ is an alkyl group; and

is a heteroaryl group having five ring atoms, including 1, 2 or 3 heteroatoms selected from O, S, and N; and pharmaceutically acceptable salts and solvates thereof, and pharmaceutically acceptable prodrugs thereof, said prodrugs being different from compounds of the formula (I); with the proviso that if the compound of formula (I) is:

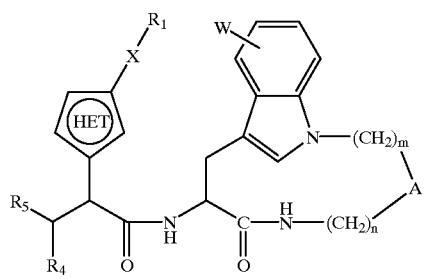

wherein $R_1$, $R_4$, and $R_5$ are as defined above, W is H, OH, a halo group, an alkyl group, or an O-alkyl group, and further wherein when m is 2, 3, or 4, n is 1, 2, 3, or 4, and A is $CH_2O$, NH, or N-alkyl; or when m is 4, 5, or 6, n is 0, and A is —CHJ—, wherein J is carboxy, alkoxycarbonyl, or carbamoyl;

or a pharmaceutically acceptable salt or solvate thereof, or a pharmaceutically acceptable prodrug thereof, said prodrug being different from a compound of the formula (I), said prodrug being different from a compound of the formula (I); then

is pyrrolyl.

More preferably the compounds of the present invention are selected from compounds of the formula I wherein X is a single bond;

Y is a single bond, —CH(OH)— or —C(O)—;

$R_1$ is an aryl group or a heteroaryl group;

$R_2$ is H, an alkyl group, an aryl group, a heteroaryl group, a cycloalkyl group, a heterocycloalkyl group, or $C(O)R_{10}$, wherein $R_{10}$ is as defined above;

$R_3$ is H, an alkyl group, a heteroaryl group, $NR_{11}R_{12}$ or $OR_{11}$, wherein $R_{11}$ and $R_{12}$ are as defined above or $R_2$ and $R_3$, together with the atoms to which they are attached, form a cycloalkyl group or heterocycloalkyl group;

$R_4$ is H, an alkyl group, OH, an O-alkyl group, $NH_2$, NH-alkyl, or a cycloalkyl group;

$R_5$ is C(O)NHOH, $C(O)OR_{13}$, SH, or $SC(O)R_{14}$,
  wherein $R_{13}$ is H, an alkyl group, or an aryl group, and
  $R_{14}$ is an alkyl group or an aryl group; and

is pyrrolyl, imidazolyl, pyrazolyl, furyl, thienyl, thiazolyl, oxazolyl, isoxazolyl, isothiazolyl, oxadiazolyl, or triazolyl;

or a pharmaceutically acceptable salt or solvate thereof, or a pharmaceutically acceptable prodrug thereof, said prodrug being different from a compound of the formula (I).

In the compounds of the present invention, and the pharmaceutically acceptable salts and solvates thereof, and pharmaceutically acceptable prodrugs thereof, preferably X is a single bond.

In particularly preferred embodiments, when Y is —CH(OH)—, preferably $R_3$ is H or an alkyl group or together with $R_2$ and the atom(s) to which $R_2$ and $R_3$ are attached forms a cycloalkyl group or heterocycloalkyl group, and more preferably $R_3$ is H. When Y is —C(O)—, preferably $R_3$ is an alkyl group, $NR_{11}R_{12}$, or $OR_{11}$, wherein $R_{11}$ and $R_{12}$ are as defined above, or together with $R_2$ and the atoms to which $R_3$ and $R_2$ are attached, forms a cycloalkyl group or heterocycloalkyl group. When Y is a single bond, preferably $R_3$ is a heteroaryl group, more preferably the heteroaryl group:

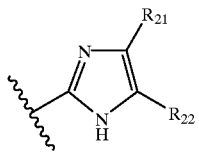

wherein $R_{21}$ and $R_{22}$ are independently any suitable organic moiety or together with the carbon atoms to which they are attached form an aryl group, a heteroaryl group, a cycloalkyl group, or a heterocycloalkyl group. Preferably $R_{21}$ and $R_{22}$ are selected from hydrogen, an alkyl group, an aryl group, a heteroaryl group, a halo group, a C(O)O-alkyl group, a carbamoyl group, a cycloalkyl group, or a heterocycloalkyl group.

Preferably $R_1$ is an aryl group or a heteroaryl group. More preferably $R_1$ is an aryl group of the formula:

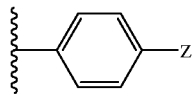

wherein Z is H, halogen, an alkyl group, an O-alkyl group, a cyano group, a hydroxy group, an aryl group, a heteroaryl group, or a heterocycloalkyl group.

Preferably $R_4$ is H, an alkyl group, or OH. More preferably $R_4$ is H or an alkyl group selected from $CHR_{16}OH$ and $CH(NHR_{17})R_{16}$, wherein $R_{16}$ is H, an alkyl group, an aryl group, a heteroaryl group, a cycloalkyl group, or a heterocycloalkyl group, and $R_{17}$ is $C(O)R_{18}$, $SO_2R_{18}$, H, an alkyl group, an aryl group, a heteroaryl group, a cycloalkyl group, or a heterocycloalkyl group, or $R_{16}$ and $R_{17}$, together with the atoms to which they are attached, form a heterocycloalkyl group; wherein $R_{18}$, is H, an alkyl group, an aryl group, a heteroaryl group, a cycloalkyl group, a heterocycloalkyl group, an O-aryl group, an O-alkyl group, or $NR_{19}R_{20}$; wherein $R_{19}$ and $R_{20}$ independently are H, an alkyl group, an aryl group, a heteroaryl group, a cycloalkyl group, or a heterocycloalkyl group, or $R_{19}$ and $R_{20}$, together with the nitrogen atom to which they are attached, form a heterocycloalkyl group.

Preferably

is pyrrolyl, imidazolyl, pyrazolyl, furyl, thienyl, thiazolyl, oxazolyl, isoxazolyl, isothiazolyl, oxadiazolyl, or triazolyl, more preferably is pyrrolyl, fuyl or thienyl, and most preferably is pyrrolyl.

Preferably $R_5$ is C(O)NHOH or C(O)OR$_{13}$, wherein $R_{13}$ is hydrogen.

Particularly preferred compounds according to the invention include:

N-[2,2-Dimethyl-1(S)-(methylcarbamoyl)propyl]-3(R)-(3-phenyl-1H-pyrrol-1-yl)succinamic Acid;

N-(8-Oxo-4-oxa-1,7-diazatricyclo[9.6.1.0$^{12,17}$]octadeca-11(18),12,14,16-tetraen-9(S)-yl)-3(R)-(3-phenyl-1H-pyrrol-1-yl)succinamic Acid;

N-[2,2-Dimethyl-1(S)-(methylcarbamoyl)propyl]-3(R)-[3-(pyridin-4-yl)-1H-pyrrol-1-yl]succinamic Acid;

3(R)-[3-(Biphenyl-4-yl)-1H-pyrrol-1-yl]-N-[2,2-dimethyl-1(S)-(methylcarbamoyl)propyl]succinamic Acid;

3(R)-[3-(Biphenyl-4-yl)-1H-pyrrol-1-yl]-N-[2-hydroxy-1(S)-[(1H-imidazol-4-yl)methyl]ethyl]succinamic Acid;

N-[2,2-Dimethyl-1(S)-(methylcarbamoyl)propyl]-3(R)-[3-(4-propylphenyl)-1H-pyrrol-1-yl] succinamic Acid;

3(R)-[3-(4-Cyanophenyl)-1H-pyrrol-1-yl]-N-[2,2-dimethyl-1(S)-(methylcarbamoyl)propyl] succinamic Acid;

N-[2,2-Dimethyl-1(S)-(hydroxymethyl)propyl]-3(R)-[3-[4-(pyridin-4-yl)phenyl]-1H-pyrrol-1-yl]succinarnic Acid;

N-(2-Hydroxy-1(S)-phenylethyl)-3(R)-[3-[4-(pyridin-4-yl)phenyl]-1H-pyrrol-1-yl]succinamic Acid;

3(R)-[3-(4'-Cyanobiphenyl-4-yl)-1H-pyrrol-1-yl]-N-[2,2-dimethyl-1(S)-(methylcarbamoyl)propyl]succinarnic Acid;

3(R)-[3-(4'-Cyanobiphenyl-4-yl)-1H-pyrrol-1-yl]-N-[2,2-dimethyl-1(S)-(pyridin-4-ylcarbamoyl)-propyl] succinamic Acid;

3(R)-[3-(4'-Carbarmoylbiphenyl-4-yl)-1H-pyrrol-1-yl]-N-[2,2-dimethyl-1(S)-(methylcarbamoyl)propyl]succinamic Acid;

3(R)-[3-(4'-Carbamoylbiphenyl-4-yl)-1H-pyrrol-1-yl]-N-[2,2dimethyl-1(S)-(pyridin-4-yl-carbamoyl)propyl] succinamic Acid;

3(R)-[3-(4'-Cyanobiphenyl-4-yl)-1H-pyrrol-1-yl]-N-[2,2-dimethyl-1 (S)-(hydroxymethyl)propyl] succinarnic Acid;

N-(2(R)-Hydroxyindan-1(R)-yl)-3(R)-[3-[4-(pyridin-4-yl)phenyl]-1H-pyrrol-1-yl] succinarnic Acid;

N-(2,2-Dimethyl-1(S)-(methylcarbamoyl)propyl)-3(R)-[3-(4-(pyridin-4-yl)phenyl)-1H-pyrrol-1-yl]succinamic Acid;

N-(4,4-Dimethyl-2-oxo-tetrahydrofuran-3(S)-yl)-3(R)-[3-[4-(pyridin-4-yl)phenyl]-1H-pyrrol-1-yl]succinamic Acid;

N-(8-Oxo-4-oxa-1,7-diazatricyclo[9.6.1.0$^{12,17}$]octadeca-11(18),12,14,16-tetraen-9(S)-yl)-3(R)-[3-[4-(pyridin-4-yl)phenyl]-1H-pyrrol-1-yl] succinamic Acid;

N-[2,2-Dimethyl-1(S)-(pyridin-4-ylcarbamoyl)propyl]-3(R)-[3-[4-(pyridin-4-yl)phenyl]-1H-pyrrol-1-yl] succinarnic Acid;

N-[1(S)-(1H-Imidazol-2-yl)-3-methylbutyl]-3(R)-[3-[4-(pyridin-4-yl)phenyl]-1H-pyrrol-1-yl] succinamic Acid;

N$^1$-[2,2-Dimethyl-1(S)-(hydroxymethyl)propyl]-N$^4$-hydroxy-2(R)-[3-[4-(pyridin-4-yl)phenyl]-1H-pyrrol-1-yl] succinamide;

N-[2,2-Dimethyl-1(S)-(methylcarbamoyl)propyl]-3(S)-[1-(4-fluorophenyl)-1H-pyrrol-3-yl]succinamic Acid;

3(S)-[1-(4'-Cyanobiphenyl-4-yl)-1H-pyrrol-3-yl]-N-[2,2-dimethyl-1(S)-(methylcarbamoyl)propyl]succinamic Acid;

3(S)-[1-(4'-Cyanobiphenyl-4-yl)-1H-pyrrol-3-yl]-N-[1(S)-(1H-imidazol-2-yl)-3-methylbutyl]succinamic Acid;

3(S)-[1-(4'-Cyanobiphenyl-4-yl)-1H-pyrrol-3-yl]-N-(4,4-dimethyl-2-oxo-tetrahydrofuran-3(S)-yl)succinamic Acid;

3(R)-[3-(4'-Cyanobiphenyl-4-yl)-1H-pyrrol-1-yl]-N-[1(S)-(1H-imidazol-2-yl)-3-methylbutyl]succinamic Acid;

3(R)-[3-(4-Cyanophenyl)-1H-pyrrol-1-yl]-N-[1(S)-(1H-imidazol-2-yl)-3-methylbutyl]succinamic Acid;

N-[2,2-Dimethyl-1(S)-(hydroxymethyl)propyl]-3(S)-[1-[4-(pyridin-4-yl)phenyl]-1H-pyrrol-3-yl] succinamic Acid;

3(R)-{3-[2-(4-Cyanophenyl)ethynyl]-1H-pyrrol-1-yl}-N-[2,2-dimethyl-1(S)(methylcarbamoyl)-propyl] succinamic Acid;

3(R)-{3-[2-(4-Cyanophenyl)ethyl]-1H-pyrrol-1-yl}-N-[2,2-dimethyl-1(S)(methylcarbamoyl)-propyl] succinamic Acid;

$N^1$-Hydroxy-$N^4$-methyl-3(R)-[3-(4-(pyridin-4-yl)phenyl)-1H-pyrrol-1-yl]succinamide;

3(R)-[3-(4'-Cyanobiphenyl-4-yl)-1H-pyrrol-1-yl]-2(S)-cyclopropyl-N-(2,2-dimethyl-1(S)(methylcarbamoyl)propyl)succinarnic Acid;

3(S)-[2-(4'-Cyanobiphenyl4-yl)furan-4-yl]-N-[2,2-dimethyl-1(S)-(methylcarbamoyl) propyl]succinamic Acid;

3(S)-[1-(4'-Cyanobiphenyl-4-yl)-1H-pyrrol-3-yl]-N-(2,2-dimethyl-1(S)-(methylcarbamoyl)propyl)-2(R)-(hydroxymethyl)succinamic Acid;

3(S)-[1-(4'-Cyanobiphenyl-4-yl)-1H-pyrrol-3-yl]-N-(2,2-dimethyl-1(S)-(methylcarbamoyl)propyl)-2(S)-(hydroxy) succinamic Acid;

3(R)-[3-(4'-Cyanobiphenyl-4-yl)-1H-pyrrol-1-yl]-N-(2,2-dimethyl-1(S)-(methylcarbamoyl)propyl)-2(S)-(hydroxy) succinamic Acid;

and the pharmaceutically acceptable salts and solvates thereof, and the pharmaceutically acceptable prodrugs thereof.

As used in the present application, the following definitions apply:

An "alkyl group" is intended to mean a straight or branched chain monovalent radical of saturated and/or unsaturated carbon atoms and hydrogen atoms, such as methyl, ethyl, propyl, isopropyl, butyl, isobutyl, t-butyl, ethenyl, pentenyl, butenyl, propenyl, ethynyl, butynyl, propynyl, pentynyl, hexynyl, and the like, which may be unsubstituted (i.e., containing only carbon and hydrogen) or substituted by one or more suitable substituents as defined below.

An "O-alkyl group" is intended to mean an oxygen bonded to an alkyl group, wherein the alkyl group is as defined above.

A "cycloalkyl group" is intended to mean a non-aromatic, monovalent monocyclic, bicyclic, or tricyclic radical containing 3, 4, 5, 6, 7, 8, 9, 10, 11, 12, 13, or 14 carbon ring atoms, each of which may be saturated or unsaturated, and which may be unsubstituted or substituted by one or more suitable substituents as defined below, and to which may be fused one or more heterocycloalkyl groups, aryl groups, or heteroaryl groups, which themselves may be unsubstituted or substituted by one or more suitable substituents. Illustrative examples of cycloalkyl groups include, but are not limited to, cyclopropyl, cyclobutyl, cyclopentyl, cyclopentenyl, cyclohexyl, cyclohexenyl, cycloheptyl, cyclooctyl, bicyclo[2.2.1.]heptyl, bicyclo[2.2.1.]hept-2-en-5-yl, bicyclo[2.2.2]octyl, bicyclo[3.2.1.]nonyl, bicyclo[4.3.0]nonyl, bicyclo[4.4.0]decyl, indan-1-yl, indan-2-yl, tetralin-1-yl, tetralin-2-yl, adamantyl, and the like.

A "heterocycloalkyl group" is intended to mean a non-aromatic, monovalent monocyclic, bicyclic, or tricyclic radical, which is saturated or unsaturated, containing 3, 4, 5, 6, 7, 8, 9, 10, 11, 12, 13, 14, 15, 16, 17, or 18 ring atoms, and which includes 1, 2, 3, 4, or 5 heteroatoms selected from nitrogen, oxygen and sulfur, wherein the radical is unsubstituted or substituted by one or more suitable substituents as defined below, and to which may be fused one or more cycloalkyl groups, aryl groups, or heteroaryl groups, which themselves may be unsubstituted or substituted by one or more suitable substituents. Illustrative examples of heterocycloalkyl groups include, but are not limited to, azetidinyl, pyrrolidyl, piperidyl, piperazinyl, morpholinyl, tetrahydro-2H-1,4-thiazinyl, tetrahydrofuryl, dihydrofuryl, tetrahydropyranyl, dihydropyranyl, 1,3-dioxolanyl, 1,3-dioxanyl, 1,4-dioxanyl, 1,3-oxathiolanyl, 1,3-oxathianyl, 1,3-dithianyl, azabicylo[3.2.1] octyl, azabicylo[3.3.1]nonyl, azabicylo[4.3.0]nonyl, oxabicylo[2.2.1]heptyl, 1,5,9-triazacyclododecyl, and the like.

An "aryl group" is intended to mean an aromatic, monovalent monocyclic, bicyclic, or tricyclic radical containing 6, 10, 14, or 18 carbon ring atoms, which may be unsubstituted or substituted by one or more suitable substituents as defined below, and to which may be fused one or more cycloalkyl groups, heterocycloalkyl groups, or heteroaryl groups, which themselves may be unsubstituted or substituted by one or more suitable substituents. Illustrative examples of aryl groups include, but are not limited to, phenyl, naphthyl, fluoren-2-yl, indan-5-yl, and the like.

A "heteroaryl group" is intended to mean an aromatic monovalent monocyclic, bicyclic, or tricyclic radical containing 5, 6, 7, 8, 9, 10, 11, 12, 13, 14, 15, 16, 17, or 18 ring atoms, including 1, 2, 3, 4, or 5 heteroatoms selected from nitrogen, oxygen and sulfur, which may be unsubstituted or substituted by one or more suitable substituents as defined below, and to which may be fused one or more cycloalkyl groups, heterocycloalkyl groups, or aryl groups, which themselves may be unsubstituted or substituted by one or more suitable substituents. Illustrative examples of heteroaryl groups include, but are not limited to, pyrrolyl, imidazolyl, pyrazolyl, furyl, thienyl, thiazolyl, oxazolyl, isoxazolyl, isothiazolyl, oxadiazolyl, triazolyl, tetrazolyl, pyrazinyl, pyridyl, pyrimidyl, pyridazinyl, indolyl, isoindolyl, benzimidazolyl, benzofuryl, isobenzofuryl, benzothienyl, quinolyl, isoquinolyl, phthalazinyl, carbazolyl, purinyl, pteridinyl, acridinyl, phenanthrolinyl, phenoxazinyl, phenothiazinyl, and the like.

An "acyl group" is intended to mean a —C(O)—R— radical, wherein R is any suitable substituent as defined below.

A "sulfonyl group" is intended to mean a —S(O)(O)—R— radical, wherein R is any suitable substituent as defined below.

The term "suitable substituent" is intended to mean any of the substituents recognizable to those skilled in the art as not adversely affecting the inhibitory activity of the inventive compounds. Illustrative examples of suitable substituents include, but are not limited to, oxo groups, alkyl groups, hydroxy groups, halo groups, cyano groups, nitro groups, cycloalkyl groups, heterocycloalkyl groups, aryl groups, heteroaryl groups, trialkylsilyl groups, groups of formula (A)

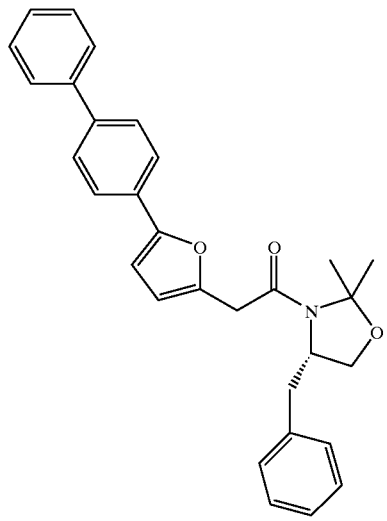

wherein $R_a$ is hydrogen, an alkyl group, a cycloalkyl group, a heterocycloalkyl group, an aryl group, or a heteroaryl group, groups of formula (B)

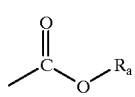
(B)

wherein $R_a$ is hydrogen, an alkyl group, a cycloalkyl group, a heterocycloalkyl group, an aryl group, or a heteroaryl group, groups of formula (C)

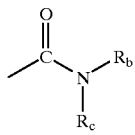
(C)

wherein $R_b$ and $R_c$ are independently hydrogen, an alkyl group, a cycloalkyl group, a heterocycloalkyl group, an aryl group, or a heteroaryl group, groups of formula (D)

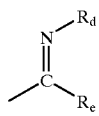
(D)

wherein $R_d$ is hydrogen, an alkyl group, a cycloalkyl group, a heterocycloalkyl group, an aryl group, a heteroaryl group, a hydroxy group, an alkoxy group, an amino group, an alkylamino group, a dialkylamino group, or an acylamino group; and $R_e$ is hydrogen, an alkyl group, a cycloalkyl group, a heterocycloalkyl group, an aryl group, a heteroaryl group, an amino group, an alkylamino group, or a dialkylamino group, groups of formula (E)

(E)

wherein $R_f$ is an alkyl group, a cycloalkyl group, a heterocycloalkyl group, an aryl group, or a heteroaryl group, groups of formula (F)

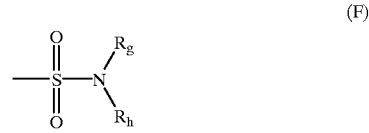
(F)

wherein $R_g$ and $R_h$ are independently hydrogen, an alkyl group, a cycloalkyl group, a heterocycloalkyl group, an aryl group, or a heteroaryl group, groups of formula (G)

(G)

wherein $R_i$ is an alkyl group, a cycloalkyl group, a heterocycloalkyl group, an aryl group, a heteroaryl group, or a group of formula (A), formula (B), formula (C), formula (H), or formula (K), groups of formula (H)

(H)

wherein $R_j$ is hydrogen, an alkyl group, a cycloalkyl group, a heterocycloalkyl group, an aryl group, a heteroaryl group, a hydroxy group, an alkoxy group, an amino group, or a group of formula (A), formula (B), formula (C) or formula (D); and wherein $R_k$ is hydrogen, an alkyl group, a cycloalkyl group, a heterocycloalkyl group, an aryl group, a heteroaryl group, or a group of formula (A), formula (B), formula (C), formula (D), formula (E), or formula (F), groups of formula (J)

(J)

wherein $R_l$ is hydrogen, an alkyl group, a cycloalkyl group, a heterocycloalkyl group, an aryl group, a heteroaryl group, or a group of formula (C), and groups of formula (K)

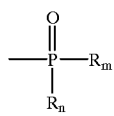

wherein $R_m$ and $R_n$ are independently an alkyl group, a cycloalkyl group, a heterocycloalkyl group, an aryl group, a heteroaryl group, a hydroxy group, an alkoxy group, an amino group, an alkylamino group, or a dialkylamino group.

The term "suitable organic moiety" is intended to mean any organic moiety recognizable to those skilled in the art as not adversely affecting the inhibitory activity of the inventive compounds. Illustrative examples of suitable organic moieties include, but are not limited to oxo groups, alkyl groups, hydroxy groups, halo groups, cyano groups, nitro groups, cycloalkyl groups, heterocycloalkyl groups, aryl groups, heteroaryl groups, trialkylsilyl groups, and groups of formulas (A), (B), (C), (D), (E), (F), (G), (H), (J), and (K), as defined above.

A "hydroxy group" is intended to mean the radical —OH.

An "oxo group" is intended to mean the divalent radical =O.

A "halo group" is intended to mean any of the radicals —F, —Cl, —Br, or —I.

A "cyano group" is intended to mean the radical —C≡N.

A "nitro group" is intended to mean the radical —NO$_2$.

A "trialkylsilyl group" is intended to mean the radical —SiR$_p$R$_q$R$_s$, where R$_p$, R$_q$, and R$_s$ are each independently an alkyl group.

A "carboxy group" is intended to mean a group of formula (B) wherein R$_t$ is hydrogen.

A "alkoxycarbonyl group" is intended to mean a group of formula (B) wherein R$_t$ is an alkyl group as defined above.

A "carbamoyl group" is intended to mean a group of formula (C) wherein R$_t$ and R$_t$ are both hydrogen.

An "amino group" is intended to mean the radical —NH$_2$.

An "alkylamino group" is intended to mean the radical —NHR$_u$, wherein R$_u$ is an alkyl group as defined above.

A "dialkylamino group" is intended to mean the radical —NR$_u$R$_v$, wherein R$_u$ and R$_v$, which are the same or different, are each an alkyl group as defined above.

A "pharmaceutically acceptable prodrug" is intended to mean a compound that may converted under physiological conditions or by solvolysis to a compound of the formula I.

A "pharmaceutically acceptable solvate" is intended to mean a solvate that retains the biological effectiveness and properties of the biologically active components of compounds of formula I.

Examples of pharmaceutically acceptable solvates include, but are not limited to, compounds of formula I in combination with water, isopropanol, ethanol, methanol, DMSO, ethyl acetate, acetic acid, or ethanolamine.

In the case of solid formulations, it is understood that the inventive compounds may exist in different forms, such as stable and metastable crystalline forms and isotropic and amorphous forms, all of which are intended to be within the scope of the present invention.

A "pharmaceutically acceptable salt" is intended to mean those salts that retain the biological effectiveness and properties of the free acids and bases and that are not biologically or otherwise undesirable.

Examples of pharmaceutically acceptable salts include, but are not limited to, sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxyenzoates, phthalates, sulfonates, xylenesulfonates, phenylacetates, phenylpropionates, phenylbutyrates, citrates, lactates, γ-hydroxybutyrates, glycolates, tartrates, methanesulfonates, propanesulfonates, naphthalene-1-sulfonates, naphthalene-2-sulfonates, and mandelates.

If the inventive compound is a base, the desired salt may be prepared by any suitable method known to the art, including treatment of the free base with an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, pyranosidyl acids such as glucuronic acid and galacturonic acid, alpha-hydroxy acids such as citric acid and tartaric acid, amino acids such as aspartic acid and glutamic acid, aromatic acids such as benzoic acid and cinnamic acid, sulfonic acids such a p-toluenesulfonic acid or ethanesulfonic acid, or the like.

If the inventive compound is an acid, the desired salt may be prepared by any suitable method known to the art, including treatment of the free acid with an inorganic or organic base, such as an amine (primary, secondary or tertiary), an alkali metal or alkaline earth metal hydroxide or the like. Illustrative examples of suitable salts include organic salts derived from amino acids such as glycine and arginine, arnmonia, primary, secondary and tertiary amines, and cyclic amines such as piperidine, morpholine and piperazine, and inorganic salts derived from sodium, calcium, potassium, magnesium, manganese, iron, copper, zinc, aluminum and lithium.

The inventive compounds may exist as single stereoisomers, racemates and/or mixtures of enantiomers and/or diastereomers. All such single stereoisomers, racemates and mixtures thereof are intended to be within the scope of the present invention. Preferably, the compounds of the present invention are used in a form that contains at least 90% of a single isomer (80% enantiomeric or diastereomeric excess), more preferably at least 95% (90% e.e. or d.e.), even more preferably at least 97.5% (95% e.e. or d.e.), and most preferably at least 99% (98% e.e. or d.e.). Compounds identified herein as single stereoisomers are meant to describe compounds used in a form that contains at least 90% of a single isomer.

The present invention is further directed to methods of inhibiting matrix metalloproteinase activity that comprise contacting the protease with an effective amount of a compound of formula I or a pharmaceutically acceptable prodrug or a pharmaceutically acceptable salt or solvate thereof. For example, one can inhibit matrix metalloproteinase activity in mammalian tissue by administering a compound of formula I or a pharmaceutically acceptable prodrug or a pharmaceutically acceptable salt or solvate thereof.

The activity of the inventive compounds as inhibitors of matrix metalloproteinase activity may be measured by any of the methods available to those skilled in the art, including in vivo and in vitro assays. Examples of suitable assays for activity measurements include the fluorometric determination of the hydrolysis rate of a fluorescently-labelled peptide substrate, which is described herein.

Administration of the compounds of the formula I, or their pharmaceutically acceptable prodrugs or pharmaceutically acceptable salts or solvates, may be performed according to any of the accepted modes of administration available to those skilled in the art. Illustrative examples of suitable modes of administration include, but are not limited to, oral, nasal, intraocular, parenteral, topical, transdermal and rectal.

The inventive compounds of formula I, and their pharmaceutically acceptable prodrugs and pharmaceutically acceptable salts and solvates, may be administered as a pharmaceutical composition in any suitable pharmaceutical form recognizable to the skilled artisan. Suitable pharmaceutical forms include, but are not limited to, solid, semisolid, liquid, or lyophilized formulations, such as tablets, powders, capsules, suppositories, suspensions and aerosols. The pharmaceutical composition may also include suitable excipients, diluents, vehicles and carriers, as well as other pharmaceutically active agents, depending upon the intended use.

Acceptable methods of preparing suitable pharmaceutical forms of the pharmaceutical compositions are known to those skilled in the art. For example, pharmaceutical preparations may be prepared following conventional techniques of the pharmaceutical chemist involving steps such as mixing, granulating and compressing when necessary for tablet forms, or mixing, filling and dissolving the ingredients as appropriate, to give the desired products for oral, parenteral, topical, intravaginal, intranasal, intrabronchial, intraocular, intraural and/or rectal administration.

Solid or liquid pharmaceutically acceptable carriers, diluents, vehicles or excipients may be employed in the pharmaceutical compositions. Illustrative solid carriers include starch, lactose, calcium sulphate dihydrate, terra alba, sucrose, talc, gelatin, pectin, acacia, magnesium stearate, and stearic acid. Illustrative liquid carriers may include syrup, peanut oil, olive oil, saline solution, and water. The carrier or diluent may include a suitable prolonged-release material, such as glyceryl monostearate or glyceryl distearate, alone or with a wax. When a liquid carrier is used, the preparation may be in the form of a syrup, elixir, emulsion, soft gelatin capsule, sterile injectable liquid (e.g. solution), or a nonaqueous or aqueous liquid suspension.

A dose of the pharmaceutical composition contains at least a therapeutically effective amount of the active compound (i.e., a compound of formula I or a pharmaceutically acceptable prodrug or a pharmaceutically acceptable salt or solvate thereof) and preferably is made up of one or more pharmaceutical dosage units. The selected dose may be administered to a mammal, for example, a human patient, in need of treatment mediated by inhibition of matrix metalloproteinase activity, by any known method of administering the dose including topical, for example, as an ointment or cream; orally, rectally, for example, as a suppository; parenterally by injection; or continuously by intravaginal, intranasal, intrabronchial, intraaural or intraocular infusion.

A "therapeutically effective amount" is intended to mean that amount of a compound of formula I or II that, when administered to a mammal in need thereof, is sufficient to effect treatment for disease conditions alleviated by the inhibition of the activity of one or more matrix metalloproteinases, such as tumor growth, invasion or metastasis, osteoarthritis, rheumatoid arthritis, osteoporosis, periodontitis, gingivitis, chronic dermal wounds, corneal ulcerations, degenerative skin disorders, multiple sclerosis, stroke, diabetic retinopathy, macular degeneration, angiofibromas, hemangiomas, chronic obstructive pulmonary disease, such as emphysema, atherosclerosis, glomerular disease, cardiac arrhythmia, endometriosis or disease conditions characterized by unwanted angiogenesis. The amount of a given compound of formula I that will correspond to a "therapeutically effective amount" will vary depending upon factors such as the particular compound, the disease condition and the severity thereof, and the identity of the mammal in need thereof, but can nevertheless be readily determined by one of skill in the art.

"Treating" or "treatment" is intended to mean at least the mitigation of a disease condition in a mammal, such as a human, that is alleviated by the inhibition of the activity of one or more matrix metalloproteinase, such as tumor growth, invasion or metastasis, osteoarthrities, rhematoid arthritis, osteoporosis, periodontis, gingivitis, chronic dermal wounds, corneal ulcerations, degenerative skin disorders, multiple sclerosis, stroke, diabetic retinophathy, macular degeneration, angiofibromas, hemangiomas, or disease conditions characterized by unwanted angiogenesis, and includes:

(a) prophalactic treatment in a mammal, particularly when the mammal is found to be predisposed to having the disease condition but not yet diagnosed as having it;

(b) inhibiting the disease condition; and/or (c) alleviating, in whole or in part, the disease condition.

The inventive compounds, and their salts, solvates and prodrugs, may be prepared by employing the techniques available in the art using starting materials that are readily available. Certain novel and exemplary methods of preparing the inventive compounds are described below.

METHODS FOR PREPARING CARBOXYLATE MATRIX METALLOPROTEASE INHIBITORS

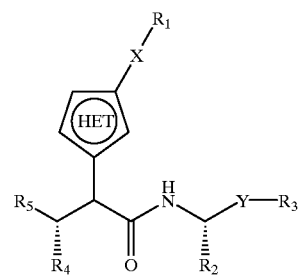

I

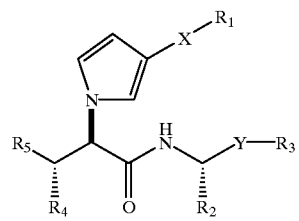

II

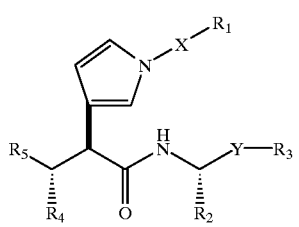

III

-continued

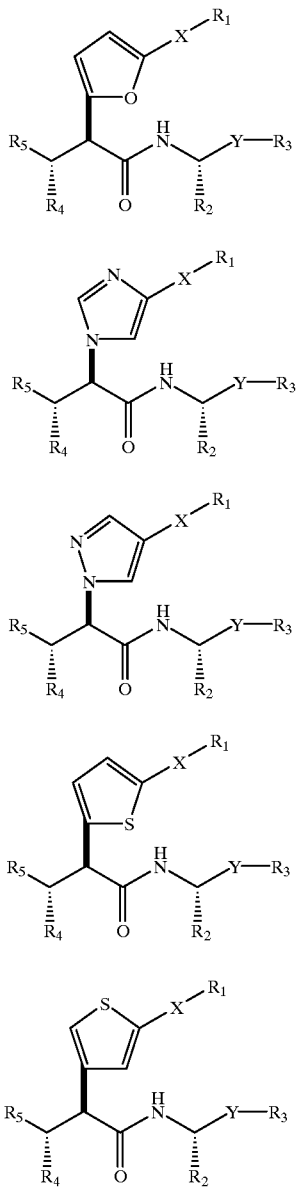

IV

V

VI

VII

VIII

PREPARATION OF COMPOUNDS OF FORMULA I

The methods of preparing compounds of Formula I, where $R_5$ is carboxyl, culminate in the deprotection of esters (1) to the corresponding carboxylates as illustrated in Reaction Scheme I below. Appropriate types of esters (1) and the cleavage of $R_5$ are described, for example, in Greene, T; Wuts, P. G. M. "*Protective Groups in Organic Synthesis,*" Wiley: 1991 and Kocienski, P. J. "*Protecting Groups,*" Thieme: 1994, which are incorporated herein by reference. Some examples and conditions encountered herein are given below.

REACTION SCHEME I (1)

I

As an example of a typical ester cleavage, an ester of Formula (1) where $R_6$ is benzyl is placed in a suspension with solvent, for example, ethyl acetate also containing metal catalyst, preferably palladium(0) in a hydrogen source such as hydrogen gas at one atmosphere or above, at ambient temperature for 30 minutes to three days, preferably four hours. The carboxylates of Formula I, where $R_5$ is —COOH, are amenable to customary isolation and purification.

For esters of Formula (1) where $R_6$ is t-butyl, the ester (1) is deprotected in a solution of solvent, preferably chloroform or dichloromethane, with excess trifluoroacetic acid, at ambient temperature for 15 minutes to 12 hours to obtain a carboxylate of Formula I.

For esters of Formula (1) where $R_6$ is allyl, the ester (1) undergoes cleavage in an inert solvent, preferably acetonitrile, with a catalytic amount of palladium catalyst, such as tetrakis(triphenylphosphine)-palladium(0), with an excess of secondary amine, such as morpholine, for 15 minutes to 12 hours at ambient temperature.

Where the above conditions are incompatible with functional groups contained in either $R_4$ or $R_5$, other protective strategies may be used. For example, simultaneous protection where $R_4$ is olefinic and $R_5$ is carboxylate may occur through their connection as in a halolactone of Formula (2) where X is halogen, as displayed in Reaction Scheme II below. The halolactone (2) undergoes reductive opening to compounds of Formula I, where $R_4$ is allyl and $R_5$ is carboxylate.

REACTION SCHEME II

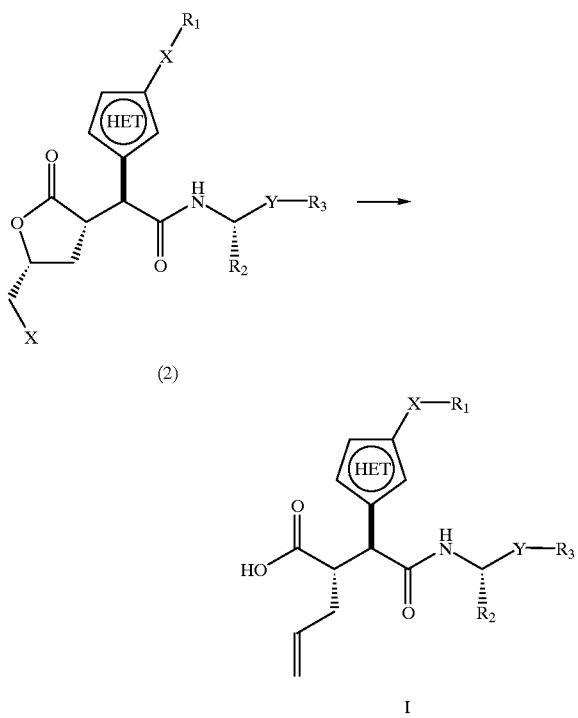

Preparation of Compounds of Formula I, where $R_4$ is Allyl and $R_5$ is Carboxylate A solution of halolactone (2) is exposed to a reductive environment, preferably excess zinc powder in acetic acid. The resulting carboxylate of Formula I where $R_4$ is allyl is isolated and purified via conventional methods.

Compounds (5) of Formula I where $R_5$ is hydroxamic acid (—C(O)NHOH) may be obtained from compounds (3) of Formula I where $R_5$ is carboxyl. Any of the numerous commercially available coupling reagents can be used for conversion either to a protected version of a compound of Formula (4) where $R_7$ is alkyl or directly to hydroxamate (5), as outlined by the Reaction Scheme III below:

Step 1—Preparation of Compounds of Formula (4) or (5)

Carboxylic acids of Formula (3) and hydroxylamine or its O-alkyl derivatives in inert solvent, preferably dimethylformamide (DMF), are coupled with any of the numerous available coupling reagents, preferably benzotriazol-1-yloxytris(dimethylamino)-phosphonium hexafluorophosphate (BOP), at ambient temperature for one to 24 hours to provide either hydroxarnates (5) or O-alkyl hydroxamates (4), respectively. The products are amenable to routine handling and purification.

Step 2—Preparation of Compounds of Formula (5) from Compounds of Formula (4)

Protected hydroxamates of Formula (4) are deprotected as determined by the nature of the protecting group $R_7$. Where $R_7$ is a trialkylsilyl, mild acid hydrolysis or fluoride cleavage in protic or aprotic solvent at ambient temperature or below for one to 12 hours is sufficient. Where $R_7$ is benzyl, selective deprotection without N—O bond cleavage proceeds in the presence of palladium on carbon, with a hydrogen source, such as hydrogen gas at atmospheric pressure, in a suitable solvent, such as dimethylformamide or methanol.

PREPARATION OF COMPOUNDS OF FORMULA II

Pyrrole compounds of Formula II can be prepared from cyclocondensation of amines of Formula (6) with tetrahydrofurans of Formula (7), as shown below in Reaction Scheme IV:

REACTION SCHEME IV

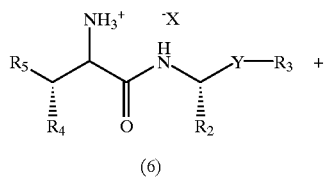

(6)

REACTION SCHEME III

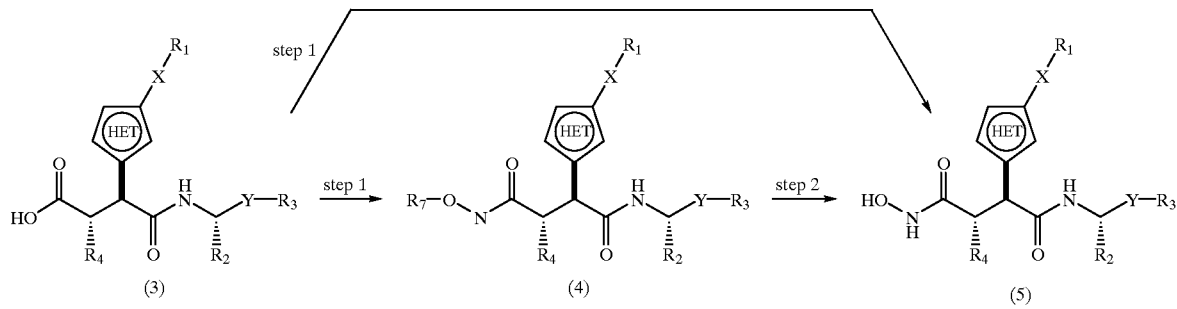

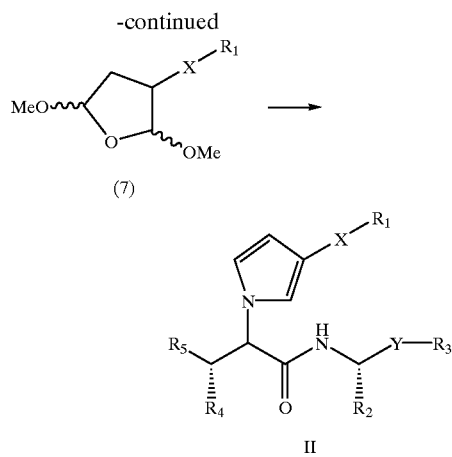

(7)

II

Preparation of Compounds of Formula II

Condensation of amine salts of Formula (6) and 2,5-dimethoxytetrahydrofurans of Formula (7) may be carried out in acetic acid for a period of one to 24 hours at temperatures from 40°–90° C. Another effective set of conditions includes heating a solution of compounds (6) and (7) in inert organic solvent, for example 1,2-dichloroethane, with or without acid, such as trifluoroacetic acid, and with or without stoichiometric amounts of water, for a period of one to 48 hours at 40°–90° C. The product of Formula II is isolated and purified by conventional means.

ALTERNATE PREPARATION OF COMPOUNDS OF FORMULA II

Another method for preparation of pyrrole compounds of Formula II involves earlier ring formation. Cyclocondensation of D-amino acids of Formula (8) with tetrahydrofurans of Formula (7) and subsequent coupling is shown below in Reaction Scheme V:

REACTION SCHEME V

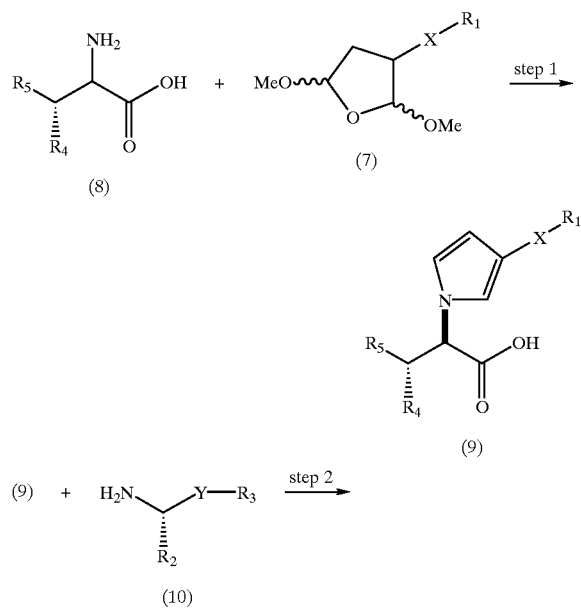

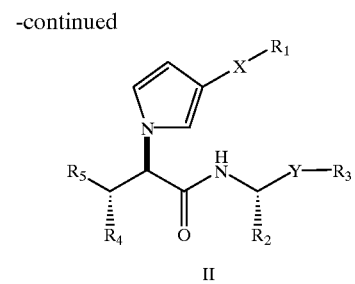

II

Step 1—Preparation of Compounds of Formula (9)

Amino acids of Formula (8) and 2,5-dimethoxytetrahydrofurans of Formula (7) are dissolved or suspended in solution in an inert organic solvent, for example 1,2-dichloroethane, with chlorotrimethylsilane, with or without acid, such as trifluoroacetic acid, and with or without a base, such as pyridine, for a period of one to 48 hours at ambient temperature to 80° C., preferably the latter. The product (9) is isolated and purified by conventional means.

Step 2—Preparation of Compounds of Formula II from Compounds of Formulas (9) and (10)

Carboxylates of Formula (9) and amines of Formula (10) are coupled under typical coupling conditions. Acids of Formula (9) may first be converted to a corresponding activated ester (i.e., acid fluoride) or used with a reagent, for example BOP, along with the amine (10) in an inert solvent such as chloroform, and with or without a base such as N-methylmorpholine (NMM), for a period of one to 48 hours at 0° C. to ambient temperature, preferably the latter. The product II is isolated and purified by conventional means.

PREPARATION OF STARTING MATERIALS

Preparation of Amines of Formula (6)

Amines of Formula (6), where $R_4$ is hydrogen and $R_5$ is an ester (—$COOR_6$) are available after two steps as shown in Reaction Scheme VI: coupling of commercially available D-aspartate derivatives (11) and various amines (10) of commercial or synthetic origin. Subsequent deprotection of protected amines (12) furnish amine salts (6).

REACTION SCHEME VI

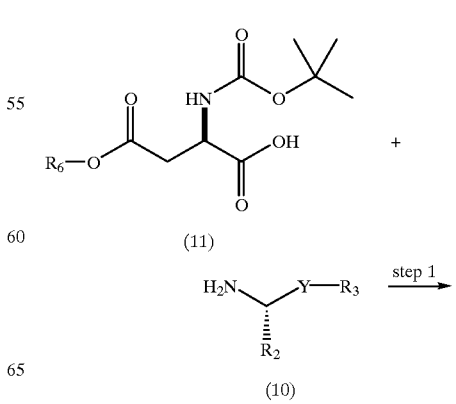

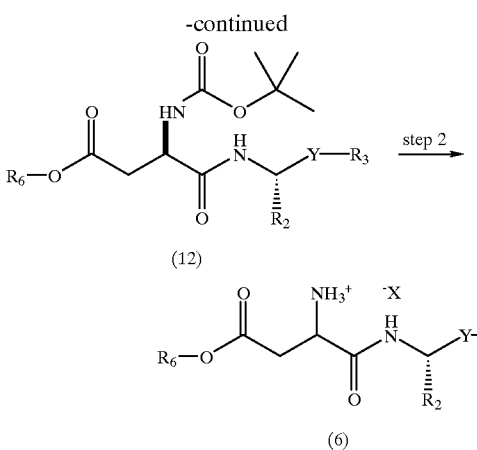

Step 1—Preparation of Compounds of Formula (12)

Carboxylates of Formula (11) and amines (10) are condensed as described above for the preparation of a compounds of formula II according to Reaction Scheme V. Typical coupling reagents, for example BOP, are used in an inert solvent such as chloroform, and with or without a base such as N-methylmorpholine, at 0° C. to ambient temperature, preferably the latter, for a period of one to 48 hours to furnish the product of Formula (12), which is isolated and purified by conventional means.

Step 2—Preparation of Amines of Formula (6)

t-Butoxycarbonylamines of Formula (12) are deprotected traditionally, for example, in an inert solvent, preferably dichloromethane or chloroform, with an excess of trifluoroacetic acid, at 0° C. to ambient temperature, preferably the former, for 30 minutes to 18 hours to obtain amine salts (6), which can be immediately used without further purification but are amenable to customary handling and purification.

Preparation of Compounds of Formula (18)

Aspartates of Formula (8) where $R_4$ is hydrogen are available for purchase, or from synthesis according to methods understood by those skilled in the art, such as those described in the literature. However, aspartates of Formula (8) where $R_4$ is alkyl must be synthesized. An example of this synthesis is shown in Reaction Scheme VII below. D-Aspartate (13) is converted via diallyl ester (14) to aspartate (15), which undergoes Ireland-Claisen rearrangement of the β-ester to allyl compound (16). Appropriate processing provides carboxylates of Formula (18) where $R_4$ is allyl, which are suitable for later conversion to lower alkyls, for example, reduction to where $R_4$ is propyl.

REACTION SCHEME VII

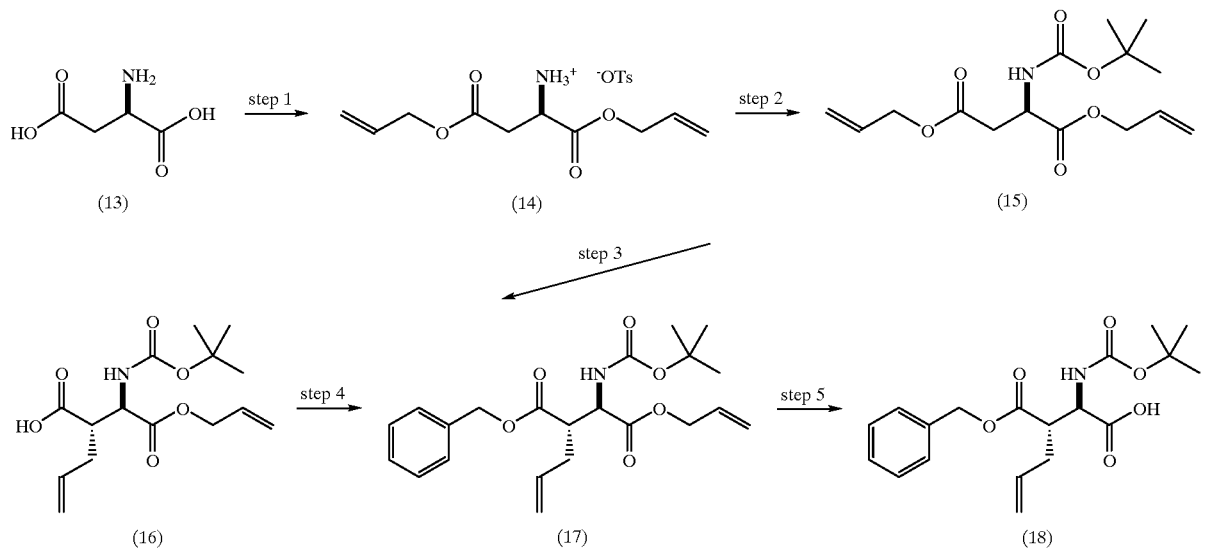

Step 1—Preparation of Compounds of Formula (14)

D-Aspartate dual esters can be produced in any of a variety of ways. For example, D-aspartate (13) is esterified with an excess of allyl alcohol, preferably in inert solvent such as benzene with stoichiometric amounts of acid, such as p-toluenesulfonic acid, for one to 12 hours, at reflux under conditions to azeotropically remove water. The salt (14) precipitates or is otherwise isolated and purified by conventional means.

Step 2—Preparation of Compounds of Formula (15)

Protection of an amine is well documented and understood by those skilled in the art. For example, amine salt (14) is treated with excess di-t-butyl-dicarbonate in appropriate solvent, preferably dichloromethane, in the presence of base, preferably triethylarnine for one to 24 hours at ambient temperature. The product (15) is isolated and purified by conventional means.

Step 3—Preparation of Compounds of Formula (16)

Esters of Formula (15) are treated with a specified stoichiometric amount of hindered lithium amide base, preferably two equivalents of lithium hexamethyldisilazide, in an inert aprotic solvent, preferably tetrahydrofiran, at −78° C. for 15 to 45 minutes, whereupon preferably two equivalents or more of trialkylsilyl chloride, preferably chlorotrimethylsilane, are added and the reaction solution is subsequently warmed at 50 to 70° C. or reflux for 30 minutes to 4 hours, then allowed to cool, and quenched with methanol. Subsequent routine aqueous workup leads to isolation of allyl compound (16), which is purified by conventional means.

Step 4—Preparation of Compounds of Formula (17)

Acids of formula (16) are esterified to distinguish carboxyl termini. This esterification can be carried out by any of a number of means understood by those skilled in the art, preferably with an appropriate isourea to prevent racemization, for example with O-benzyl-N,N'-diisopropylurea, in inert solvent such as chloroform, at reflux for 3 to 6 hours. The diester (17) is isolated and purified by conventional means.

Step 5—Preparation of Compounds of Formula (18)

Selective mono-deprotection of diesters of Formula (17) is effected preferentially by means of routine allyl ester cleavage conditions, as discussed above for Reaction Scheme I. A solution of the diester (17) is placed in polar aprotic solvent, preferably acetonitrile, with palladium catalyst, for example with palladium (0) tetrakis-(triphenylphosphine) and excess secondary amine base, preferably morpholine at ambient temperature for 15 minutes to four hours, preferably 30 minutes. The product acid of Formula (18) is isolated and purified in routine manner.

Preparation of Compounds of Formula (2)

For the simultaneous protection of $R_4$ and $R_5$ functionality for certain compounds of Formula I, for example where $R_4$ is allyl and $R_5$ is carboxyl, the halolactone-amide of Formula (2) is prepared. The synthesis of these compounds of Formula (2) uses methods described for Formula II in Reaction Scheme V, as shown in Reaction Schemes VIII and IX below.

In Reaction Scheme VIII, the monoacid (19) undergoes conventional coupling (as described for Reaction Scheme V) with amine of Formula (10) to give amide of Formula (20), which is deprotected to amine of Formula (21). The pyrrole ring is formed (as in the preparation of pyrroles in Reaction Scheme V) on amine (21) with dimethoxy-furan (7) to obtain products of Formula (2).

REACTION SCHEME VIII

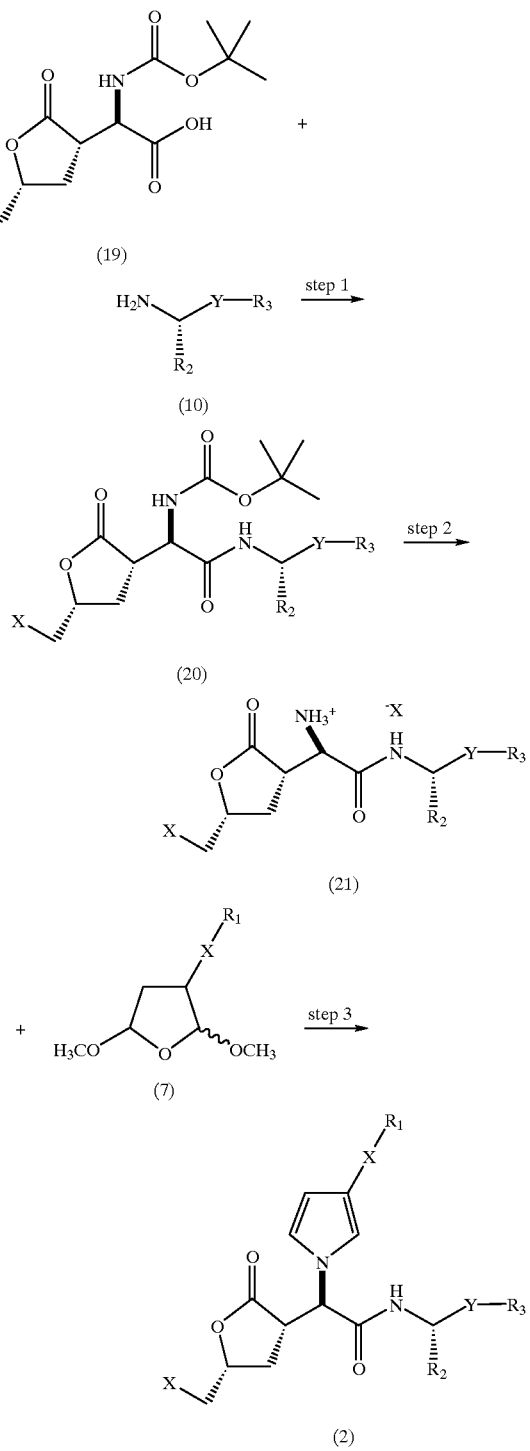

Step 1—Preparation of Compounds of Formula (20)

The coupling of acid (19) and amine (10) is accomplished with the routine peptide amide forming conditions as described above in Reaction Scheme V, Step 2.

Step 2—Preparation of Compounds of Formula (21)

The deprotection of amine (20) to amine salt (21) is accomplished as described above for the preparation of amines of Formula (6) in Reaction Scheme VI, Step 2.

Step 3—Preparation of Compounds of Formula (2)

The formation of pyrroles of Formula (2) from (21) and (7) can be accomplished as described above in Reaction Scheme V, Step 1.

An alternate route to compounds of Formula (2) proceeds via formation of pyrrole (23) prior to a coupling, as illustrated by Reaction Scheme IX below:

REACTION SCHEME IX

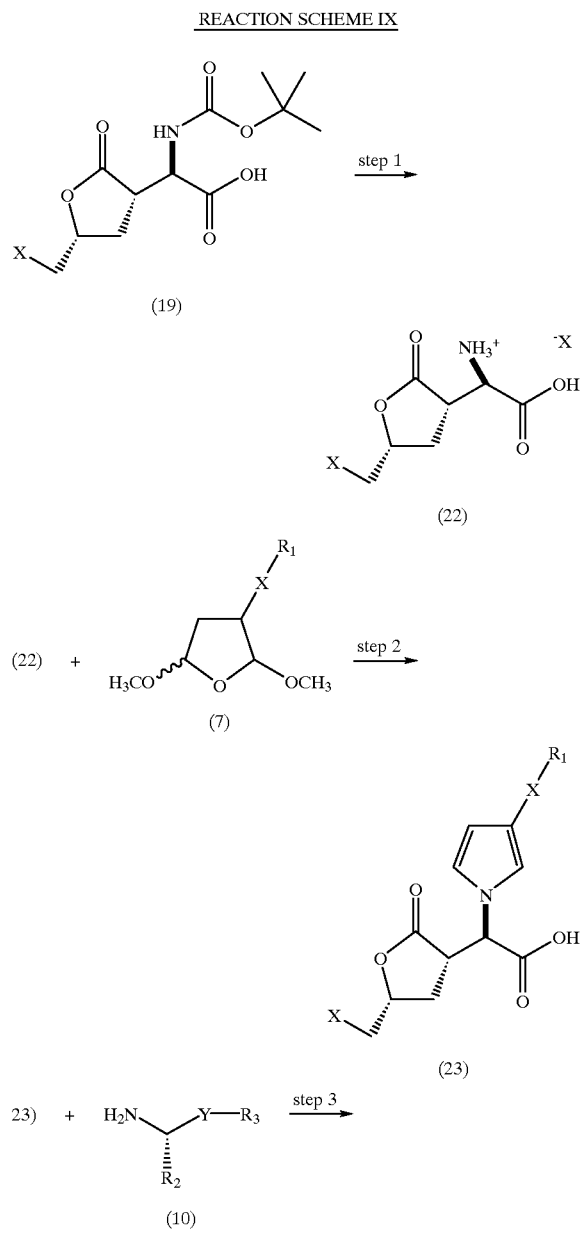

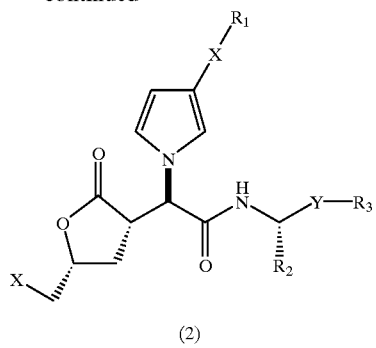

(2)

Step 1—Preparation of Compounds of Formula (22)

The deprotection of monoacid (19) to amine salt (22) is as described above for the preparation of amines of Formula (6) in Reaction Scheme VI, Step 2.

Step 2—Preparation of Compounds of Formula (23)

The condensation and cyclization of compounds (22) and (7) provides pyrroles of Formula (23) in the same manner as discussed above for Reaction Scheme V, Step 1.

Step 3—Alternate Preparation of Compounds of Formula (2)

The coupling of acid (23) and amine (10) is accomplished with the routine peptide amide formation conditions described above for Reaction Scheme V, Step 2.

For the preparation of late stage intermediates of Formula (2), aspartate derivatives of Formula (19) are needed. As shown in Reaction Scheme X below, intermediate (16) is alternatively cyclized to afford halolactones (25), which simultaneously protect the ultimate $R_5$ carboxylate and olefin of $R_4$ at an early stage.

REACTION SCHEME X

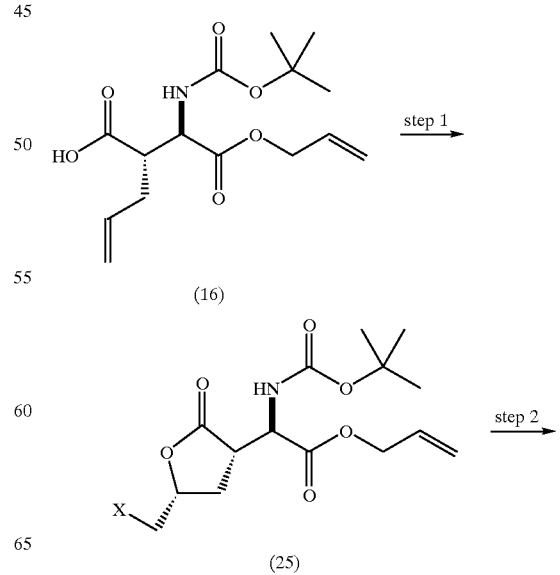

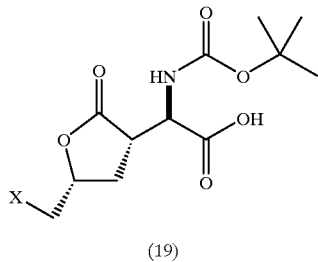

(19)

Step 1: Preparation of Compounds of Formula (25)

Carboxy-olefins of Formula (16) in a suspension of inert solvent, for example tetrahydrofuran or acetonitrile, and excess aqueous alkali, preferably sodium bicarbonate, are exposed to excess halogen, preferably iodine, initially at −10 to 0° C., then allowed to warm and equilibrate at ambient temperature over a period of 2 to 24 hours. The product halolactone (25) is isolated and purified according to routine methods.

Step 2: Preparation of Compounds of Formula (19)

Compound (19) is prepared from compound of Formula (25) in a manner identical to that described above for the preparation of compounds of Formula (18) in Reaction Scheme VII, Step 5.

Preparation of Tetrahydrofurans of Formula (7)

The tetrahydrofuran of Formula (7) where $R_1$ is hydrogen and X is a single bond is commercially available. More often 3-substituted furans (26) are treated with bromine in methanol to provide 2,5-dimethoxy-dihydrofurans (27), which are in turn hydrogenated to produce tetrahydrofurans (7). The overall approach is illustrated in Reaction Scheme XI below:

REACTION SCHEME XI

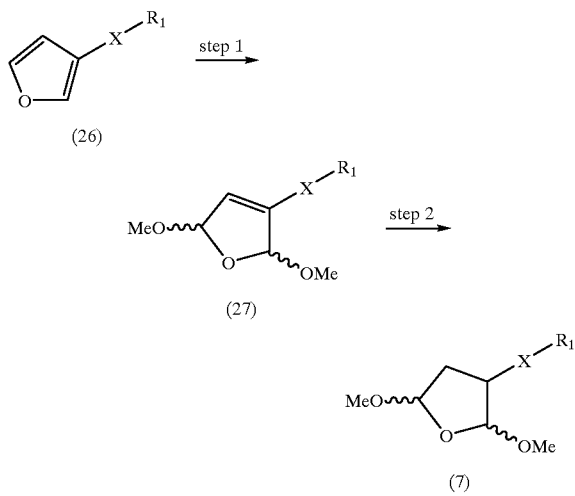

Step 1—Preparation of Compounds of Formula (27)

Furans of Formula (26) are treated with stoichiometric amounts of bromine in methanol as solvent or in mixtures with less polar solvents, at temperatures of −20° C. to ambient temperature, preferably −10° C., for 10 minutes to 8 hours, preferably for 90 minutes. The products (27) are isolated and purified by conventional means.

Step 2—Preparation of Compounds of Formula (7)

Olefins of Formula (27) are reduced in a suitable protic or aprotic solvent under hydrogen at one atmosphere or above in the presence of metal catalyst, preferably rhodium on alumina or palladium on carbon, in the temperature range from about 0° C. to 40° C., for about 1–8 hours, preferably 3 hours. Compounds (7) are isolated and purified by conventional means.

The tetrahydrofairan (7a) of Formula (7) where X is a single bond and $R_1$ is formyl (—CHO) is commercially available. Construction of various X and $R_1$ combinations are possible through elaboration upon the carboxaldehyde. One possible scenario is displayed in Reaction Scheme XII below.

REACTION SCHEME XII

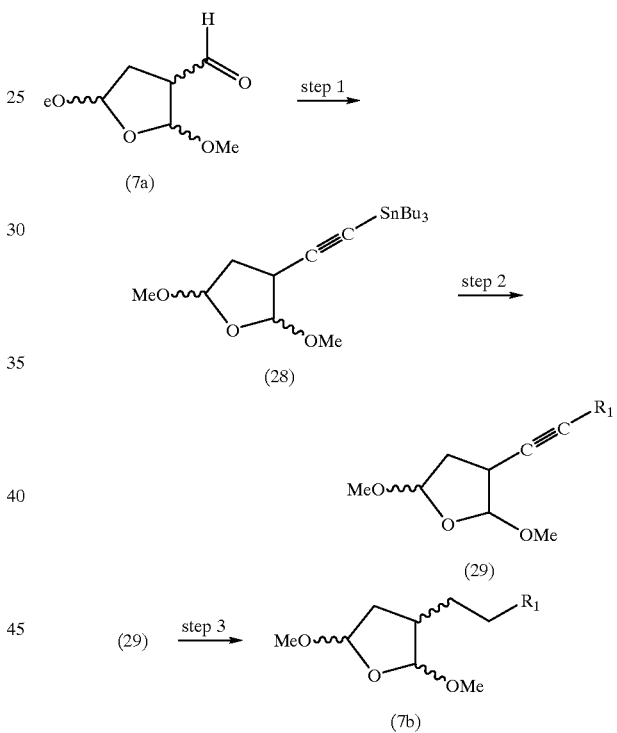

Step 1—Preparation of the Compound of Formula (28)

As an example, the aldehyde of Formula (7a) is added to a mixture with at least two equivalents of the reagent formed from carbon tetrabromide, triphenylphosphine, and zinc powder in dichlormethane over 24 hours at ambient temperature. After 60 minutes at ambient temperature, the desired intermediate 1,1-dibromoolefin can be isolated and purified in conventional manner. The alkyne product of Formula (28) is produced from treatment of 1,1-dibromoolefin with alkyllithium, preferably n-butyllithium, in inert, aprotic solvent, preferably tetrahydrofuran, at low temperature, −78° C. to 0° C. after 60 minutes, and subsequent capping with trialkylstannyl halide, such as chlorotributyl-tin (IV). The product (28) can be handled and purified with routine methods.

Step 2—Preparation of the Compounds of Formula (29)

The alkyne (28) is elaborated through an alkylation with the corresponding anion for compounds of Formula (7) where X is —C≡C—, and $R_1$ is alkyl, or the alkyne (28) is coupled in a Stille-type reaction to a compound of Formula (7) where X is a —C≡C— and $R_1$ is aryl. For the former compounds of Formula (29) where $R_1$ is alkyl, a solution of the alkyne (28) in inert solvent at low temperature, ambient or below, undergoes metal exchange with a suitable alkyllithium, and is subsequently alkylated with a suitable alkylating reagent, for example primary alkyl halides. For compounds of Formula (29) where $R_1$ is vinyl or aryl, the alkyne (28) and vinyl or aryl halide couple in the presence of palladium catalyst, such as tetrakis-(triphenylphosphine) palladium(0), with aprotic solvent at below or above ambient temperature. The products of Formula (29) are isolable and can be purified by conventional techniques.

Step 3—Preparation of the Compounds of Formula (7b)

The alkyne (29) can be hydrogenated in suitable solvent, with a hydrogen source, such as hydrogen gas at atmospheric pressure, in the presence of a catalyst, such as palladium on carbon, to furnish, for example, compounds (7b) of Formula (7) where X is —CH$_2$CH$_2$—. The products of Formula (7b) can be subjected to routine handling and purification.

Other tetrahydrofurans of Formula (7) where X is a single bond and $R_1$ is vinyl or aryl are available from the corresponding furans. The appropriately functionalized furans arise from substituent elaboration via coupling of appropriate vinyl or aryl partners: carefully choreographed sequential Suzuki, Heck, or Stille-style couplings with olefins, haloaryls, arylboronic acids, aryltriflates and/or aryltinalkyls can be used to prepare arylfurans (22), as exemplified in Reaction Schemes XIII, XIV, XV, and XVI below.

An example of a Suzuki-style coupling to develop $R_1$ is shown below in Reaction Scheme XIII.

REACTION SCHEME XIII

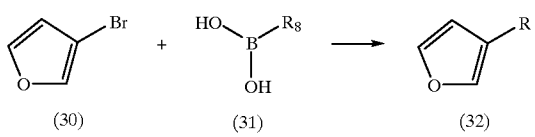

Preparation of Compounds of Formula (32)

3-Bromofuran (30) and boronic acids of Formula (31) where $R_8$ is aryl or vinyl, in a mixture of inert solvent, for example benzene, and aqueous alkali, preferably sodium carbonate, in the presence of a suitable metal catalyst, are heated at 30° to reflux temperature for one to 24 hours. Suitable metal catalysts include palladium(0) tetrakis (triphenylphosphine) or palladium(II) acetate as examples. The product (32) is isolable and can be processed in routine fashion.

Alternatively, the roles of the reaction partners can be reversed, for example as shown in Scheme XIV below wherein furan-3-yl-boronic acid (33) and unsaturated halides of Formula (34), where X is bromide, iodide, or triflate and $R_8$ is vinyl or aryl, couple to result in compounds (32).

REACTION SCHEME XIV

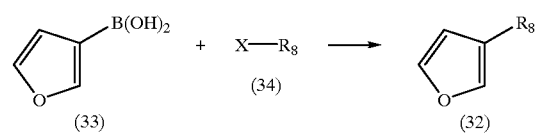

Preparation of Compounds of Formula (32)

Furan-3-ylboronic acid (33) and vinyl or aryl halides of Formula (34) are reacted under conditions similar to those described above for Reaction Scheme XIII.

The Heck coupling represents additional useful methodology to introduce and elaborate substituents on unsaturated systems as displayed in Reaction Scheme XV as follows:

REACTION SCHEME XV

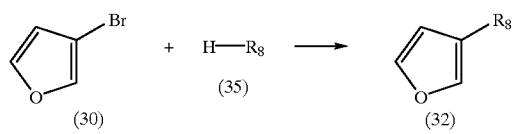

Alternate Preparation of Compounds of Formula (32)

3-Bromofuran (30) and olefinic compounds of Formula (35) where $R_8$ is aryl or vinyl, are placed in a suspension of inert solvent, in the presence of metal catalyst, preferably palladium(0) tetrakis(triphenylphosphine) or palladium(II) acetate with catalytic tertiary phosphine, preferably tri(o-tolyl)phosphine or tri(o-tolyl)arsine, at ambient to reflux temperature for one to 24 hours. The product (32) is isolable and can be processed in routine fashion.

For larger $R_1$ groups, further elaboration of smaller $R_1$ groups can be obtained from different coupling conditions, complimentary to those reactions depicted in Reaction Schemes XIII, XIV, and XV above. For example, once the above methods are used to prepare a furan of Formula (36), it can in turn be manipulated to join an additional vinyl or aryl group as shown in Reaction Scheme XVI below:

REACTION SCHEME XVI

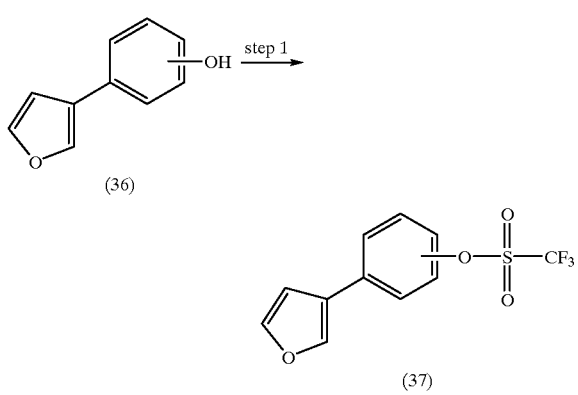

-continued

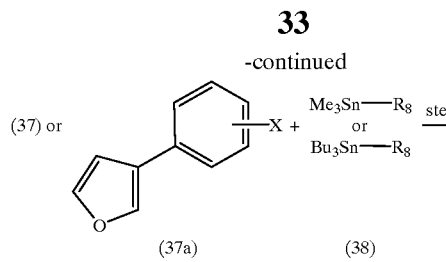

(37) or (37a) (38)

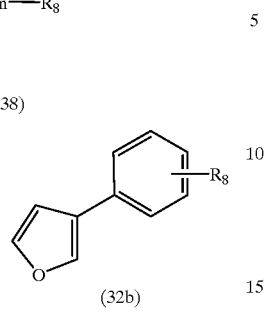

(32b)

Step 1: Preparation of Compounds of Formula (37)

Phenol of Formula (36) in a solution of inert solvent, for example chloroform, in the presence of amine base, preferably 2,6-lutidine, at a temperature of −10° C. or above, preferably 0° C., is treated with a stoichiometric amount of trifluoromethanesulfonic anhydride. The product triflate (37) is potentially reactive; it may be isolated and purified under anhydrous conditions in inert atmosphere, and should be used quickly.

Step 2: Alternate Preparation of Compounds of Formula (32b)

Either triflate of Formula (37) or vinyl halide of Formula (37a) is coupled with trialkyl-vinyl or aryl tin(IV) of Formula (38) in a solution of inert solvent, such as benzene, in the presence of metal catalyst, such as palladium(II) acetate, with a stoichiometric amount of lithium chloride at ambient temperature or above. The coupled product (32b) is amenable to conventional isolation and purification.

The furan building components in Reaction Schemes XIII, XIV, XV, and XVI are readily available. 3-Bromofuran (30) can be purchased from Aldrich. Furan-3-yl-boronic acid can be prepared, for example, as described in Thompson, W. J.; Gaudino, G. *J. Org, Chem.* 1984, 49, 5237–5243. Furans of Formula (36) can be synthesized using the methodology outlined above for Reaction Schemes XIII, XIV, XV, and XVI. Boronic acids of Formula (31) are known in the literature or can be synthesized. Organotin(IV) compounds of Formula (38) are also known in the literature or can be synthesized.

PREPARATION OF COMPOUNDS OF FORMULAS III, IV, V, VI, VII, AND VIII

All compounds of Formulas III, IV, V, VI, VII, and VIII where $R_5$ is carboxyl can be produced from the corresponding esters as described, above for Formula I in Reaction Scheme I. Compounds of Formulas III, IV, V, VI, VII, and VIII where $R_5$ is N-hydroxycarbamoyl (—C(O)NHOH) can be produced by the method described above for Reaction Scheme II.

The heterocyclic acetic acid derivatives of Formula (40) where $R_9$ is alkoxy, alkylamino, or oxazolidin-3-yl, are alkylated with α-haloesters of Formula (39) where X is chloride, bromide, iodide, or triflate to target esters of Formula (41) as shown below in Reaction Scheme XVII. The $R_9$ group of compounds of Formula (40) can serve as a chiral auxiliary to help establish the absolute stereochemistry of compounds of Formula (41).

REACTION SCHEME XVII

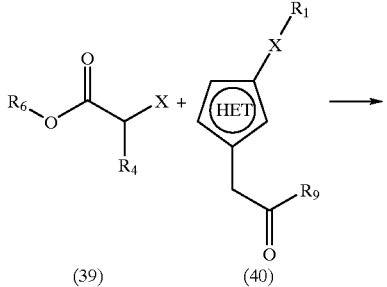

(39) (40)

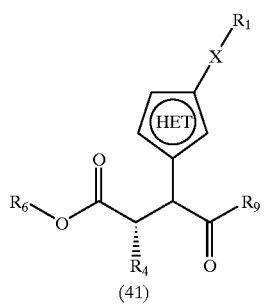

(41)

Solutions of compounds of Formula (40) in inert solvent, preferably tetrahydrofuran, are added to solutions with stoichiometric and/or defined amounts of a suitable base, for example, sodium hexamethyldisilazane or lithium diisopropylamide, in inert solvent, preferably tetrahydrofuran, at low temperature, preferably −78 to −15° C., for five minutes to one hour, are suitable to effect formation of the corresponding anion. Then α-haloesters of Formula (39) are added alone or in a solution of inert solvent. The cold reaction mixture is allowed to stir for 30 minutes to 24 hours, preferably one hour, to form target esters (41), which are isolated and purified by routine methods.

For an example of the alkylation process outlined by Reaction Scheme XVII where $R_9$ is a chiral auxiliary, see Reaction Scheme XVIII below. According to this scheme, amides of Formula (40) where $R_9$ are chiral oxazolidines (see Formula (42) below) can undergo stereoselective alkylation to provide products of Formula (43), which in turn can furnish hydroxyethylamides of Formula (44) (Formula I where $R_5$ is an ester, Y is —CH(OH)—).

REACTION SCHEME XVIII

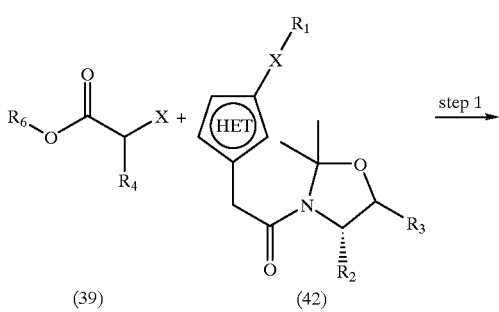

(39) (42)

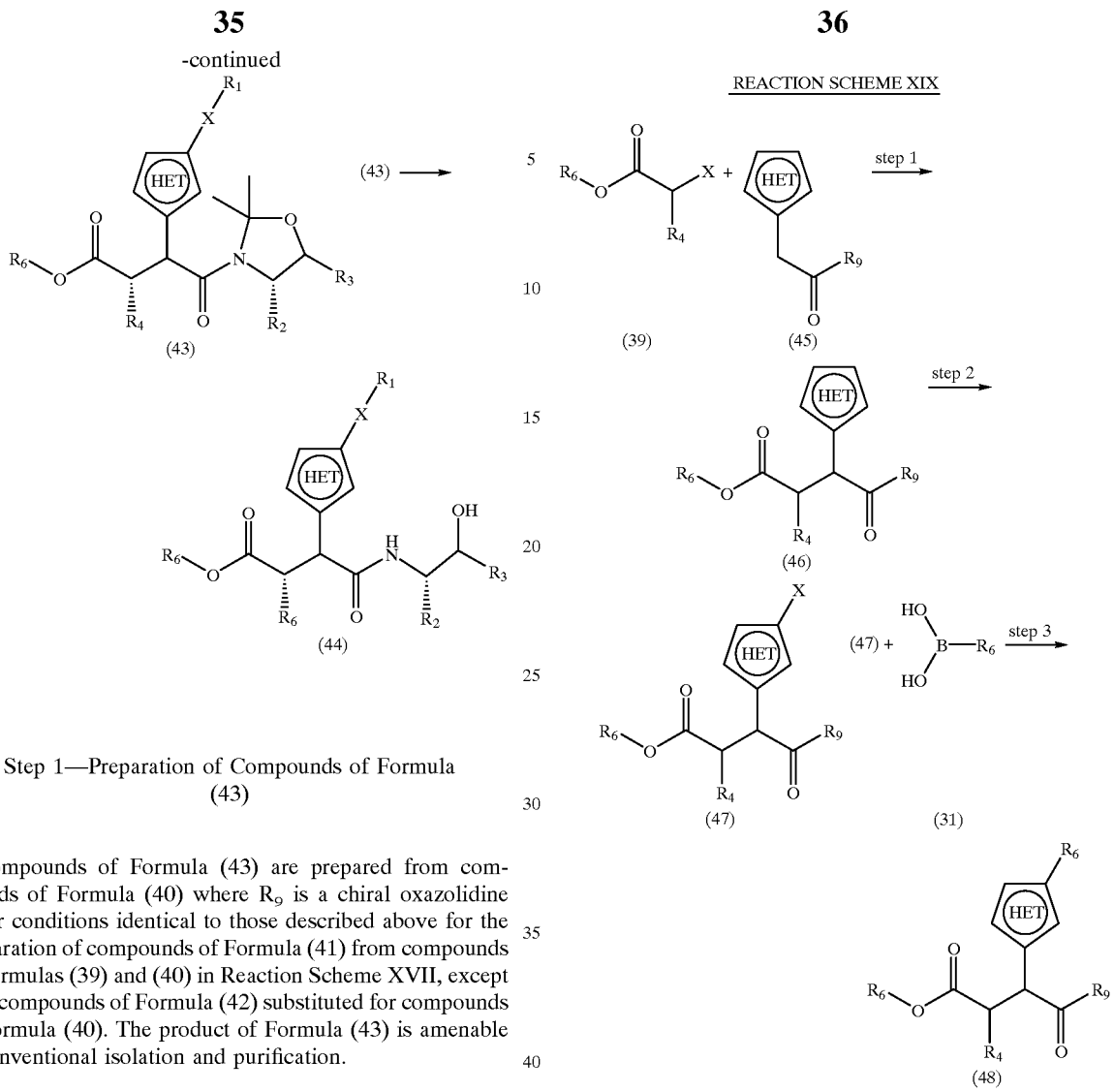

Step 1—Preparation of Compounds of Formula (43)

Compounds of Formula (43) are prepared from compounds of Formula (40) where $R_9$ is a chiral oxazolidine under conditions identical to those described above for the preparation of compounds of Formula (41) from compounds of Formulas (39) and (40) in Reaction Scheme XVII, except with compounds of Formula (42) substituted for compounds of Formula (40). The product of Formula (43) is amenable to conventional isolation and purification.

Step 2—Preparation of Compounds of Formula (44)

Compounds of Formula (43) in solvent, such as tetrahydrofuran, is treated with excess acid, preferably dilute, 0.5 molar aqueous hydrochloric acid, at ambient to reflux temperature, preferably the former. The product of Formula (44) is isolated and purified via routine methods.

The disubstituted heterocycles of Formula (41) may also be assembled in a variation in the order of execution shown above in Reaction Scheme XVIII. The alkylations in the above Schemes XVII and XVIII can precede the installation or elaboration of the portion that contains X and $R_1$. Late stages use appropriate sequences of coupling methods discussed in Reaction Schemes XIII, XIV, XV, and XVI. For example, in Reaction Scheme XIX below, monosubstituted heterocycle of Formula (46) might be halogenated to an appropriately disubstituted heterocycle of Formula (47), which in turn is a coupling partner for methodology outlined in Reaction Schemes XIII, XIV, XV, and XVI. In this example, a Suzuki coupling with boronic acid of Formula (31) is used to give a compound of Formula (48).

PREPARATION OF STARTING MATERIALS

α-Haloesters of Formula (39) where $R_4$ is hydrogen are commercially available. When $R_4$ is alkyl, many compounds of Formula (39) can be prepared by syntheses described in literature. For example, many amino acids can be converted to optically active compounds of Formula (39) where $R_4$ is alkyl as described in Coppola, G. M., Schuster, H. F. *Asymmetric Synthesis: Construction of chiral molecules using amino acids;* J. Wiley & Sons: New York, 1987.

Certain heterocyclic acetic acid derivatives of Formula (40) are commercially available in certain cases (for example, 2- or 3-thiophene acetic acid), but usually must be synthesized in various ways, as described below.

Direct alkylation on the nitrogen of an appropriate heterocycle of Formula (49), where T, U, and V are each independently carbon or nitrogen, by the a-haloacetic acid derivatives of Formula (50), where X is halogen or triflate, produces the desired intermediates of Formula (51), as shown in Reaction Scheme XX below:

REACTION SCHEME XX

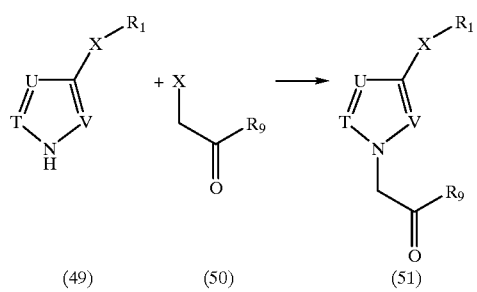

Step 1—Preparation of Compounds of Formula (51)

Nitrogen-containing heterocycles of Formula (49) (for example, pyrazole) are placed in aprotic solvent such as N,N-dimethylformamide, and if warranted, deprotonated with a base such as sodium hydride and treated with α-haloacetamides of Formula (50) where X is halogen or triflate, at room temperature or above for one to 24 hours. The products of Formula (51) are amenable to routine techniques for isolation and purification.

An analogous straightforward substitution of the heterocyclic ring involves the alkylation of an organometallic derivative of Formula (53) where M is, for example, lithium, magnesium, or copper, with an α-halo acetic acid derivative of Formula (50), as shown in Reaction Scheme XXI below:

REACTION SCHEME XXI

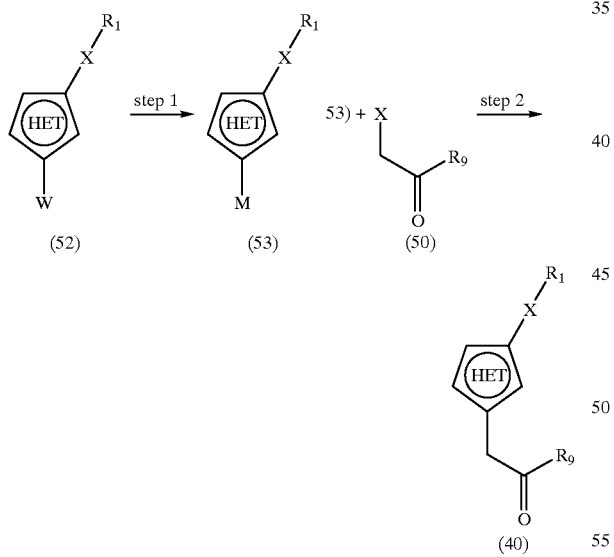

Step 1—Preparation of Compounds of Formula (53)

Heterocyclic metallo derivatives of Formula (53) are available in customary fashion from a heterocycle of Formula (52). Principal methods include deprotonation of parent of Formula (52) where W is hydrogen, or from halogen-metal exchange of the corresponding halo-heterocycle of Formula (52) where W is halogen. These reactions are typically carried out in inert, aprotic solvent such as tetrahydrofuran, at ambient temperature or below, in 15 minutes to 24 hours. The organometallics of Formula (53) are typically unstable to atmosphere and moisture. They are routinely formed in situ and used immediately without isolation.

Step 2—Alternate Preparation of Compounds of Formula (40)

The organometallics of Formula (53) are alkylated by stoichiometric or excess amounts of acetate or acetamide of Formula (50) in inert solvent, preferably tetrahydrofuran, at low temperatures of −78 to 0° C., in ten to 90 minutes. The product of Formula (40) is isolated and purified with routine methods.

As another alternative, an acylation can be carried out with oxalates or oxamates of Formula (54) where $R_{10}$ is, for example, halogen, alkoxy, or imidazol-1-yl, to ketoesters or ketoamides of Formula (55), which are subsequently deoxygenated in several steps to ester or amides of Formula (40), as shown in Reaction Scheme XXII below.

REACTION SCHEME XXII

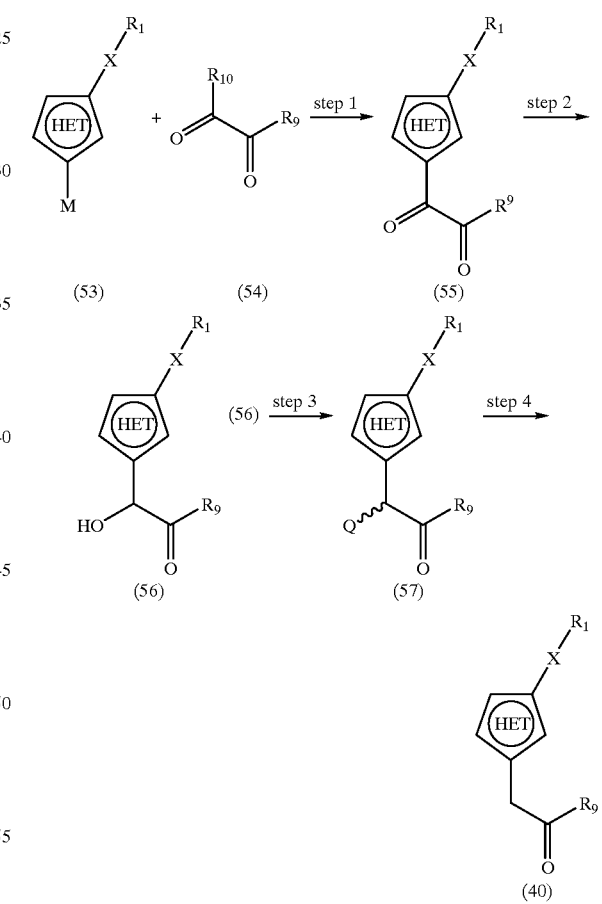

Step 1—Preparation of Compounds of Formula (55)

Heterocyclic organometallic derivatives of Formula (53) where M is lithium can be prepared as shown in Reaction Scheme XXI above and acylated by an oxalate or oxamate of Formula (54) where $R_{10}$ is typically halogen, alkoxy, or imidazol-1-yl in inert solvent, preferably tetrahydrofuran, at low temperatures of −78 to 0C., in ten to 90 minutes. The product of Formula (55) is isolated and purified with routine methods.

Step 2—Preparation of Compounds of Formula (56)

The ketoester or amide of Formula (55) in solvent, preferably ethanol, at temperatures of −15 to 0° C., is treated with hydride reducing agent, preferably sodium borohydride, for five minutes to four hours to provide products of Formula (56), which are isolable and purified with conventional techniques.

Step 3—Preparation of Compounds of Formula (57)

Alcohols of Formula (56) can be processed for deoxygenation by conversion to various moieties designated Q, preferably where Q is an ester or halide. Typically they are acylated in aprotic solution, for example chloroform, with excess acylating agent, for example acetic anhydride or acetyl chloride in the presence of excess amine base, preferably pyridine, with or without catalytic amounts of (4-dimethylamino)pyridine to give acetates of Formula (57) where Q is acetoxy, which are handled and purified in usual fashion.

Step 4—Preparation of Compounds of Formula (40)

α-Halides or acetates of Formula (57) where Q is halogen or acetoxy, respectively, are reduced to products of Formula (40) with a metal catalyst, preferably palladium on carbon, and a source of hydrogen, preferably ammonium formate. The products (40) are handled and purified in customary manner.

The disubstituted heterocycles of Formula (40) can also be constructed in a differently ordered sequence: late formation of the portion that contains X and $R_1$ utilizing appropriate sequences of coupling methods discussed in Reaction Schemes XIII, XIV, XV, and XVI.

Many of the monosubstituted heterocycles that are commercially available bear only one carbon in the substituent, and additional processing is necessary to prepare disubstituted heterocycles of Formula (40), as shown in Reaction Scheme XXIII below. Commercially available monosubstituted heterocycles of Formula (58) where $R_{11}$ is hydrogen, hydroxy, or alkoxy (for example, 3-furan carboxaldehyde or 3-furfural, where $R_{11}$ is hydrogen) can be homologated through any of numerous suitable methods known to those skilled in the art, for example, that described in Martin, S. F. *Synthesis* 1979, 633–665, to furnish 2-heterocyclic acetic acid derivatives (59), which can be further substituted, for example as a halide of Formula (60). Alternatively, the heterocycles Formula (58) are substituted as halides of Formula (61), then homologated to derivatives of Formula (60). Subsequent linkage of a compound of Formula (60) with an appropriate coupling partner such as a compound of Formula (31) gives esters or amides of Formula (62). As recognized by those skilled in the art, the versatility of the methods in Reaction Scheme XXIII allows interchangability of the steps. For example, the substitution of halides of Formula (61) with boronic acids of Formula (31) may precede a homologation to desired intermediates of Formula (62) (not shown).

REACTION SCHEME XXIII

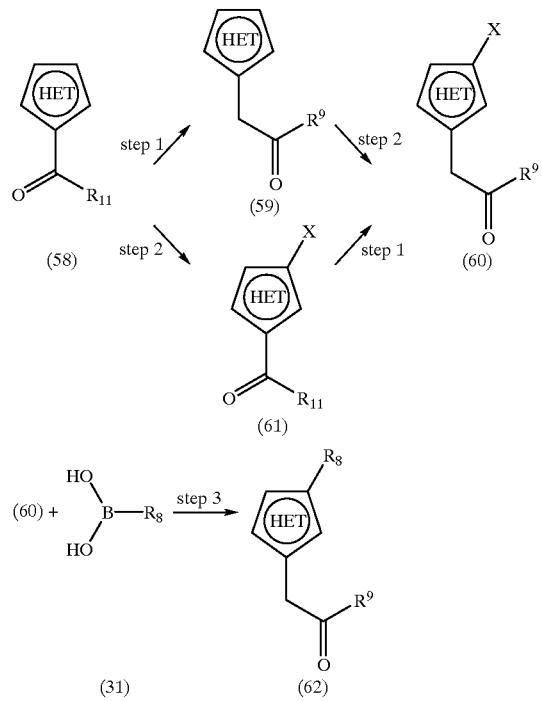

Step 1—Preparations of Compounds of Formulas (59) and (60)

The heterocycles of Formulas (58) and (61) are homologated to compounds of Formulas (59) and (60), respectively, depending upon the nature of $R_{11}$ and $R_9$. See, for example, Martin, S. F. *Synthesis* 1979, 633–665. As an example, for compounds (58) and (61) when $R_{11}$ is hydrogen, the anion of 2-trimethylsilyl-1,3-dithiane is used in inert aprotic solvent, preferably tetrahydrofuran at low temperature, 0° to −78° C. for 30 minutes to several hours, to obtain the corresponding dithiane adduct, which is subsequently converted through any of a variety of methods to derivatives of Formula (59). An example of dithiane removal uses mercuric chloride in water and alcohol to afford an ester of Formula (59) where $R_9$ is alkoxy. The products of Formula (59) are amenable to conventional handling and purification.

Step 2—Preparations of Compounds of Formulas (60) and (61)

As an example of the introduction of the second heteroaromatic substituents, compounds of Formulas (59) and (58) in an inert solvent are halogenated, for example, with a bromine source, such as bromine or N-bromosuccinimide, at ambient temperature or below, for an hour to a day. The resultant hetereoaryl halides of Formulas (60) and (61), respectively, are subject to routine purification and manipulation.

Step 3—Preparations of Compounds of Formula (62)

The coupling of heteroaryls of Formula (60) are carried out analogous to that described for Reaction Schemes XIII, XV, or XVI to obtain compounds of Formula (62).

Amides with the generic Formula (40) where $R_9$ is alkylamino are often available from the corresponding carboxylic acid or activated esters of Formula (40) where $R_9$ is alkoxy or hydroxy, as exemplified in Reaction Scheme XXIV below:

REACTION SCHEME XXIV

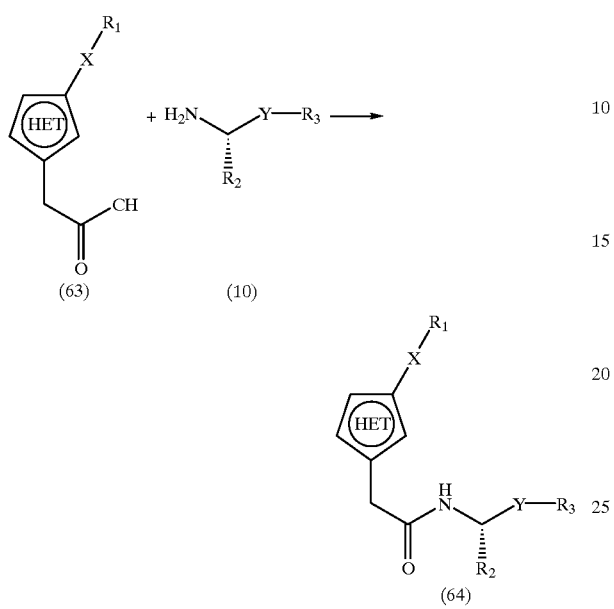

The formation of amides (64) (i.e., Formula (40) where $R_9$ is alkylamine) results from acids of Formula (63) coupling with amines of Formula (10) under the same conditions as described above for Reaction Scheme V, Step 2. The products of Formula (64) are isolated and purified by conventional methods.

Oxazolidines of Formula (42) can be made from the acetamides of Formula (65) where Y in terms of formula I is —CH(OH)—, as shown in Reaction Scheme XXV below:

REACTION SCHEME XXV

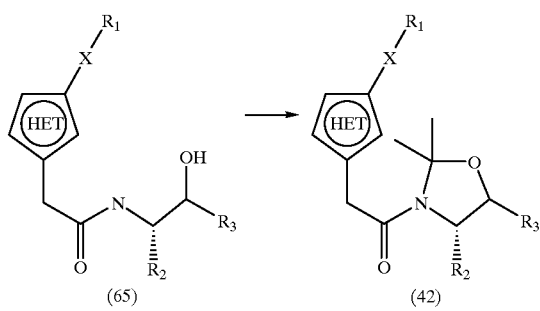

The hydroxyamides of Formula (65) are placed in solution containing acetone or its equivalent, preferably 2-methoxypropene, with a catalytic amount of acid, such as p-toluenesulfonic acid, under dehydrating conditions, such as trapping of water with a Dean-Stark apparatus, at ambient temperature to reflux, for a suitable amount of time to convert starting material (65). The product (42) is amenable to routine processing for isolation and purification.

A preferable avenue to oxazolidines of Formula (42) involves coupling of oxazolidines of Formula (67) to acetic acids of Formula (63), as shown in Reaction Scheme XXVI below. The oxazolidines (67) in turn originate from amino-alcohols of Formula (66) of commercial and synthetic origin.

REACTION SCHEME XXVI

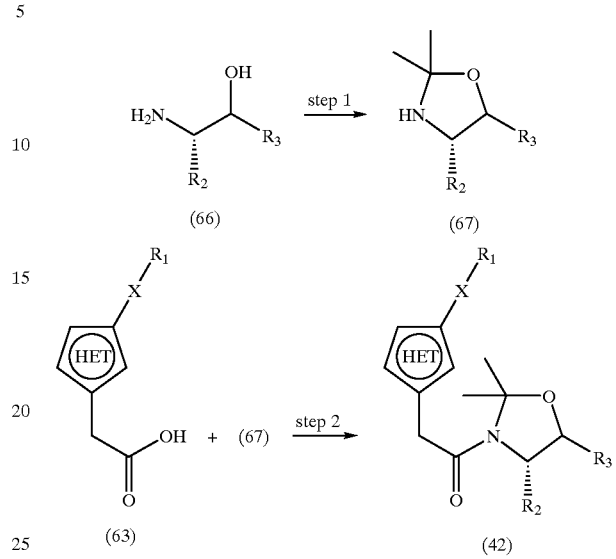

Step 1—Preparation of Compounds of Formula (67)

Compounds of Formula (67) are prepared from compounds of Formula (66) using a method similar to that described above for the preparation of compounds of Formula (42) Reaction Scheme XXV, except lower temperatures are preferred. The products of Formula (67) can be somewhat unstable and are routinely used in situ or immediately in the next reaction without purification.

Step 2—Alternative Preparation of Compounds of Formula (42)

Conditions for the formation of amides with typical coupling reagents as discussed above for Reaction Scheme V, Step 2, apply to the preparation of compounds of Formula (42).

For mono-substituted heterocycles that are not available commercially, the rings may be constructed. For example, for the compounds of Formula III, as shown below in Reaction Scheme XXVII, tetrahydrofurans of Formula (68) where $R_{12}$ is hydrogen or alkyl are condensed with amines of Formula (69) to provide pyrroles of Formula (70). Depending on the nature of X and $R_1$, $R_{12}$ of pyrrole (70) may be converted from hydrogen to a halogen and subsequently an alkyl (as in Reaction Scheme XXII, for example).

REACTION SCHEME XXVII

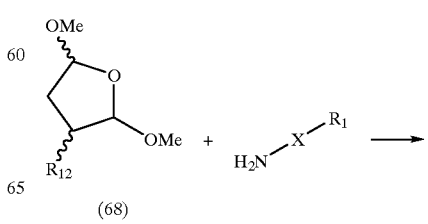

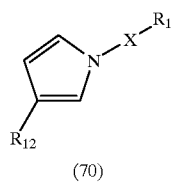

(70)

Preparation of Compounds of Formula (70)

Compounds of Formula (70) can be prepared from compounds of Formulas (68) and (69) using the conditions identical to those described for the preparation of pyrroles of Formula II in Reaction Scheme IV.

EXAMPLES

The following examples are merely illustrative of the invention and should not be construed as limiting the invention. The examples include preferred embodiments of the inventive compounds. One skilled in the art can make, without undue experimentation, various substitutions and variations.

Example 1(a)

N-(1(S)-Benzyl-2-hydroxyethyl)-3(R)-[3-(biphenyl-4-yl)-1H-pyrrol-1-yl]succinamic Acid

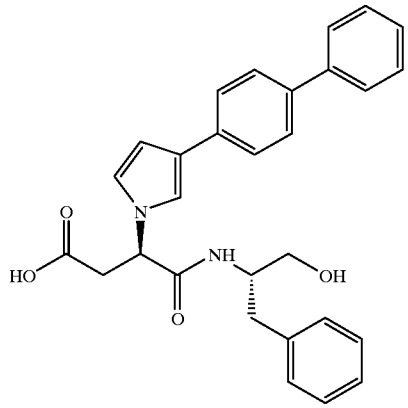

A suspension of 10% Pd/C (wet DeGussa type, 15 mg) and N-(1(S)-benzyl-2-hydroxyethyl)-3 (R)-[3-(biphenyl-4-yl)-1H-pyrrol-1-yl]succinamic acid benzyl ester (68 mg, 0.12 mmol) in EtOAc (5 mL) was stirred under $H_2$ for 20 hours. The catalyst was filtered onto Celite and rinsed with MeOH. The filtrate was concentrated under reduced pressure to give a yellow oil, which was purified via flash column chromatography with a 1% HOAc/2–5% MeOH/$CH_2Cl_2$ stepwise gradient elution to provide 47 mg (82%) of N-(1(S)-benzyl-2-hydroxyethyl)-3(R)-[3-(biphenyl-4-yl)-1H-pyrrol-1-yl]succinamic acid as a white solid.

$^1$H NMR (CDCl$_3$): 67 7.66–7.48 (m, 3H), 7.42 (t, 2H, J=7.2 Hz), 7.34–7.28 (m, 1H), 7.21–7.12 (m, 2H), 7.04–6.96 (m, 1H), 6.94 (bs, 1H), 6.68 (dd, 1H, J=2.5, 2.5 Hz), 6.55 (dd, 1H, J=1.6, 1.6 Hz), 5.78 (bd, 1H, J=7.5 Hz), 4.90 (t, 1H, J=7.2 Hz), 4.36–4.02 (m, 1H), 3.68 (dd, 1H, J=3.4, 11.2 Hz), 3.50 (dd, 1H, J=5.3, 9.0 Hz), 3.31 (dd, J=5.9, 7.4 Hz), 3.12 (dd, 1H, J=7.2, 17.1 Hz), 2.74 (ddd, 1H, J=6.2, 14.3, 14.3 Hz), 2.68 (ddd, J=8.7, 14.0, 14.3 Hz). IR (film): 3387, 3028, 2931, 1715, 1660, 1532, 1494, 1204, 702, 698 cm$^{-1}$. HRFABMS: Calculated for $C_{29}H_{28}N_2O_4Cs$ (M+Cs$^+$): 643.1209. Found: 643.1185. Anal. calculated for $C_{29}H_{28}N_2O_4 \cdot 0.1$ CHCl$_3 \cdot 0.35$ H$_2$O: C, 71.80; H, 5.96; N, 5.75. Found: C, 71.92; H, 5.87; N, 5.77.

The starting material, N-(1(S)-benzyl-2-hydroxyethyl)-3(R)-[3-(biphenyl-4-yl)-1H-pyrrol-1-yl] succinamic acid benzyl ester, was prepared as follows:

N-(1(S)-Benzyl-2-hydroxyethyl)-3(R)-(t-butoxycarbonylamino)succinamic Acid Benzyl Ester

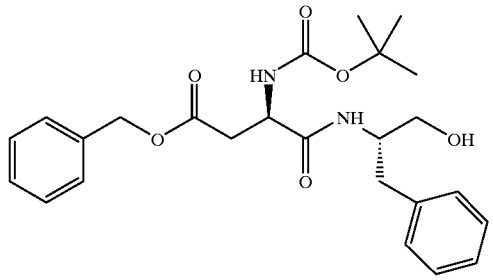

To a solution of N-t-butoxycarbonyl-D-aspartic acid β-benzyl ester (2.00 g, 6.20 mmol) in CHCl$_3$ (80 mL) at 0° C. was added in succession 1-(3-dimethylaminopropyl)-3-ethyl-carbodiimide hydrochloride (EDC, 1.30 g, 6.82 mmol) and N-hydroxybenzotriazole hydrate (HOBt.H$_2$O, 1.04 g, 6.82 mmol). After 10 min at 0° C., 2S-amino-3-phenyl-1-propanol (936 mg, 6.20 mmol) was added and the resultant mixture was allowed to warm to ambient temperature overnight. After 20 hours, the mixture was stirred with 10% aqueous HCl (5 mL) and saturated aqueous NH$_4$Cl (25 mL). The separated aqueous layer was extracted with more CHCl$_3$ (2×10 mL). The combined organic extracts were washed with saturated aqueous NaHCO$_3$:H$_2$O (25:25 mL) two times, dried over Na$_2$SO$_4$, and concentrated in vacuo to a yellow foam, 2.84 g, which was recrystallized from EtOAc/hex in successive crops to afford 2.34 g (83%) of N-(1(S)-benzyl-2-hydroxyethyl)-3(R)-(t-butoxycarbonylamino) succinamic acid benzyl ester as white microneedles, mp 94–95° C.

$^1$H NMR (CDCl$_3$): δ7.40–7.10 (m, 10H), 6.81 (d, 1H, J=10.8 Hz), 5.55 (d, 1H, J=7.2 Hz), 5.11 (ddd, 2H, J=1.2, 6.9, 7.4 Hz), 4.50–4.32 (bm, 1H), 4.21–4.04 (m, 1H), 3.68 (dd, 1H, J=3.4, 11.2 Hz), 3.52 (dd, 1H, J=5.3, 11.5 Hz), 3.03 (dd, 1H, J=4.7, 17.1 Hz), 2.86 (dd, 1H, J=7.2, 13.7 Hz), 2.83 (dd, 1H, J=7.2, 13.7 Hz),2.64 (dd, 1H, J=5.9, 17.1 Hz), 1.43 (s, 9H). IR (KBr): 3442, 3381, 3307, 1729, 1676, 1656, 1554, 1522, 1300, 1164, 1041, 701 cm$^{-1}$. Anal. Calculated for $C_{25}H_{32}N_2O_6$: C, 65.77; H, 7.07; N, 6.14. Found: C, 65.74; H, 7.10; N, 6.20.

4-Biphenylboronic acid

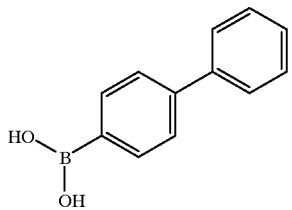

3-(Biphenyl-4-yl)-2,5-dihydro-2,5-dimethoxyfuran

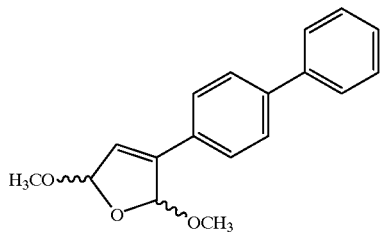

4-Biphenylboronic acid was prepared differently than described in the literature (see Yabroff, D. L.; Branch, G. E.; Bettman, B. *J. Am. Chem. Soc.* 1934, 56, 1850–1857). To a solution of 4-bromobiphenyl (2.00 g, 8.58 mmol) in THF (20 mL) at −78° C. was added n-butyllithium (4.0 mL of 2.5 M in hexanes) in a slow stream via syringe. After 15 minutes, triisopropylborate (3.0 mL, 13 mmol) was added in a slow stream via syringe. After 10 minutes, the resultant homogeneous solution was allowed to warm to ambient temperature over 45 minutes and partitioned between EtOAc (50 mL) and 10% aqueous HCl (50 mL). The aqueous layer was separated and extracted with more EtOAc. The combined organic layers were washed with brine, dried over $Na_2SO_4$ and concentrated to give a crude product which was triturated with hexanes to yield 1.53 g (90%) of 4-biphenylboronic acid as a white solid.

$^1$H NMR (DMSO-$d_6$): δ8.05 (s, 2H), 7.83 (d, 2H, J=8.5 Hz), 7.65 (d, 2H, J=7.0 Hz), 7.60 (d, 2H, J=8.1 Hz), 7.43 (t, 2H, J=7.4 Hz), 7.33 (t, 1H, J=7.2 Hz). Anal. $C_{12}H_{11}BO_2$: C, 72.78; H, 5.60. Found: C, 72.51; H, 5.62.

3-(Biphenyl-4-yl)furan

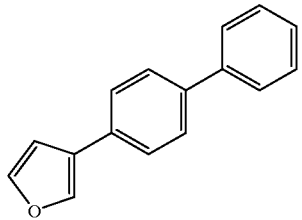

A biphasic mixture of 3-bromofuran (2.90 mL, 32.1 mmol), benzene (70 mL), and 2N aqueous $Na_2CO_3$ (50 mL) was degassed and purged with argon. Tetrakis(triphenylphosphine) palladium(0) (3.7 g, 3.2 mmol) arid a solution of 4-biphenylboronic acid (6.3 g, 32.1 mmol) in EtOH (50 mL) were added sequentially. The mixture was heated at 80° C. for 18 hours, allowed to cool, and partitioned between $CH_2Cl_2$ and $H_2O$. The aqueous layer was separated and extracted with $CH_2Cl_2$ two times. The combined organic layers were washed with brine, dried over $Na_2SO_4$, and concentrated to a crude product, which was dissolved in a minimal amount of $CH_2Cl_2$ and applied to a flash chromatography column packed with hexanes. Elution with 10% $CH_2Cl_2$/hex led to some mixed fractions, which were rechromatographed. A total of 5.37 g (76%) of 3-(biphenyl-4-yl)furan was obtained as a pale yellow oil.

$^1$H NMR: δ8.28 (s, 1H), 7.64–7.55 (m, 6H), 7.50 (s, 1H), 7.45 (t, 2H, J=7.35 Hz), 7.40 (t, 1H, J=7.35 Hz), 6.75 (s, 1H). Anal. calculated for $C_{16}H_{12}O$: C., 87.25; H, 5.49. Found: C, 87.15; H, 5.52.

To a slurry of 3-(biphenyl-4-yl)furan (100 mg, 0.450 mmol) and $Na_2CO_3$ (48 mg, 0.45 mmol) in benzene (1 mL) and MeOH (1 mL) at −10° C. was added bromine (22 μL, 0.43 mmol) dropwise via syringe. After 30 minutes at −10° C., the mixture was diluted with EtOAc and filtered twice. The filtrate was concentrated to give a crude solid which was purified via flash column chromatography with a 0–1% EtOAc/$CH_2Cl_2$ gradient eluant to provide 90 mg (74%) of a diasteromeric mixture of 3-(biphenyl-4-yl)-2,5-dihydro-2,5-dimethoxyfuran as a colorless oil.

$^1$H NMR (CDCl$_3$): δ7.70–7.28 (m, 9H), 6.35 (dd, 0.75H, major isomer, J=0.9, 0.9 Hz), 6.30 (d, 0.25H, minor isomer, J=6.0 Hz), 6.04–6.03 (m, 1H, major+minor isomer), 5.71 (d, 0.75H, major isomer, J=0.9 Hz), 3.60–3.40 (m, 6H). Anal. Calculated for $C_{18}H_{18}O_3$: C, 76.57; H, 6.43 Found: C, 76.52; H, 6.38.

3-(Biphenyl-4-yl)-2,5-dimethoxytetrahydrofuran

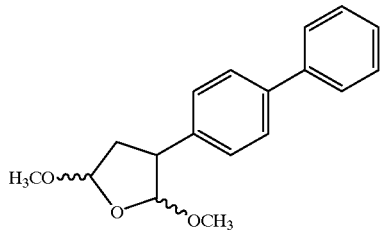

A mixture of 3-biphenyl-4-yl-2,5-dihydro-2,5-dimethoxyfuran (1.00 g, 3.55 mmol) and 5% Pd/C (300 mg) in EtOH:EtOAc (1:2) was stirred under $H_2$ atmosphere for 1.75 hours. The catalyst was filtered onto Celite. The filtrate was concentrated to provide 0.97 g (97%) of a diastereomeric mixture of 3-biphenyl4-yl-2,5-dimethoxy-tetrahydrofuran as a colorless oil which was typically used without purification.

$^1$H NMR: δ7.60–7.53 (m, 4H), 7.45–7.28 (m, 5H), 5.26 (t, 1H, J=5.5 Hz), 5.02 (d, 1H, J=4.4 Hz), 3.54 (s, 3H), 3.36 (s, 3H), 2.63–2.53 (m, 1H), 2.41–2.30 (m, 1H). Anal. calculated for $C_{18}H_{20}O_3$: C, 76.03; H, 7.09. Found: C, 75.74: H, 6.92.

N-(1(S)-Benzyl-2-hydroxyethyl)-3(R)-[3-(biphenyl-4-yl)-1H-pyrrol-1-yl]succinamic Acid Benzyl Ester

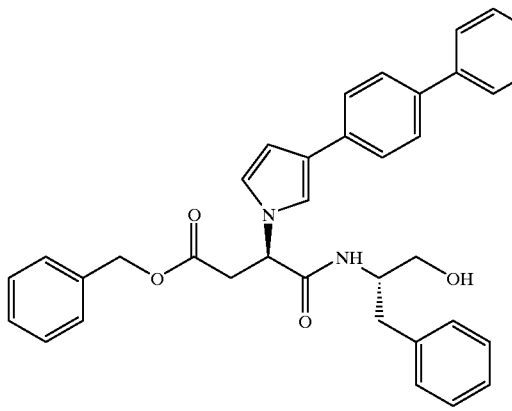

To a solution of N-(1(S)-benzyl-2-hydroxyethyl)-3 (R)-(t-butoxycarbonylamino) succinamic acid benzyl ester (389 mg, 0.851 mmol) in CH$_2$Cl$_2$ (5 mL) was added trifluoroacetic acid (1 mL). After 2.5 h at ambient temperature, the solvent was removed in vacuo to give 3(R)-amino-N-(1(S)-benzyl-2-hydroxyethyl)succinamic acid benzyl ester trifluoroacetate salt as a yellow foam that was placed with 3-(biphenyl-4-yl-)2,5-dimethoxytetrahydrofuran (182 mg, 0.641 mmol) in HOAc (1 mL) and heated to 50° C. After 2 hours, the mixture was allowed to cool, carefully stirred with saturated aqueous NaHCO$_3$ (25 mL), and extracted into CHCl$_3$ (3×15 mL). The combined organic layers were dried over Na$_2$SO$_4$ and evaporated to give a brown oil, 685 mg. Flash column chromatography with 10% MeOH/CH$_2$Cl$_2$ as eluant provided 276 mg (64%) of N-(1(S)-benzyl-2-hydroxyethyl)-3(R)-(3-(biphenyl-4-yl)-1H-pyrrol-1-yl) succinamic acid benzyl ester as a yellow solid.

$^1$H NMR (CDCl$_3$): δ7.70–7.48 (m, 10H), 7.44 (dd, 2H, J=7.2, 7.8 Hz), 7.38–7.12 (m, 5H), 7.08–6.98 (m, 2H), 6.89 (bm, 1H), 6.63 (dd, 1H, J=2.5, 2.5 Hz), 6.54 (dd, 1H, J=1.2, 1.2 Hz), 5.76 (d, 1H, J=7.5 Hz), 5.10 ( dd, 2H, J=12.1, 15.9 Hz), 4.95 (dd, 1H, J=5.0, 8.7 Hz), 4.34–4.00 (bm, 1H), 3.66 (dd, 1H, J=3.7, 11.2 Hz), 3.49 (dd, 1H, J=5.3, 11.2 Hz), 3.3 7 (dd, 1H, J=5.0, 16.8 Hz), 3.18 (dd, 1H, J=8.7, 16.8 Hz), 2.74 (ddd, 2H, J=6.5, 13.7, 15.9 Hz). IR (KBr): 3314, 3029, 2925, 1731, 1658, 1548, 1495, 1355, 1196, 1165, 761, 698 cm$^{-1}$; Anal. calculated for C$_{36}$H$_{34}$N$_2$O$_4$.0.5 H$_2$O: C, 76.17; H, 6.22; N, 4.94. Found: C, 76.24; H, 6.18; N, 4.97.

The following were prepared in a similar manner:

Example 1(b)

N-[2,2-Dimethyl-1(S)-(methylcarbamoyl)propyl]-3(R)-(3-phenyl-1H-pyrrol-1-yl)succinamic acid

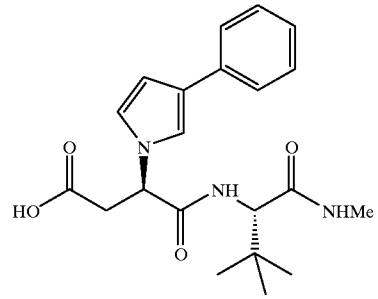

According to the procedure described in Example 1(a), N-[2,2-dimethyl-1(S)-(methylcarbamoyl)propyl]-3(R)-(3-phenyl-1H-pyrrol-1-yl)succinamic acid benzyl ester (371 mg, 0.781 mmol) in MeOH (15 mL) was hydrogenolyzed to provide 301 mg (100%) of N-[2,2-dimethyl-1(S)-(methylcarbamoyl)propyl]-3(R)-(3-phenyl-1H-pyrrol-1-yl) succinamic acid as a yellow foam.

$^1$H NMR (CDCl$_3$): δ7.50–7.20 (m, 4H), 7.15 (tt, 1H, J=1.2, 7.3 Hz), 7.06 (dd, 1H, J=2.0, 2.0 Hz), 6.78 (dd, 1H, J=2.5, 2.5 Hz), 6.48 (dd, 1H, J=1.6, 2.8 Hz), 5.20 (t, 1H, J=6.9 Hz), 4.20 (d, 1H, J=9.3 Hz), 3.34 (dd, 1H, J=6.9, 17.4 Hz), 3.06 (dd, 1H, J=7.2, 17.4 Hz), 2.69 (d, 3H, J=4.7 Hz), 0.93 (s, 9H); IR (KBr): 3318, 2966, 1718, 1654, 1559, 1542, 1202, 745 cm$^{-1}$. HRFABMS: Calcd for C$_{21}$H$_{27}$N$_3$O$_4$Cs (M+Cs$^+$): 518.1056. Found: 518.1037. Anal. Calculated for C$_{21}$H$_{27}$N$_3$O$_4$.0.3 CHCl$_3$: C, 60.73; H, 6.53; N, 9.97. Found: C, 60.7; H, 658; N, 9.84.

The starting material, N-[2,2-dimethyl-1(S)-(methylcarbamoyl)propyl]-3(R)-(3-phenyl-1H-pyrrol-1-yl) succinamic acid benzyl ester, was furnished as follows:

3(R)-t-Butoxycarbonylamino-N-(2,2-dimethyl-1(S)-(methylcarbamoyl)propyl)-succinamic Acid Benzyl Ester

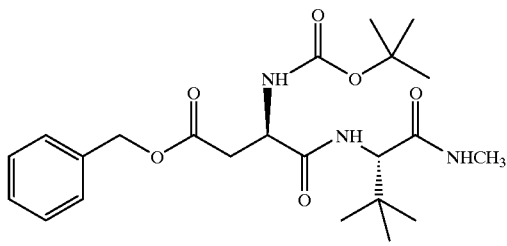

To a solution of N-t-butoxycarbonyl-D-aspartic acid β-benzyl ester (2.19 g, 6.77 mmol) in DMF (40 mL) was added in succession 4-methylmorpholine (NMM, 13.5 mmol, 1.49 mL), 2-(1H-benzotriazole-1-y)-N,N,N',N'-tetramethyluronium tetrafluoroborate (TBTU; 2.17 g, 6.77 mmol) and a solution of L-t-leucine N-methylamide (see Malon, P.; Pancoska, P.; Budesinsky, M.; Hlavacek, J.; Pospisek, J.; Blaha, K. *Coll Czech. Chem. Commun.* 1983, 48, 2844–2861; 886 mg, 6.15 mmol) in DMF (10 mL). After 3 hours at ambient temperature, the mixture was stirred with 10% aqueous $KHSO_4$ (25 mL) and water (100 mL) and extracted with $CHCl_3$ (100 mL) three times. The $CHCl_3$ extracts were washed with 10% aqueous $KHSO_4$:$H_2O$ (10:250 mL), saturated aqueous $NaHCO_3$:$H_2O$ (100:200 mL), and water (200 mL) three times, dried over $Na_2SO_4$, and evaporated to give 2.49 g (90%) of 3(R)-t-butoxycarbonylamino-N-(2,2-dimethyl-1(S)-(methylcarbamoyl)propyl)succinamic acid benzyl ester as a yellow foam, typically used without further purification. Flash column chromatagraphy with 3% $MeOH/CHCl_3$ as eluant afforded analytically pure amorphous solid.

$^1$H NMR: δ7.40–7.30 (m, 5H), 7.03 (d, 1H, J=9.0 Hz), 5.90 (bd, 1H, J=4.7 Hz), 5.56 (bd, 1H, J=8.5 Hz), 5.13 (dd, 2H, J=2.5, 17.4 Hz), 4.56 (bd, 1H, J=7.5 Hz), 4.11 (d, 1H, J=9.0 Hz), 3.00 (dd, 2H, J=4.0, 16.2 Hz), 2.85 (d, 3H, J=4.7 Hz), 1.00 (s, 9H). Anal. Calculated for $C_{23}H_{35}N_3O_6$: C, 61.45; H, 7.85; N, 9.35. Found: C, 61.56; H, 7.83; N, 9.27.

2,5-Dihydro-2,5-dimethoxy-3-phenylfuran

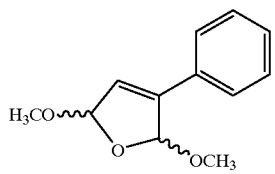

According to the procedure described in Example 1(a) for the preparation of 3-biphenyl-4-yl-2,5-dihydro-2,5-dimethoxyfuran, 3-phenylfuran (see Pridgen, L. N.; Jones, S. S. *J. Org. Chem.* 1982, 47, 1590–1592 and Yang, Y.; Wong, H. N. C. *Tetrahedron* 1994, 32, 9583–9608; 848 mg, 5.89 mmol) provided 1.00 g (82%) of 2,5-dihydro-2,5-dimethoxy-3-phenylfuran as a yellow oil, which was an approximately 80:20 mixture of diastereomers by $^1$H NMR and used without further purification.

$^1$H NMR (CDCl$_3$): δ7.64–7.52 (m, 2H), 7.44–7.30 (m, 3H), 6.36–6.30 (m, 0.9H, major+minor isomer), 6.28 (dd, 0.1H, minor isomer, J=1.2, 3.7 Hz), 6.04–6.00 (m, 0.9H, major+minor isomer), 5.70 (d, 0.8H, major isomer, J=1.2 Hz), 3.52 (s, 2.2H, major isomer), 3.46 (s, 0.60H, minor isomer), 3.43 (s, 2.2H, major isomer), 3.40 (s, 0.60H, minor isomer); Anal. Calculated for $C_{12}H_{14}O_3$.0.04 Br$_2$: C, 67.78; H, 6.64. Found: C, 67.79; H, 6.45.

2,5-Dimethoxy-3-phenyl-tetrahydrofuran

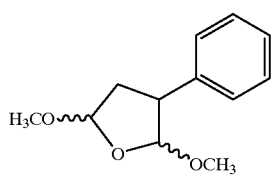

A mixture of 2,5-dihydro-2,5-dimethoxy-3-phenylfuran (590 mg, 2.86 mmol) and 10% Rh/Al$_2$O$_3$ (110 mg) in EtOAc (10 mL) was stirred under H$_2$ atmosphere for 24 hours. The catalyst was filtered onto Celite and rinsed with EtOAc. The filtrate was concentrated in vacuo to afford 583 mg (98%) of 2,5-dimethoxy-3-phenyl-tetrahydrofuran as a colorless oil which was typically used without further purification.

$^1$H NMR: δ7.40–7.18 (m, 5H), 5.30–4.80 (m, 2H), 3.70–3.40 (m, 6H), 2.78–2.43 (m, 1.2H), 2.34 (ddd, 0.75H, J=5.6, 12.7, 18.3 Hz), 2.17 (dd, 0.1H, J=8.4, 12.8 Hz). Anal. Calcd for $C_{12}H_{16}O_3$.0.2 H$_2$O: C, 68.03; H, 7.80. Found: C, 68.11; H, 7.60.

3(R)-Amino-N-(2,2-dimethyl-1(S)-(methylcarbamoyl)propyl)succinamic Acid Benzyl Ester Trifluoroacetate Salt

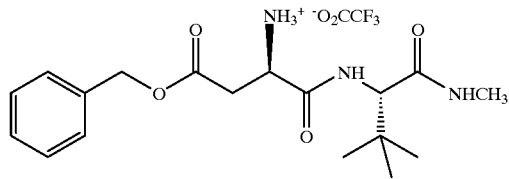

To a solution of 3(R)-butoxycarbonyl-amino-N-(2,2-dimethyl-1(S)-(methylcarbamoyl)propyl)succinamic acid benzyl ester (2.05 g, 4.57 mmol) in CHCl$_3$ (15 mL) was added trifluoroacetic acid (3 mL). After 2.5 hours at ambient temperature, more trifluoroacetic acid was added (3 mL), and after 90 minutes, the solvent was removed in vacuo to give crude 3(R)-amino-N-[2,2-dimethyl-1(S)-(methylcarbamoyl)propyl]succinamic acid benzyl ester trifluoroacetate salt as a yellow oil that was used without further purification.

$^1$H NMR: δ7.50–7.20 (m, 5H), 5.14 (dd, 2H, J=12.1, 15.6 Hz), 4.57 (t, 1H, J=6.2 Hz), 4.33 (d, 1H, J=8.7 Hz), 3.13 (d, 1H, J=6.2 Hz), 2.74 (d, 3H, J=4.7 Hz), 0.93 (s, 9H).

N-[2,2-Dimethyl-1(S)-methylcarbamoyl)propyl]-3 (R)-(3-phenyl1H-pyrrol-1-yl)-succinamic Acid Benzyl Ester

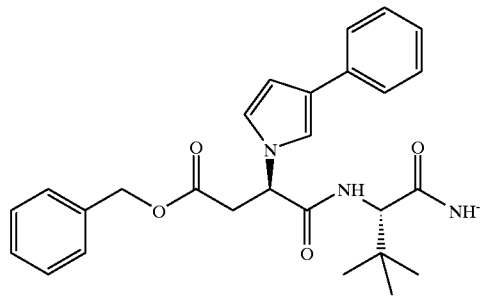

A solution of crude 3)R)-amino-N-[2,2-dimethyl-1(S)-(methylcarbamoyl)propyl]-succinamic acid benzyl ester trifluoroacetate salt (2.33 mmol), 2,5-dimethoxy-3-phenyl-tetrahydrofuran (583 mg, 2.80 mmol), trifluoroacetic acid (216 μL, 2.80 mmol), and water (50 μL, 2.8 =mol) in 1,2-dichloroethane (1 mL) was heated at 70° C. After 20 hours, the mixture was allowed to cool and concentrated in vacuo to give a brown oil, which was purified via flash column chromatography with 0.5% HOAc/35% EtOAc/hex as eluant to afford 407 mg (37%) of N-(2,2-dimethyl-1(S)-(methylcarbamoyl)propyl)-3(R)-(3-phenyl-1H-pyrrol-1-yl) succinamic acid benzyl ester as a yellow foam.

$^1$H NMR: δ7.52–7.44 (m, 2H), 7.38–7.15 (m, 3H), 7.04 (dd, 1H, J=1.8, 1.8 Hz), 6.78 (t, 1H, J=2.5 Hz), 6.56 (dd, 1H, J=1.6,2.5 Hz), 6.42 (d, 1H, J=9.0hz), 5.95 (bd, 1H, J=4.0 Hz), 5.18–5.04 (m, 3H), 4.30 (d, 1H, J=9.0 Hz), 3.38 (dd, 1H,

J=5.9, 16.8 Hz), 3.10 (dd, 1H, J=8.4, 16.8 hz), 2.72 (d, 3H, J=5.0 Hz), 0.93 (s, 9H). IR: 3301, 2960, 1736, 1645, 1542, 1166, 752, 695 cm$^{-1}$. HRFABMS: Calculated for $C_{28}H_{33}N_3O_4Cs$ (M$^+$Cs+): 608.1525. Found: 608.1549. Anal. Calculated for $C_{28}H_{33}N_3O_4 \cdot 0.2$ $H_2O$: C, 70.18; H, 7.03; N, 8.77. Found: C, 70.45; H, 6.99; N, 8.84.

Example 1(c)

N-(8-Oxo-4-oxa-1,7-diazatricyclo[9.6.1.0$^{12,17}$] octadeca-11(18), 12,14,16-tetraen-9(S)-yl)-3(R)-(3-phenyl-1H-pyrrol-1-yl)succinamic Acid

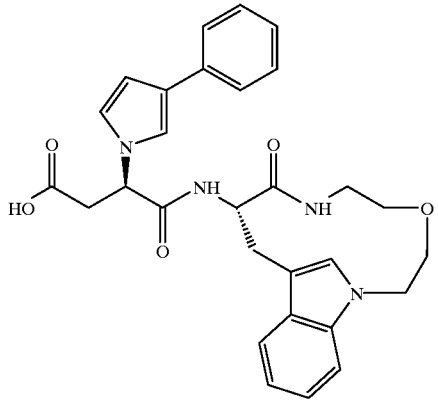

According to the procedure described in Example 1(a), N-(8-oxo-4-oxa-1,7-diaza-tricyclo[9.6.1.0$^{12,17}$]octadeca-11 (18),12,14,16-tetraen-9S-yl)-3(R)-(3-phenyl-1H-pyrrol-1-yl)succinamic acid benzyl ester was hydrogenolyzed to give in 94% yield N-(8-oxo-4-oxa-1,7diazatricyclo[9.6.1.0$^{12,17}$] octadeca-11(18),12,14,16-tetraen-9(S)-yl)-3(R)-(3-phenyl-1H-pyrrol-1-yl)succinamic acid as an amorphous solid.

$^1$H NMR (CD$_3$CN): δ7.65 (d, 1H, J=7.4 Hz), 7.48 (d, 2H, J=7.7 Hz), 7.39 (d, 1H, J=8.1 Hz), 7.33 (t, 2H, J=7.7 Hz), 7.23–7.13 (m, 3H), 7.11 (s, 1H), 6.97 (s, 1H), 6.78–6.71 (m, 2H), 6.43 (t, 1H, J=2.0 Hz), 5.46–5.43 (bm, 1H), 5.11 (t, 1H, J=7.2 Hz), 4.42–4.34 (m, 1H), 4.28–4.10 (m, 2H), 3.45–3.24 (m, 5H), 3.07–2.76 (m, 5H). Anal. Calcd for $C_{29}H_{30}N_4O_5 \cdot 0.35$ $H_2O \cdot 0.1$ MTBE: C, 66.89; H, 6.07; N, 10.58. Found: C, 66.99; H, 6.06; N, 10.33.

The starting material, N-(8-oxo-4-oxa-1,7-diaza-tricyclo [9.6.1.0$^{12,17}$]octadeca-11(18),12,14,16-tetraen-9S-yl)-3(R)-(3-phenyl-1H-pyrrol-1-yl)succinamic acid benzyl ester, was available as follows:

3(R-t-Butoxycarbonylamino-N-(8-Oxo-4-oxa-1,7-diaza-tricyclo[9.6.1.0$^{12,17}$]octadeca-11(18),12,14,16-tetraen-9S-yl)succinamic Acid Benzyl Ester

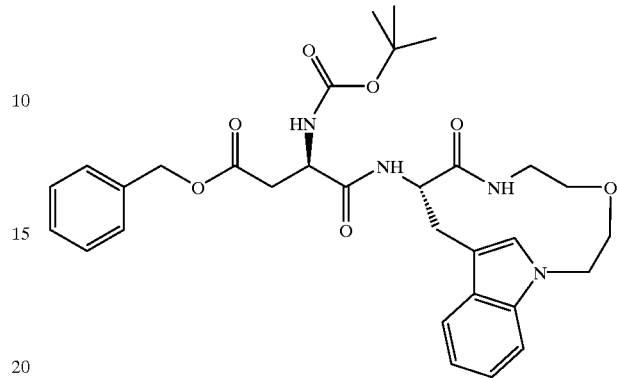

According to the procedure described in Example 1(b) for the preparation of 3(R)-amino-N-(2,2-dimethyl-1(S)-(methylcarbamoyl)propyl) succinamic acid benzyl ester trifluoroacetate salt, 9S-t-butoxycarbonylamino-4-oxa-1,7-diaza-tricyclo-[9.6.1.0$^{12,17}$]-octadeca-11(18),12,14,16-tetraen-8-one (see Castelhano, A. L.; Liak, T. J.; Horne, S.; Yuan, Z.; Krantz, A. Int. Patent Appl. WO95/04735-A1, Feb. 16, 1995) was deprotected with trifluoroacetic acid. According to the procedure described in Example 1(b) for the preparation of N-(2,2-dimethyl-1(S)-(methylcarbamoyl) propyl)-3(7)-t-butoxycarbonylaminosuccinamic acid benzyl ester, the crude amine salt and N-t-butoxycarbonyl-D-aspartatic acid β-benzyl ester was coupled with TBTU to afford in 70% yield 3(R)-t-butoxycarbonylamino-N-(8-oxo-4-oxa-1,7-diaza-tricyclo-[9.6.1.0$^{12,17}$]-octadeca-11(18),12, 14,16-tetraen-9S-yl)succinamic acid benzyl ester. Trituration with MTBE gave an off-white amorphous solid that was suitable for further use without additional purification.

$^1$H NMR (DMSO-d$_6$): δ7.76 (d, 1H, J=8.1 Hz), 7.49–7.28 (m, 8H), 7.14 (d, 1H, J=8.1 Hz), 7.08 (s, 1H), 7.04 (d, 1H, J=7.7 Hz), 6.98 (t, 1H, J=7.0 Hz), 5.07 (s, 2H), 4.38–4.15 (m, 4H), 3.47–3.38 (m, 2H), 2.96–2.75 (m, 5H), 2.65–2.53 (m, 2H), 1.34 (s, 9H). Anal. Calculated for $C_{31}H_{38}N_4O_7$: C, 64.34; H, 6.62; N, 9.68. Found: C, 64.24; H, 6.65; N, 9.61.

N-(8-Oxo-4-oxa-1,7-diaza-tricyclo[9.6.1.0^{12,17}] octadeca-11(18),12,14,16-tetraen-9S-yl)-3(R)-(3-phenyl-1H-pyrrol-1-yl)succinamic Acid Benzyl Ester

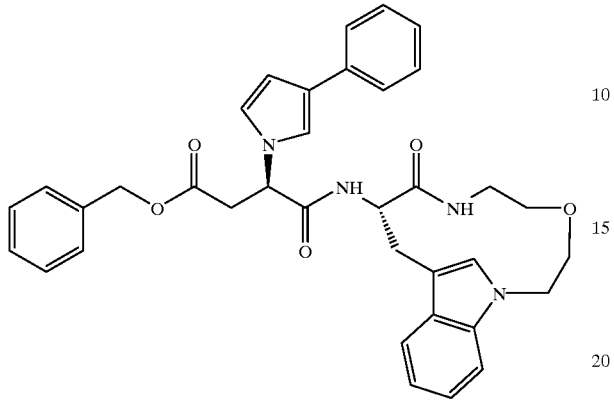

According to the procedure described in Example 1(b) for the preparation of 3(R)-amino-N-(2,2-dimethyl-1(S)-(methylcarbamoyl)propyl)succinamic acid benzyl ester trifluoroacetate salt, 3(R)-t-butoxycarbonylamino-N-(8-oxo-4-oxa-1,7-diaza-tricyclo-[9.6.1.0$^{12,17}$]-octadeca-11(18), 12,14,16-tetraen-9S-yl)succinamic acid benzyl ester (157 mg, 0.27 mmol) was deprotected with trifluoroacetic acid. A solution of dried crude amine salt and 2,5-dimethoxy-3-phenyl-tetrahydrofuran (67 mg, 0.32 mmol, from Example 1(b)) in anhydrous 1,2-dichloroethane (2 mL) was heated at ~75° C. for 17 hours, allowed to cool, and partitioned between EtOAc/ pH7 phosphate buffer. The combined organic layers were dried over Na$_2$SO$_4$ and concentrated to give a residue which was purified via flash column chromatography with 0–25% EtOAc/CH$_2$Cl$_2$ gradient eluant and triturated with MTBE to provide 70 mg (43%) of N-(8-oxo-4-oxa-1,7-diaza-tricyclo-[9.6.1.0$^{12,17}$]-octadeca-11(18),12, 14,16-tetraen-9S-yl)-3(R)-(3-phenyl-1H-pyrrol-1-yl) succinamic acid benzyl ester as an off white solid, mp 163–6° C.

$^1$H NMR (CDCl3): δ7.68 (d, 1H, J=6.6 Hz), 7.37–7.13 (m, 12H), 6.95 (s, 1H), 6.64 (s, 1H), 6.45 (t, 1H, J=2.2 Hz), 6.32 (s, 1H), 6.17 (d, 1H, J=7.7 Hz), 5.14 (s, 2H), 4.96 (t, 1H, J=7.2 Hz), 4.62–4.56 (m, 1H), 4.44–4.40 (m, 1H), 4.12 (t, 2H, J=4.4 Hz), 3.49–3.40 (m, 3H), 3.35–3.26 (m, 1H), 3.09–2.96 (m, 3H), 2.92–2.85 (m, 2H), 2.77–2.69 (m, 1H). Anal.Calculated for C$_{36}$H$_{36}$N$_4$O$_5$.0.4 H20: C, 70.66; H, 6.06;N, 9.16. Found: C, 70.69; H, 6.11; N, 8.99.

Example 1(d)

N-[2,2-Dimethyl-1(S)-(methylcarbamoyl)propyl]-3(R)-[3-(pyridin-4-yl)-1H-pyrrol-1-yl]succinamic acid

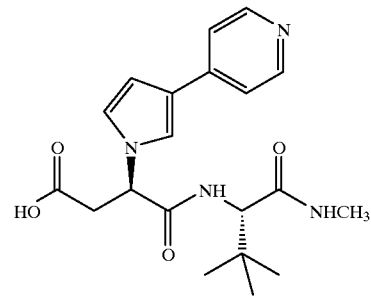

According to the procedure described in Example 1(a), N-[2,2-dimethyl-1(S)-(methylcarbamoyl)propyl]-3(R)-[3-(pyridin-4-yl)-1H-pyrrol-1-yl]succinamic acid benzyl ester was hydrogenolyzed in MeOH to give 60 mg (95%) of N-[2,2-dimethyl-1(S)-(methylcarbamoyl)propyl]-3(R)-[3-(pyridin-4-yl-1H-pyrrol-1-yl)]succinamic acid as a yellow powder, mp 145–8° C.:

$^1$H NMR (CD$_3$OD): δ8.48 (d, 2H, J=6.2 Hz), 7.62 (d, 2H, J=6.2 Hz), 7.58 (s, 1H), 6.94 (t, 1H, J=2.5 Hz), 6.64 (t, 1H, J=2.2 Hz), 5.30 (t, 1H, J=7.3 Hz), 2.98 (dd, 1H, J=7.2, 16.5 Hz), 2.64 (d, 3H, J=3.7 Hz), 1.00 (s, 9H). IR (KBr): 3315, 2959, 1710, 1654, 1545, 1400, 1206 cm$^{-1}$. HRFABMS: Calculated for C$_{20}$H$_{26}$N$_4$O$_4$Cs (M+Cs)$^+$: 519.1008. Found: 519.1026. Anal. Calcd for C$_{20}$H$_{26}$N$_4$O$_4$.0.1 EtOAc.0.2 CHCl$_3$: C, 59.03; H, 6.49; N, 1337. Found: C, 59.24; H, 6.75; N, 13.10.

The starting materials were furnished as follows:

4-Furan-3-yl-pyridine

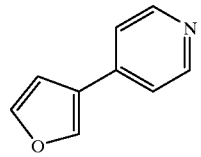

According to the procedure described in Example 1(a) for the preparation of 3-biphenyl-4-yl-furan, 4-bromopyridine hydrochloride (500 mg, 2.57 mmol) was coupled to fresh 3-furanboronic acid (see Thompson, W. J.; Gaudino, G. *J. Org. Chem.* 1984, 49, 5237–5243) to furnish 373 mg (100%) of crude 4-furan-3-yl-pyridine as an unstable solid that was used immediately. NMR and IR matched that of literature (see Ribereau, P.; Queguiner, G. *Can. J. Chem.* 1983, 61, 334–342 and Ishikura, M.; Ohta, T.; Terashima, M. *Chem. Pharm. Bull.* 1985, 33, 4755–4763).

4-(2,5-Dimethoxy-2,5-dihydro-furan-3-yl)pyridine

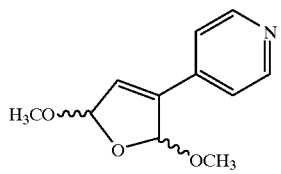

According to the procedure describe in Example 1(a) for the preparation of 3-biphenyl-4-yl-2,5-dihydro-2,5-dimethoxyfuran, crude 4-furan-3-yl-pyridine (2.57 mmol) was treated with bromine in MeOH at −15° C. in the presence of $Na_2CO_3$ to provide 450 mg (85%) of a mixture of diastereomers of 4-(2,5-dimethoxy-2,5-dihydro-furan-3-yl)pyridine as a yellow oil, which was used without further purification:

$^1$H NMR (CDCl3): δ8.62 (d, 2H, J=5.0 Hz), 7.44–7.38 (m, 2H), 6.52 (d, 1H, J=0.9 Hz), 6.02 (dd, 0.5H, J=0.9, 3.7 Hz), 6.00 (dd, 0.5H, J=0.9, 3.7 Hz), 5.98 (s, 0.5H), 5.71 (d, 0.5H, J=1.2 Hz), 3.48–3.40 (m, 6H). IR: 2933, 1597, 1547, 1438, 1369, 1193, 1118, 1039, 974, 918, 889, 821 cm$^{-1}$. HRFABMS: Calculated for $C_{11}H_{14}NO_3$ (M+H$^+$): 208.0974. Found: 208.0968.

4-(2,5-Dimethoxy-tetrahydro-furan-3-yl)pyridine

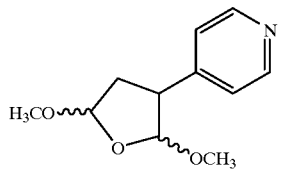

According to the procedure described in Example 1(a) for the preparation of 3-biphenyl-4-yl-2,5-dimethoxy-tetrahydro-furan, a mixture of 4-(2,5-dimethoxy-2,5-dihydro-furan-3-yl)pyridine (500 mg, 2.41 mmol) was hydrogenated in MeOH (2 mL) and EtOAc (8 mL) for 2 h to give 500 mg (100%) of a mixture of diastereomers by NMR of 4-(2,5-dimethoxy-tetrahydro-furan-3-yl)pyridine as a yellow oil.

$^1$H NMR (CDCl3): δ8.52–8.48 (m, 2H), 5.34–4.98 (m, 2H), 3.60–3.20 (m, 6H), 2.76–1.94 (m, 3H). IR (KBr): 2920, 1601, 1120, 988, 860 cm$^{-1}$. HRFABMS: Calculated for $C_{11}H_{16}NO_3$ (M+H$^+$): 210.1130. Found: 210.1137.

N-(2,2-Dimethyl-1(S)-methylcarbamoylpropyl)-3 (R)-(3-pyridin-4-yl[-1H-pyrrol-1-yl)succinamic Acid Benzyl Ester

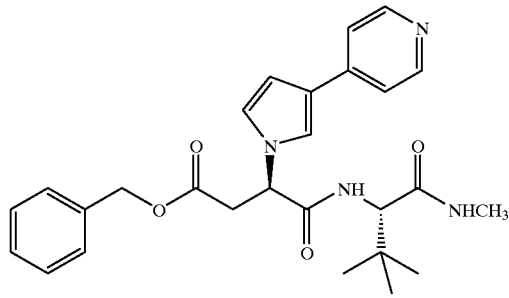

A solution of crude 3(R)-amino-N-(2,2-dimethyl-1(S)-methylcarbamoylpropyl)succinamic acid benzyl ester trifluoroacetate salt (0.44 mmol), 4-(2,5-dimethoxy-tetrahydro-furan-3-yl)pyridine (101 mg, 0.482 mmol), pyridine (156 μL, 1.92 mmol), and chlorotrimethylsilane (366 μL, 2.88 mmol) in 1,2-dichloroethane (5 mL) was heated at 90° C. After 3 days, the mixture was allowed to cool and concentrated in vacuo to give a brown oil which was purified via flash column chromatography with 0.5% HOAc/10% MeOH/CH$_2$Cl, as eluant to afford 90 mg (43%) of N-(2,2-dimethyl-I(S)-methylcarbarnoylpropyl)-3(R)-(3-pyridin-4-yl-1H-pyrrol-1-yl)succinamic acid benzyl ester as a pale yellow powder, mp 130–3° C.

$^1$H NMR (CD$_3$OD): δ8.36 (bs, 2H), 7.98 (d, 2H, J=4.4 Hz), 7.51 (d, 2H, J=5.0 Hz), 7.48 (t, 1H, J=1.8 Hz), 6.93 (t, 1H, J=2.5 Hz), 6.61 (dd, 1H, J=1.7, 3.0 Hz), 5.34 (t, 1H, J=7.6 Hz), 5.10 (dd, 2H, J=2.5, 14.3 Hz), 4.16 (s, 1H), 3.14 (dd, 1H, J=7.8 Hz, 16.5 Hz), 2.60 (d, 3H, J=3.4 Hz), 0.92 (s, 9H). IR (KBr): 3314, 2965, 1734, 1648, 1604, 1543, 1400, 1167 cm$^{-1}$. HRFABMS: Calcd for $C_{27}H_{32}N_4O_4Cs$ (M+Cs$^+$): 609.1478. Found: 609.1499. Anal: Calculated for $C_{27}H_{32}N_4O_4$·0.1 $CH_2Cl_2$·MeOH: C, 65.27; H, 7.06; N, 10.83. Found: C, 65.52; H, 6.89; N, 10.52.

Example 1(e)

3(R)-[3-(Biphenyl-4-yl)-1H-pyrrol-1-yl]-N-[2,2-dimethyl-1(S)-(methylcarbamoyl)propyl]succinamic Acid

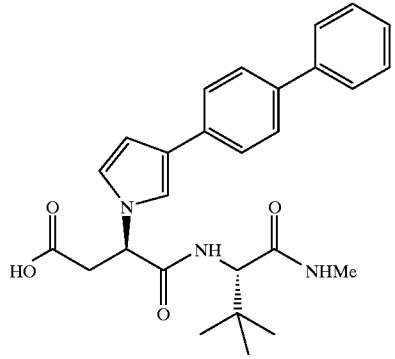

According to the procedure described in Example 1(a), 3(R)-[3-(biphenyl-4-yl)-1H-pyrrol-1-yl]-N-[2,2-dimethyl-1

(S)-(methylcarbamoyl)propyl]succinamic acid benzyl ester was hydrogenolyzed to give 310 mg (95%) of 33(R)-[3-(biphenyl-4-yl)-1H-pyrrol-1-yl]-N-[2,2-dimethyl-1(S)-(methylcarbamoyl)propyl]succinamic acid as an amorphous solid.

$^1$H NMR (CDCl$_3$): δ7.56 (d, 2H, J=7.4 Hz), 7.51 (s, 4H), 7.40 (t, 2H, J=7.4 Hz), 7.32–7.26 (m, 2H), 7.11 (s, 1H), 6.81 (s, 1H), 6.51 (s, 1H), 5.96–5.93 (bm, 1H), 5.23 (t, 1H, J=6.8 Hz), 4.17 (d, 1H, J=9.6 Hz), 3.34 (dd, 1H, J=6.4, 17.1 Hz), 3.09 (dd, 1H, J=7.6, 17.5 Hz), 2.71 (d, 3H, J=4.8 Hz), 0.90 (s, 9H); Anal. Calculated for C$_{27}$H$_{31}$N$_3$O$_4$.0.3 MTBE.0.1 H$_2$O: C, 69.89; H, 7.16; N, 8.58. Found: C, 70.02; H, 7.33; N, 8.25.

The starting material was prepared as follows:

3(R)-[3-(Biphenyl-4-yl)-1H-pyrrol-1-yl]-N-[2,2-dimethyl-1(S)-(methylcarbamoyl)propyl]succinamic Acid Benzyl Ester

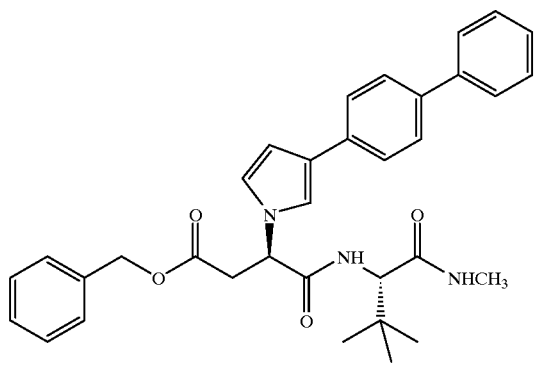

According to the procedure described in Example 1(c) for the preparation of N-(8-oxo-4oxa-1,7-diaza-tricyclo-[9.6.1.0$^{12,17}$]-octa-deca-11(18),12,14,16-tetraen-9S-yl)-3(R)-(3-phenyl-1H-pyrrol-1-yl)succinamic acid benzyl ester, 3(R)-amino-N-(2,2-dimethyl-1(S)-(methylcarbamoyl)propyl)succinamic acid benzyl ester (prepared as described in Example 1(b))was condensed with 3-biphenyl-4-yl-2,5-dimethoxy-tetrahydrofuran (prepared as described in Example 1(a)) in 1,2-dichloroethane with trifluoroacetic acid to provide in 35% yield 3(R)-[3-(biphenyl-4-yl)-1H-pyrrol-1-yl]-N-[2,2-dimethyl-1(S)-(methylcarbamoyl)propyl]succinamic acid benzyl ester as an amorphous solid.

$^1$H NMR (CDCl3): δ7.63–7.57 (m, 6H), 7.44 (t, 2H, J=7.6 Hz), 7.35–7.25 (m, 6H), 7.09 (s, 1H), 6.80 (t, 1H, J=2.4 Hz), 6.61 (t, 1H, J=2.0 Hz), 6.28 (d, 1H, J=8.8 Hz), 5.99–5.71 (bm, 1H), 5.17–5.08 (m, 3H), 4.02 (d, 1H, J=8.0 Hz), 3.40 (dd, 1H, J=5.7, 16.7 Hz), 3.12 (dd, 1H, J=8.5, 16.9 Hz), 2.76 (d, 3H, J=4.8 Hz), 0.87 (s, 9H). Anal. Calculated for C$_{34}$H$_{37}$N$_3$O$_4$: C, 74.02; H, 6.76; N, 7.62. Found: C, 73.87; H, 6.93; N, 7.39.

Example 1(f)

N-(1(S)-Benzyl-2-methoxyethyl)-3(R)-3-(biphenyl-4-yl)-1H-pyrrol-1-yl]succinamic Acid

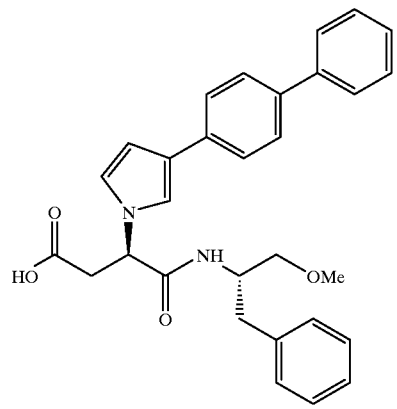

According to the procedure described in Example 1(a), N-(1(S)-benzyl-2-methoxyethyl)-3(R)-[3-(biphenyl-4-yl)-1H-pyrrol-1-yl]succinamic acid benzyl ester was hydrogenolyzed in 90% yield to N-(1(S)-benzyl-2-methoxyethyl)-3(R)-[3-(biphenyl-4-yl)-1H-pyrrol-1-yl]succinamic acid as an amorphous solid, mp 247° C.

$^1$H NMR (CDCl3): δ7.64–7.53 (m, 6H), 7.44 (t, 2H, J=7.5 Hz), 7.34 (t, 1H, J=7.4 Hz), 725–7.19 (m, 3H) 7.10 (d, 2H, J=8.1 Hz), 6.98 (s, 1H), 6.70 (s, 1H), 6.59 (s, 1H), 5.83 (d, 1H), J=7.7 Hz), 4.97 (t, 1H, J=7.0 Hz), 4.22–4.15 (m, 1H), 3.43 (dd, 1H, J=6.6, 16.5 Hz), 3.29–3.16 (m, 5H), 3.00 (dd, 1H, J=7.4, 16.9 Hz), 2.78 (d, 2H, J=7.0 Hz). Anal. Calculated for C$_{30}$H$_{30}$N$_2$O$_4$.0.25 H$_2$O: C, 73.97; H, 6.3 1; N, 5.75. Found: C, 73.99: H, 6.59; N, 5.45.

The starting materials were furnished as follows:

N-(1(S)-Benzyl-2-methoxyethyl)-3-(R)-(t-butoxycarbonylamino)succinamic Acid Benzyl Ester

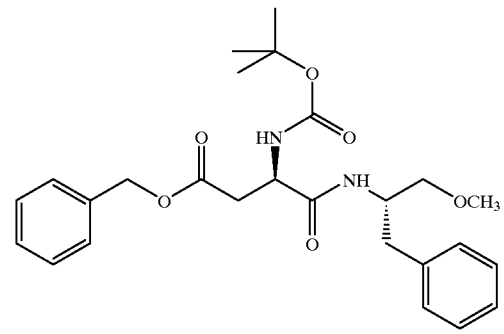

A mixture of N-t-butoxycarbonyl-D-aspartic acid β-benzyl ester (480 mg, 1.50 mmol), 2S-amino-1-methoxy-3-phenylpropane hydrochloride (300 mg, 1.50 mmol), benzotriazole-1-yloxytris(dimethylamino)phosphonium hexafluorophosphate (BOP; 663 mg, 1.50 mmol) and triethylamine (0.5 mL, 3.6 mmol) in DMF (5 mL) was stirred at ambient temperature for 4 hours. The mixture was poured into H$_2$O (75 mL) and extracted with EtOAc:hex (3:1; 2×50 mL). The combined organic extracts were washed with 1N aqueous NaHSO$_4$ (2×25 mL), saturated aqueous NaHCO$_3$ (25 mL) two times, and brine (25 mL), dried over NaSO₄, and evaporated to give upon hexane trituration 545 mg (76%) of N-(1(S)-benzyl-2-methoxyethyl)-3(R)-(t-butoxycarbonylamino)succinamic acid benzyl ester as a solid, mp 60–3° C.

¹H NMR (CDCl3): δ7.37–7.16 (m, 10H), 6.74 (bs, 1H), 5.64 (bd, 1H, J=6.6 Hz), 5.12 (dd, 2H, J=12.1, 17.7 Hz), 4.48–4.46 (m, 1H), 4.25–4.20 (m, 1H), 3.34 (s, 3H), 3.31–3.23 (m, 2H), 2.98 (dd, 1H, J=4.4, 16.9 Hz), 2.82 (d, 2H, J=7.4 Hz), 2.62–2.57 (m, 1H), 1.44 (s, 9H). Anal. Calculated for $C_{26}H_{33}N_2O_6 \cdot 0.25\ H_2O$: C, 65.87; H, 7.12; N, 5.91. Found: C, 65.73; H, 7.29; N, 5.89.

N-(1(S)-Benzyl-2-methoxyethyl)-3(R)-[3-(biphenyl4-yl)-1H-pyrrol-1-yl]succinamic Acid Benzyl Ester

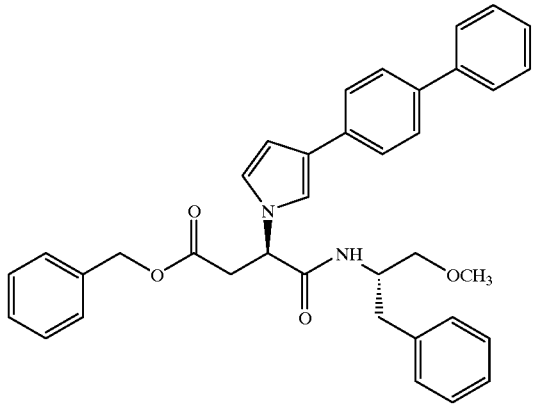

According to the proecdure described in Example 1(a) for the preparation of N-(1(S)-benzyl-2-hydroxyethyl)-3(R)-[3-(biphenyl-4-yl)-1H-pyrrol-1-yl]succinamic acid benzyl ester, N-(1(S)-benzyl-2-methoxy-ethyl)-3(R)-(t-butoxycarbonylamino)succinamic acid benzyl ester was deprotected and the crude salt condensed in HOAc with 3-(biphenyl-4-yl)-2,5-dimethoxytetrahydrofuran (prepared as described in Example 1(a)) to provide in 54% yield N-(1(S)-benzyl-2-methoxyethyl)-3(R)-[3-(biphenyl-4-yl)-1H-pyrrol-1-yl]succinamic acid benzyl ester as an oil, which was used without further purification.

¹H NMR (CDCl3): δ7.65–7.62 (m, 6H), 7.57 (t, 2H, J=7.4 Hz), 7.48–7.16 (m, 9H), 7.10 (d, 2H, J=7.7 Hz), 6.98 (s, 1H), 6.69 (s, 1H), 6.57 (s, 1H), 5.78 (d, 1H, J=8.5 Hz), 5.10 (s, 2H), 5.01 (dd, 1H, J=5.5, 9.2 Hz), 4.2–4.16 (m, 1H), 3.43 (dd, 1H, J=5.3, 16.7 Hz), 3.28–3.15 (m, 5H), 3.02 (dd, 1H, J=9.2, 16.6 Hz), 2.76 (d, 2H, J=7.4 Hz); IR: 3315, 3063, 3030, 2930, 2891, 1738, 1682, 1526, 1495, 1204, 1167, 764, 737, 698 cm⁻¹. HRFABMS: Calculated for $C_{37}H_{36}N_2O_4$ (M+H⁺): 572.2675. Found: 572.2674.

Example 1(g)

3(R)-[3-(Biphenyl-4-yl)-1H-pyrrol-1-yl]-N-[2-hydroxy-1(S)-[(1H-imidazol-4-yl)methyl]ethyl] succinamic Acid Trifluoroacetate Salt

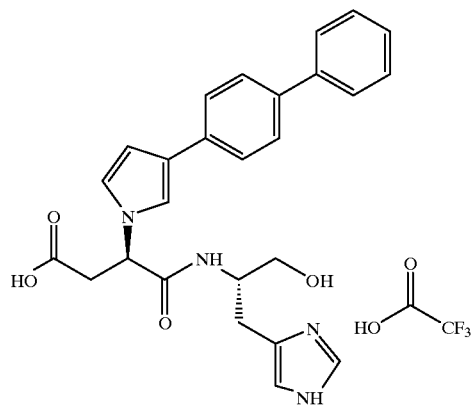

According to the provedure described in Example 1(a), 3(R)-[3-(biphenyl-4-yl)-1H-pyrrol-1-yl]-N-[2-hydroxy-1(S)-[(1H-imidazol-4-yl)methyl]ethyl]succinamic acid benzyl ester was hydrogenolyzed and, after purification via reversed-phase HPLC, (12%) of 3(R)-[3-(biphenyl-4-yl)-1H-pyrrol-1-yl]-N-[2-hydroxy-1(S)-[(1H-imidazol-4-yl)methyl]ethyl]succinamic acid trifluoroacetate salt was obtained as a rust-colored amorphous solid.

¹H NMR (CD₃OD): δ8.74 (s, 1H), 7.61–7.51 (m, 6H), 7.41 (t, 2H, J=7.5 Hz), 7.34–7.27 (m, 2H), 7.19 (s, 1H), 6.81 (t, 1H, J=2.2 Hz), 6.48 (s, 1H), 5.00 (dd, 1H, J=5.9, 8.8 Hz), 4.17–4.12 (m, 1H), 3.58–3.46 (m, 2H), 3.30–3.21 (m, 1H), 3.06 (dd, 1H, J=4.8, 15.1 Hz), 2.95–2.87 (m, 2H). Anal. Calculated for $C_{26}H_{26}N_4O_4 \cdot 1.0\ TFA \cdot 1.4\ H_2O \cdot 0.15\ C_6H_{14}$: C, 56.84; H, 5.27; N, 9.17. Found: C, 57.04; H, 5.00; N, 8.94.

The starting material was furnished as follows:

3(R)-(t-Butoxycarbonylamino)-N-[2-hydroxy-1(S)-[(1H-imidazol-4-yl)methyl]ethyl]succinamic Acid Benzyl Ester

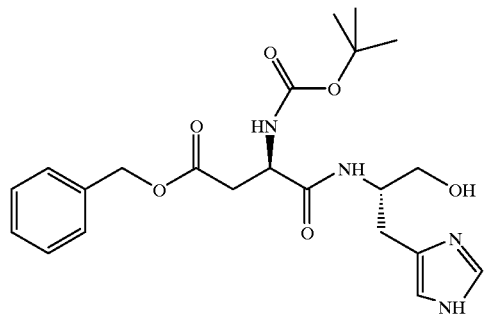

According to the procedure described in Example 1(b) for the preparation of 3(R)-t-butoxycarbonylamino-N-(2,2-dimethyl-1(S)-(methylcarbamoyl)propyl)succinamic acid benzyl ester, N-t-butoxycarbonyl-D-aspartic acid β-benzyl ester and L-histidinol dihydrochloride were coupled with TBTU to furnish 410 mg (92%) of 3(R)-(t-butoxycarbonylamino)-N-[2-hydroxy-1(S)-[(1H-imidazol-4-yl)methyl]ethyl]succinamic acid benzyl ester as a solid which was used without further purification.

3(R)-[3-(Biphenyl-4-yl)-1H-pyrrol-1-yl]-N-[2-hydroxy-1(S)-[(1H-imidazol-4-yl)methyl]ethyl]succinamic Acid Benzyl Ester

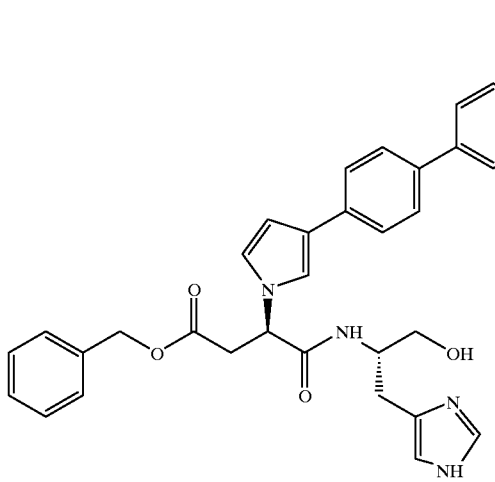

According to the procedure described in Example 1(c) for the preparation of N-(8-oxo-4-oxa-1,7-diaza-tricyclo-[9.6.1.0$^{12,17}$]-octadeca-11(18),12,14,1 6-tetraen-9S-yl)-3(R)-(3-phenyl-1H-pyrrol-1-yl)succinamic acid benzyl ester, 3(R)-(t-butoxycarbonylamino)-N-[2-hydroxy-1(S)-[(1H-imidazol4-yl)methyl]ethyl]succinamic acid benzyl ester was deprotected, and the resultant crude amine salt was condensed with 3-(biphenyl-4-yl)-2,5-dimethoxy-tetrahydrofuran (produced as described in Example 1(a)) in 1,2-dichloroethane in the presence of trifluoroacetic acid to give in 37% yield 3(R)-[3-(biphenyl-4-yl)-1H-pyrrol-1-yl]-N-[2-hydroxy-1(S)-[(1H-imidazol-4-yl)methyl]ethyl]succinamic acid benzyl ester as a yellow solid.

$^1$H NMR (CDCl3): δ7.65–7.59 (m, 4H), 7.53 (d, 2H, J=8.5 Hz), 7.45 (t, 2H, J=7.4 Hz), 7.37–7.26 (m, 7H), 6.95 (s, 1H), 6.70 (t, 1H, J=2.2 Hz), 6.65 (s, 1H), 6.52 (s, 1H), 6.45 (bs, 1H), 5.10 (s, 2H), 5.06–5.02 (m, 1H), 4.13–4.11 (m, 1H), 3.69 (dd, 1H, J=3.9, 11.6 Hz), 3.56 (dd, 1H, J=4.8, 11.8 Hz), 3.42 (dd, 1H, J=5.5, 16.9 Hz), 3.06 (dd, 1H, J=8.8, 16.9 Hz), 2.84 (t, 2H, J=4.8 Hz). Anal. Calculated for $C_{33}H_{32}N_4O_4$·0.8 $H_2O$·0.15 MTBE: C, 70.34; H, 6.19; N, 9.72. Found: C, 70.51; H, 6.05; N, 10.15.

Example 1(h)

3(R)-[3-(Biphenyl-4-yl)-1H-pyrrol-1-yl]-N-(2(R)-hydroxycyclohex-1(R)-yl)succinamic Acid

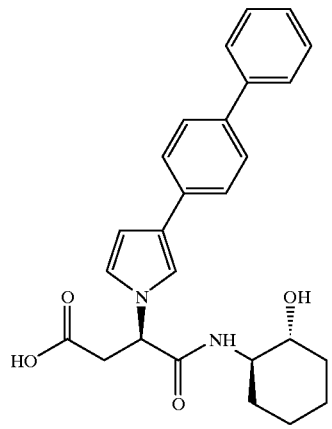

According to the procedure described in Example 1(a), 3(R)-[3-(biphenyl4-yl)-1H-pyrrol-1-yl]-N-(2(R)-hydroxycyclohex-1(R)-yl)succinamic acid benzyl ester was hydrogenolyzed to obtain in 81% yield 3(R)-[3-(biphenyl-4-yl)-1H-pyrrol-1-yl]-N-(2(R)-hydroxycyclohex-1(R)-yl) succinamic acid as an amorphous solid.

$^1$H NMR (CD$_2$O D): δ8.00 (d, 1H, J=8.9 Hz), 7.61 (d, 2H, J=7.4 Hz), 7.56 (s, 4H), 7.40 (t, 2H, J=7.5 Hz), 7.28 (t, 1H, J=7.5 Hz), 7.23 (s, 1H), 6.86 (t, 1H, J=2.6 Hz), 6.48 (t, 1H, J=2.2 Hz), 5.07 (t, 1H, J=7.4 Hz), 3.59–3.53 (m, 1H), 2.98 (dd, 1H, J=7.7, 16.9 Hz), 2.01–1.95 (m, 1H), 1.83–1.78 (m, 1H), 1.72–1.61 (m, 2H), 1.34–1.11(m, 4H). Anal. Calculated for $C_{26}H_{28}N_2O_4$·0.5 $H_2O$: C, 70.73; H, 6.62;N, 6.35. Found: C, 70.79; H, 6.61; N, 6.26.

The starting material was prepared as follows:

3(R)-t-Butoxycarbonylamino-N-(2(R)-hydroxycyclohex-1R-yl)succinamic Acid Benzyl Ester

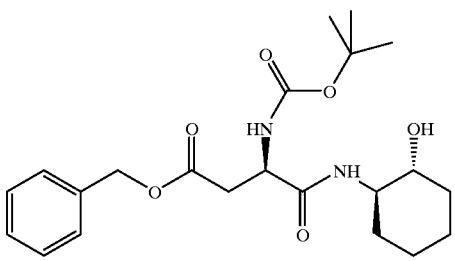

According to the procedure described in Example 1(f) for the preparation of N-(1(S)-benzyl-2-methoxyethyl)-3(R)-t-butoxycarbonyl-amino-succinamic acid benzyl ester, N-t-butoxycarbonyl-D-aspartic acid β-benzyl ester and racemic trans-2-aminocyclohexanol were coupled with BOP to give a crude solid which was triturated with MTBE/hex, and then successively recrystallized from MTBE/isooctane and MTBE/cyclohexanes/isooctane to provide 260 mg (20%) of the single diastereomer 3(R)-t-butoxycarbonylamino-N-(2(R)-hydroxy-cyclohex-1R-yl)succinamic acid benzyl ester as an off-white solid, mp 124–5° C.

$^1$H NMR (DMSO-d$_6$): δ7.52 (d, 1H, J=7.0 Hz), 7.36–7.31 (m, 5H), 7.09 (d, 1H, J=9.2 Hz), 5.08, 5.05 (AB quartet, 2H, J=12.1 Hz), 4.48 (d, 1H, J=5.2 Hz), 4.34–4.27 (m, 1H), 3.26–3,18 (m, 1H), 2.76 (dd, 1H, J=4.4, 16.2 Hz), 2.56 (dd, 1H, J=9.2, 16.2 Hz), 1.82–1.70 (m, 2H), 1.60–1.50 (m, 2H), 1.36 (s, 9H), 1.20–1.08 (m, 4H). Anal. Calculated for C$_{22}$H$_{32}$N$_2$O$_6$: C, 62.84; H, 7.67; N, 6.66. Found: C, 63.10; H, 7.69; N, 6.60.

3(R)-[3-(Biphenyl-4-yl)-1H-pyrrol-1-yl]-N-(2(R)-hydroxycyclohex-1(R)-yl)succinamic Acid Benzyl Ester

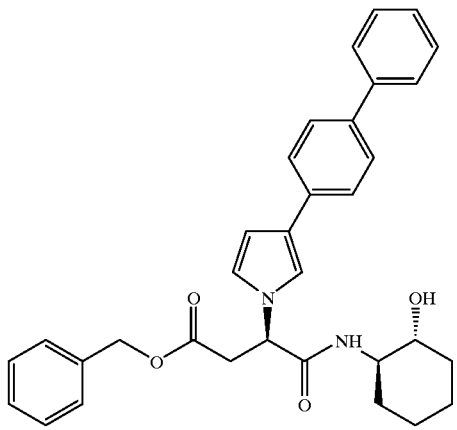

As described in Example 1(a) for the preparation of N-(1(S)-benzyl-2-hydroxyethyl)-3(R)-(3-(biphenyl-4-yl)-1H-pyrrol-1-yl)succinamic acid benzyl ester, 3(R)-t-butoxycarbonylamino-N-(2(R)-hydroxycyclohex-1(R)-yl) succinamic acid benzyl ester and 3-biphenyl-4-yl-2,5-dimethoxy-tetrahydrofuran (prepared as described in Example 1(a)) were condensed in acetic acid to furnish in 41% yield 3(R)-[3-(biphenyl-4-yl)-1H-pyrrol-1-yl]-N-(2(R)-hydroxycyclohex-1(R)-yl)succinamic acid benzyl ester as an amorphous off-white solid.

$^1$H NMR (CDCl3): δ7.63–7.54 (m, 6H), 7.45 (t, 2H, J=7.5 Hz), 7.36–7.26 (m, 6H), 7.06 (s, 1H), 6.76 (t, 1H, J=2.4 Hz), 6.58 (s, 1H), 5.46 (d, 1H, J=7.0 Hz), 5.15–5.10 (m, 3H), 3.61–3.55 (m, 1H), 3.49 (dd, 1H, J=5.5, 16.6 Hz), 3.27–3.21 (m, 1H), 3.06 (dd, 1H, J=8.3, 16.7 Hz), 2.04–1.98 (m, 1H), 1.85–1.78 (m, 1H), 1.71–1.51 (m, 2H), 1.32–1.02 (m, 4H). Anal. Calculated for C$_{33}$H$_{34}$N$_2$O$_4$.H$_2$O: C, 73.31; H, 6.71; N, 5.18. Found: C, 72.93; H, 6.72; N, 4.93.

Example 1(i)

3(R)-[3-(Biphenyl4-yl)-1H-pyrrol-1-yl]-N-[2-hydroxy-1(S)-(hydroxymethyl)-2-methylpropyl] succinamic Acid

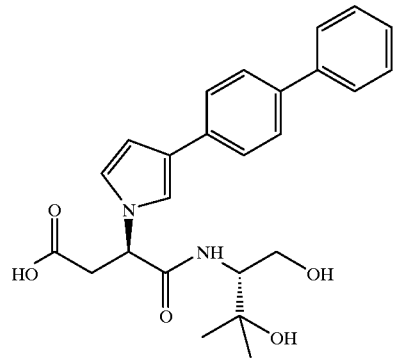

According to the procedure described in Example 1(a), a mixture of 3(R)-[3-(biphenyl-4-yl)-1H-pyrrol-1-yl]-N-[2-hydroxy-1(S)-(hydroxymethyl)-2-methylpropyl]succinamic acid benzyl ester (137 mg, 0.26 mmol) in EtOH (2.5 mL) and EtOAc (2.5 mL) was hydrogenolyzed after 110 minutes to give a white solid, which was triturated with CH$_2$Cl$_2$/hex to provide 85 mg (75%) of 3(R)-[3-(biphenyl-4-yl)-1H-pyrrol-1-yl]-N-[2-hydroxy-1(S)-(hydroxymethyl)-2-methylpropyl]succinamic acid as a white solid, mp 150–2° C.

$^1$H NMR (acetone-d$_6$): δ7.67–7.61 (m, 6H), 7.46–7.39 (m, 3H), 7.33 (t, 1H, J=7.4 Hz), 7.09 (bd, 1H, J=8.5 Hz), 6.97 (t, 1H, J=2.4 Hz), 6.53 (t, 1H, J=2.2 Hz), 5.28 (t, 1H, J=7.2 Hz), 3.81–3.67 (m, 3H), 3.35 (dd, 1H, J=7.4, 16.9 Hz), 3.02 (dd, 1H, J=7.4, 16.9 Hz), 1.24 (s, 3H), 1.12 (s, 3H). Anal. Calculated for C$_{25}$H$_{28}$N$_2$O$_5$: C, 68.79; H, 6.47; N, 6.42. Found: C, 68.54; H, 6.50; N, 6.39.

The starting material was furnished as follows:

3-Benzyloxycarbonyl-2,2-dimethyl4R-(1-hydroxy-1-methylethyl)oxazolidine

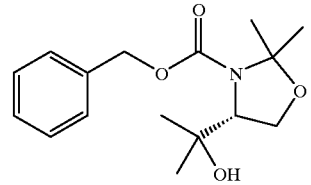

To a solution of methyl 2-(3-benzyloxycarbonyl-2,2-dimethyloxazolidin-4R-yl)acetate (see Delacotte, J. -M.; Galons, H.; Schott, D.; Morgat, J. -L. *J Labelled Comp. Radiopharm.* 1991, 29, 1141–1146; 500 mg, 1.70 mmol) in dry THF (10 mL) at –78° C. was added dropwise via syringe a solution of methylmagnesium bromide (1.5 mL of 3M in ether). After 15 minutes, the reaction vessel was placed in a 0° C. ice bath. After 2 hours, the mixture was cooled to –78° C. and more methylmagnesium bromide (0.5 mL of 3M in ether) was added. The mixture was allowed to warm to 0° C. over 2 hours, then quenched with acetone (1 mL) and partitioned between EtOAc (50 mL) and 1M pH7 phosphate buffer (50 mL). The separated organic layer was washed with 1M pH7 phosphate buffer (50 mL) and brine (25 mL), cried over Na₂SO₄, and concentrated to a residue which was purified via flash column chromatography with 0–12% EtOAc/CH₂Cl₂ gradient eluant to furnish 280 mg (56%) of 3-benzyloxycarbonyl-2,2-dimethyl-4R-(1-hydroxy-1-methyl-ethyl)-oxazolidine as a colorless oil.

¹H NMR (CD₃CN): δ7.52–7.45 (m, 5H), 5.35–5.2 (bm, 2H), 4.68 (bs, 1H), 4.15–3.95 (bm, 3H), 1.67 (s, 3H), 1.57 (s, 3H), 1.21 (s, 6H). Anal. Calculated for C₁₆H₂₃NO₄.0.3 H₂O: C, 64.32; H, 7.96; N, 4.69. Found: C, 64.48; H, 7.87; N, 4.67.

3(R)-t-Butoxycarbonylamino-N-[2-hydroxy-1(S)-(hydroxymethyl)-2-methylpropyl]succinamic Acid Benzyl Ester

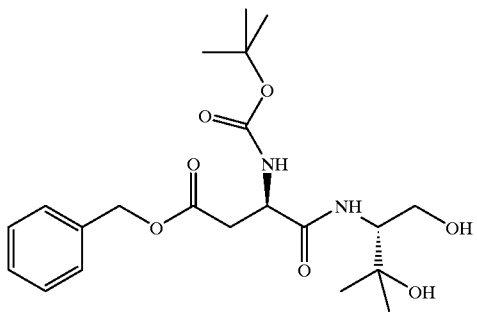

3-Benzyloxycarbonyl-2,2-dimethyl4R-(1-hydroxy-1-methyl-ethyl)-oxazolidine was hydrogenolyzed in the presence of HCl according to conditions described in Example 1(a) to provide crude 2(R)-amino-3-methyl-butane-1,3-diol hydrochloride. According to the procedure described in Example 1(b) for the preparation of 3(R)-t-butoxycarbonylamido-N-(2,2 -dimethyl-1(S)-(methylcarbamoyl)propyl)succinamic acid benzyl ester, the crude amine salt was coupled to N-t-butoxycarbonyl-D-aspartic acid β-benzyl ester with TBTU. Purification via column chromatography with EtOAc/CH₂Cl₂ (1:1) to 10% MeOH/CH₂Cl₂ gradient elution led to isolation in 52% yield of 3(R)-t-butoxycarbonylamino-N-[2-hydroxy-1(S)-(hydroxymethyl)-2-methylpropyl]succinamic acid benzyl ester, which was used without further purification.

¹H NMR (CD₃CN): δ7.51 (s, 5H), 6.99 (bs, 1H), 5.99 (bs, 1H), 5.25 (s, 2H), 4.57–4.50 (m 1H), 3.83–3.76 (m, 3H), 3.00 (dd, 1H, J=5.7, 16.4 Hz), 2.87 (dd, 1H, J=7.2, 16.6 Hz), 1.55 (s, 9H), 1.34 (s, 3H), 1.22 (s, 3H). Anal. Calculated for C₂₁H₃₂N₂O₇.0.5 H₂O.0.1 O=C[N(CH₃)₂]₂: C, 58.02; H, 7.74; N, 6.92. Found: C, 58.29; H, 7.75; N, 6.82.

3(R)-[3-(Biphenyl-4-yl)-1H-pyrrol-1-yl]-N-[2-hydroxy1(S)-(hydroxymethyl)-2-methylpropyl] succinamic Acid Benzyl Ester

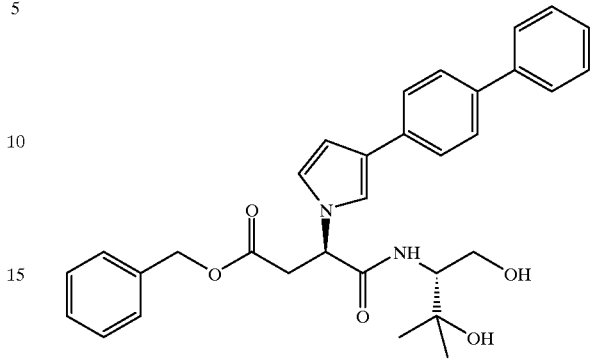

According to the procedure described in Example 1(c) for N-(8-oxo-4-oxa-1,7-diaza-tricyclo-[9.6.1.0$^{12,17}$]-octa-deca-11(18),12,14,16-tetraen-9S-yl)-3(R)-(3-phenyl-1H-pyrrol-1-yl)succinamic acid benzyl ester, 3(R)-t-butoxycarbonylamino-N-(2-hydroxy-1(S)-hydroxymethyl-2-methyl-propyl)succinamic acid benzyl ester was deprotected with trifluoroacetic acid. The crude amine salt and 3-biphenyl-4-yl-2,5-dimethoxy-tetrahydrofuran (prepared as described in Example 1(a)) were condensed in anhydrous 1,2-dichloroethane with trifluoroacetic acid to give in 11% yield 3(R)-[3-(biphenyl-4-yl)-1H-pyrrol-1-yl]-N-[2-hydroxy-1(S)-(hydroxymethyl)-2-methylpropyl] succinamic acid benzyl ester as an amorphous solid.

¹H NMR (acetone-d₆): δ7.67–7.61 (m, 6H), 7.48 (t, 2H, J=7.7 Hz), 7.39 (t, 1H, J=1.8 Hz), 7.37–7.27 (m, 6H), 7.09 (bd, 1H, J=9.2 Hz), 6.96 (t, 1H, J=2.6 Hz), 6.53 (dd, 1H, J=1.7, 2.8 Hz), 5.35 (t, 1H, J=7.4 Hz), 5.11 (s, 2H), 3.81–3.62 (m, 3H), 3.39 (dd, 1H, J=6.8, 16.4 Hz), 3.12 (dd, 1H, J=7.7, 16.6 Hz), 1.24 (s, 3H), 1.21 (s, 3H). Anal. Calculated for C₃₂H₃₄N₂O₅: C, 72.98; H, 6.51; N, 5.32. Found: C, 72.83; H, 6.60; N, 5.24.

Example 1(j)

N-[2,2-Dimethyl-1(S)-(methylcarbamoyl)propyl]-3(R)-[3-(4-propylphenyl)-1H-pyrrol-1-yl]succinamic Acid

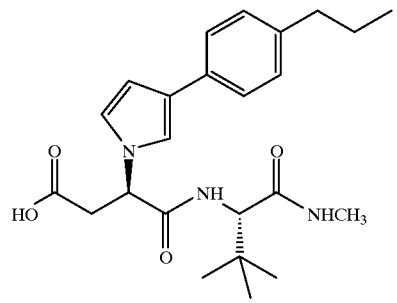

According to the procedure described in Example 1(a), N-[2,2-dimethyl-1(S)-(methylcarbamoyl)propyl]-3(R)-[3-(4-propylphenyl)-1H-pyrrol-1-yl]succinamic acid benzyl ester in MeOH and EtOAc was hydrogenolyzed to provide 30 mg (91%) of N-[2,2-dimethyl-1(S)-(methylcarbamoyl)propyl]-3(R)-[3-(4-propylphenyl)-1H-pyrrol-1-yl]succinamic acid as a yellow powder, mp 104–6° C.

$^1$H NMR (CD$_3$O D): δ7.95 (bs, 1H), 7.60 (bs, 1H), 7.48 (d, 2H, J=7.5 Hz), 7.16 (bs, 1H), 7.08 (d, 2H, J=7.5 Hz), 6.86 (bs, 1H), 6.42 (bs, 1H), 5.34 (t, 1H, J=7.0 Hz), 4.15 (bd, 1H, J=5.9 Hz), 2.83 (dd, 1H, J=6.2, 16.0 Hz), 2.62 (s, 3H), 2.6–2.50 (m, 2H), 1.7–1.58 (m, 2H), 0.95 (s, 9H). IR (KBr): 3300, 2960, 1642, 1560, 1195, 775 cm$^{-1}$. HRFABMS: Calculated for C$_{24}$H$_{33}$N$_3$O$_4$Cs (M+Cs$^+$): 560.1525. Found: 560.1509. Anal. Calculated for C$_{24}$H$_{33}$N$_3$O$_4$·0.3 EtOAc: C, 66.67; H, 7.86; N, 9.26. Found: C, 66.93; H, 7.78; N, 8.89.

The starting materials were made as follows:

3-(4-Propylphenyl)-furan

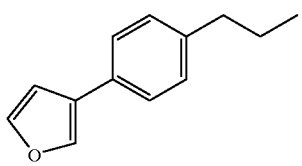

As described in Example 1(d) for the preparation of 4-furan-3-yl-pyridine, 1-iodo-4-propylbenzene (500 mg, 2.03 mmol) was coupled to 3-furanboronic acid to furnish in high yield 3-(4-propylphenyl)-furan as a light brown oil that was unstable and used immediately without further purification.

$^1$H NMR (CDCl3): δ7.69 (t, 1H, J=0.9 Hz), 7.46 (t, 1H, J=1.7 Hz), 7.40 (d, 2H, J=8.1 Hz), 7.18 (d, 2H, J=7.8 Hz), 6.68 (t, 1H, J=0.9 Hz), 2.59 (t, 2H, J=75 Hz), 1.66–1.60 (m, 2H), 0.95 (t, 3H, J=7.5 Hz).

2,5-Dimethoxy-3-(4-propylphenyl)-2,5-dihydro-furan

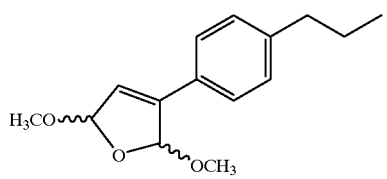

As described in Example 1(a) for the preparation of 3-biphenyl4-yl-2,5-dihydro-2,5-dimethoxy-tetrahydrofuran, crude 3-(4-propylphenyl)-furan was converted to 490 mg (98% from 1-iodo-4-propylbenzene) of 2,5-dimethoxy-3-(4-propylphenyl)-2,5-dihydro-furan as a light brown oil that was unstable and used immediately without further purification.

$^1$H NMR (CDCl3): δ7.47 (dd, 2H, J=1.4, 8.1 Hz), 7.17 (d, 2H, J=8.1 Hz), 6.25, (dd, 1H, J=0.6, 1.2 Hz), 6.00 (d, 1H, J=0.6 Hz), 5.69 (d, 1H, J=1.6 Hz), 3.49 (s, 2H), 3.43 (s, 1H), 3.40 (s, 2H), 3.38 (s, 1H), 2.59 (t, 2H, J=7.5 Hz), 1.64 (q, 2H, J=7.5 Hz), 0.94 (t, 3H, J=7.5 Hz). IR: 2930, 1514, 1464, 1192, 1105cm$^{-1}$.

2,5-Dimethoxy-3-(4-propylphenyl)-tetrahydrofuran

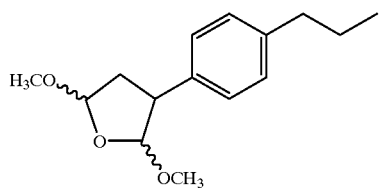

As described in Example 1(b) for the preparation of 2,5-dimethoxy-3-phenyl-tetrahydrofuran, 2,5-dihydro-2,5-dimethoxy-3-(4-propylphenyl)-furan (320 mg, 1.29 mmol) was hydrogenated to give 322 mg (100%) of a diastereomeric mixture of 2,5-dimethoxy-3-(4-propylphenyl)-tetrahydrofuran as a viscous colorless oil that was unstable and used immediately without further purification.

$^1$H NMR (CDCl3): δ7.24 (d, 2H, J=8.1 Hz), 7.12 (d, 2H, J=8.1 Hz), 5.24 (t, 1H, J=5.9 Hz), 3.60–3.30 (m, 6H), 2.59 (d, 1H, J=7.5 Hz), 2.52 (d, 1H, J=8.1 Hz), 2.32 (bs, 3H), 1.62 (q, 2H, J=7.5 Hz), 0.92 (t, 3H, J=7.5 Hz).

N-[2,2-Dimethyl-1(S)-methylcarbamoyl)propyl]-3(R)-(4-propyl-3-phenyl-4-yl-1H-pyrrol-1-yl)succinamic Acid Benzyl Ester

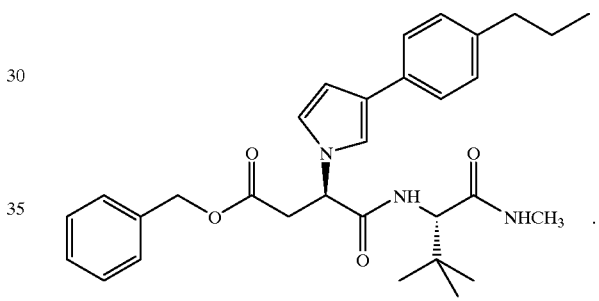

As described in Example 1(d) for the preparation of N-(2,2-dimethyl-1(S)-methylcarbamoylpropyl)-3(R)-(3-pyridin4-yl-1H-pyrrol-1-yl)succinamic acid benzyl ester, 3(R)-amino-N-[2,2-dimethyl-1(S)-(methylcarbamoyl)propyl]succinamic acid benzyl ester trifluoroacetate salt (prepared as described in Example 1(b); 522 mg, 1.16 mmol) was condensed with crude 2,5-dimethoxy-3-(4-propylphenyl)-tetrahydrofuran (1.29 mmol) in 1,2-dichloroethane with chlorotrimethylsilane at 90° C. over 3 days. The crude dark oil was purified via flash column chromatography with 1% HOAc/10% MeOH/CH$_2$Cl$_2$ as eluant to provide 40 mg (7%) of N-[2,2-dimethyl-1(S)-(methylcarbamoyl)propyl]-3(R)-[3-(4-propylphenyl)-1H-pyrrol-1 -yl]succinamic acid benzyl ester as a solid, mp 63–5° C.:

$^1$H NMR (CDCl3): δ7.40 (d, 2H, J=8.1 Hz), 7.34–7.20 (m, 5H), 7.14 (d, 2H, J=8.1 Hz), 7.00 (t, 1H, J=1.9 Hz), 6.78 (t, 1H, J=2.5 Hz), 6.56 (t, 1H, J=1.9 Hz), 6.24 (d, 1H, J=8.7 Hz), 5.70 (d, 1H, J=4.7 Hz), 5.16–4.96 (m, 3H), 4.00(d, 1H, J=9.0 Hz), 3.38(dd, 1H, J=5.6, 16.8 Hz), 3.10 (dd, 1H, J=8.7, 16.8 Hz), 2.76 (d, 3H, J=5.0 Hz), 2.59 (d, 1H, J=7.2 Hz), 2.56 (d, 1H, J=7.8 Hz), 1.65 (q, 2H, J=7.5 Hz), 0.96 (t, 3H, J=7.5 Hz), 0.86 (s, 9H). IR (KBr): 3314, 2959, 1736, 1648, 1560, 1165, 697 cm$^{-1}$. HRFABMS: Calculated for C$_{31}$H$_{39}$N$_3$O$_4$Cs (M+Cs$^+$): 650.1995. Found: 650.1977. Anal: Calculated for C$_3$H$_{39}$N$_3$O$_4$·0.3 C$_6$H$_{14}$: C, 72.33; H, 7.62; N, 7.71. Found: C, 72.36; H, 7.77; N, 7.38.

Example 1(k)

4-[2S-[2(R)-[3-(Biphenyl4-yl)-1H-pyrrol-1-yl]-3-carboxy-propionylamino]-4-methyl-pentanoylamino] benzoic Acid Methyl Ester

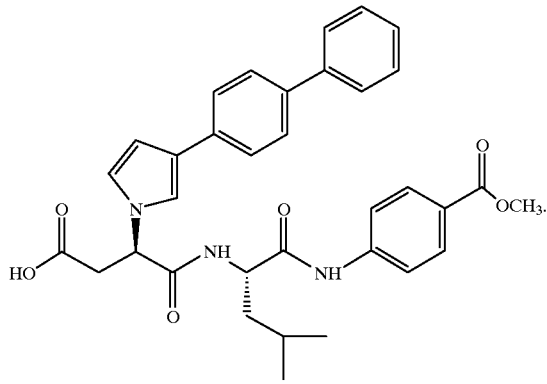

According to the procedure described in Example 1(a), 4-{2S-[2(R)-(3-biphenyl-4-yl-1H-pyrrol-1-yl)-3-carbobenzyloxy-propionyl-amino]-4-methyl-pentanoylamino}-benzoic acid methyl ester was hydrogenolyzed in quantitative yield to furnish 4-{2S-[2(R)-(3-biphenyl-4-yl-1H-pyrrol-1-yl)-3-carbobenzyloxy-propionyl-amino]4-methyl-pentanoylamino}-benzoic acid methyl ester as a solid, mp 209–11° C.

$^1$H NMR (CD$_3$OD): δ7.81 (d, 2H, J=8.8 Hz), 7.60–7.50 (m, 8H), 7.40 (t, 2H, J=7.4 Hz), 7.28 (t, 1H, J=7.4 Hz), 7.20 (s, 1H), 6.88 (s, 1H), 6.48 (s, 1H), 5.16 (t, 1H, J=7.2 Hz), 4.54 (t, 1H, J=7.2 Hz), 3.77 (s, 3H), 2.98 (dd, 1H, J=6.4, 17.1 Hz) 1.75–1.64 (m, 3H), 0.95 (t, 6H, J=5.9 Hz). Anal. Calculated for C$_{34}$H$_{35}$N$_3$O$_6$.0.6 H$_2$O: C, 68.92; H, 6.16; N, 7.09. Found: C, 68.98; H, 6.20; N, 6.98.

The starting material was available as follows:

4-[2S-(3-Benzyloxycarbonyl2(R)-t-butoxycarbonylamino-propionylamino)-4-methyl-pentanoyl-amino]-benzoic Acid Methyl Ester

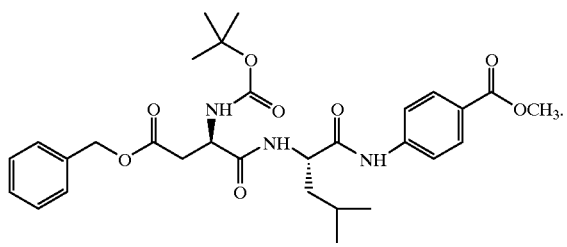

As described in Example 1(f) for the preparation of N-(1(S)-benzyl-2-methoxyethyl)-3(R)-(t-butoxycarbonylamino)succinamic acid benzyl ester, N-t-butoxycarbonyl-D-aspartate β-benzyl ester and 4-(2S-amino-4-methyl-pentanoylamino)benzoic acid methyl ester (Castelhano, A. L.; Yuan, Z.; Horne, S.; Liak, T. J. WO95/12603-A1, May 11, 1995) were coupled with BOP to furnish in 91% yield 4-[2S-(3-benzyloxycarbonyl-2(R)-t-butoxycarbonylamino-propionylamino)-4-methyl-pentanoyl-amino]-benzoic acid methyl ester, which was used crude, without any purification.

$^1$H NMR (CDCl3): δ8.62 (s, 1H), 7.98 (d, 2H, J=8.8 Hz), 7.73 (d, 2H, J=8.8 Hz), 7.38–7.26 (m, 5H), 6.68 (bd, 1H, J=8.5 Hz), 5.45 (bm, 1H), 5.09 (dd, 2H, J=12.1, 29 Hz), 4.60–4.51 (m, 2H), 3.89 (s, 3H), 3.34–3.26 (m, 1H), 2.82 (dd, 1H, J=4.8, 18.0 Hz), 2.01–1.95 (m, 1H), 1.70–1.53 (m, 2H), 1.45 (s, 9H), 0.98–0.93 (m, 6H); Anal. Calculated for C$_{30}$H$_{39}$N$_3$O$_8$.0.4 H$_2$O: C, 62.46; H, 6.95; N, 7.28. Found: C, 62.47; H, 6.98; N, 7.36.

4-{2S-[3-Benzyloxycarbonyl-2(R)-(3-bilphenyl-4-yl-1H-pyrrol-1-yl)-propionylamino]-4-methyl-pentanoylamino}-benzoic Acid Methyl Ester

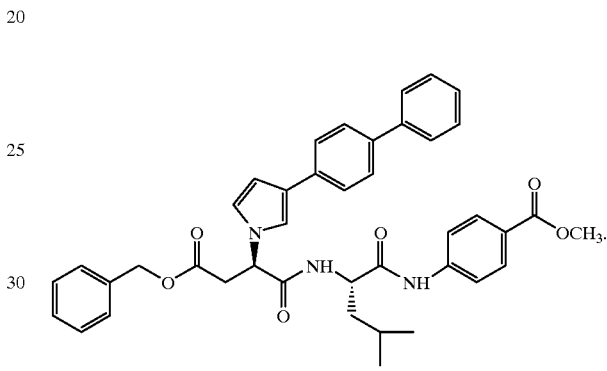

As described in Example 1(b) for the preparation of 3(R)-amino-N-(2,2-dimethyl-1S-methylcarbanoyl-propyl) succinamic acid benzyl ester, 4-[2S-(3-benzyloxycarbomyl-2(R)-t-butoxycarbonylamino-propionylamino)-4-methylpentanoylamino] benzoic acid methyl ester was deprotected with trifluoroacetic acid.

As described in Example 1(b) for the preparation of N-(2,2-dimethyl-1(S)-methylcarbamoylpropyl)-3(R)-(3-phenyl-1H-pyrrol-1-yl)succinamic acid benzyl ester, crude 4-[2S-(2(R)-amino-3-benzyloxycarbonyl-propionylamino)-4-methyl-pentanoyl-amino]-benzoic acid methyl ester trifluoroacetate salt and 3-biphenyl-4-yl-2,5-dimethoxy-tetrahydrofuran (prepared as described in Example 1(a)) were condensed in 1,2-dichloroethane with trifluoroacetic acid and water to give in 27% yield 4-{2S-[3-benzyloxycarbonyl-2(R)-(3-biphenyl-4-yl-1H-pyrrol-1-yl)-propionylamino]4-methyl-pentanoylamino}-benzoic acid methyl ester as a solid, mp 186–8° C.

$^1$H NMR (CDCl3): δ8.49 (s, 1H), 7.95 (d, 2H, J=8.8 Hz), 7.69–7.26 (m, 16H), 6.78 (s, 1H), 6.61 (s, 1H), 5.80 (s, 1H), 5.25–5.05 (m, 3H), 4.54–4.50 (m, 1H), 3.88 (s, 3H), 3.38–3.35 (m, 2H), 1.89–1.80 (m, 1H), 1.54–1.40 (m, 2H), 0.89 (d, 6H, J=6.3 Hz). Anal. Calculated for C$_{41}$H$_{41}$N$_3$O$_6$: C, 73.30; H, 6.15; N, 6.26. Found: C, 73.21; H, 6.16; N, 6.25.

Example 1(l)

3(R)-(3-Biphenyl-4-yl-1H-pyrrol-1-yl)-N-[1(S)-(N-methoxy-N-methylcarbamoyl)-3-methylbutyl] succinamic Acid

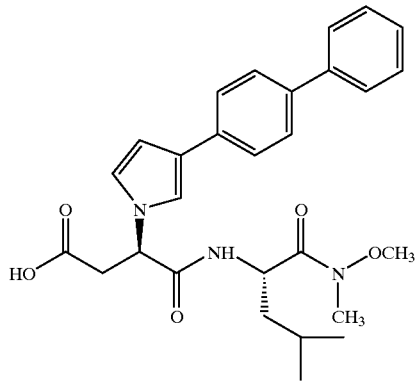

According to the procedure described in Example 1(a), 3(R)-[3-(biphenyl-4-yl)-1H-pyrrol-1-yl)-N-[1(S)-(N-methoxy-N-methylcarbamoyl)-3-methyl-butyl]succinamic acid benzyl ester was hydrogenolyzed to give in 97% yield 3(R)-(3-biphenyl-4-yl-1H-pyrrol-1-yl)-N-[1(S)-(N-methoxy-N-methylcarbamoyl)-3-methyl-butyl]succinamic acid as an amorphous solid.

$^1$H NMR (CDCl3): δ7.59–7.53 (m, 6H), 7.40 (t, 2H, J=7.2 Hz), 7.33–7.26 (m, 1H), 6.88 (bd, 1H, J=9.2 Hz), 6.80 (s, 1H), 6.54 (s, 1H), 5.13 (t, 1H, J=6.8 Hz), 5.03–5.00 (m, 1H), 3.76 (s, 3H), 3.39 (dd, 1H, J=6.4, 17.5 Hz), 3.16 (s, 3H), 3.00 (dd, 1H, J=7.2, 17.1 Hz), 1.60–1.42 (m, 3H), 0.92 (d, 3H, J=6.6 Hz), 0.89 (d, 3H, J=6.6 Hz). Anal. Calculated for $C_{28}H_{33}N_3O_5 \cdot 0.25\ H_2O \cdot 0.20\ C_6H_{14}$: C, 68.32; H, 7.13; N, 8.19. Found: C, 68.28; H, 7.08; N, 7.93.

The starting material was available as follows:

3(R)-t-Butoxycarbonylamino-N-[1(S)-(N-methoxy-N-methylcarbamoyl)-3-methyl-butyl]succinamic Acid Benzyl Ester

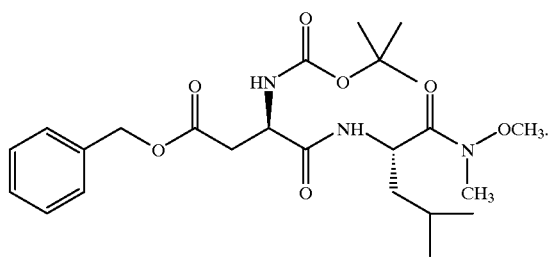

As described in Example 1(b) for the preparation of N-(2,2-dimethyl-1(S)-methylcarbamoylpropyl)-3(R)-(3-phenyl-1H-pyrrol-1-yl)succinamic acid benzyl ester, 2S-butoxycarbonylamino-N-methoxy-4-methyl-pentanoylamide was deprotected with trifluoroacetic acid. The resultant amine salt and N-t-butoxycarbonyl-D-aspartic acid β-benzyl ester were coupled with TBTU to provide in 89% yield 3(R)-t-butoxycarbonylamino-N-[1(S)-(N-methoxy-N-methylcarbamoyl)-3-methyl-butyl]succinamic acid benzyl ester as an oil, which was used without further purification.

$^1$H NMR (CDCl3): δ7.34 (s, 5H), 6.90 (d, 1H, J=8.5 Hz), 5.61 (d, 1H, J=7.4 Hz), 5.13, 5.11 (AB quartet, 2H, J=12.3 Hz), 5.04–4.98 (m, 1H), 4.61–4.54 (m, 1H), 3.76 (s, 3H), 3.19 (s, 3H), 3.02 (dd, 1H, J=4.4, 16.6 Hz), 2.74 (dd, 1H, J=5.2, 16.6 Hz), 0.93 (d, 3H, J=6.4 Hz), 0.90 (d, 3H, J=6.4 Hz). Anal. Calculated for $C_{24}H_{37}N_3O_7 \cdot 0.3\ H_2O$: C, 59.44; H, 7.82; N, 8.66. Found: C, 59.41; H, 7.69; N, 8.63.

3(R)-(3-Biphenyl-4-yl-1H-pyrrol-1-yl)-N-[1(S)-(N-methoxy-N-methylcarbamnoyl)-3-methyl-butyl] succinamic Acid Benzyl Ester

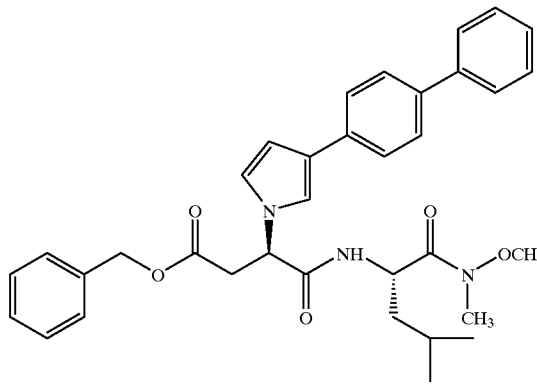

As described in Example 1(c) for the preparation of N-(8-oxo-4-oxa-1,7-diaza-tricyclo-[9.6.1.0$^{12,17}$]-octadeca-11(18),12,14,16-tetraen-9-yl)-3-(3-phenyl-1H-pyrrol-1-yl) succinamic acid benzyl ester, 3(R)-amino-N-(1(S)-(N-methoxy-N-methylcarbamoyl)-3-methyl-butyl)succinamic acid benzyl ester was deprotected. The crude amine salt and 3-biphenyl-4-yl-2,5-dimethoxy-tetrahydrofuran (prepared as described in Example 1(a)) were condensed in anhydrous 1,2-dichloroethane with trifluoroacetic acid to provide in 48% yield 3(R)-(3 -biphenyl-4-yl-1H-pyrrol-1-yl)-N-[1(S)-(N-methoxy-N-methylcarbamoyl)-3-methyl-butyl] succinamic acid benzyl ester as an amorphous solid.

$^1$H NMR (CDCl3): δ7.62 (d, 2H, J=7.4 Hz), 7.58 (s, 3H), 7.44 (t, 2H, J=7.7 Hz), 7.35–7.21 (m, 7H), 7.10 (s, 1H), 6.80 (t, 1H, J=2.2 hz), 6.60 (bs, 1H), 5.17–1.13 (m, 1H), 5.10 (s, 2H), 4.97–4.92 (m, 1H), 3.77 (s, 3H), 3.44 (dd, 1H, J=5.7, 17.1 Hz), 3.17 (s, 3H), 3.03 (dd, 1H, J=8.8, 16.5 Hz), 1.67–1.36 (m, 3H), 0.92 (d, 3H, J=6.25 Hz), 0.87 (d, 3H, J=6.3 Hz). Anal. Calculated for $C_{35}H_{39}N_3O_5$: C, 72.27; H, 6.76; N, 7.22. Found: C, 72.19; H, 6.78; N, 7.16.

Example 1(m)

3(R)-[3-(4-Cyanophenyl)-1H-pyrrol-1-yl]-N-[2,2-dimethyl-1(S)-(methylcarbamoyl)propyl]succinamic Acid

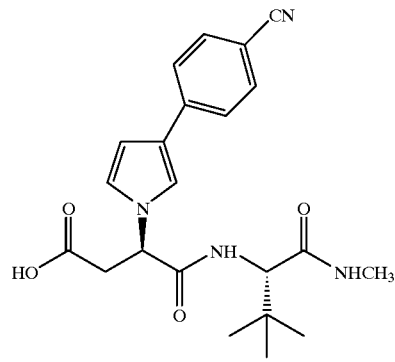

According to the procedure described in Example 1(a), 3(R)-[3-(4-cyanophenyl)-1H-pyrrol-1-yl]-N-[2,2-dimethyl-1(S)-(methylcarbamoyl)propyl]succinamic acid benzyl ester in MeOH and EtOAc was hydrogenolyzed to provide 1.2 g (90%) of 3(R)-[3-(4-cyanophenyl)-1H-pyrrol-1-yl]-N-[2,2-dimethyl-1(S)-(methylcarbamoyl)propyl]succinamic acid as a yellow powder, mp 138–40° C.

$^1$H NMR (CD$_3$O D): δ7.98 (bs, 1H), 7.82 (bd, 1H, J=8.4 Hz), 7.68 (d, 2H, J=8.7 Hz), 7.50 (d, 2H, J=8.4 Hz), 7.38 (t, 1H, J=1.6 Hz), 6.92 (t, 1H, J=2.5 Hz), 6.55 (t, 1H, J=2.2 Hz), 5.28 (t, 1H, J=7.5 Hz), 4.19 (d, 1H, J=9.0 Hz), 2.98 (dd, 1H, J=6.9, 16.5 Hz), 2.64 (d, 3H, J=4.7 Hz), 0.98 (s, 9H). IR (KBr): 3317, 2963, 2225, 1648, 1550, 1410, 1180 cm$^{-1}$. HRFABMS: Calculated for C$_{22}$H$_{26}$N$_4$O$_4$ Cs (M+Cs$^+$): 543.1008. Found 543.1021. Anal. Calculated for C$_{22}$H$_{26}$N$_4$O$_4$.0.4 EtOAc: C, 63.60; H, 6.60; N, 12.57. Found: C, 63.80; H, 6.77; N, 12.57.

Starting materials were available as follows:

3-(4-Cyanophenyl)-furan

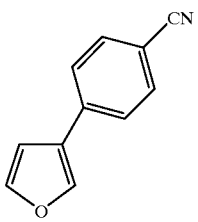

As described in Example 1(d) for the preparation of 3-(pyridin-4-yl)furan, 4-bromobenzonitrile (4.00 g, 22.0 mmol) was coupled to 3-furanboronic acid to furnish in high yield crude 3-(4-cyanophenyl)-furan as a brown solid, mp 55–7° C., which was used immediately without further purification.

$^1$H NMR (CDCl3): δ7.82 (bs, 1H), 7.67 (d, 2H, J=8.4 Hz), 7.59 (d, 2H, J=8.4 Hz), 7.52 (t, 1H, J=1.9 Hz), 6.72 (bs, 1H). IR (KBr): 2214, 1608, 1160, 796 cm$^-$. Anal. Calculated for C$_{11}$H$_7$NO.0.1 C$_6$H$_6$: C, 78.72; H, 4.33; N, 7.91. Found: C, 78.32; H, 4.60; N, 7.65.

3-(4-Cyanophenyl)-2,5-dihydro-2,5-dimethoxyfuran

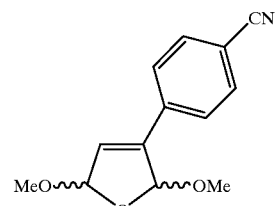

As described in Example 1(a) for the preparation of 3-biphenyl-2,5-dihydro-2,5-dimethoxy-tetrahydrofuran, crude 3-(4-cyanophenyl)furan was converted. Flash column chromatography with EtOAc:hex (30:70) as eluant furnished 3.8 g (73% from 4-bromobenzonitrile) of 3-(4-cyanophenyl)-2,5-dihydro-2,5-dimethoxyfuran as a yellow solid, mp 71–2° C.

$^1$H NMR (CDCl3): δ7.62 (s, 4H), 6.46 (d, 1H, J=0.9 Hz), 6.22 (dd, 0.5H, J=0.9, 3.7 Hz), 6.00 (dd, 0.5H, J=0.9, 3.7 Hz), 5.97 (d, 0.5H, J=0.6 Hz), 5.71 (d, 0.5H, J=1.3 Hz), 3.48–3.40 (m, 6H). IR: 2933, 28322, 2227, 1607, 1505, 1369 cm$^{-1}$. Anal. Calculated for C$_{13}$H$_{13}$NO$_3$: C, 67.52; H, 5.67; N, 6.06. Found: C, 67.39; H, 5.71; N, 6.14.

3-(4-Cyanophenyl)-2,5-dimethoxy-tetrahydrofuran

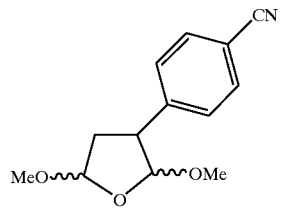

As described in Example 1(a) for the preparation of 3-(biphenyl-4-yl)-2,5-dimethoxy-tetrahydrofuran, 3-(4-cyano-phenyl)-2,5-dihydroxy-2,5-dimethoxyfuran (3.8 g, 16.43 mmol) was reduced to give 3.70 g (97%) of a diastereomeric mixture of 3-(4-cyanophenyl)-2,5-dimethoxy-tetrahydrofuran as an oily white solid, which was used without further purification.

$^1$H NMR (CDCl3): δ7.60 (d, 2H J=7.8 Hz), 7.42 (d, 2H, J=8.1 Hz), 5.30–4.94 (m, 2H), 3.60–3.20 (m, 6H), 2.78–1.92 (m, 3H). IR: 2912, 2833, 2227, 1607, 1511 cm$^{-1}$.

3(R)-[-3-(4-Cyanophenyl)-1H-pyrrol-1-yl]-N-2,2-dimethyl-1(S)-(methylcarbamoyl)propyl] succinnamic Acid Benzyl Ester

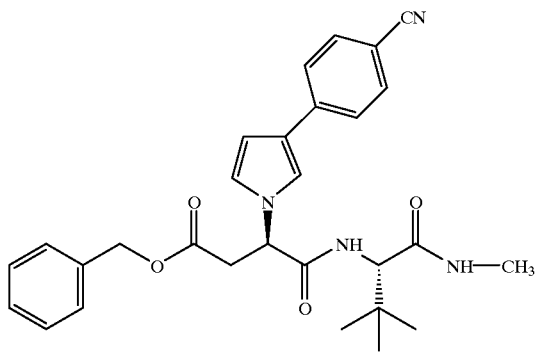

According to the procedure described in Example 1(c) for the preparation of N-(1,7-diaza-4-oxa-8-oxo-tricyclo-(9.6.1.0$^{12,17}$]-octadeca-11(18),12,14,16-tetraen-9S-yl)-3(R)-(-3-phenyl-1H-pyrrol-1-yl)-succinamic acid benzyl ester, crude 3(R)-amino-N-(2,2-dimethyl-1(S)-methylcarbamoylpropyl)succinamic acid benzyl ester trifluroacetate salt (prepared as described in Example 1(b)) and 3-(4-cyanophenyl)-2,5-dimethoxy-tetrahydrofuran were condensed. Drying the crude product via azeotrope with benzene gave 1.70 g (41%) of 3(R)-[-3-(4-cyanophenyl)-1H-pyrrol-1-yl]-N-[2,2-dimethyl-1(S)-(methylcarbamoyl) propyl] succinamic acid benzyl ester as a yellow solid, mp 102–4° C.

$^1$H NMR (CDCl3): 7.60–7.55 (m, 4H), 7.30–7.25 (m, 5H), 7.12 (t, 1H, J=2.2 Hz), 6.80 (t, 1H, J=2.5 Hz), 6.56 (t, 1H, J=2.8 Hz), 6.32 (d, 1H, J=8.7 Hz), 5.60 (d, 1H, J=5.0 Hz), 5.18–5.05 (m, 3H), 4.05 (d, 1H, J=9.0 Hz), 3.38 (dd, 1H, J=5.9, 17.0 Hz), 3.08 (dd, 1H, J=8.7, 16.8 Hz), 2.76 (d, 3H, J=5.0 Hz), 0.92 (s, 9H). IR: 3310, 2958, 2227, 1736, 1648, 1547 cm$^{-1}$. HRFABMS: Calculated for $C_{29}H_{32}N_4O_4Cs$ (MH+Cs$^+$): 633.1478. Found: 633.1452. Anal. Calculated for $C_{29}H_{32}N_4O_4 \cdot 0.4\ C_6H_6$: C, 70.91; H, 6.52; N, 10.53. Found: C, 70.97; H, 6.15; N, 10.26.

Example 1(n)

4-[2S-(3-Carboxy-2(R)-1H-pyrrol-1-yl-propionylamido)-4-methyl-pentanoylamino]benzoic Acid Ethyl Ester

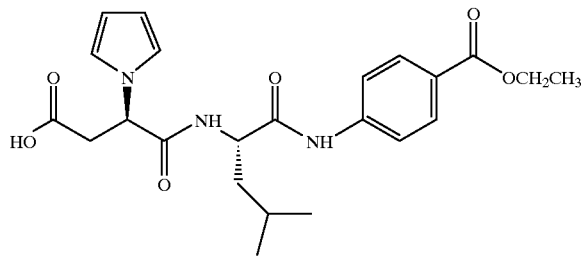

According to the procedure described in Example 1(a), 4-[2S-(3-carbobenzyloxy-2(R)-1H-pyrrol-1-yl-propionylamido)-4-methyl-pentanoylamino]-benzoic acid ethyl ester in EtOH and THF was hydrogenolyzed. The crude product was successively purified via flash column chromatography with a 20–40% EtOAc/hex-5% MeOH/ CH$_2$Cl$_2$ stepwise gradient and preparative RPHPLC (C18) with 50% CH$_3$CN/1M aqueous NH$_4$OAc to provide 45 mg of 4-[2S-(3-carboxy-2(R)-1H-pyrrol-1-yl-propionyl-amido)-4-methyl-pentanoylamino]-benzoic acid ethyl ester as fluffy crystals, mp 111–4° C.

FABMS: 444.1 ($C_{23}H_{30}N_3O_6$; M) +H$^+$).

The starting materials were available as follows:

4-[2S-(3-Benzyloxycarbonyl-2(R)-t-butoxycarbonylamino-propionylamino)-4-methyl-pentanoyl-amino]-benzoic Acid Ethyl Ester

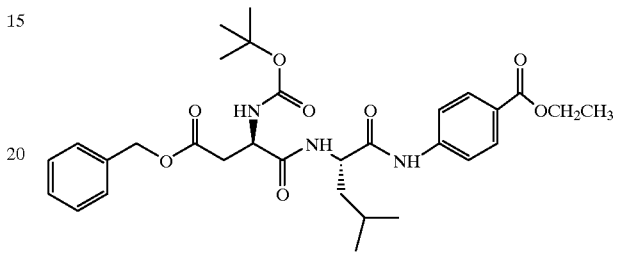

According to the procedure described in Example 1(a) for the preparation of N-(1(S)-benzyl-2-hydroxyethyl)-3(R)-t-butoxycarbonylamino-succinamic acid benzyl ester, N-t-butoxycarbonyl-D-aspartate β-benzyl ester and 4-(2S-amino-4-methyl-pentanoylamino)benzoic acid ethyl ester (Castelhano, A. L.; Yuan, Z.; Horne, S.; Liak, T. J. WO95/12603-A1, May 11, 1995) were coupled with EDC to furnish 2.4 g (67%) of 4-[2S-(3-benzyloxycarbonyl-2(R)-t-butoxycarbonylamino-propionylamino)-4-methyl-pentanoyl-amino]-benzoic acid ethyl ester as a glassy solid, which was used without further purification.

4-[2S-(2(R)-Amino-3-benzyloxycarbonyl-propionylamino)-4-methyl-pentanoyl-amino]benzoic Acid Ethyl Ester

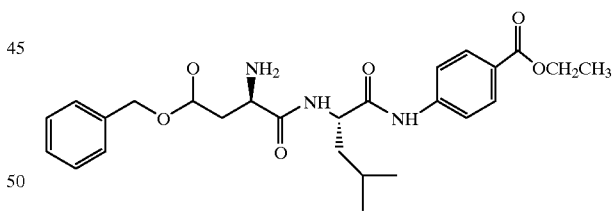

As described in Example 1(b) for the preparation of 3(R)-amino-N-(2,2-dimethyl-1(S)-(methylcarbamoyl) propyl)succinamic acid benzyl ester trifluoroacetate salt, 4-[2S-(3-benzyloxycarbonyl-2(R)-t-butoxycarbonylamino-propionylamino)-4-methyl-pentanoyl-amino]-benzoic acid ethyl ester was deprotected with trifluroacetic acid, except that a solution of the resultant salt was neutralized by washing a CH$_2$Cl$_2$ solution with 1N aqueous NaOH. Removal of the solvent under reduced pressure afforded 2.00 g (100%) of 4-[2S-(2(R)-amino-3-benzyloxycarbonyl-propionyl-amino)-4-methyl-pentanoyl-amino]-benzoic acid ethyl ester as a viscous yellow oil, which was used without further purification.

4-[2S-(3-Carbobenzyloxy-2(R)-1H-pyrrol-1-yl-propionylamido)-4-methyl-pentanoylamino]-benzoic Acid Ethyl Ester

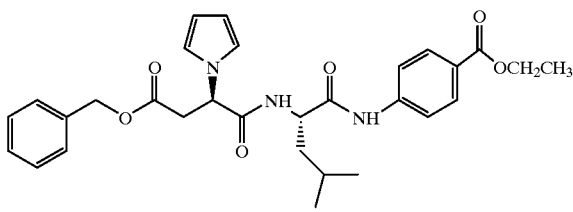

A mixture of 4-[2S-(2(R)-amino-3-benzyloxycarbonyl-propionyl-amino)-4-methyl-pentanoyl-amino]-benzoic acid ethyl ester (150 mg, 0.310 mmol), 2,5-dimethoxy-tetrahydrofuran (43 mg, 0.33 mmol), sodium acetate (153 mg, 1.86 mmol), and glacial HOAc (3 mL) was heated at reflux for 30 minutes. The mixture was allowed to cool, poured onto ice, diluted with $H_2O$ (30 mL), and extracted with EtOAc (2×50 mL). The combined extracts were washed with brine, dried over $MgSO_4$, and concentrated in vacuo. Flash column chromatography with 15–20–25–30% EtOAc/hex stepwise gradient furnished 107 mg (65%) of 4-[2S-(3-carbobenzyloxy-2(R)-1H-pyrrol-1-yl-propionylamido)-4-methyl-pentanoylamino]-benzoic acid ethyl ester.

Example 1(o)

N-(9-Oxo-1,8-diaza-tricyclo[10.6.1.0$^{13,18}$]nonadeca-12(19),13,15,17-tetraen-10S-yl)-3(R)-1H-pyrrol-1-yl-succinamic Acid

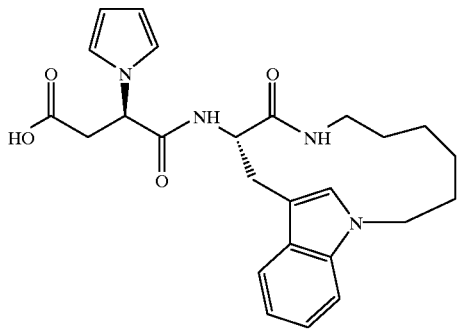

According to the procedure described in Example 1(a), N-(9-oxo-1,8-diaza-tricyclo[10.6.1.0$^{13,18}$]nonadeca-12(19), 13,15,17-tetraen-10S-yl)-3(R)-1H-pyrrol-1-yl-succinamic acid benzyl ester was hydrogenolyzed in EtOH and THF. Crystallization from $CH_2Cl_2$ provided 120 mg (36%) of N-(9-oxo-1,8-diaza-tricyclo[10.6.1.0$^{13,18}$]nonadeca-12(19), 13,15,17-tetraen-10S-yl)-3(R)-1H-pyrrol-1-yl-succinamic acid as fluffy colorless crystals, mp 139–44° C.

FABMS: 451 ($C_{25}H_{31}N_4O_4$; M+H$^+$).

Example 1(p)

3(R)-[3-[(4-Cyanophenyl)acetyl]-1H-pyrrol-1-yl]-N-[2,2-dimethyl-1(S)-(methylcarbamoyl)propyl]succinamic Acid

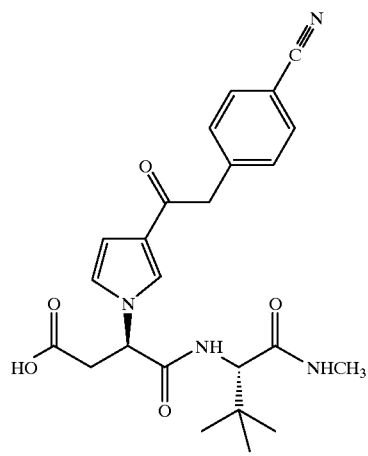

Routine allyl ester cleavage conditions were previously described by Friedrich-Bochnitschek, S.; Waldmann, H.; Kunz, H. *J. Org. Chem.* 1989, 54, 751–756. To a solution of 3 (R)-[3-[(4-cyanophenyl)acetyl]-1H-pyrrol-1-yl]-N-[2,2-dimethyl-1(S)-(methylcarbamoyl)propyl]succinamic acid allyl ester (247 mg, 0.501 mmol) in acetonitrile (2 mL) was added in succession Pd(PPh$_3$)$_4$ (29 mg, 0.026 mmol) and morpholine (226 µL, 2.60 mmol). The resultant mixture was carefully purged with argon. After 30 min, the resultant green mixture was stirred with 10% aqueous $KHSO_4$ (20 mL) and extracted with CHCl$_3$ (35 mL). The organic layer was washed with 10% aqueous $KHSO_4$ (20 mL), dried over $Na_2SO_4$, and concentrated. Flash column chromatography with 1% HOAc/3% MeOH/CHCl$_3$ and drying via azeotrope with n-heptane gave 243 mg (94%) of 3(R)-[3-[(4-cyanophenyl)acetyl]-1H-pyrrol-1-yl]-N-[2,2-dimethyl-1(S)-(methylcarbamoyl)propyl]succinamic acid as a yellow solid.

$^1$H NMR (CD$_3$OD): δ8.09 (d, 1H, J=8.7 Hz), 8.05 (dd, 1H, J=2.8, 6.9 Hz), 7.78 (dd, 1H, J=1.9, 1.9 Hz), 7.66 (d, 2H, J=8.4 Hz), 7.46 (d, 2H, J=8.4 Hz), 6.90 (dd, 1H, J=2.2,2.2 Hz), 6.59 (dd, J=1.9,3.1 Hz), 5.33 (t, 1H, J=7.5 Hz), 4.22–4.15 (m, 3H), 3.24 (t, 1H, J=8.7 Hz), 2.98 (dd, 1H, J=5.3, 17.4 Hz), 2.66 (d, 3H, J=4.7 Hz), 0.99 (s, 9H). IR (KBr): 3332, 2696, 2230, 1719, 1654, 1532, 1412, 1177 cm$^{-1}$. HRFABMS: Calculated for $C_{24}H_{29}N_4O_5$ (M+H$^+$): 453.2125. Found: 453.2125. Anal. Calculated for $C_{24}H_{28}N_4O_5$·0.5 HOAc·0.3 CHCl$_3$: C, 58.62; H, 5.89; N, 10.81. Found: C, 58.41; H, 5.72; N, 10.50.

The starting materials were available as follows:

3(R)-(t-Butoxycarbonylamino)-N-(2,2-dimethyl-1(S)-(methylcarbamoyl)propyl)succinamic Acid Allyl Ester

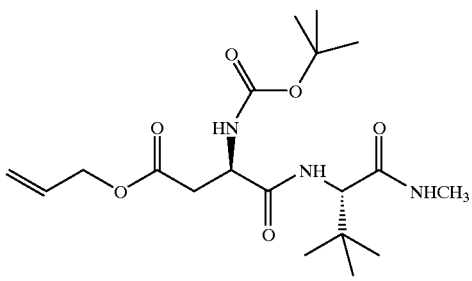

According to Example 1(b) for 3 (R)-t-butyloxycarbonylamino-N-(2,2-dimethyl-1(S)-(methylcarbamoyl)propyl)succinamic acid benzyl ester, β-allyl-N-t-butoxycarbonyl-D-aspartate (Belshaw, P.; Mzengeza, S.; Lajoie, G. *Syn Commun* 1990, 20, 3157–3160; 2.00 g, 7.32 mmol) and L-t-leucine N-methylarnide (Malon, P.; Pancoska, P.; Budesinsky, M.; Hlavacek, J.; Pospisek, J.; Blaha, K. *Coll. Czech. Chem Commun.* 1983, 48, 2844–2861; 1.05 g, 7.32 mmol) were coupled with TBTU. The resultant yellow oil was routinely used without further purification. Flash column chromatography with 2% MeOH/$CH_2Cl_2$ provided 2.44 g (84%) of 3(R)-(t-butoxycarbonylamino)-N-(2,2-dimethyl-1(S)-(methylcarbamoyl)propyl)succinamic acid allyl ester as a pale yellow oil.

1H NMR (CDCl3): δ7.05 (d, 1H, J=9.0 Hz), 5.98 (d, 1H, J=4.4 Hz), 5.77 (ddt, 1H, J=5.6, 10.3, 16.2 Hz), 5.29 (ddd, 1H, J=1.5, 2.8, 15.6 Hz), 5.23 (dd, 1H, J=1.3, 10.5 Hz), 4.57 (dddd, 2H, J=1.6,3.1, 5.6, 12.1 Hz), 4.11 (d, 1H, J=9.4 Hz), 2.77 (d, 3H, J=5.0 Hz), 1.46 (s, 9H), 0.99 (s, 9H).

3(R)-Amino-N-(2,2-dimethyl-1(S)-(methylcarbamoyl)propyl)succinamic Acid Allyl Ester Trifluoroacetate Salt

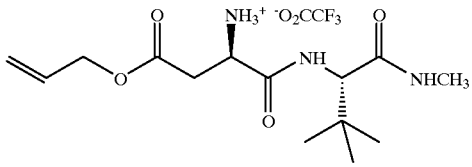

As described in Example 1(b) for the preparation of 3(R)-amino-N-(2,2-dimethyl-1(S)-(methylcarbamoyl)propyl)succinamic acid benzyl ester trifluoroacetate salt, crude 3(R)-(t-butoxycarbonylamino)-N-(2,2-dimethyl-1(S)-(methylcarbamoyl)propyl)succinamic acid allyl ester was deprotected after 2 hours. Flash column chromatography with 0.5% TFA17% MeOH/$CHCl_3$ gave 2.46 g (87%) of 3(R)-amino-N-(2,2-dimethyl-1(S)-(methylcarbamoyl)propyl)succinamic acid allyl ester trifluoroacetate salt as a colorless foam.

1H NMR ($CD_3OD$): δ5.96 (ddt, 1H, J=5.6, 10.6, 17.1 Hz), 5.35 (ddd, 1H, J=1.6, 3.1, 17.1 Hz), 5.25 (ddd, 1H, J=1.2, 2.5, 10.3 Hz), 4.66 (ddd, 2H, J=1.2, 1.3, 5.9 Hz), 4.34 (dd, 1H, J=5.6, 7.8 Hz), 4.21 (s, 1H), 3.03 (dd, 1H, J=5.6, 17.4 Hz), 2.94 (dd, 1H, J=7.5, 17.4 Hz), 2.71 (d, 3H, J=5.0 Hz), 1.46 (s, 9H), 0.99 (s, 9H). IR (KBr): 3413, 2966, 1672, 1656, 1207, 1143 $cm^{-1}$. HRFABMS: Calculated for $C_{14}H_{25}N_3O_4Na$ (M+Na$^+$): 322.1743. Found: 322.1747. Anal. Calculated for $C_{14}H_{25}N_3O_4$·2.5 $F_3COOH$·0.5 $CHCl_3$: C, 36.36; H, 4.38; N, 6.52. Found: C, 36.34; H, 4.25; N, 6.51.

3-(2,2-Dibromoethenyl)-2,5-dimethoxy-tetrahydrofuran

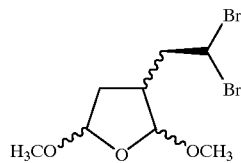

A mixture of Zn powder (1.65 g, 25.0 mmol), triphenylphosphine (6.54 g, 25.0 mmol), and $CBr_4$ (8.30 g, 25.0 mmol) in dry $CH_2Cl_2$ (40 mL) was stirred at ambient temperature. After 24 hours, 2,5-dimethoxy-tetrahydrofaran-3-carboxaldehyde (2.00 g, 12.5 mmol) was added and an exothermic reaction ensued. After 30 minutes, pet ether (100 mL) was added and the resultant upper layer separated. The lower layer was twice diluted with $CH_2Cl_2$ (50 mL) and pet ether (50 mL), and the upper layer reserved. The combined upper layers were combined, passed through a pad of $SiO_2$, and concentrated under reduced pressure at 30° C. or below to give 2.18 g (55%) of 3-(2,2-dibromoethenyl)-2,5-dimethoxy-tetrahydrofuran as a volatile colorless oil, which was a mixture of diastreomers by 1H NMR and used immediately without further purification.

2,5-Dimethoxy-3-(2-tributylstannylethynyl)-tetrahydrofuran

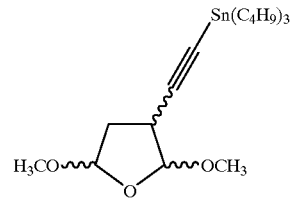

To solution of crude 3-(2,2-dibromoethenyl)-2,5-dimethoxy-tetrahydrofuran (1.78 g, 5.64 mmol) in ether (30 mL) at –78° C. was added n-butyllithium (9.02 mL of 1.25 M in hex). After 1 hour at –78° C., tributyltin chloride (1.68 mL, 6.20 mmol) was added, and the mixture was allowed to warm to ambient temperature. After 16 hours, ether (35 mL) and saturated aqueous $NH_4Cl$ (30 mL) were added. The organic layer was separated, washed with saturated aqueous $NH_4Cl$ (30 mL), $H_2O$ (25 mL), and saturated aqueous $NaHCO_3$ (25 mL), dried over $K_2CO_3$, and evaporated to give an orange oil, which was purified via flash column chromatography with 2% MTBE/hex to furnish 1.92 g (77%) of 2,5-dimethoxy-3-(2-tributylstannylethynyl)-tetrahydrofuran as a colorless oil. A mixture of diastereomers was evident in the 1H NMR spectrum, which was used immediately without further purification.

IR: 2923, 1456, 1374, 1215, 1105, 1017, 967 $cm^{-1}$. Anal. Calculated for $C_{20}H_{38}O_3Sn$: C, 53.96; H, 8.60. Found: C, 54.21; H, 8.66.

3-[2-(4-Cyanophenyl)-ethynyl]-2,5-dimethoxy-tetrahydrofuran

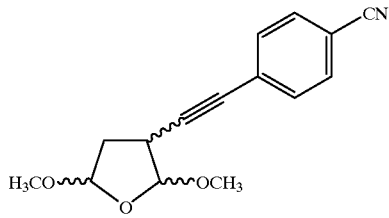

A mixture of 2,5-dimethoxy-3-(2-tributylstannylethynyl)-tetrahydrofuran (1.86 g, 4.18 mmol), 4-iodobenzonitrile (1.15 g, 5.02 mmol), and tetrakis(triphenylphosphine)palladium(0) (145 mg, 0.125 mmol) in toluene (25 mL) was heated at 100° C. After 5.5 hours, the resultant red solution was allowed to cool, and the solvent was removed under reduced pressure. Flash column chromatography twice with 10% EtOAc/hex provided 1.10 g (100%) of 3-[2-(4-cyanophenyl)-ethynyl]-2,5-dimethoxy-tetrahydrofuran as an orange oil. A mixture of diastereomers was observed by $^1$H NMR, which was used without further purification.

$^1$H NMR (CDCl3): 3.12 (ddd, J=2.8, 6.6, 9.0 Hz), 2.57 (ddd, J=5.6, 9.3, 13.4 Hz), 2.08 (dd, J=2.5,4.7 Hz), 2.04 (dd, J=3.1,4.3 Hz). IR: 2227, 1603, 1216, 1102, 1012, 841 cm$^{-1}$. Anal. Calculated for $C_{15}H_{15}NO_3$·0.1 EtOAc: C, 69.51; H, 5.98; N, 5.26. Found: C, 69.52; H, 5.76; N, 5.32.

3(R)-[3-[(4-Cyanophenyl)acetyl]-1H-pyrrol-1-yl]-N-[2,2-dimethyl-1(S)-(methylcarbamoyl)propyl]succinamic Acid Allyl Ester

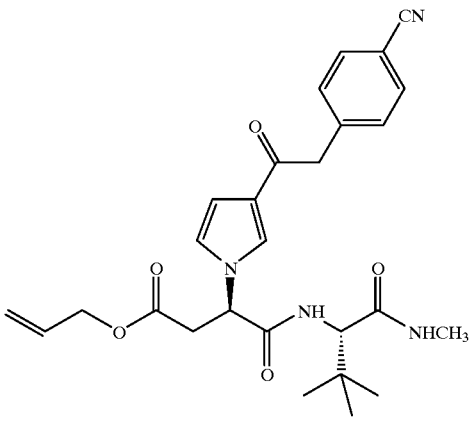

As described in Example 1(c) for the preparation of N-(8-oxo-4-oxa-1,7-diaza-tricyclo[9.6. 1.0$^{12,17}$]octadeca-11(18),12,14,16-tetraen-9-yl)-3-(3-phenyl-1H-pyrrol-1-yl)succinamic acid benzyl ester, 3 (R)-amino-N-(2,2-dimethyl-1(S)-(methylcarbamoyl)propyl)succinamic acid allyl ester trifluoroacetate salt and 3-[2-(4-cyanophenyl)-ethynyl]-2,5-dimethoxy-tetrahydrofuran were heated with trifluoroacetic acid (1 equiv) at 70° C. for 4 hours. Flash column chromatography twice with 0.5% HOAc/15% EtOAc/CH$_2$Cl$_2$ as eluant and azeotrope with n-heptane afforded 800 mg (36%, 43% based on recovered furan) of 3(R)-[3-[(4-cyanophenyl)acetyl]-1H-pyrrol-1-yl]-N-[2,2-dimethyl-1(S)-(methylcarbamoyl)propyl]succinamic acid allyl ester as a brown oil.

$^1$H NMR (CDCl3): δ7.58 (d, 2H, J=8.1 Hz), 7.47 (dd, 1H, J=1.9, 1.9 Hz), 7.36 (d, 2H, J=8.1 Hz), 6.84 (d, 1H, J=9.0 Hz), 6.74 (dd, 1H, J=2.8,2.8 Hz), 6.63 (dd, 1H, J=1.6,2.8 Hz), 6.08 (dd, J=2.8, 6.8 Hz), 5.82 (ddt, 1H, J=5.9, 10.3, 17.1 Hz), 5.26 (ddd, 1H, J=1.2, 2.8, 17.1 Hz), 5.19 (q, 1H, J=7.2 Hz), 4.56 (dddd, 2H, J=1.6, 2.8, 4.4, 15.9 Hz), 4.18 (d, 1H, J=9.0 Hz), 4.05 (s, 2H), 3.34 (dd, 1H, J=7.2, 16.8 Hz), 2.99 (dd, 1H, J=7.2, 16.8 Hz), 2.72 (d, 3H, J=5.0 Hz), 0.90 (s, 9H). $^{13}$C NMR (CDCl3): δ191.2,170.2, 169.4, 168.0, 140.6, 132.2, 131.3, 130.3, 125.7, 125.7, 122.0, 119.0, 118.9, 110.5, 110.4, 66.0, 61.0, 59.4,46.1, 37.5, 34.8, 31.9, 29.0, 26.5, 26.0. IR (KBr): 3320, 2965, 229, 1736, 1648, 1531, 1173 cm$^{-1}$. HRFABMS: Calculated for $C_{27}H_{33}N_4O_5$ (M+H$^+$): 493.2451. Found 493.2462. Anal. Calculated for $C_{27}H_{32}N_4O_5$·0.2 H$_2$O·0.2 CH$_2$Cl$_2$: C, 63.66; H, 6.44; N, 10.92. Found: C, 63.86; H, 6.56; N, 10.58.

Example 2

N-(1(S)-Acetyl-3-methylbutyl)-3(R)-[3-(biphenyl-4-yl)-1H-pyrrol-1-yl)succinamic Acid

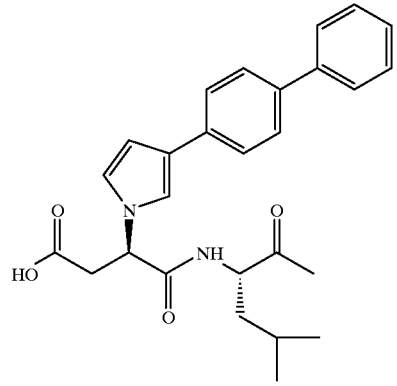

To a solution of 3(R)-(3-biphenyl-4-yl-1H-pyrrol-1-yl)-N-[1(S)-N-methoxy-N-methylcarbamoyl)-3-methyl-butyl]succinamic acid (prepared as described in Example 1(1); 209 mg, 0.425 mmol) in THF (5 mL) at −78° C. was added methylmagnesium bromide (3 M in ether, 0.7 mL) dropwise via syringe. After 15 minutes at −70° C. and 2 hours at 0° C., the mixture was quenched with acetone (50 μL), and then added to EtOAc/1N NaHSO$_4$. The aqueousueous phase was extracted with EtOAc. The combined organic layers were dried over Na$_2$SO$_4$ and concentrated. After 3 days at ambient temperature, the dark residue began to crystallize, and trituration with MTBE/hexanes provided 90 mg (46%) of pure N-(1(S)-acetyl-3-methylbutyl)-3(R)-[3-(biphenyl-4-yl)-1H-pyrrol-1-yl)succinamic acid as an off-white solid.

$^1$H NMR (CDCl3): δ7.62–7.55 (m, 6H), 7.44 (t, 2H, J=7.5 Hz), 7.33 (t, 1H, J=7.0 Hz), 7.11 (s, 1H), 6.81 (t, 1H, J=2.4 Hz), 6.62 (dd, 1H, J=1.3, 2.4 Hz), 6.07 (d, 1H, J=8.5 Hz), 5.12 (t, 1H, J=6.8 Hz), 4.6–14.54 (m, 1H), 3.46 (dd, 1H, J=6.4, 16.7 Hz), 3.01 (dd, 1H, J=7.4, 16.9 Hz), 2.16 (s, 3H), 1.58–1.51 (m, 2H), 1.33 (d, 1H, J=7.4 Hz), 0.92 (d, 3H, J=6.3 Hz), 0.87 (d, 3H, J=6.3 Hz). Anal. Calculated for $C_{27}H_{30}N_2O_4$·0.5 H$_2$O: C, 71.18; H, 6.86; N, 6.15. Found: C, 71.01; H, 6.78; N, 6.40.

Example 3

3(R)-[3-(Biphenyl-4-yl)-1H-pyrrol-1-yl]-N-[1(S)-(1(RS)-hydroxy-ethyl)-3-methylbutyl]succinamic Acid

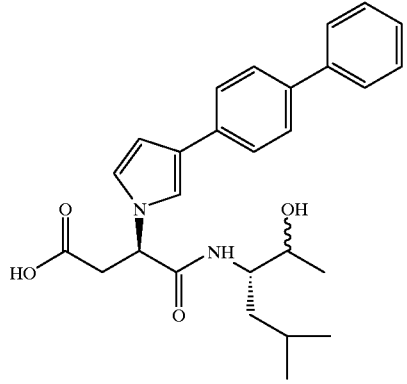

To a solution of N-(1(S)-acetyl-3-methylbutyl)-3(R)-(biphenyl-4-yl-1H-pyrrol-1-yl)succinamic acid (prepared as described in Example 2; 45 mg, 0.10 mmol) in THF (2 mL) and EtOH (1 mL) at −78° C. was added a solution of NaBH$_4$ (19 mg, 0.50 mmol) in EtOH (1 mL). After 2 hours at −78° C., the reaction was quenched with acetone (0.5 mL) and concentrated in vacuo to afford a residue which was partitioned with EtOAc and pH 4.5 citrate buffer. The aqueous phase was further extracted with EtOAc. The combined organic layers were dried over Na$_2$SO$_4$ and evaporated to give a solid that was dissolved in MTBE and precipitated with hexanes to give 30 mg (67%) of 3(R)-[3-(biphenyl-4-yl)-1H-pyrrol-1-yl)-N-[1(S)-(1RS-hydroxy-ethyl)-3-methylbutyl]succinamic acid as an amorphous solid.

$^1$H NMR (CDCl3): δ7.60–7.56 (m, 6H), 7.44 (t, 2H, J=7.4 Hz), 7.33 (t, 1H, J=6.8 Hz), 7.11 (s, 1H), 6.82 (s, 1H), 6.61 (s, 1H), 5.70 (m, 1H, minor isomer), 5.49 (d, 1H, J=8.1 Hz, major isomer), 5.05 (t, 1H, J=6.3 Hz), 4.04–4.01 (m, 1H, major isomer), 3.86–3.82 (m, 1H), 3.76–3.74 (m, 1H, minor isomer), 3.41 (dd, 1H, J=5.9, 16.9 Hz), 3.16 (dd, 1H, J=6.6, 10.7 Hz), 1.75–1.42 (m, 1H), 1.28–1.13 (m, 2H), 1.08 (d, 3H, J=6.3 Hz, minor isomer), 1.01 (d, 3H, J=6.3 Hz, major isomer), 0.87 (d, 6H, J=6.6 Hz). Anal. Calculated for C$_{27}$H$_{32}$N$_2$O$_4$ .0.8 H$_2$O: C, 70.04; H, 7.32; N, 6.05. Found: C, 69.89; H, 7.33; N, 5.97.

Example 4(a)

N-(1(S)-Benzyl-2-hydroxyethyl)-3(R)-[3-(4'-cyanobiphenyl-4-yl)-1H-pyrrol-1-yl]succinamic Acid

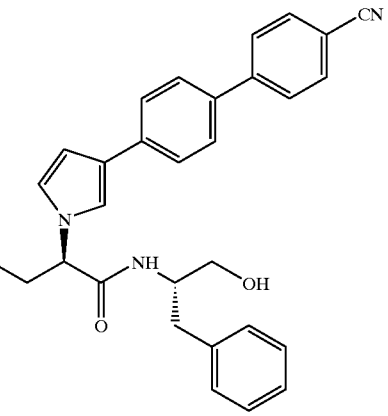

According to the procedure described in Example 1(a), N-(1(S)-benzyl-2-hydroxyethyl)-3(R)-[3-(4'-cyanobiphenyl-4-yl)-1H-pyrrol-1-yl]succinamic acid benzyl ester (50 mg, 0.070 mmol) hydrogenolyzed in MeOH:EtOAc (2:3 mL) after 2 hours to give a yellow powder, which was washed with CHCl$_3$ and hexane to furnish 35 mg (100%) of N-(1(S)-benzyl-2-hydroxyethyl)-3(R)-[3-(4'-cyanobiphenyl-4-yl)-1H-pyrrol-1-yl]succinamic acid as a yellow powder, mp 189–92° C.:

$^1$H NMR (DMSO-d$_6$): δ8.82–8.78 (bm, 1H), 7.90 (s, 4H), 7.72 (d, 2H, J=8.1 Hz), 7.50 (d, 2H, J=8.1 Hz), 7.20 (m, 6H), 6.82 (s, 1H), 6.45 (s, 1H), 4.95 (t, 1H, J=7.2 Hz), 3.88–3.78 (m, 1H), 2.84 (d, 1H, J=5.9 Hz), 2.75–2.60 (m, 3H). IR (KBr): 3396, 3029, 2925, 2229, 1654, 1602, 1560, 1495 cm$^{-1}$. HRFABMS: Calculated for C$_{30}$H$_{27}$N$_3$O$_4$Na (MH+ Na$^+$): 516.1899. Found: 516.1912. Anal. Calculated for C$_{30}$H$_{27}$N$_3$O$_4$.0.81 CHCl$_3$: C, 62.69; H, 4.75; N, 7.12. Found: C, 62.64; H, 4.89; N, 7.23.

The starting material was made as follows:

4'-Bromo-biphenyl-4-carbonitrile

As described in Example 1(a) for the preparation of 3-biphenyl-4-yl-furan, 4-bromobenzonitrile (9.42 g, 51.8 mmol) and 4-bromophenylboric acid (5.20 g, 25.9 mmol)

were coupled in EtOH to afford 4.50 g (67%) of 4'-bromo-biphenyl-4-carbonitrile as a grey powder, mp 147–8° C. (lit 153–5° C.; McNamara, J.; Gleason, W. B. *J. Org Chem.* 1976, 41, 1071). The material had an NMR spectrum that matched literature (see Amatore, C.; Juland, A.; Negri, S. *J. Organomet. Chem.* 1990, 390, 389–398) and was typically used without further purification.

4'-(Furan-3-yl)-biphenyl-4-carbonitrile

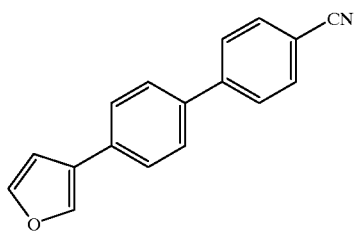

As described in Example 1(a) for the preparation of 3-biphenyl-4-yl-furan, crude 4'-bromo-biphenyl-4-carbonitrile (200 mg, 0.775 mmol) and 3-fuiranboronic acid (see Thompson, W. J.; Gaudino, G. *J. Org. Chem.* 1984, 49, 5237–5243; 105 mg, 0.937 mmol) in MeOH (2 mL) were coupled to give a yellow solid, which was purified via preparative TLC. Elution with EtOAc:benzene (1:99) provided 100 mg (53%) of 4'-furan-3-yl-biphenyl-4-carbonitrile as a grey powder, mp 199–203° C.

$^1$H NMR (CDCl3): δ7.81 (bs, 1H), 7.72 (d, 4H, J=1.9 Hz), 7.61 (s, 4H), 7.51 (bs, 1H), 6.75 (s, 1H). IR (KBr): 2225, 1604, 1503, 1396, 1162, 1102, 1058 cm$^{-1}$. Anal. Calculated for $C_{17}H_{11}NO.0.3$ EtOAc.0.2 $C_6H_6$: C, 80.78; H, 5.05; N, 5.01. Found: C, 80.96; H, 4.88; N, 5.00.

4'-(2,5-Dimethoxy-2,5-dihydro-furan-3-yl)-biphenyl-4-carbonitrile

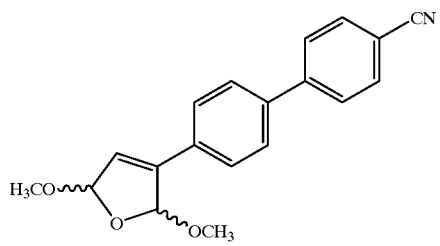

According to the procedure for the preparation of 3-biphenyl-4-yl-furan described in Example 1(a), 4'-furan-3-yl-biphenyl-4-carbonitrile (1.29 g, 5.26 mmol) was converted into 4'-(2,5-dimethoxy-2,5-dihydro-furan-3-yl)-biphenyl-4-carbonitrile. The crude product was recrystallized from EtOAc/hex to furnish 1.03 g (64%) of a mixture of diastereomers by NMR as a pale white powder, mp 136–7° C.

$^1$H NMR (CDCl3): δ7.80–7.58 (m, 8H), 6.40 (s, 1H), 6.30 (d, 0.5H, J=3.7 Hz), 6.06 (s, 0.5H), 6.01 (d, 0.5H, J=3.7 Hz), 5.72 (d, 0.5H, J=1.6 Hz), 3.55 (s, 1.5 H), 3.48 (s, 1.5H), 3.44 (s, 1.5H), 3.02 (s, 1.5H). IR (KBr): 2933, 2831, 2229, 1654, 1604, 1560, 1498 cm$^{-1}$. HRFABMS: Calculated for $C_{19}H_{18}NO_3$ (M+H$^+$): 308.1287. Found: 308.1275. Anal. Calculated for $C_{19}H_{17}NO_3$: C, 74.25; H, 5.58; N, 4.56. Found: C, 74.11; H, 5.63; N, 4.49.

4'-(2,5-Dimethoxy-tetrahydrofuran-3-yl)-biphenyl-4-carbonitrile

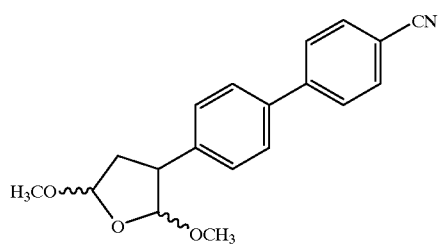

As described in Example 1(a) for the preparation of 3-biphenyl-4-yl-2,5-dimethoxy-tetrahydrofuran, 4'-(2,5-dimethoxy-2,5-dihydro-furan-3-yl)-biphenyl-4-carbonitrile (260 mg, 0.846 mmol) was reduced in 2 hours to give 260 mg (99%) of 4'-(2,5-dimethoxy-tetrahydrofuran-3-yl)-biphenyl-4-carbonitrile as a white solid, mp 149–50° C., which was used without further purification.

1H NMR (CDCl3): δ7.78–7.26 (m, 8H), 5.30–5.00 (m, 2H), 3.52–3.22 (m, 6H), 2.78–2.00 (m, 3H). IR (KBr): 2910, 2220. 1606, 1498, 1448, 1380, 1224, 1190 cm$^{-1}$. Anal. Calculated for $C_{19}H_{19}NO_3.0.3$ $H_2O$: C, 72.28; H, 6.28; N, 4.45. Found: C, 72.28; H, 6.19; N, 4.11.

N-(1(S)-Benzyl-2-hydroxyethyl)-3(R)-[3-(4'-cyanobiphenyl-4-yl)1H-pyrrol-1-yl]succinamic Acid Benzyl Ester

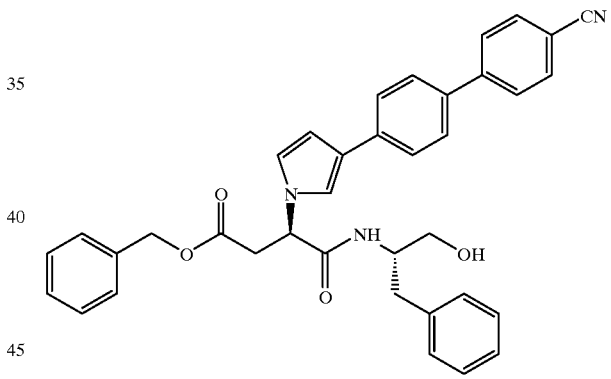

As described in Example 1(b) for the preparation of 3(R)-amino-N-(2,2-dimethyl-1(S)-(methylcarbamoyl)propyl)succinamic acid benzyl ester trifluroacetate salt, crude 3(R)-amino-N-(1(S)-benzyl-2-hydroxyethyl) succinamic acid benzyl ester trifluoroacetate salt (prepared as described in Example 1(a); 0.876 mmol) was condensed with 4'-(2,5-dimethoxy-tetrahydrofuran-3-yl)-biphenyl-4-carbonitrile (326 mg, 1.05 mmol) in 1,2-dichloroethane (5 mL). The solution was heated at 85–90° C. for 5 hours, allowed to cool, and evaporated to give a brown oil which was purified via flash column chromatography with 1% HOAc/30% EtOAc/hex as eluant. HOAc was removed via azeotrope with n-heptane layers to provide 200 mg (39%) of N-(1(S)-benzyl-2-hydroxyethyl)-3(R)-[3-(4'-cyanobiphenyl4-yl)-1H-pyrrol-1-yl]succinamic acid benzyl ester as a pale yellow powder, mp 149–50° C.

$^1$H NMR (CDCl3): δ7.74 (s, 4H), 7.59 (d, 4H, J=4.1 Hz), 7.32–7.18 (m, 10H), 7.05 (bm, 2H), 6.94 (t, 1H, J=2.2 Hz), 6.64 (t, 1H, 2.5 Hz), 6.58 (bm, 1H), 5.48 (d, 1H, J=7.8 Hz), 5.10 (d, 2H, J=3.1 Hz), 5.00 (dd, 1H, J=5.0, 9.3 Hz), 4.46–4.32 (m, 2H), 4.22–4.12 (m, 1H), 3.41 (dd, 1H, J=5.3, 17.1 Hz), 3.04 (dd, 1H, J=9.1, 17.1 Hz), 2.70–2.63 (m, 2H). IR: 3389, 3030, 2948, 2225, 1735, 1665, 1603, 1528, 1495 cm$^{-1}$. HRFABMS: Calculated for $C_{37}H_{33}N_3O_4Cs$ (MH+ Cs$^+$): 716.1525. Found: 716.1503. Anal. Calculated for $C_{37}H_{33}N_3O_4 \cdot 0.4\ CH_2Cl_2$: C, 72.73; H, 5.52; N, 6.80. Found: C, 72.67, H, 5.53; N, 6.81.

The following compounds were made in a similar manner:

Example 4(b)

N-(1-Benzyl-2-hydroxyethyl)-3(R)-[3-(4'-carbamoylbiphenyl-4-yl)-1H-pyrrol-1-yl]succinamic acid

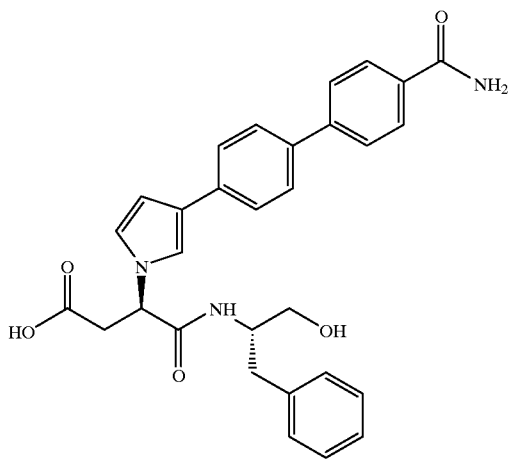

According to the procedure described in Example 1(a), N-(1(S)-benzyl-2-hydroxyethyl)-3(R)-[3-(4'-carbamoylbiphenyl-4-yl)-1 H-pyrrol-1-yl]succinamic acid benzyl ester was hydrogenolyzed to N-(1(S)-benzyl-2-hydroxyethyl)-3(R)-[3-(4'-carbamoylbiphenyl-4-yl)-1H-pyrrol-1-yl]succinamic acid in 95% yield, mp 218–20° C.

1H NMR (DMSO-d$_6$): δ8.12 (d, 1H, J=8.5 Hz), 7.97 (s, 1H), 7.88 (d, 2H, J=8.5 Hz), 7.72 (d, 2H, J=8.5 Hz), 7.57 (d, 2H, J=8.1 Hz), 7.33 (bs, 1H), 7.24 (s, 1H), 7.22–7.11 (m, 6H), 6.80 (bs, 1H), 6.42 (bs, 1H), 4.98–4.90 (bm, 1H), 4.80–4.72 (m, 1H), 3.82–3.76 (m, 1H), 2.82–2.70 (m, 2H), 2.62–2.50 (m, 1H). IR (KBr): 3402, 2925, 1658, 1601, 1400, 1202, 825, 782, 702, 633 cm$^{-1}$. HRFABMS: Calculated for $C_{30}H_{29}N_3O_5Cs$ (M+Cs$^+$): 644.1162. Found: 644.1147. Anal. Calculated for $C_{30}H_{29}N_3O_5 \cdot 0.3\ CHCl_3$: C, 66.49; H, 5.40; N, 7.68. Found: C, 66.30; H, 5.50; N, 7.50.

The starting materials were furnished as follows:

3-(4'-Carboxamidobiphenyl-4-yl)-2,5-dimethoxytetrahydrofuran

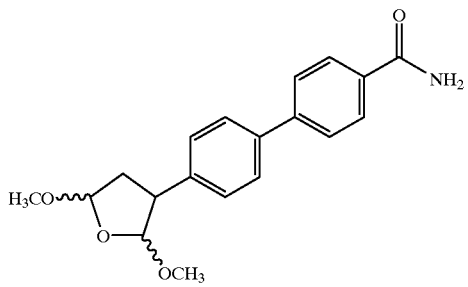

To a solution of 4'-(2,5-dimethoxy-tetrahydrofuran-3-yl)-biphenyl-4-carbonitrile (100 mg, 0.32 mmol) in 95% EtOH (1.5 mL) was added 30% hydrogen peroxide (114 μL, 1.12 mmol) and 6N aqueous NaOH (13 μL, 0.08 mmol). The resultant mixture was heated at 50° C. for 5 hours, allowed to cool, neutralized to pH7 by pH paper with 5% $H_2SO_4$, diluted with water (10 mL), and extracted with $CHCl_3$ (2×30 mL). The organic layers were dried over $MgSO_4$ and evaporated under reduced pressure to give a solid, which was precipitated from EtOAc/hex to give 1.04 g (100%) of 3-(4'-carboxamidobiphenyl-4-yl)-2,5-dimethoxytetrahydrofuran as a white powder, mp 184–6° C.

1H NMR (CDCl3): δ7.87 (d, 2H, J=8.1 Hz), 7.66 (d, 2H, J=8.1 Hz), 7.56 (d, 2H, J=8.1 Hz), 7.42 (d, 2H. J=8.1 Hz), 5.26–5.00 (m, 2H), 3.54–3.29 (m, 6H), 2.78–2.00 (m, 3H); IR (KBr): 3383, 3191, 2908, 1654, 1612, 1400, 1116, 983, 857, 779 cm$^{-1}$. HRFABMS: Calculated for $C_{19}H_{22}N_3O_4$ (M+H$^+$): 328.1549. Found: 328.1560. Anal. Calculated for $C_{19}H_{21}NO_4$: C, 69.69; H, 6.47; N, 4.28. Found: C, 69.68, H, 6.43; N, 4.19.

N-(1-Berzyl-2-hydroxyethyl)-3-[3-(4'-carbamoylbiphenyl-4-yl)-1H-pyrrol-1-yl]succinamic Acid Benzyl Ester

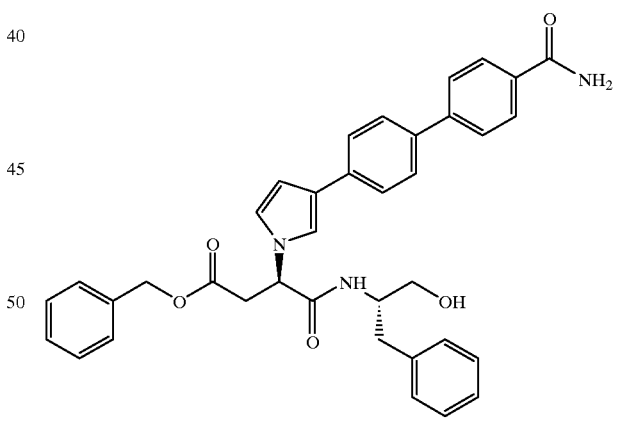

As described in Example 4(a) for the preparation of N-(1(S)-benzyl-2-hydroxyethyl)-3(R)-[3-(4'-cyano-biphenyl-4-yl)-1H-pyrrol-1-yl]succinamic acid benzyl ester, N-(1(S)-benzyl-2-hydroxyethyl)-3(R)-butoxycarbonyl-amino-succinamic acid benzyl ester (0.320 mmol) was deprotected. A solution of the resultant crude N-(1(S)-benzyl-2-hydroxyethyl)-3(R)-amino-succinamic acid benzyl ester trifluoroacetate salt and crude 3-(4'-carboxamidobiphenyl-4-yl)-2,5-dimethoxytetrahydrofuran (110 mg, 0.330 mmol) in 1,2-dichloroethane condensed in 18 hours to give a brown solid, which was purified via flash column chromatography with 5% MeOH/CH$_2$Cl$_2$ as eluant to provide 60 mg (31%) of N-(1-benzyl-2-hydroxyethyl)-3-[3-(4'-carbamoylbiphenyl-4-yl)-1H-pyrrol-1-yl]succinamic acid benzyl ester as a pale yellow solid, mp 192–4° C.

1H NMR (DMSO-d$_6$): δ8.18 (d, 1H, J=8.5 Hz), 8.00 (s, 1H), 7.94 (d, 2H, J=8.1 Hz), 7.76 (d, 2H, J=8.5 Hz), 7.68 (d, 2H, J=8.5 Hz), 7.58 (d, 2H, J=8.5 Hz), 7.36–7.14 (bm, 7H), 6.84 (t, 1H, J=2.2 Hz), 6.47 (s, 1H), 5.10–4.95 (m, 3H), 4.81 (t, 1H, J=5.1 Hz), 3.88–3.75 (m, 1H), 3.00 (d, 2H, J=7.4 Hz), 2.80 (dd, 1H, J=5.5, 13.2 Hz), 2.67–2.60 (m, 1H). IR (KBr): 3330, 2962, 1729, 1655, 1606, 1560, 1498, 1261, 1092 cm$^{-1}$. FABMS: 602 (M+H$^+$). Anal. Calculated for C$_{37}$H$_{35}$N$_3$O$_5$.0.4 CH$_2$Cl$_2$: C, 70.67; H, 5.68; N, 6.61. Found: C, 70.78; H, 5.86; N, 6.98.

Example 4(c)

3(R)-[3-(4'-Carbamoylbiphenyl4-yl)-1H-pyrrol-1-yl]-N-(1(S)-hydroxymethyl-2,2-dimethyl-propyl) succinamic Acid

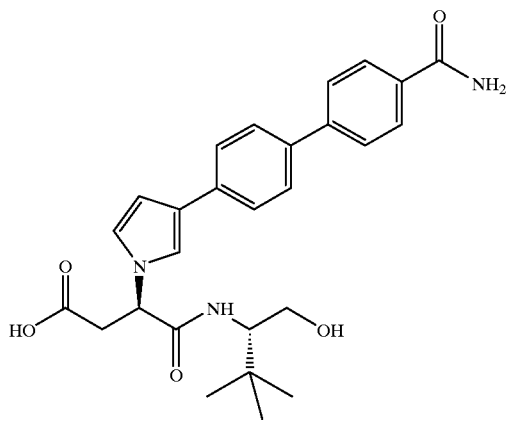

According to the procedures described in Example 1(a), 3(R)-[3-(4'-carbamnoylbiphenyl-4-yl)-1H-pyrrol-1-yl]-N-(1(S)-hydroxy-methyl-2,2-dimethyl-propyl)succinamic acid benzyl ester in MeOH and EtOAc was hydrogenolyzed to afford in 88% yield 3(R)-[3-(4'-carbamoylbiphenyl-4-yl)-H-pyrrol-1-yl]-N-(1(S)-hydroxymethyl-2,2-dimethyl-propyl)succinamic acid as a white powder, mp 192–4° C.

$^1$H NMR (CD$_3$OD): δ7.95 (d, 2H, J=8.4 Hz), 7.72 (d, 2H, J=8.1 Hz), 7.60 (s, 4H), 7.32 (d, 1H, J=1.6 Hz), 6.92 (t, 1H, J=2.5 Hz), 6.51 (s, 1H), 5.20 (t, 1H, J=7.5 Hz), 3.85–3.75 (m, 2H), 3.02 (dd, 1H, J=7.2, 17.0 Hz), 0.92 (s, 9H). IR (KBr): 3360, 2961, 1710, 1658, 1404, 1201, 770 cm$^{-1}$; HRFABMS: Calculated for C$_{27}$H$_{32}$N$_3$O$_5$ (M+H)$^+$: 478.2342. Found: 478.2360. Anal. Calculated for C$_{27}$H$_{31}$N$_3$O$_5$ .0.25 CH$_2$Cl$_2$: C, 65.62; H, 6.37; N, 8.42. Found: C, 65.86, H, 6.69; N, 8.30.

The starting materials were available as follows:

3(R)-(t-Butoxycarbonylamino)-N-(1(S)-hydroxymethyl-2,2-dimethyl-propyl)succinamic Acid Benzyl Ester

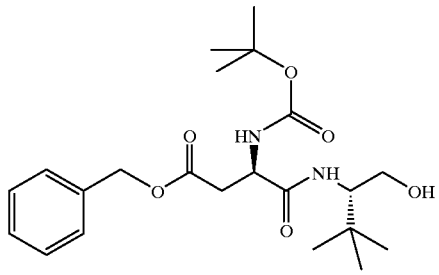

As described in Example 1(f) for the preparation of N-(1(S)-benzyl-2-methoxyethyl)-3(R)-(t-butoxycarbonylamino)succinamic acid benzyl ester, N-t-butoxycarbonyl-D-aspartic acid β-benzyl ester (1.00 g, 3.10 mmol) and L-t-leucinol (400 mg, 3.40 mrnol) were coupled with BOP to afford 1.20 g (90%) of 3(R)-(t-butoxycarbonylamino)-N-(1(S)-hydroxymethyl-2,2-dimethyl-propyl)succinamic acid benzyl ester as a white powder, mp 186–7° C.

$^1$H NMR (CDCl3): δ7.22 (s, 5H), 6.52 (d, 1H, J=9.3 Hz), 5.62–5.52 (m, 1H), 5.25 (dd, 2H, J=12.1, 18.7 Hz), 4.58–4.48 (m, 1H), 3.90–3.78 (m, 2H), 3.58–3.50 (m, 1H), 3.22–3.10 (m, 1H), 2.78 (dd, 1H, J=5.9, 17.7 Hz), 2.52–2.45 (m, 1H), 1.22 (s, 9H), 0.98 (s, 9H). IR: 3322, 2960, 1730, 1664 1528, 1367, 1249, 1165, 1050 cm$^{-1}$. Anal. Calculated for C$_{22}$H$_{34}$N$_2$O$_6$: C, 62.52; H, 8.12; N, 6.63. Found: C, 62.20; H, 8.13; N, 6.62.

3(R)-[3-(4'-Carbarnoylbiphenyl-4-yl)-1H-pyrrol-1-yl]-N-(1(S)-hydroxymethyl-2,2-dimethyl-propylsuccinamic Acid Benzyl Ester

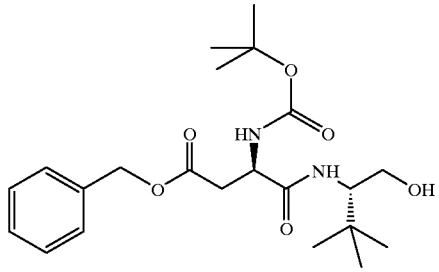

As described for Example 4(a) for the preparation of N-(1(S)-benzyl-2-hydroxyethyl)-3(R)-[3-(4'-cyano-biphenyl4-yl)-1H-pyrrol-1-yl]succinamic acid benzyl ester, crude 3-(4'-carboxamidobiphenyl)-2,5-dimethoxy-tetrahydrofuran and 3(R)-amino-N-(1-hydroxymethyl-2,2-dimethyl-propyl)succinamic acid benzyl ester trifluoroacetate salt were condensed in 1,2-dichloroethane to furnish 110 mg (41%) of 3(R)-[3-(4'-carbamoylbiphenyl-4-yl)-1H-pyrrol-1-yl]-N-(1(S)-hydroxymethyl-2,2-dimethyl-propyl) succinamic acid benzyl ester as a solid, mp 201–3° C.

$^1$H NMR (CDCl3): δ7.88 (d, 2H, J=8.1 Hz), 7.69 (d, 2H, J=8.4 Hz), 7.61 (d, 2H, J=8.4 Hz), 7.56 (d, 2H, J=8.7 Hz), 7.36–7.26 (m, 5H), 7.10 (d, 1H, J=1.9 Hz), 6.81 (d, 1H, J=2.5 Hz), 6.61 (t, 1H, J=1.6 Hz), 5.60–5.56 (m, 1H), 5.10–5.02 (m, 3H), 3.80–3.70 (m, 2H), 3.50–3.38 (m, 3H), 3.24 (dd, 1H, J=4.0, 17.0 Hz), 0.80 (s, 9H). IR (KBr): 3356, 2961, 1735, 1655, 1606, 1560, 1542, 1406, 1200 cm$^{-1}$. Anal. Calculated for $C_{34}H_{37}N_3O_5 \cdot 0.25\ CH_2Cl_2$: C, 69.85; H, 6.42; N, 7.14. Found: C, 69.82, H, 6.67; N, 7.12.

Example 5(a)

N-[2,2-Dimethyl-1(S)-(hydroxymethyl)propyl]-3(R)-[3-[4-(pyridin-4-yl)phenyl]-1H-pyrrol-1-yl] succinamic Acid

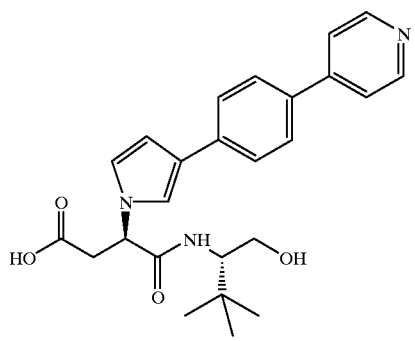

A mixture of N-(1-benzyloxycarbonyloxy-3,3-dimethylbut-2(R)-yl)-3(R)-[3-[4-(pyridin-4-yl)phenyl]-1H-pyrrol-1-yl]succinamic acid benzyl ester (140 mg, 0.212 mmol) and Pd(OH)$_2$ (60 mg of 20% Pd by content) in MeOH (1mL) and EtOAc (9 mL) was stirred under H$_2$ atmosphere for 3 hours. The catalyst was filtered onto Celite and rinsed with 10% MeOH/CHCl$_3$ (75 mL). The filtrate was concentrated in vacuo to provide a yellow solid, which was precipitated from hot CHCl$_3$ solution with hexane to furnish 68 mg (95%) of N-[2,2-dimethyl-1(S)-(hydroxymethyl)propyl]-3(R)-[3-[4-(pyridin-4-yl)phenyl]-1H-pyrrol-1-yl]succinamic acid as a yellow solid, mp 192–4° C.

$^1$H NMR (CD$_3$OD): δ8.56 (d, 1H, J=5.9 Hz), 7.78–7.60 (m, 7H), 7.37 (t, 1H, J=1.9 Hz), 6.96 (t, 1H, J=2.5 Hz), 6.54 (t, 1H, J=1.6 Hz), 5.22 (dd, 1H, J=2.5 Hz), 3.83–3.70 (m, 2H), 3.45–3.40 (m, 1H), 3.22 (d, 1H, J=7.5 Hz), 3.02 (dd, 1H, J=7.2, 16.8 Hz), 0.90 (s, 9H). IR (KBr): 3405, 2960, 1718, 1656, 1602, 1560, 1408, 1364, 1203, 922, 818, 783 cm$^{-1}$. HRFABMS: Calculated for $C_{25}H_{29}N_3O_4Cs$ (M+Cs$^+$): 568.1212. Found: 568.1189. Anal. Calculated for $C_{25}H_{29}N_3O_4 \cdot 0.10\ CHCl_3$: C, 67.38; H, 6.55; N, 9.39. Found: C, 67.69, H, 6.90; N, 9.65.

The starting material was made as follows:

4-(4-Bromo-phenyl)-pyridine

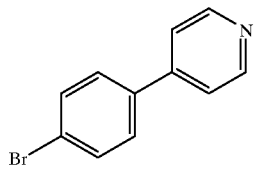

According to the procedure described in Example 1(a) for the preparation of 3-biphenyl-4-yl-furan, 4-bromopyridine (700 mg, 3.00 mmol) underwent coupling to 4-bromophenylboronic acid to give 2.38 g (100%) of 4-(4-bromo-phenyl)-pyridine as a yellow solid, which had an NMR that matched literature (Boy, P.; Combellas, C.; Thiebault, A.; Amatore, C.; Jutand, A. *Tetrahedron Lett.* 1992, 33, 491–494) and was used without further purification.

IR (KBr): 1593, 1474, 1412, 1075, 1006, 807, 756, 693, 498 cm$^{-1}$.

3-(4'-Pyridylphenyl-4-yl)furan

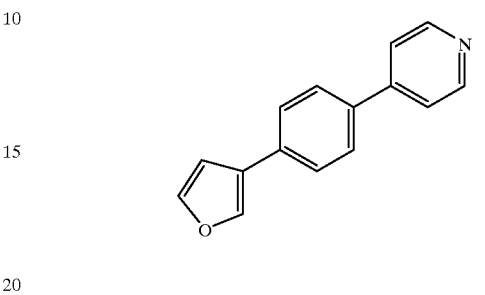

According to the procedure described in Example 1(a) for the preparation of 3-biphenyl-4-yl-furan, 4-(4-bromophenyl)pyridine (700 mg, 3.00 mmol) underwent coupling to 3-fuiranboronic acid (see Thompson, W. J.; Gaudino, G. *J. Org. Chem.* 1984, 49, 5237–5243). Purification via flash column chromatography with 2% MeOH/CH$_2$Cl$_2$ as eluant led to obtention of 640 mg (97%) of 3-(4'-pyridylphenyl4-yl)furan as a yellow solid, which was used in the next reaction.

$^1$H NMR (CDCl3): δ8.68 (d, 2H, J=5.9 Hz), 7.82 (dd, 1H, J=0.6, 1.6 Hz), 7.76–7.43 (m, 7H), 6.76 (dd, 1H, J=0.9, 1.8 Hz). Anal. Calculated for $C_{15}H_{11}NO$: C, 81.43; H, 5.01; N, 6.33. Found: C, 81.32, H, 5.08; N, 6.28.

2,5-Dihydro-2,5-dimethoxy-3-(4-(pyridin4-yl) phenyl)furan

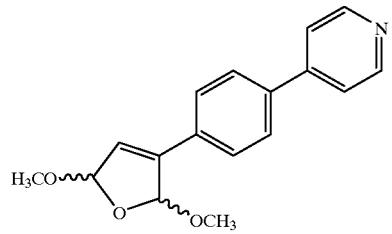

According to the procedure described in Example 1(a) for the preparation of3-biphenyl-4-yl-2,5-dihydro-2,5-dimethoxyfuran, 3-(4'-pyridylphenyl-4-yl)furan (470 mg, 2.12 mmol) was converted and purified via flash column chromatography with 2% MeOH/CH$_2$Cl$_2$ as eluant to afford 600 mg (100%) of 2,5-dihydro-2,5-dimethoxy-3-(4-(pyridin-4-yl)phenyl)furan as a tan solid.

$^1$H NMR (CDCl3): δ8.68 (d, 2H, J=4.0 Hz), 7.68 (s, 4H), 7.52 (d, 2H, J=5.9 Hz), 6.40 (s, 1H), 6.30 (d, 0.5H, J=3.7 Hz), 6.05 (s, 0.5H), 6.02 (d, 0.5H, J=3.7 Hz), 5.72 (s, 0.5H), 3.52 (s, 1.5H), 3.48 (s, 1.5H), 3.45 (s, 1.5H), 3.43 (s, 1.5H). HRFABMS: Calculated for $C_{17}H_{18}NO_3$: (M+H$^+$): 284.1287. Found: 284.1294. Anal. Calculated for $C_{17}H_{17}NO_3$: C,72.07; H, 6.05 N, 4.94. Found: C, 71.97, H, 6.05; N, 4.95.

2,5-Dimethoxy-3-(4-(pyridin-4-yl phenyl) tetrahydrofuran

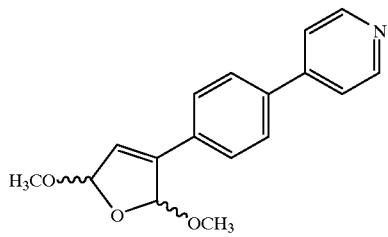

According to the procedure described in Example 1(a) for the preparation of 3-biphenyl-4-yl-2,5-dimethoxy-tetrahydrofuran, 2,5-dihydro-2,5-dimethoxy-3-(4-(pyridin-4-yl)phenyl)furan (300 mg, 1.06 mmol) was hydrogenated in MeOH after 6 hours to furnish 300 mg (100%) of 2,5-dimethoxy-3-(4-(pyridin-4-yl)phenyl)tetrahydrofuran as a yellow oil, which was a mixture of diastereomers by NMR, and which was used without further purification.

$^1$H NMR (CDCl3): δ8.68 (bs, 2H), 7.76–7.36 (m, 6H), 5.34–4.94 (m, 2H), 3.72–3.20 (m, 7H), 2.75 (ddd, 0.15H, minor isomer, J=5.9, 10.0, 13.7 Hz), 2.35 (ddd, 0.74H, major isomer, J=5.6, 12.8, 12.8 Hz), 2.20 (dd, 0.0.19H, minor isomer, J=6.9, 12.0 Hz), 2.12 (ddd, 0.16H, minor isomer, J=3.7, 5.9, 13.7 Hz); Anal. Calculated for $C_{17}H_{19}NO_3 \cdot 0.2 H_2O$: C, 70.66; H, 6.77; N, 4.85. Found: C, 70.49; H, 6.74; N, 4.76.

N-(1(S)-Benzyloxycarbonyloxymethyl-2,2-dimethylpropyl)-3(R)-(t-butoxycarbonylamino) succinamic Acid Benzyl Ester

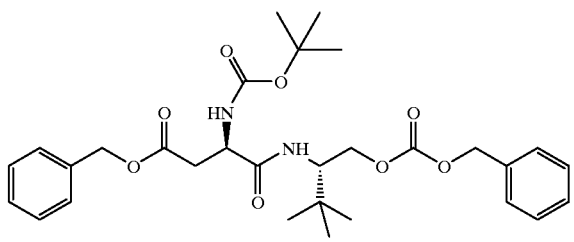

To a solution of 3(R)-(t-butoxycarbonylamino)-N-(2,2-dimethyl-1(S)-hydroxymethyl-propyl)succinamic acid benzyl ester (1.27 g, 3.01 mmol; prepared as described in Example 4(c)) and DMAP (920 mg, 7.51 mmol) in CHCl3 (5 mL) was added benzyl chloroformate (1.07 mL, 7.51 mmol). After 2 hours, 10% aqueous KHSO4 (15 mL) was added. The aqueousueous layer was extracted with more CHCl3 (15 mL) two time. The combined CHCl3 layers were washed with 10% aqueous KHSO4 (10 mL), saturated aqueous NaHCO3 (10 mL), and H2O (10 mL), dried over Na2SO4 and evaporated to give a crude solid, which was purified via flash column chromatography to afford 1.42 g (85%) of N-(1(S)-benzyloxycarbonyl-oxymethyl-2,2-dimethyl-propyl)-3(R)-(t-butoxycarbonylamino)succinamic acid benzyl ester as a white solid, mp 69–71° C.

$^1$H NMR (CDCl3): δ7.37–7.27 (bm, 10H), 6.63 (d, 1H, J=9.3 Hz), 5.61 (d, 1H, J=7.5 Hz), 5.16 (s, 2H), 5.15 (d, 1H, J=12.3 Hz), 4.97 (d, 1H, J=12.3 Hz), 4.51 (d, 1H, J=5.6 Hz), 4.29 (dd, 1H, J=3.7, 11.2 Hz), 4.15 (dd, 1H, 7.8, 11.2 Hz), 4.05 (ddd, 1H, J=3.7, 7.8, 9.6 Hz), 3.01 (dd, 1H, J=4.7, 17.1 Hz), 2.72 (dd, 1H, J=6.5, 17.1 Hz), 1.44 (s, 9H), 0.93 (s, 9H). IR: 3340, 2951, 1753, 1707, 1671, 1533, 1507, 1456, 1364, 1272, 1175, 790, 734 cm$^{-1}$. HRLSIMS: Calculated for $C_{30}H_{40}N_2O_8Cs$ (M+Cs$^+$): 689.1839. Found: 689.1826. Anal. Calculated for $C_{30}H_{40}N_2O_8$: C, 64.72; H, 7.24; N, 5.03. Found: C, 64.82; H, 7.25; N, 4.98.

N-(1-Benzyloxycarbonyloxy-3,3-dimethylbut-2(R)-yl)-3(R)-[3-[4-(pyridin-4-yl)phenyl]-1H-pyrrol-1-yl] succinamic Acid Benzyl Ester

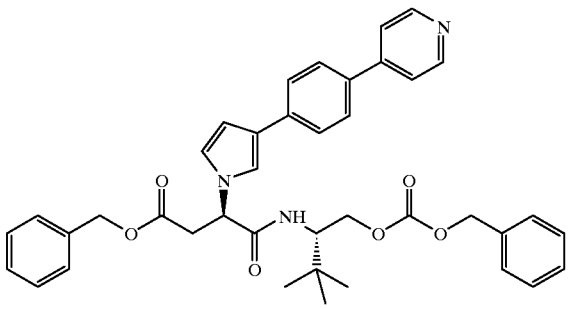

According to the procedure described in Example 1(b) for the preparation of 3(R)-t-butoxycarbonylamino-N-(2,2-dimethyl-1(S)-methylcarbamoylpropyl)succinamic acid benzyl ester, N-(1R-benzyloxy-carbonyloxymethyl-2,2-dimethyl-propyl)-3(R)-(t-butoxycarbonylamino)succinamic acid benzyl ester was deprotected. The corresponding amine salt and 2,5-dimethoxy-3-(4'-pyridylphenyl-4-yl)-tetrahydro-furan was condensed in wet 1,2-dichloroethane at 80–90° C. after 18 hours to furnish a crude product, which was purified via flash column chromatography with 1% HOAc/5% MeOH/CH2Cl2 as eluant to furnish 160 mg (54%) of N-(1-benzyloxycarbonyloxy-3,3-dimethylbut-2(R)-yl)-3(R)-[3-[4-(pyridin-4-yl)phenyl]-1H-pyrrol-1-yl] succinamic acid benzyl ester as a yellow solid, mp 74–6° C.

$^1$H NMR (CDCl3): δ8.65 (d, 2H, J=5.9 Hz), 7.58 (d, 5H, J=2.2 Hz), 7.55–7.43 (m, 4H), 7.34–7.22 (m, 7H), 7.08 (t, 1H, J 1.9 Hz), 6.74 (t, 1H, J=2.5 Hz), 6.54 (dd, 1H, J=1.9, 2.8 Hz), 5.46 (d, 1H, 9.3 Hz), 5.18–5.05 (m, 4H), 5.03 (s, 2H), 4.30 (dd, 1H, J=2.5, 12.0 Hz), 4.00 (m, 2H), 3.46 (dd, 1H, J=5.3, 15.0 Hz), 3.00 (dd, 1H, J=9.3, 15.0 Hz), 0.83 (s, 9H). IR (KBr): 2961, 1748, 1666, 1600, 1560, 1263, 1118, 815, 783, 737, 695, 541 cm$^{-1}$. HRFABMS: Calculated for $C_{40}H_{41}N_3O_6Cs$ (M+Cs$^+$): 792.2050. Found: 792.2034. Anal. Calculated for $C_{40}H_{41}N_3O_6 \cdot 0.2$ CHCl3$\cdot 0.3$ $C_6H_{14}$: C, 71.10; H, 6.45; N, 5.92. Found: C, 71.01, H, 6.36; N, 5.59.

The following compounds were made in a similar manner:

Example 5(b)

N-(2-Hydroxy-1(S)-phenylethyl)-3(R)-[3-[4-(pyridin-4-yl)phenyl]-1H-pyrrol-1-yl]succinamic Acid

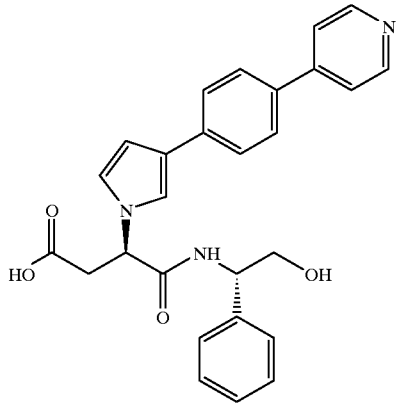

According to the procedure described in Example 5(a), N-(2-benzyloxycarbonyloxy-1(S)-phenylethyl)-3(R)-[3-[4-(pyridin-4-yl)phenyl]-1H-pyrrol-1-yl]succinamic acid benzyl ester was hydrogenolyzed to afford 60 mg (68%) of N-(2-hydroxy-1(S)-phenylethyl)-3(R)-3(R)-[3-[4-(pyridin-4-yl)phenyl]-1H-pyrrol-1-yl]succinamic acid.

$^1$H NMR (CD$_3$OD): δ8.56 (d, 2H, J=5.9 Hz), 7.78–7.60 (m, 7H), 7.38 (t, 1H, J=1.9 Hz), 6.95 (t, 1H, J=2.5 Hz), 6.55 (dd, 1H, J=1.6, 2.8 Hz), 5.22 (dd, 1H, J=7.2, 7.4 Hz), 3.76–3.64 (bm, 2H), 3.02 (dd, 1H, J=7.2, 16.8 Hz). IR (KBr): 3315, 1718, 1670, 1654, 1602, 1560, 1491, 1406, 1202cm$^{-1}$. HRFABMS: Calculated for C$_{27}$H$_{25}$N$_3$O$_4$Cs (M+Cs$^+$): 588.0899. Found: 588.0914. Anal. Calculated for C$_{27}$H$_{25}$N$_3$O$_4$.0.2 CHCl$_3$: C, 68.15; H, 5.30; N, 8.77. Found: C, 68.19, H, 5.63; N, 8.38.

The starting materials were made as follows:

3(R)-(t-Butoxycarbonylamino)-N-(2-hydroxy-1(S)-phenyl-ethyl)succinamic Acid Benzyl Ester

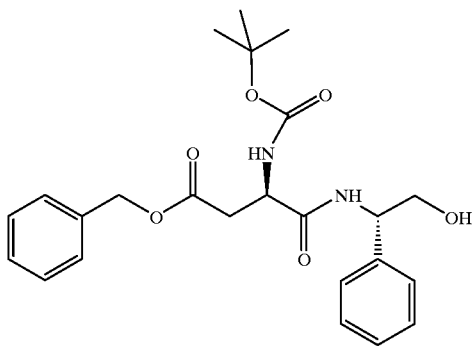

According to the procedure described in Example 1(f) for the preparation of N-(1(S)-benzyl-2-methoxy-ethyl)-3(R)-t-butoxycarbonyl-amino-succinamic acid benzyl ester, N-t-butoxycarbonyl-D-aspartic acid β-benzyl ester and 2S-phenylglycinol were coupled with BOP to provide 290 mg (85%) of 3(R)-(t-butoxycarbonylarnino)-N-(2-hydroxy-1(S)-phenyl-ethyl)succinamic acid benzyl ester, mp 117–8° C.

$^1$H NMR (CDCl3): δ7.40–7.22 (m, 10H), 7.10 (bd, 1H, J=9.3 Hz), 5.66 (bd, 1H, J=9.3 Hz), 5.14 (dd, 2H, J=12.1, 18.4 Hz). 5.08–5.02 (m, 1H), 4.58–4.50 (m, 1H), 3.94–3.80 (m, 2H), 3.12 (dd, 1H, J=4.4, 17.1 Hz), 2.75 (dd, 1H, J=5.9, 17.4 Hz), 2.42–2.36 (m, 1H), 1.20 (s, 9H). IR: 3322, 2965, 1730, 1660, 1367, 1166 cm$^{-1}$. Anal. Calculated for C$_{24}$H$_{30}$N$_2$O$_6$.0.25 H$_2$O: C, 64.49; H, 6.88; N, 6.27. Found: C, 64.34; H, 6.73; N, 6.29.

N-(2-Benzyloxycarbonyloxy-1(S-phenylethyl)-3(R)-t-(butoxycarbonylamino)Succinamic Acid Benzyl Ester

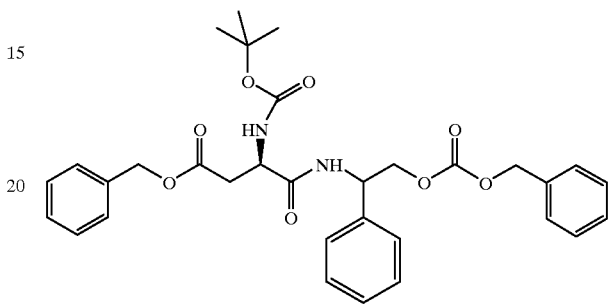

According to the procedure described in Example 5(a) for the preparation of N-(1 R-benzyloxycarbonyloxymethyl-2,2-dimethyl-propyl)-3(R)-(-butoxycarbonylamino) succinamic acid benzyl ester, N-(2-hydroxy-1(S)-phenyl-ethyl)-3(R)-(t-butoxycarbonylamino)succinamic acid benzyl ester was acylated to provide crude product, which was purified via flash column chromatography with 30% EtOAc/hex as eluant: to give 333 mg (96%) of N-(2-benzyloxycarbonyloxy-1(S)-phenyl-ethyl)-3(R)-(t-butoxycarbonylamino)succinamic acid benzyl ester as a white solid, mp 105–6° C.

$^1$H NMR (CDCl3): δ7.40–7.18 (m, 15H), 5.63 (bs, 1H), 5.24 (q, 1H, J=6.6 Hz), 5.12 (s, 2H), 5.06 (q, 2H. J=10.3 Hz), 4.50 (bs, 1H), 4.55 (ddd, 2H, J=5.0, 6.8, 11.2 Hz), 2.99 (dd, 1H, J=4.4, 17.0 Hz), 2.66 (dd, 1H, J=6.2, 17.0 Hz), 2.42–2.36 (m, 1H), 1.40 (s, 9H). IR: 3320, 2981, 1742, 1692, 1657, 1518, 1458, 1394, 1313, 1277, 1171 cm$^{-1}$. Anal. Calculated for C$_{32}$H$_{36}$N$_2$O$_8$: C, 66.65; H, 6.29; N, 4.86. Found: C, 66.57; H, 6.31; N, 4.88.

N-(2-Benzyloxycarbonyloxy-1(S)-phenylethyl)-3(R)-[3-[4-(pyridin-4-yl)phenyl]-1H-pyrrol-1-yl] succinamic Acid Benzyl Ester

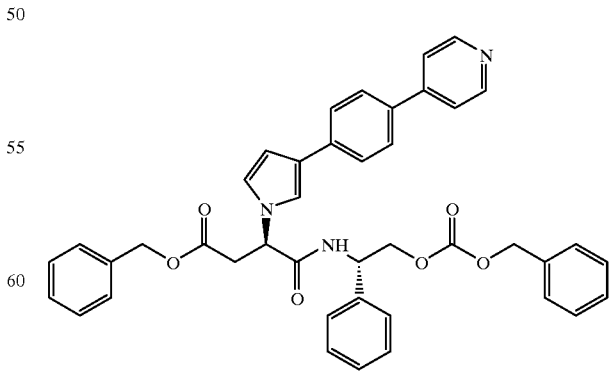

According to the procedure described in Example 1(b) for the preparation of N-(2,2-dimethyl-1(S)- methylcarbamoylpropyl)-3(R)-(3-phenyl-1H-pyrrol-1-yl) succinamic acid benzyl ester, N-(2-benzyloxycarbonyloxy-1(S)-phenyl-ethyl)-3(R)-(t-butoxycarbonylamino) succinamic acid benzyl ester and 2,5-dimethoxy-3-(4-pyridin-4-yl-phenyl)-tetrahydrofuran (prepared as described in Example 5(a)) were condensed in wet 1,2-dichloroethane at 80–90° C. after 18 hours. Flash column chromatagraphy with 4% MeOH/CH$_2$Cl$_2$ as eluant gave 140 mg (56%) of N-(2-benzyloxycarbonyloxy-1(S)-phenylethyl)-3(R)-[3-[4-(pyridin-4-yl)phenyl]-1H-pyrrol-1-yl]succinamic acid benzyl ester as a yellow solid, mp 138–40° C.

$^1$H NMR (CDCl3): δ8.66 (bs, 2H), 7.60 (s, 5H), 7.50 (d, 3H, J=5.3 Hz), 7.34–7.22 (m, 10H), 7.19 (d, 1H, J=2.2 Hz), 7.17 (d, 1H, J=1.9 Hz), 7.09 (t, 1H, J=1.9 Hz), 6.77 (dd, 1H, J=2.5, 2.8 Hz), 6.57 (bt, 1H, J=1.9, 2.5 Hz), 6.24 (d, 1H, J=7.8 Hz), 5.26 (m, 1H), 4.25 (dd, 1H, J=7.2, 11.5 Hz), 3.44 (dd, 1H, J=7.2, 16.8 Hz), 3.00 (dd, 1H, 8.7, 16.8 Hz). IR (KBr): 2985, 1738, 1657, 1598, 1560, 1495, 1202, 815, 697 cm$^{-1}$. HRFABMS: Calculated for C$_{42}$H$_{37}$N$_3$O$_6$Cs (M+Cs$^+$): 812.1737. Found: 812.1712. Anal. Calculated for C$_{42}$H$_{37}$N$_3$O$_6$.0.25 CHCl$_3$: C, 71.51; H, 5.29. Found: C, 71.72; H, 5.60.

Example 5(c)

3(R)-[3-(4'-Cyanobiphenyl-4-yl)-1H-pyrrol-1-yl]-N-[2,2-dimethyl-1(S)-(methylcarbamoyl)propyl] succinamic Acid

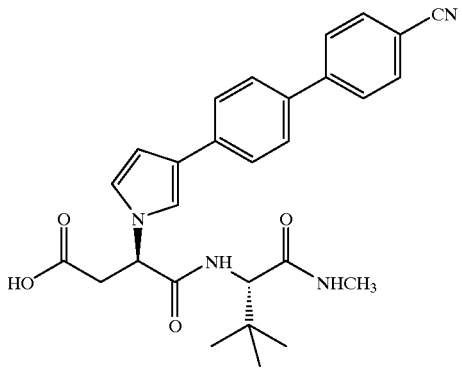

According to the procedure described in Example 1(a), 3(R)-[3-(4'-cyanobiphenyl-4-yl)-1H-pyrrol-1-yl]-N-[2,2-dimethyl-1(S)-(methylcarbamoyl)propyl]succinamic acid benzyl ester (58 mg, 0.101 mmol) was hydrogenolyzed to afford 31 mg (63%) of 3(R)-[3-(4'-cyanobiphenyl-4-yl)-1H-pyrrol-1-yl]-N-[2,2-dimethyl-1(S)-(methylcarbamoyl) propyl]succinamic acid as a solid, mp 142–4° C.

$^1$H NMR (CDCl3): δ7.61 (dd, 4H, J=8.4, 15.2 Hz), 7.45 (dd, 4H, J=8.2, 16.6 Hz), 7.12 (s, 1H), 6.77 (s, 1H), 6.44 (s, 1H), 6.31 (bs, 1H), 5.26 (t, 1H, J=6.8 Hz), 4.29 (d, 1H, J=9.3 Hz), 4.03 (bs, 1H), 3.32 (dd, 1H, J=6.5, 17.1 Hz), 3.07 (dd, 1H, J=7.6, 17.3 Hz), 2.66 (d, 3H, J=4.05 Hz), 0.92 (s, 9H). IR (KBr): 3354, 2955, 2367, 1737, 1719, 1655, 1561 cm$^{-1}$. HRFABMS: Calculated for C$_{28}$H$_{31}$N$_4$O$_4$ (M+H$^+$): 487.2345. Found: 487.2356. Anal. Calculated for C$_{28}$H$_{30}$N$_4$O$_4$.1.2 EtOAc: C, 66.51; H, 6.74; N, 9.46. Found: C, 66.57, H, 6.54; N, 9.28.

The starting material was available as follows:

3(R)-[3-(4'-Cyanobiphenyl-4-yl)-1H-pyrrol-1-yl]-N-[2,2-dimethyl-1(S)-(methylcarbamoyl)propyl] succinamic Acid Benzyl Ester

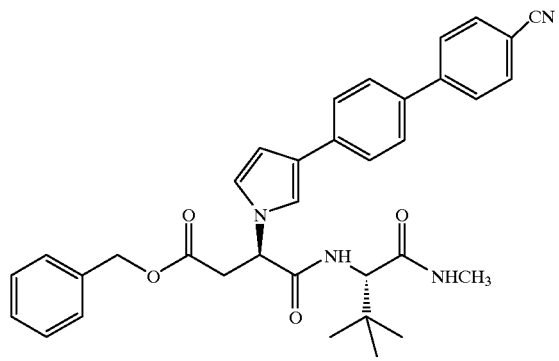

According to the procedure as described in Example 1(c) for N-(1,7-diaza-4-oxa-8-oxo-tricyclo-[9.6.1.0$^{12,17}$]-octadeca-11(18),12,14,16-tetraen-9S-yl)-3(R)-(3-phenyl-1H-pyrrol-1-yl)-succinamic acid benzyl ester, crude 3(R)-amino-N-(2,2-dimethyl-1(S)-methylcarbamoylpropyl) succinamic acid benzyl ester trifluoroacetate salt (prepared as described in Example 1(b)) and 4'-(2,5-dimethoxy-tetrahydrofuran-3-yl)-biphenyl4-carbonitrile (prepared as described in Example 4(a)) were condensed to give 84 mg (48%) of 3(R)-[3-(4'-cyanobiphenyl4-yl)-1H-pyrrol-1-yl]-N-[2,2-dimethyl-1 (S)-(methylcarbamoyl)propyl] succinamic acid benzyl ester as a yellow solid, mp 120° C.

$^1$H NMR (CDCl3): δ7.72 (s, 4H), 7.59 (s, 4H), 7.32–7.28 (m, 2H), 7.26 (s, 3H), 7.12 (t, 1H, J=2.1 Hz), 6.82 (t, 1H, J=2.7 Hz), 6.61 (dd, 1H, J=1.8,3.0 Hz), 6.27 (d, 1H, J=9.0 Hz), 5.58 (m, 1H), 5.13 (s, 2H), 5.12 (m, 1H), 4.01 (d, 2H, 8.7 Hz), 3.41 (dd, 1H, J=5.8, 16.7 Hz), 3.11 (dd, 1H, 8.7, 16.8 Hz), 2.78 (d, 3H, J 5.0 Hz), 0.87 (s, 9H). IR (KBr): 2960, 2221, 1736, 1685, 1654, 1562, 1542 cm$^{-1}$. HRFABMS: Calculated for C$_{35}$H$_{37}$N$_4$O$_4$ (M+H$^+$): 577.2815. Found: 577.2832. Anal. Calculated for C$_{35}$H$_{36}$N$_4$O$_4$.0.2 DMF 0.5 H$_2$O: C, 71.23; H, 6.45; N, 9.80. Found: C, 71.14, H, 6.23; N, 10.19.

Example 5(d)

3(R)-[3-(4'-Cyanobiphenyl-4-yl)-1H-pyrrol-1yl]-N-[2,2-dimethyl-1(S)-(pyridin-4-ylcarbamoyl)propyl] succinamic Acid Formate Salt

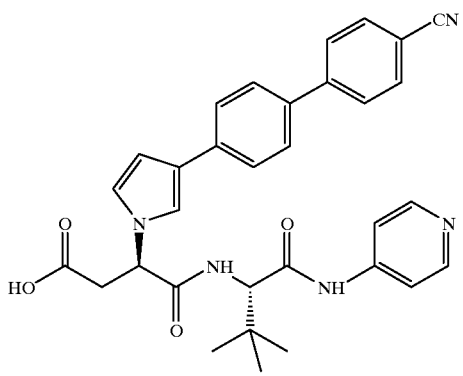

A mixture of palladium on carbon and 3(R)-[3-(4'-cyanobiphenyl-4-yl)-1 H-pyrrol-1-yl]-N-[2,2-dimethyl-1

(S)-(pyridin-4-ylcarbamoyl)propyl]succinamic acid benzyl ester (72 mg, 0.112 mmol) in MeOH with formic acid afforded 30 mg (49%) of 3(R)-[3-(4'-cyanobiphenyl-4-yl)-1H-pyrrol-1yl]-N-[2,2-dimethyl-1(S)-(pyridin4-ylcarbamoyl)propyl]succinamic acid formate salt as a solid, mp 134–6° C.

¹H NMR (DMSO-d6): δ8.39–8.35 (m, 3H), 7.81 (d, 2H, J=5.9 Hz), 7.63 (s, 2H), 7.34–7.23 (m, 4H), 7.28 (d, 2H, J=10.3 Hz), 7.24 (s, 1H), 6.96–6.92 (m, 1H), 6.52 (dddd, 1H, J=1.8, 2.9, 4.8, 7.4 Hz), 5.35–5.29 (m, 1H), 3.39–3.18 (bm, 1H), 3.09–2.91 (bm, 1H), 1.06 (s, 9H). IR (KBr): 2966, 2225, 1719, 1654, 1594, 1560, 1507, 1396, 1196 cm⁻¹. HRFABMS: Calculated for $C_{28}H_{31}N_4O_4$ (M+H⁺): 550.2454. Found: 550.2450. Anal. Calculated for $C_{32}H_{31}N_5O_4 \cdot 1.0\, HCO_2H \cdot 2.5\, CH_3OH$: C, 63.10; H, 6.41; N, 10.36. Found: C, 63.03, H, 6.75; N, 10.38.

The starting material was available as follows:

2S-t-Butoxycarbonylamino-3,3-dimethyl-N-pyridin-4-yl-butanamide

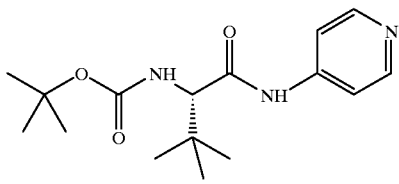

To a mixture of N-t-butoxycarbonyl-L-t-leucine (made according to Shiosaki, K.; Tasker, A. S.; Opgenorth, T. J. WO 92/13545, Nov. 8, 1991 and matched with data from Pospisek, J.; Blaha, K. Coll. Czech. Chem. Commun. 1977, 42, 1069–1076; 200 mg, 0.860 mmol) and 4-aminopyridine (356 mg, 1.72 mmol) in anhydrous DMF was added morpholine (284 μL, 2.58 mmol). After cooling to 0° C., tetrafluoroformarnidinium hexafluorophosphate (TFFH; see Carpino, L. A.; El-Faham, A. J. Am. Chem. Soc. 1995, 117, 5401–5402; 340 mg, 1.29 mmol) was added. The mixture was allowed to warm to ambient temperature and stirred overnight. The resultant mixture was diluted with $CH_2Cl_2$ (50 mL), washed with saturated aqueous $NH_4Cl$ (25 mL), saturated aqueous $NaHCO_3$ (25 mL) and brine (25 mL), dried over $MgSO_4$ and concentrated at reduced pressure to provide a yellow solid, which was purified via flash column chromatography to give 167 mg (67%) of 2S-t-butoxycarbonylamino-3,3-dimethyl-N-pyridin-4-yl-butanamide as a white solid.

¹H NMR: δ8.60 (bs, 1H), 8.42 (bs, 2H), 7.34 (bs, 2H), 5.34 (bd, 1H, J=8.7 Hz), 4.08 (bs, 1H, J=8.7 Hz), 1.42 (s, 9H), 1.02 (s, 9H). IR (KBr): 3286, 2971, 1682, 1594, 1518, 1367, 1169 cm⁻¹. HRFABMS: Calculated for $C_{16}H_{26}N_3O_3$ (M+H⁺): 308.1974. Found: 308.1967. Anal. Calculated for $C_{16}H_{25}N_3O_3 \cdot 0.37\, H_2O$: C, 61.19; H, 8.26; N, 13.38. Found: C, 61.52; H, 8.18; N, 12.99.

2S-Amino-3,3-dimethyl-N-4-pyridinyl-butanamide

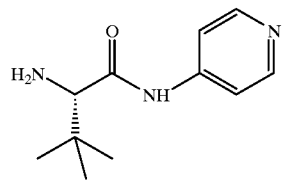

To a solution of 2S-t-butoxycarbonylamino-3,3-dimethyl-N-pyridin-4-yl-butanamide (3.00 g, 9.75 mmol) in $CH_2Cl_2$ (10 mL) was added trifluoroacetic acid (3 mL). After 3 hours at ambient temperature, the solvent was removed in vacuo and azeotropically dried with hexane twice to furnish a colorless foam, which was dissolved in MeOH (50 mL) and neutralized upon stirring with IRA-400 anion exchange resin (⁻$HCO_3$ form; 3 g) over 3 hours. The resin was filtered off and the solution concentrated in vacuo to furnish a white solid, which recrystallized from hexanes to give 1.18 g (90%) of 2S-amino-3,3-dimethyl-N-4-pyridinyl-butanamide as a white powder (cited in Chapman, K. T.; Hagmann, W. K.; Durette, P. L.; Esser, C. K.; Kopka, I. E.; Caldwell, C. G. WO 9412169, Nov. 18, 1995).

¹H NMR: δ9.40 (bs, 1H), 8.50 (d, 1H, J=4.7 Hz), 7.50 (d, 2H, J=4.7 Hz), 3.15 (s, 3H), 1.02 (s, 9H). IR (KBr): 3250, 2962, 1686, 1592, 1517, 1418 cm⁻¹. Anal. Calculated for $C_{11}H_{17}N_3O$: C, 63.74; H, 8.27; N, 20.27. Found: C, 63.79; H, 8.23; N, 20.35.

3(R)-t-Butoxycarbonylamino-N-[2,2-dimethyl-1(S)-(N-pyridin-4-ylcarbamoyl)propyl]succinamic Acid Benzyl Ester

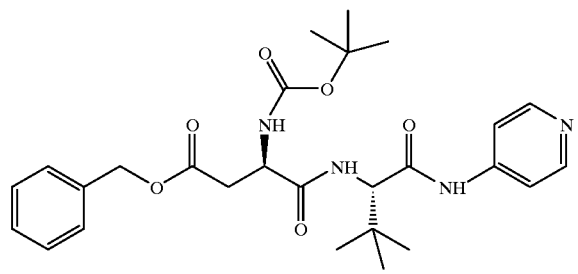

To a solution of 2S-amino-3,3-dimethyl-N-4-pyridinyl-butanamide (100 mg, 0.482 mmol) and N-t-butoxycarbonyl-L-aspartate β-benzyl ester (156 mg, 0.482 mmol) in dry DMF (3 mL) at 0° C. was added sequentially diethylcyanophosphonate (81 μL, 0.482 mmol) and triethylamine (200 μL, 1.46 mmol). After 30 minutes at 0° C., the mixture was allowed to warm to ambient temperature. After 4, the resultant orange mixture was stirred with saturated aqueous $NaHCO_3$ and extracted with EtOAc three times. The combined organic layers were washed with 5% aqueous citric acid, $H_2O$, and brine, dried over $Na_2SO_4$, and evaporated to give a viscous yellow oil, which was purified via flash column chromatography with EtOAc as eluant to afford 150 mg (61%) of 3(R)-t-butoxycarbonylamino-N-[2,2-dimethyl-1(S)-(N-pyridin-4-yl-carbamoyl)-propyl]succinamic acid benzyl ester as a yellow oil.

¹H NMR: δ9.11 (bs, 1H), 8.37 (d, 2H, J=5.0 Hz), 7.43 (d, 2H, 4.7 Hz), 7.28 (m, 5H), 5.90 (bs, 1H), 5.09 (d, 1H, J=12.1 Hz), 5.01 (d, 1H, J=12.1 Hz), 4.60 (dd, 1H, J=5.5, 12.6 Hz), 4.35 (d, 1H, 8.1 Hz), 3.03 (ddd, 1H, J=4.6, 4.6, 17.1 Hz), 2.83 (dd, 1H, 5.6, 17.1 Hz), 1.47 (s, 9H), 1.05 (s, 9H). IR (KBr): 3319, 2966, 1737, 1719, 1701, 1666, 1596, 1525, 1420, 1367, 1290 cm$^{-1}$. HRFABMS: Calculated for $C_{27}H_{37}N_4O_6$ (M+H$^+$): 513.2713. Found: 513.2726. Anal. Calculated for $C_{27}H_{36}N_4O_6$: C, 63.26; H, 7.09; N, 10.92. Found: C, 63.11; H, 7.12; N, 10.89.

3(R)-[3-(4'-Cyanobiphenyl-4-yl)-1H-pyrrol-yl]-N-[2,2-dimethyl-1(S)-(pyridin-4-ylcarbamoyl)propyl] succinamic Acid Benzyl Ester

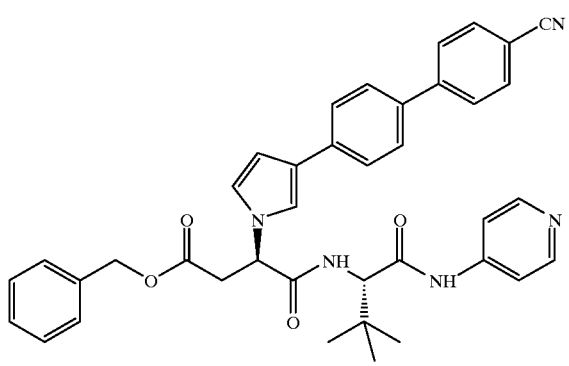

According to the procedure described in Example 1(c) for the preparation N-(1,7-diaza-4-oxa-8-oxo-tricyclo-[9.6.1.0$^{12,17}$]-octadeca-11(18),12,14,16-tetraen-9S-yl)-3(R)-(3-phenyl-1H-pyrrol-1-yl)succinamic acid benzyl ester, crude 3(R)-amino-N-[2,2-dimethyl-1(S)-(pyridin-4-ylcarbamoyl)propyl]succinamic acid benzyl ester trifluoroacetate salt and 4'-(2,5-dimethoxy-tetrahydrofuiran-3-yl)-biphenyl-4-carbonitrile were condensed to give 75 mg (42%) of 3(R)-[3-(4'-cyanobiphenyl-4-yl)-1H-pyrrol-1yl]-N-[2,2-dimethyl-1(S)-(pyridin-4-ylcarbamoyl)propyl] succinamic acid benzyl ester as an off-white powder, mp 115–6° C.

$^1$H NMR: δ8.42 (d, 2H, J=5.6 Hz), 7.72 (s, 2H), 7.58 (s, 2H), 7.50 (d, 2H, J=5.0 Hz), 7.31 (s, 2H), 7.26 (s, 7H), 7.12 (m, 1H), 6.85 (dd, 1H, J=2.5, 2.5 Hz), 6.64 (dd, 1H, J=1.6, 2.8 Hz), 6.25 (m, 1H), 5.20–5.10 (m, 3H), 4.15 (d, 1H, J=8.1 Hz), 3.39 (dd, 1H, J=5.5, 17.3 Hz), 3.25 (dd, 1H, J=7.9, 17.3 Hz), 0.94 (s, 9H). IR (KBr): 3331, 2959, 2225, 1735, 1687, 1655, 1602, 1559, 1511, 1288, 1203, 825 cm$^{-1}$. HRFABMS: Calculated for $C_{35}H_{37}N_4O_4$ (M+H$^+$): 640.2924. Found: 640.2908. Anal. Calculated for $C_{39}H_{37}N_5O_4$·1.1 EtOAc: C, 70.76; H, 6.27; N, 9.51. Found: C, 70.73; H, 6.19; N, 9.16.

Example 5(e)

3(R)-[3-(4'-Carbamoylbiphenyl-4-yl)-1H-pyrrol-1-yl]-N-(2,2-dimethyl-1(S)-(methylcarbamoyl)propyl) succinamic Acid

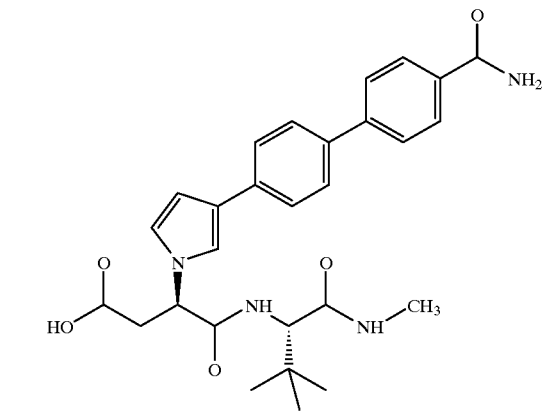

According to the procedure described in Example 5(a), 3(R)-[3-(4'-carbamoylbiphenyl-4-yl)-1H-pyrrol-1-yl]-N-(2,2-dimethyl-1(S)-(methylcarbamoyl)propyl)succinamic acid benzyl ester was hydrogenolyzed to provide 45 mg (90%) of 3(R)-[3-(4'-carbamoylbiphenyl-4-yl)-1H-pyrrol-1-yl]-N-(2,2-dimethyl-1(S)-(methylcarbamoyl)propyl)succinamic acid as a yellow solid.

$^1$H NMR (CD$_3$OD): δ7.98 (d, 2H, J=8.1 Hz), 7.78 (d, 2H, J=8.1 Hz), 7.62 (s, 4H), 7.30 (bs, 1H), 6.92 (bs, 1H), 6.54 (bs, 1H), 5.98 (1H, J=2.8 Hz), 5.39 (t, 1H, J=6.5 Hz), 4.19 (d, 1H, J=9.3 Hz), 3.02 (dd, 1H, J=7.2, 16.5 Hz), 2.60 (s, 3H), 0.98 (s, 9H). IR (KBr): 3332, 2915, 1658, 1547, 1408 cm$^{-1}$. Anal. Calculated for $C_{28}H_{32}N_4O_5$·0.7 H$_2$O: C, 65.03; H, 6.51; N, 10.83. Found: C, H, 6.74; N, 10.43.

The starting material was made as follows:

3(R)-[3-(4'-Carbamoylbiphenyl-4-yl)-1H-pyrrol-1-yl]-N-(2,2-dimethyl-1(S)-(methylcarbamoyl)propyl) succinamic Acid Benzyl Ester

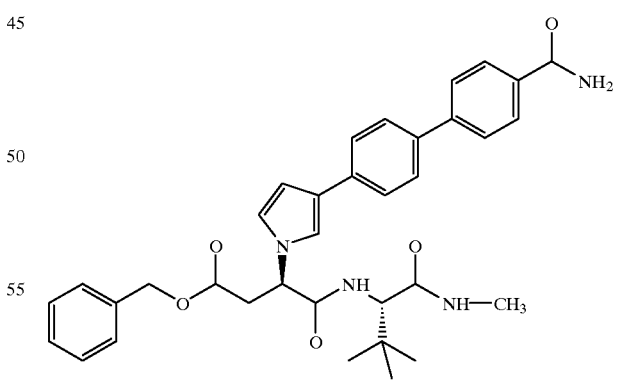

According to the procedure described in Example 1(b) for the preparation of N-(2,2-dimethyl-1(S)- methylcarbamoylpropyl)-3(R)-(3-phenyl-1H-pyrrol-1-yl)succinamic acid benzyl ester, 3(R)-t-butoxycarbonylamino-N-(2,2-dimethyl-1(S)-methylcarbamoylpropyl)succinamic acid benzyl ester was deprotected. The crude amine salt and crude 3-(4'-carboxamidobiphenyl-4-yl)-2,5-dimethoxy-tetrahydrofuran (prepared as described in Example 4(b)) were condensed in wet 1,2-dichloroethane at 90–100° C. to yield 180 mg (55%) of 3(R)-[3-(4'-carbarnoylbiphenyl-4-yl)-1H-pyrrol-1-yl]-N-(2,2-dimethyl-1(S)-(methylcarbamoyl)propyl)succinamic acid benzyl ester.

$^1$H NMR: δ7.90 (d, 2H, J=8.4 Hz), 7.70 (d, 2H, J=8.7 Hz), 7.60 (dd, 3H, J=8.7, 11.5 Hz), 7.38–7.22 (m, 8H), 7.10 (t, 1H, J=2.2 Hz), 6.82 (t, 1H, J=2.5 Hz), 6.62 (t, 1H, J=3.0 Hz), 6.32 (d, 1H, J=9.0 Hz), 5.63 (d, 1H, J=4.70 Hz), 5.14 (d, 3H, J=3.7 Hz), 4.00 (d, 1H, J=8.7 Hz), 3.48 (dd, 1H, J=7.2, 13.1 Hz), 3.39 (d, 1H, J=5.9 Hz), 3.14 (dd, 1H, J=8.7, 16.8 Hz), 2.78 (d, 3H, J=4.7 Hz), 0.92 (s, 9H). IR (KBr): 3356, 2929, 1735, 1657, 1402 cm$^{-1}$. Anal. Calculated for $C_{35}H_{39}N_4O_5 \cdot 0.5\ H_2O$: C, 69.63; H, 6.51; N, 9.28. Found: C, 69.85, H, 6.46; N, 9.14.

Example 5(f)

3(R)-[3-(4'-Carbamoylbiphenyl-4-yl)-1H-pyrrol-1-yl]-N-[2,2-dimethyl-1(S)-(N-(pyridin-4-yl)carbamoyl)propyl]succinamic Acid

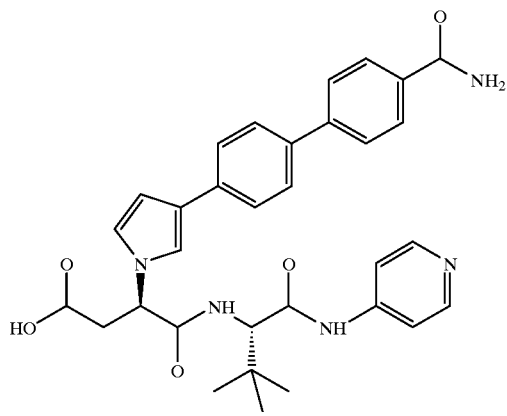

According to the procedure described in Example 5(a), 3(R)-[3-(4'-carbamoylbiphenyl-4-yl)-1H-pyrrol-1-yl]-N-[2,2-dimethyl-1(S)-(N-(pyridin-4-yl)carbamoyl)propyl]succinamic acid benzyl ester was hydrogenolyzed in MeOH/EtOAc to provide 35 mg (81%) of 3(R)-[3-(4'-carbamoylbiphenyl-4-yl)-1H-pyrrol-1-yl]-N-[2,2-dimethyl-1(S)-(N-(pyridin-4-yl)carbamoyl)propyl]succinamic acid as a yellow solid, mp 194–6° C.

$^1$H NMR (CD$_3$OD): δ8.35 (d, 2H, J=6.5 Hz), 7.95 (d, 2H, J=8.4 Hz), 7.75 (d, 3H, J=8.4 Hz), 7.70–7.52 (m, 6H), 7.28 (t, 1H, J=2.0 Hz), 6.90 (t, 1H, J 2.8 Hz), 6.52 (dd, 1H, J=6.9, 16.8 Hz), 1.20 (s, 9H). IR (KBr): 3400, 2962, 1665, 1606, 1511, 1402 cm$^{-1}$. HRFABMS: Calculated for $C_{32}H_{34}N_5O_5$ (M+H$^+$): 568.2560. Found: 568.2575. Anal. Calculated for $C_{32}H_{33}N_5O_5 \cdot 0.7\ HOAc \cdot 0.5\ CHCl_3$: C, 60.83; H, 5.47; N, 10.46. Found: C, 60.93, H, 5.88; N, 10.19.

The starting materials were made as follows:

3(R)-[3-(4'-Carbamoylbiphenyl-4-yl)-1H-pyrrol-1-yl]-N-[2,2-dimethyl-1(S)-(N-(pyridin-4-yl)carbamoyl)propyl]succinamic Acid Benzyl Ester

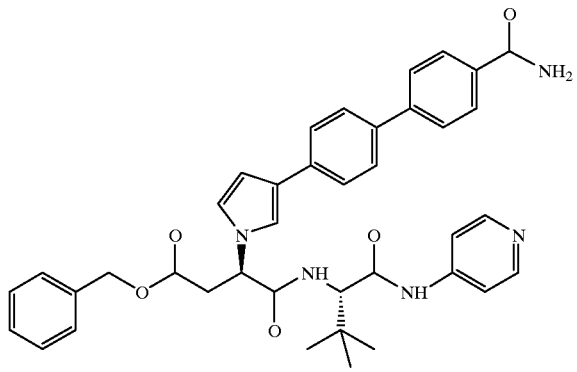

According to the procedure described in Example 1(b) for the preparation of N-(2,2-dimethyl-1(S)-methylcarbamoylpropyl)-3(R)-(3-phenyl-1H-pyrrol-1-yl)succinamic acid benzyl ester, 3(R)-t-butoxycarbonylamino-N-[2,2-dimethyl-1(S)-(pyridin-4-yl)carbamoylpropyl]succinamic acid benzyl ester was deprotected. The crude amine salt and crude 3-(4'-carboxamidobiphenyl-4-yl)-2,5-dimethoxy-tetrahydrofuran (prepared as described in Example 4(b)) were condensed in wet 1,2-dichloroethane at 90–100° C. to yield 130 mg (36%) of 3(R)-[3-(4'-carbamoylbiphenyl-4-yl)-1H-pyrrol-1-yl]-N-[2,2-dimethyl-1(S)-(N-(pyridin-4-yl)carbamoyl)propyl]succinamic acid benzyl ester.

$^1$H NMR (CD$_3$OD): δ8.35 (bs, 2H), 7.95 (d, 2H, J=8.4 Hz), 7.72 (d, 2H, J=8.7 Hz), 7.60 (dd, 6H), J=8.7, 13.4 Hz), 7.28 (s, 5H), 6.90 (t, 1H, ZJ=2.8 Hz), 6.52 (dd, 1H, 1.6, 2.8 Hz), 5.38 (t, 1H, J=7.5 Hz), 5.12 (d, 2H, J=1.9 Hz), 4.40 (s, 1H), 1.00 (s, 9H). IR (KBr): 2725, 1735, 1664, 1510 cm$^{-1}$. Anal. Calculated for $C_{39}H_{39}N_5O_5 \cdot 1.0\ HOAc$: C, 68.38; H, 6.05; N, 9.76. Found: C, 68.38, H, 6.05; N, 9.38.

Example 5(g)

3(R)-[3-(4'-Cyanobiphenyl-4-yl)-1H-pyrrol-1-yl]-N-[2,2-dimethyl-1(S)-(hydroxymethyl)propyl]succinamic Acid Triethylammonium Salt

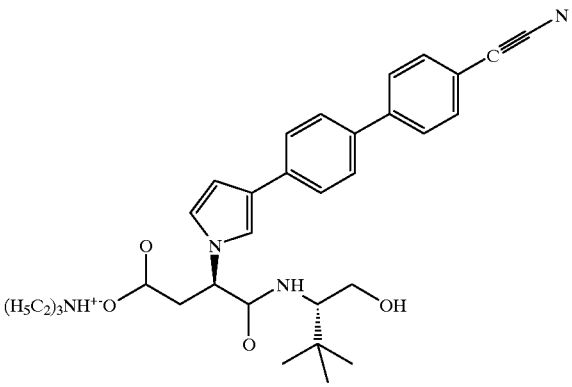

According to the procedure described in Example 1(a), a mixture of N-(2-benzyloxycarboxymethyl-1(S)-dimethylpropyl)-3(R)-[3-(4'-cyanobiphenyl-4-yl)-1H- pyrrol-1-yl]succinamic acid benzyl ester and N-(2-benzyloxycarboxymethyl-1(S)-dimethylpropyl)-3(R)-[3-(4-cyanophenyl)-1H-pyrrol-1-yl]succinamic acid benzyl ester was hydrogenolyzed to give a mixture which was separated via preparative RPHPLC (C18) with HOAc/Et₃N/MeOH/CH₂Cl₂ as eluant to give 50 mg of 3(R)-[3-(4'-cyanobiphenyl-4-yl)-1H-pyrrol-1-yl]-N-[2,2-dimethyl-1(S)-(hydroxymethyl)propyl]succinamic acid as a solid, mp 110–2° C.:

$^1$H NMR (CD$_3$OD): δ7.82 (d, 2H, J=8.3 Hz), 7.77 (d, 2H, J=8.3 Hz), 7.65–7.60 (bm, 4H), 7.34 (s, 1H), 6.93 (s, 1H), 6.50 (s, 1H), 5.19 (dd, 1H, J=3.6, 3.6 Hz), 3.45 (dd, 1H, J=8.2, 12.1 Hz), 3.16 (q, 6H, J=7.4 Hz), 1.28 (t, 9H, J=7.4 Hz), 0.91 (s, 9H). IR (KBr): 3389, 2955, 2226, 1655, 1601, 1561, 1396, 1367, 1202, 920, 826, 779 cm$^{-1}$. HRFABMS: Calculated for C$_{27}$H$_{29}$N$_3$O$_4$Cs (MH+Cs$^+$): 592.1212. Found: 592.1230. Anal. Calculated for C$_{27}$H$_{29}$N$_3$O$_4$.Et$_3$N. 2.5 H$_2$O: C, 65.42; H, 7.87; N, 9.11. Found: C, 65.43; H, 8.15; N, 9.25.

Example 5(h)

3(R)-[3-(4-Cyanophenyl)-1H-pyrrol-1-yl]-N-(2,2-dimethyl-1(S)-(hydroxymethyl)propyl)succinamic Acid Triethylammonium Salt

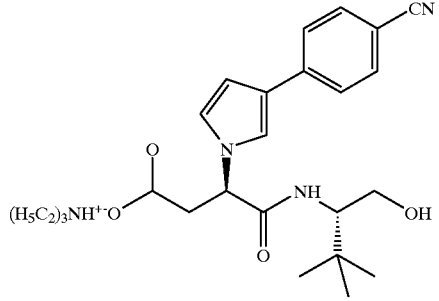

Separation via preparative HPLC of the mixture obtained as described in Example 5(g) afforded 50 mg of 3(R)-[3-(4-cyanophenyl)-1H-pyrrol-1-yl]-N-[2,2-dimethyl-1(S)-(hydroxymethyl)propyl]succinamic acid:

$^1$H NMR: δ7.66 (d, 2H, J=8.1 Hz), 7.60 (d, 2H, J=8.1 Hz), 7.42 (s, 1H), 6.94 (s, 1H), 6.51 (s, 1H), 5.18 (bs, 1H), 3.45 (dd, 1H, J=9.2, 12.1 Hz), 3.16 (q, 6H, J=7.4 Hz), 1.96 (bs, 1H), 1.28 (t, 9H, J=7.4 Hz), 0.91 (s, 9H). IR (KBr): 3378, 2955, 2214, 1655, 1602, 1561, 1489, 1396, 1172, 1094, 920, 838, 785 cm$^{-1}$. FABMS: 516. Anal. Calculated for C$_{21}$H$_{25}$N$_3$O$_4$.Et$_3$N, HOAc.1.7 H$_2$O: C, 60.70; H, 8.05; N, 9.51. Found: C, 60.54; H, 8.30; N, 9.74.

Example 6(a)

N-(2(R)-Hydroxyindan-1(R)-yl)-3(R)-[3-[4-(pyridin4-yl)phenyl]-1H-pyrrol-1-yl]succinamic Acid

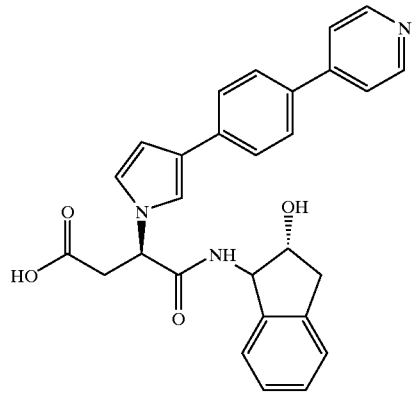

According to the procedure described in Example 1(a), N-(2(R)-hydroxyindan-1(R)-yl)-3(R)-[3-[4-(pyridin-4-yl)phenyl]-1H-pyrrol-1-yl]succinamic acid benzyl ester was hydrogenolyzed to obtain in 61% yield N-(2(R)-hydroxyindan-1(R)-yl)-3(R)-[3-[4-(pyridin-4-yl)phenyl]-1H-pyrrol-1-yl]succinamic acid as a yellow amorphous solid.

$^1$H NMR (DMSO-d$_6$): δ 12.52 (bs, 1H), 8.59 (d, 2H, J=5.9 Hz), 8.24 (d, 1H, J=8.5 Hz), 7.77 (d, 2H, J=8.5 Hz), 7.71 (d 2H, J=6.3 Hz), 7.64 (d, 2H, J=8.5 Hz), 7.45 (s, 1H), 7.30–7.15 (m, 4H), 6.97 (t, 1H, J=2.4 Hz), 6.51 (s, 1H), 5.34 (t, 1H, J=7.5 Hz), 5.17 (dd, 1H, J=5.0, 8.7 Hz), 5.11 (d, 1H, J=3.7 Hz), 4.35 (d, 1H, J=3.3 Hz), 3.27–2.94 (m, 2H), 2.76 (d, 1H, J=16.0 Hz). Anal. Calculated for C$_{28}$H$_{25}$N$_3$O$_4$.0.2 EtOAc: C, 71.30; H, 5.53; N, 8.66. Found: C, 71.24; H, 5.59; N, 8.52.

The starting material was available as follows:

2(R)-[3-[4-(Pyridin-4-yl)phenyl]-1H-pyrrol-1-yl) succinic Acid 4-Benzyl Ester Hydrochloride

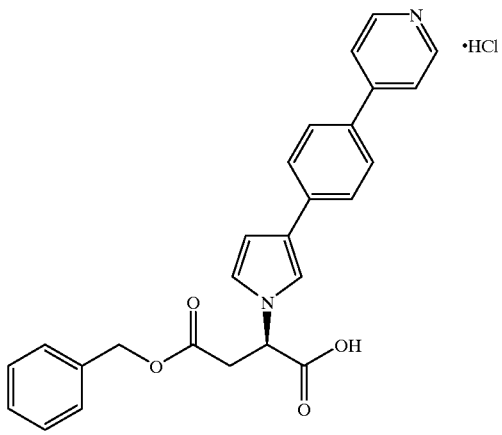

According to the procedure as described in Example 1(d) for the preparation of N-(2,2-dimethyl-1(S)-methylcarbamoylpropyl)-3(R)-(3-pyridin-4-yl-1H-pyrrol-1-yl)succinamic acid benzyl ester, to a solution of D-aspartate β-benzyl ester (223 mg, 1.00 mmol) and 2,5-dimethoxy-3-(4-(pyridin-4-yl)phenyl)tetrahydrofuran (350 mg, 1.20 mmol; prepared as described in Example 5(a)) in 1,2-dichloroethane was added sequentially pyridine (0.16 mL, 2.0 mmol), trifluoroacetic acid (0.08 mL, 1 mmol), and chlorotrimethylsilane (0.38 mL, 3.0 mmol). After 17 hours at 80° C., the mixture was allowed to cool to ambient temperature. Filtration led to isolation of 408 mg (87%) of 2(R)-[3-[4-(pyridin-4-yl)phenyl]-1H-pyrrol-1-yl]succinic acid 4-benzyl ester hydrochloride as a yellow solid, mp 203–5° C. (d).

$^1$H NMR (DMSO-d$_6$): δ8.86 (d, 2H, J=6.3 Hz), 8.38 (d, 2H, J=6.6 Hz), 8.02 (d, 2H, J=8.5 Hz), 7.74 (d, 2H, J=8.5 Hz), 7.58 (s, 1H), 7.31–7.24 (m, 5H), 6.96 (t, 1H, J=2.4 Hz), 6.58 (s, 1H), 5.23 (t, 1H, J=7.4 Hz), 5.10 (s, 2H), 3.36 (dd, 1H, J=6.6, 16.6 Hz), 3.21 (dd, 1H. J=7.7, 16.9 Hz). Anal. Calculated for C$_{26}$H$_{22}$N$_2$O$_4$.HCl.0.3 H$_2$O: C, 66.68; H, 5.08; N 5.98; Cl, 7.57. Found: C, 66.56; H, 5.01; N, 5.98; Cl, 7.80.

N-(2(R)-Hydroxyindan-1(R)-yl)-3(R)-[3-[4-(pyridin-4-yl)phenyl]-1H-pyrrol-1-yl]succinamic Acid Benzyl Ester

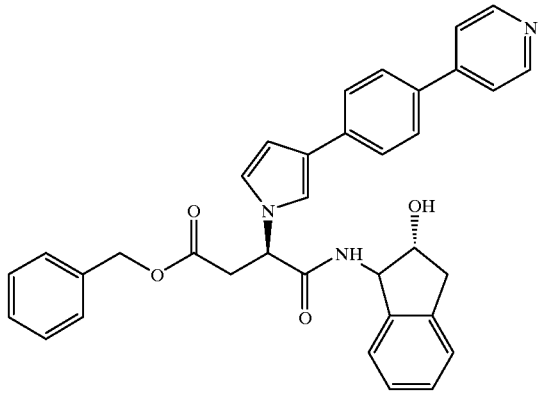

According to the procedure as described in Example 1(f) for 3(R)-t-butoxycarbonylarnino-N-(1(S)-benzyl-2-methoxy-ethyl)succinamic acid benzyl ester, 2(R)-[3-(4'-pyridin-4-yl-phenyl)-1H-pyrrole-1-yl]succinic acid 4-benzyl ester hydrochloride and 1(S)-amino-2(R)-hydroxyindane were coupled with BOP to afford in 60% yield N-(2(R)-hydroxyindan-1(R)-yl)-3(R)-[3-[4-(pyridin-4-yl)phenyl]-1H-pyrrol-1-yl]succinamic acid benzyl ester as an off-white solid, mp 199–202° C. (d).

$^1$H NMR (DMSO-d$_6$): δ_8.66 (d, 2H, J=5.9 Hz), 8.34 (d, 1H, J=8.8 Hz), 7.84 (d, 2H, J=8.5 Hz), 7.79 (d, 2H, J=6.3 Hz), 7.73 (d, 2H, J=6.3 Hz), 7.69 (s, 1H), 7.36 (s, 5H), 7.29–7.21 (m, 4H), 7.04 (t, 1H, J=2.2 Hz), 6.58 (s, 1H), 5.49 (t, 1H, J=7.2 Hz), 5.25–5.12 (m, 4H), 4.43–4.39 (m, 1H), 3.48 (dd, 1H, J=7.5, 16.5 Hz), 3.26 (dd, 1H, J=7.7, 16.5 Hz), 3.09 (dd, 1H, J=4.6, 15.6 Hz), 2.83 (d, 1H, J=16.2 Hz). Anal. Calculated for C$_{35}$H$_{31}$N$_3$O$_4$.0.6 H$_2$O: C, 73.95; H, 5.71; N, 7.39. Found: C, 73.70; H, 5.61; N, 7.26.

The following were made in a similar manner:

Example 6(b)

N-(2,2-Dimethyl-1(S)-(methylcarbamoyl)propyl)-3(R)-[3-(4-(pyridin-4-yl)phenyl)-1H-pyrrol-1-yl] succinamic Acid

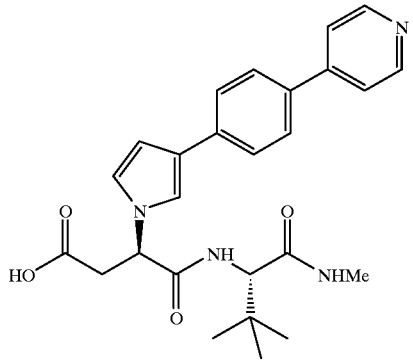

According to the procedure described in Example 1(a), N-(2,2-dimethyl-1(S)-(methylcarbamoyl)propyl)-3(R)-[3-(4-(pyridin-4-yl)phenyl)-1H-pyrrol-1-yl]succinamic acid benzyl ester was hydrogenolyzed in MeOH after 20 hours. Purification via flash column chromatography with 1% HOAc/10% MeOH/CHCl$_3$ as eluant and azeotrope with n-heptane furnished 24 mg (32%) of N-(2,2-dimethyl-1(S)-(methylcarbamoyl)propyl)-3(ER)-[3-(4-(pyridin-4-yl)phenyl)-1H-pyrrol-1-yl]succinamic acid as yellow crystals.

$^1$H NMR (CD$_3$OD): δ8.54 (d, 2H, J=5.6 Hz), 7.99 (bd, 1H, J=4.4 Hz), 7.80–7.59 (m, 6H), 7.34 (t, 1H, J=1.9 Hz), 6.92 (t, 1H, J=2.5 Hz),6.55 (dd, 1H, J=1.9, 2.8 Hz), 5.28 (t, 1H, J=7.2 Hz), 4.17 (s, 1H), 3.23 (dd, 1H, J=7.5, 16.7 Hz), 3.01 (dd, 1H, J=7.2, 16.7 Hz), 2.66 (d, 3H, J=3.5 Hz), 0.95 (s, 9H). IR(KBr): 3422, 1654, 1598, 1562, 1535 cm$^{-1}$. HRFABMS: Calculated for C$_{26}$H$_{31}$N$_4$O$_4$ (M+H$^+$): 463.2345. Found: 463.2356. Anal. Calculated for C$_{26}$H$_{30}$N$_4$O$_4$.1.15 H$_2$O.0.1 CHCl$_3$: C, 63.30; H, 6.59; N, 11.31. Found: C, 63.28; H, 6.58; N, 11.08.

The starting material was available in the following manner:

N-(2,2-Dimethyl-1(S)-(methylcarbamoyl)propyl)-3(R)-[3-(4-(pyridin4-yl)phenyl)-1H-pyrrol-1-yl] succinamic Acid Berzyl Ester

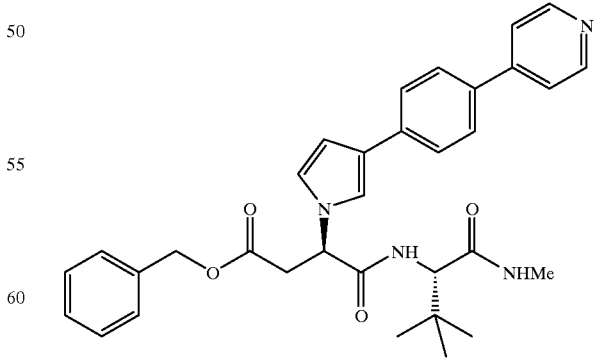

According to the procedure described in Example 1(b) for the preparation of N-(2,2-dimethyl-1(S)-(methylcarbarnoyl) propyl)-3(R)-t-butoxycarbonylamino-succinamic acid benzyl ester, 2(R)-[3-(4'-pyridin-4-yl-phenyl)-1H-pyrrole-1-yl]succinic acid 4-benzyl ester hydrochloride and L-t-leucine-N-methylamide trifluoroacetate salt (prepared as described in Example 5(d)) were coupled with TBTU to provide in 86% yield N-(2,2-dimethyl-1(S)-(methylcarbamoyl)propyl)-3(R)-[3-(4-(pyridin-4-yl)phenyl)-1H-pyrrol-1-yl]succinamic acid benzyl ester.

¹H NMR: δ8.80–8.57 (bs, 2H), 7.76–7.50 (m, 6H), 7.36–7.22 (m, 5H), 7.12 (d, 1H, J=1.6 Hz), 6.82 (t, 1H, J=1.9 Hz), 6.60 (dd, 1H, J=1.2, 1.2 Hz), 5.20–5.15 (m, 3H), 4.09(dd, 1H, J=2.8,9.0 Hz), 3.41 (dd, 1H, J=5.3, 16.5 Hz), 3.10 (dd, 1H, J=8.4, 16.5 Hz), 2.76 (dd, 3H, J=2.5, 4.4 Hz), 0.90 (s, 9H). IR (KBr): 3314, 2959, 1736, 1652, 1598, 1560, 1550, 1409, 1166 cm⁻¹. LSIMS: 553 (MH⁺). Anal. Calculated for $C_{33}H_{36}N_4O_4 \cdot 0.5\ H_2O$: C, 70.56; H, 6.64; N, 9.98. Found: C, 70.70; H, 6.62; N, 9.78.

Example 6(c)

N-(4,4-Dimethyl-2-oxo-tetrahydrofuran-3(S)-yl)-3(R)-[3-[4-(pyridin-4-yl)phenyl]-1H-pyrrol-1-yl]succinamic Acid

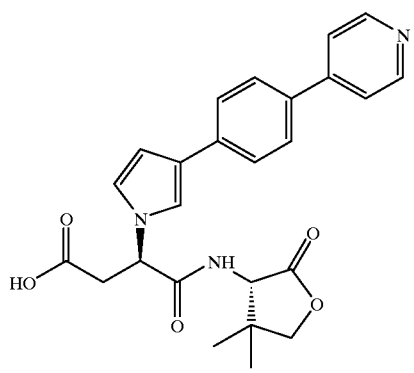

According to the procedure described in Example 1(a), N-(4,4-dimethyl-2-oxo-tetrahydrofuran-3(S)-yl)-3(R)-[3-[4-(pyridin-4-yl)phenyl]-1H-pyrrol-1-yl]succinamic acid benzyl ester was hydrogenolyzed to obtain in 70% yield N-(4,4-dimethyl-2-oxo-tetrahydrofuran-3(S)-yl)-3(R)-[3-[4-(pyridin-4-yl)phenyl]-1H-pyrrol-1-yl]succinamic acid as an amorphous solid.

¹H NMR (DMSO-d₆): δ12.60 (bs, 1H), 8.82 (d, 1H, J=8.8 Hz), 8.59 (d, 2H, J=5.9 Hz), 7.77 (d, 2H, J=8.1 Hz), 7.71 (d, 2H, J=5.9 Hz), 7.64 (d, 2H, J=8.5 Hz), 7.41 (s, 1H), 6.92 (s, 1H), 6.52 (s, 1H), 5.16–5.11 (m, 1H), 4.75 (d, 1H, J=8.8 Hz), 4.08, 4.00 (AB quartet, 2H, J=8.3 Hz), 3.22 (dd, 1H, J=9.2, 16.6 Hz), 2.93 (dd, 1H, J=5.9, 16.9 Hz), 1.05 (s, 3H), 0.96 (s, 3H). Anal. Calculated for $C_{25}H_{25}N_3O_5 \cdot 0.2\ MTBE \cdot 0.2\ H_2O$: C, 66.62; H, 5.98; N, 8.97. Found: C, 66.55; H, 5.90; N, 8.98.

The starting material was available as follows:

N-(4,4-Dimethyl-2-oxo-tetrahydrofuran-3(S)-yl)-3(R)-[3-[4-(pyridin-4-yl)phenyl]-1H-pyrrol-1-yl]succinamic Acid Benzyl Ester

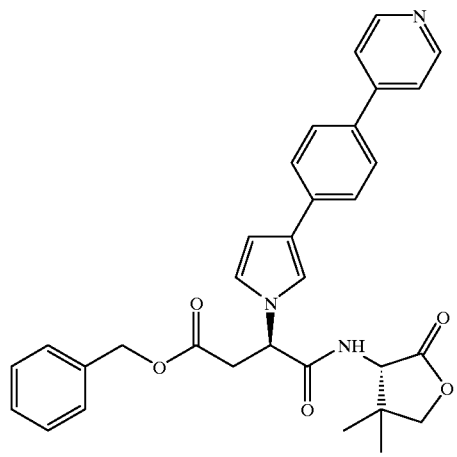

According to the procedure described in Example 1(f) for the preparation of 3(R)-t-butoxycarbonylamino-N-(1(S)-benzyl-2-methoxy-ethyl)succinamic acid benzyl ester, 2(R)-[3-(4'-pyridin-4-yl)-1H-pyrrole-1-yl]succinic acid 2-benzyl ester hydrochloride and 3(R)-amino-4,4-dimethyl-2-oxo-tetrahydrofuran (see Freskos, J. N. *Syn. Commun.* 1994, 24, 557–563) were coupled using BOP reagent to provide in 55% yield N-(4,4-dimethyl-2-oxo-tetrahydrofuran-3(S)-yl)-3(R)-[3-[4-(pyridin-4-yl)phenyl]-1H-pyrrol-1-yl]succinamic acid benzyl ester as a white solid, mp 175–7° C.

¹H NMR: δ8.64 (d, 2H, J=6.3 Hz), 7.64 (d, 2H, J=8.5 Hz), 7.59 (d, 2H, J=8.8 Hz), 7.53 (d, 2H, J=6.3 Hz), 7.32–7.26 (m, 5H), 7.13 (s, 1H), 6.83 (t, 1H, J=2.4 Hz), 6.61 (dd, 1H, J=1.7, 2.8 Hz), 5.23 (dd, 1H, J=5.9, 8.5 Hz), 5.13 (s, 2H), 4.59 (d, 1H, J=8.1 Hz), 4.01 (s, 2H), 3.50 (dd, 1H, J=5.9, 16.9 Hz), 3.09 (dd, 1H, J=8.5, 16.9 Hz), 1.20 (s, 3H), 0.86 (s, 3H). Anal. Calculated for $C_{32}H_{31}N_3O_5$: C, 71.49; H, 5.81; N, 7.82. Found: C, 71.57; H, 5.84; N, 7.77.

Example 7(a)

N-(8-Oxo-4-oxa-1,7-diazatricyclo[9.6.1.0$^{12,17}$] octadeca-11(18), 12,14,16-tetraen-9(S)-yl)-3(R)-[3-[4-(pyridin-4-yl)phenyl]-1H-pyrrol-1-yl]succinamic Acid

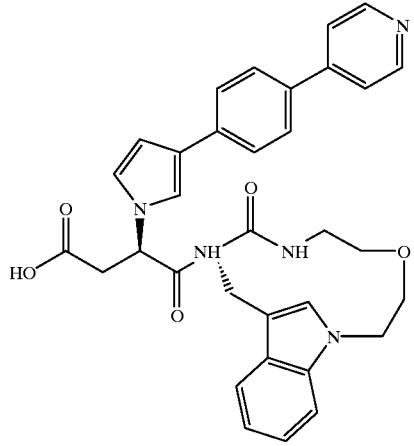

To a solution of N-(8-oxo-4-oxa-1,7-diazatricyclo [9.6.1.0$^{12,17}$]octadeca-11(18),12,14,1 6-tetraen-9(S)-yl)-3 (R)-[3-[4-(pyridin-4-yl)phenyl]-1H-pyrrol-1-yl]succinamic acid benzyl ester (185 mg, 0.280 mmol) in EtOAc/EtOH/ THF was added in succession 10% palladium on carbon (50 mg) and 88% formic acid (0.1 mL). After 1.5 hours, HOAc (1 mL) was added. After 16 hours, more 10% palladium on carbon (25 mg), 88% formic acid (0.1 mL), and HOAc (1 mL) was added. At 24 hours, more 10% palladium on carbon (25 mg) was added. After 25 hours total elapsed time, the catalyst was filtered off. The filtrate was concentrated to a crude solid. The product dissolved in a minimal amount of MeOH/EtOAc, and inorganic particulates were filtered away. The filtrate was concentrated to a solid that was triturated with CH$_2$Cl$_2$/hex to give 76 mg (46%) of N-(8-oxo-4-oxa-1,7-diazatricyclo[9.6.1.0$^{12,17}$]octadeca-11(18), 12,14,16-tetraen-9(S)-yl)-3(R)-[3-[4-(pyridin-4-yl)phenyl]-1H-pyrrol-1-yl]succinamic acid as a yellow solid, mp >172° C. (d).

$^1$H NMR (CD$_3$COOD): δ8.91 (d, 2H, J=6.6 Hz), 8.23 (d, 2H, J=6.6 Hz), 7.93 (d, 2H, J=8.5 Hz), 7.75 (d, 2H, J=8.5 Hz), 7.62 (d, 1H, J=7.4 Hz), 7.40–7.33 (m, 2H), 7.17 (t, 1H, J=7.5 Hz), 7.10 (t, 1H, J=7.4 Hz), 7.04 (s, 1H), 6.93 (t, 1H, J=2.6 Hz), 6.79 (bm, 1H, partially exchanged), 6.58 (s, 1H), 5.34 (t, 1H, J=7.5 Hz), 4.72 (dd, 1H, J=4.6, 11.2 Hz), 4.35–4.30 (m, 1H), 4.23–4.15 (m, 1H), 3.74–3.65 (m, 2H), 3.56–3.42 (m, 2H), 3.31–3.00 (m, 4H), 2.91–2.85 (m, 1H), 2.74–2.67 (m, 1H). Anal. Calculated for C$_{34}$H$_{33}$N$_5$O$_5$.0.4 H$_2$O: C, 68.19; H, 5.69; N, 11.70. Found: C, 68.13; H, 5.77; N, 11.81.

The starting material was available as follows:

N-(8-Oxo-4-oxa-1,7-diazatricyclo[9.6.1.0$^{12,17}$] octadeca-11(18)12,14,16-tetraen-9(S)-yl)-3(R)-[3-[4-(pyridin-4-yl)phenyl]-1H-pyrrol-1-yl]succinamic Acid Benzyl Ester

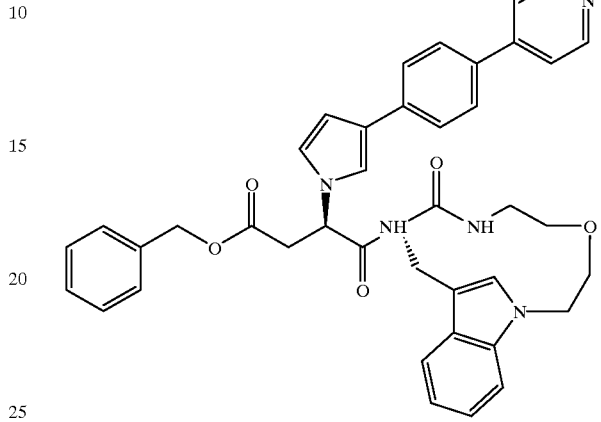

According to the procedure described in Example 1(b) for N-(2,2-dimethyl-1(S)-(methylcarbamoyl)propyl)-3(R)-(t-butoxycarbonylamino)succinamic acid benzyl ester, 2(R)-[3-[4-(pyridin-4-yl)phenyl]-1H-pyrrol-1-yl]succinic acid 4-benzyl ester hydrochloride (prepared as described in Example 6(a)) and 9S-t-butoxycarbonylarmino-4-oxa-1,7-diazatricyclo-[9.6.1.0$^{12,17}$]-octadeca-11(18),12,14,16-tetraen-8-one (see Castelhano, A. L.; Liak, T. J.; Horne, S.; Yuan, Z.; Krantz, A. Int. Patent Appl. WO95/04735-A1, Feb. 16, 1995) were coupled with TBTU to provide in 77% yield, after purification via column chromatography with 5% MeOH/EtOAc and trituration with MTBE/hex, N-(8-oxo-4-oxa-1,7-diazatricyclo[9.6.1.0$^{12,17}$]octadeca-11(18),12,14, 16-tetraen-9(S)-yl)-3(R)-[3-[4-(pyridin-4 -yl)phenyl]-1H-pyrrol-1-yl]succinamic benzyl ester as a pale yellow amorphous solid.

$^1$H NMR: δ8.91 (d, 2H, J=6.6 Hz), 8.23 (d, 2H, J=6.6 Hz), 7.93 (d, 2H, J=8.5 Hz), 7.74 (d, 2H, J=8.5 Hz), 7.59 (d, 1H, J=7.4 Hz), 7.37–7.25 (m, 7H), 7.17 (t, 1H, J=7.4 Hz), 7.10 (t, 1H, J=7.4 Hz), 7.03 (s, 1H), 6.90 (t, 1H, J=2.2 Hz), 7.79 (bd, 1H, partially exchanged), 6.57 (s, 1H), 5.37 (t, 1H, J=7.5 Hz), 5.18 (s, 2H), 4.70 (dd, 1H, J=5.0, 11.2 Hz), 4.35–4.30 (m, 1H), 4.23–4.15 (m, 1H), 3.70–3.65 (m, 2H), 3.56–3.43 (m, 2H), 3.31–3.15 (m, 3H), 3.02 (t, 1H, J=12.7 Hz), 2.91–2.84 (m, 1H), 2.72–2.67 (m, 1H). Anal. Calculated for C$_{41}$H$_{38}$N$_5$O$_5$.0.5 H$_2$O: C, 71.39; H, 5.70; N, 10.15. Found: C, 71.47; H, 5.82; N, 10.26.

The following were available in a similar manner:

Example 7(b)

N-[2,2-Dimethyl-1(S)-(pyridin-4-ylcarbamoyl)propyl]-3(R)-[3-[4-(pyridin-4-yl)phenyl]-1H-pyrrol-1-yl]succinamic Acid

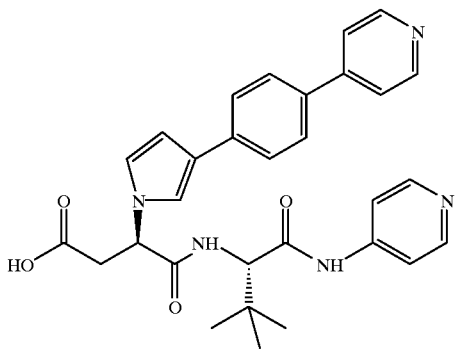

According to the procedure described in Example 7(a), N-[2,2-dimethyl-1(S)-(pyridin4-ylcarbamoyl)propyl]-3(R)-[3-[4-(pyridin-4-yl)phenyl]-1H-pyrrol-1-yl]succinamic acid benzyl ester (185 mg, 0.280 mmol) was hydrogenolyzed in EtOH (10 mL) and HOAc (1 mL) and furnished a solid that was triturated with EtOAc to give 60 mg (41%) of N-[2,2-dimethyl-1(S)-(pyridin-4-ylcarbamoyl)propyl]-3 (R)-[3-[4-(pyridin-4-yl)phenyl]-1H-pyrrol-1-yl]succinamic acid as a yellow solid.

$^1$H NMR (CD$_3$OD): δ8.54 (d, 2H, J=6.6 Hz), 8.33 (d, 2H, J=6.6 Hz), 7.73–7.68 (m, 4H), 7.64–7.59 (m, 4H), 7.32 (s, 1H), 6.91 (t, 1H J=2.4 Hz), 6.52 (dd, 1H, J=1.8, 2.9 Hz), 5.31 (t, 1H, J=7.5 Hz), 4.41 (s, 1H), 2.99 (dd, 1H, J=6.8, 16.7 Hz), 1.03 (s, 9H). Anal. Calculated for C$_{30}$H$_{31}$N$_5$O$_4$.0.6 H$_2$O.0.2 EtOAc: C, 66.77; H, 6.15; N, 12.64. Found: C, 66.72; H, 5.99; N, 12.62.

The starting material was available as follows:

N-[2,2-Dimethyl-1(S)-(pyridin-4-ylcarbamoyl)propyl]-3(R)-[3-[4-(pyridin-4-yl)phenyl]-1H-pyrrol-1-yl]succinamic Acid Benzyl Ester

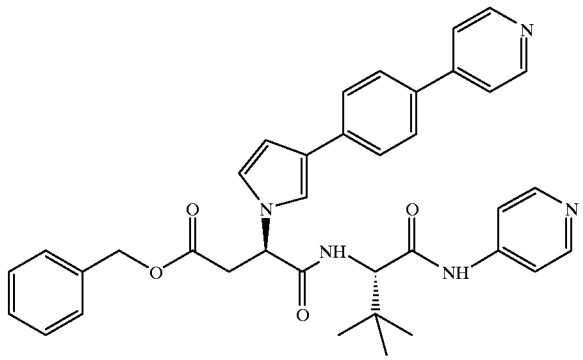

According to the procedure described in Example 1(b) for the preparation of N-(2,2-dimethyl-1(S)-(methylcarbamoyl) propyl)-3(R)-t-butoxycarbonylamino-succinamic acid benzyl ester, 2S-t-butoxycarbonylamino-3,3-dimethyl-N-(pyridin-4-yl)-butanamide (prepared as described in Example 5(d)) was deprotected with trifluoroacetic acid. The crude amine salt and 2(R)-[3-[4-(pyridin-4-yl)phenyl]-1H-pyrrol-1-yl]succinic acid 4-benzyl ester hydrochloride (prepared as described in Example 6(a)) were coupled with TBTU to provide after purification via column chromatography with 5% MeOH/CH$_2$Cl$_2$ and trituration with MTBE/hex, in 76% yield N-[2,2-dimethyl-1(S)-(pyridin-4-ylcarbamoyl)propyl]-3(R)-[3-[4-(pyridin-4-yl)phenyl]-1H-pyrrol-1-yl]succinamic acid benzyl ester as a pale yellow amorphous solid, which was used without further purification.

$^1$H NMR: δ8.65 (d, 2H, J=5.9 Hz), 8.43 (d, 2H, J=6.3 Hz), 8.26 (s, 1H), 7.64 (d, 2H, J=8.5 Hz), 7.58 (d, 2H, J=8.5 Hz), 7.53 (d, 2H, J=6.3 Hz), 7.40 (d, 2H, J=6.3 Hz), 7.32–7.24 (m, 5H), 7.12 (s, 1H), 6.85 (t, 1H, J=2.4 Hz), 6.64 (dd, 1H, J=1.8, 2.9 Hz),6.23 (d, 1H, J=8.1 Hz), 5.19–5.08 (m, 3H), 4.19 (d, 1H, J=8.1 Hz), 3.39 (dd, 1H, J=5.2, 16.9 Hz), 3.23 (dd, 1H, J=8.1, 17.3 Hz),0.93 (s, 9H). Anal. Calculated for C$_{37}$H$_{37}$N$_5$O$_4$.0.9 H$_2$O: C, 70.32; H, 6.19; N, 11.08. Found: C, 70.37; H, 6.11; N, 10.94.

Example 7(c)

N-[1(S)-(1H-Imidazol-2-yl)-3-methylbutyl]-3(R)-[3-[4-(pyridin-4-yl)phenyl]-1H-pyrrol-1-yl]succinamic Acid Formate Salt

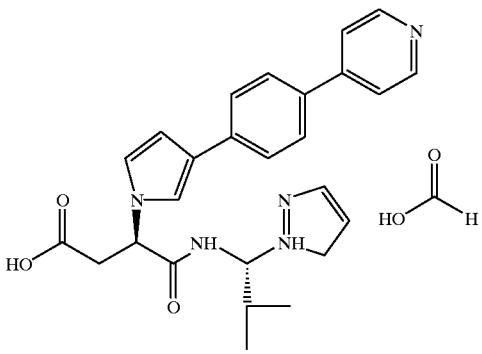

According to the procedure described in Example 7(a), N-[1(S)-(1H-imidazol-2-yl)-3-methylbutyl]-3(R)-[(3-[4-(pyridin-4-yl)phenyl]-1H-pyrrol-1-yl]succinamic acid benzyl ester was hydrogenolyzed in EtOH:THF (1:1) to yield in 81% yield N-[1(S)-(1H-imidazol-2-yl)-3-methylbutyl]-3 (R)-[3-[4-(pyridin-4-yl)phenyl]-1H-pyrrol-1-yl]succinamic acid formate salt as a yellow amorphous solid.

$^1$H NMR (DMSO-d$_6$): δ12.30 (bs, 1H), 8.65 (d, 1H, J=8.1 Hz), 8.59 (d, 2H, J=4.4 Hz), 8.13 (s, 1H), 7.75 (d, 2H, J=8.5

Hz), 7.71 (d, 2H, J=4.4 Hz), 7.60 (d, 2H, J=8.5 Hz), 7.34 (s, 1H), 6.91–6.83 (m, 3H), 6.44 (s, 1H), 5.08 (t, 1H, J=7.5 Hz), 4.97 (dd, 1H, J=8.1, 16.2 Hz), 3.10 (dd, 1H, J=8.1, 16.6 Hz), 2.90 (dd, 1H, J=7.2, 16.7 Hz), 1.68 (t, 2H, J=7.2 Hz), 1.52–1.45 (m, 1H), 0.86 (d, 3H, J=7.0 Hz), 0.83 (d, 3H, J=6.6 Hz). Anal. Calculated for $C_{27}H_{29}N_5O_3 \cdot HCO_2H \cdot 0.5$ EtOAc: C, 64.15; H, 6.28; N, 12.47. Found: C, 64.21, H, 6.40; N, 12.60.

The starting materials were made as follows:

N-(1(S-(1H-Imidazol-2-yl)-3-methylbutyl]-3(R)-[3-[4-(pyridin-4-yl)phenyl]-1H-pyrrol-yl]succinamic Acid Benzyl Ester

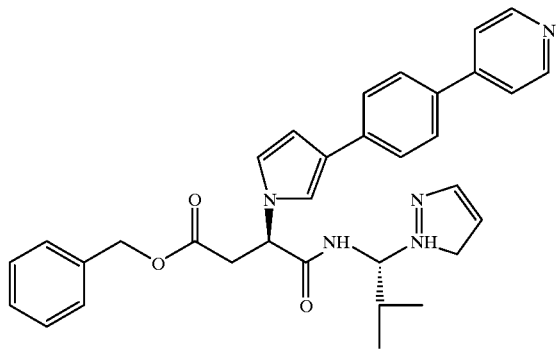

According to the procedure described in Example 1(b) for the preparation of 3(R)-t-butyloxycarbonylamino-N-(2,2-dimethyl-1(S)-(methylcarbamoyl)propyl)succinamic acid benzyl ester, 2-(1(S)-amino-3-methyl-butyl)-imidazole (See Chen, J. J.; Zhang, Y.; Hammond, S.; Dewdney, N.: Ho, T.; Browner, M. F.; Castelhano, A. L., submitted for publication; and Abel-Meguid, S. S.; Metcalf B. W.; Caw, T. J.; DeMarsh, P.; Des Jarlais, R. L.; Fisher, S.; Green, D. W.; et al. *Biochemistry,* 1994, 33, 11671–11677) and 2(R)-[3-(4-(pyridin-4-yl)phenyl]-1H-pyrrol-1-yl]succinic acid 4-benzyl ester hydrochloride (prepared as described in Example 7(a)) were coupled with TBTU. Flash column chromatography with 0–5% MeOH/CH$_2$Cl$_2$ gradient eluant and recrystallization from EtOAc gave in 41% yield N-[1(S)-(1H-imidazol-2-yl)-3-methylbutyl]-3(R)-[3-[4-(pyridin-4-yl)phenyl]-1H-pyrrol-1-yl]succinamic acid benzyl ester as white crystals, mp 179–81° C. (d).

$^1$H NMR (DMSO-d$_6$): δ11.84 (bs, 1H), 8.68 (d, 1H, J=8.5 Hz), 8.59 (d, 2H, J=4.4 Hz), 7.76 (d, 2H, J=8.5 Hz), 7.71 (d, 2H, J=6.3 Hz), 7.60 (d, 2H, J=8.5 Hz), 7.36 (s, 1H), 7.30 (s, 5H), 6.94–6.80 (m, 3H), 6.46 (s, 1H), 5.17 (t, 1H, J=7.5 Hz), 5.11, 5.05 (AB quartet, 2H, J=12.7 Hz), 4.97 (dd, 1H, J=7.7, 15.4 Hz), 3.24 (dd, 1H, J=7.4, 12.9 Hz), 3.11 (dd, 1H, J=7.7, 16.6 Hz), 1.67 (t, 2H, J=7.7 Hz), 1.48–1.40 (m, 1H), 0.85 (d, 3H, J=6.6 Hz), 0.81 (d, 3H, J=6.6 Hz). Anal. Calculated for $C_{34}H_{35}N_5O_3$: C, 72.70; H, 6.28; N, 12.47. Found: C, 72.43, H, 6.33; N, 12.34.

Example 7(d)

N-Methyl-3(R)-[3-[4-(pyridin-4-yl)phenyl]-1H-pyrrol-1-yl]succinamic Acid

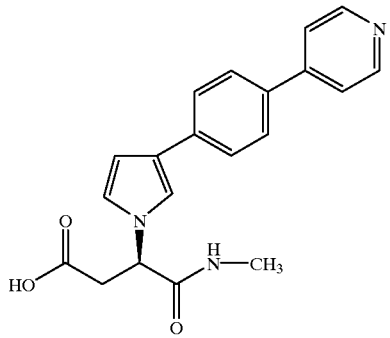

According to the procedure described in Example 7(a), N-methyl-3(R)-[3-[4-(pyridin-4-yl)phenyl]-1H-pyrrol-1-yl]succinamic acid benzyl ester was hydrogenolyzed in acetic acid to yield in 90% yield N-methyl-3(R)-[3-[4-(pyridin4-yl)phenyl]-1H-pyrrol-1-yl]succinamic acid as a yellow amorphous solid.

$^1$HNMR (DMSO-d$_6$): δ8.58 (d, 2H, J=5.9 Hz), 7.75 (d, 2H, J=8.1 Hz), 7.71 (d, 2H, J=6.2 Hz), 7.61 (d, 2H, J=8.4 Hz), 7.29 (s, 1H), 6.77 (t, 1H, J=2.2 Hz), 6.42 (t, 1H, J=2.2 Hz), 4.80 (d, 1H, J=10.7 Hz), 3.16 (dd, 1H, J=15.8, 11.0 Hz), 2.36 (s, 3H). Anal. Calculated for $C_{20}H_{19}N_3O_3 \cdot 10 H_2O \cdot 0.33$ AcOH: C, 64.08; H, 5.81; N, 10.85 Found: C, 64.23, 64.16; H, 5.66, 5.67; N, 10.83, 10.78.

The starting materials were made as follows:

N-Methyl-3(R)-[3-[4-(pyridin-4-yl)phenyl]-1H-pyrrol-1-yl]succinamic Acid Benyl Ester

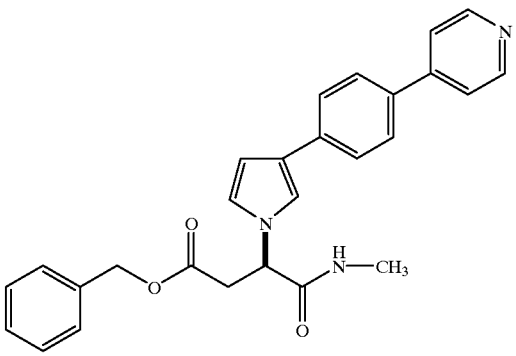

According to the procedure described in Example 1(b) for the preparation of 3(R)-t-butyloxycarbonylarnino-N-(2,2-dimethyl-1(S)-(methylcarbamoyl)propyl)succinamic acid benzyl ester, 2(R)-[3-[4-(pyridin-4-yl)phenyl]-1H-pyrrol-1-yl]succinic 4-benzyl ester hydrochloride (prepared as described in Example 7(a)) and excess 40% aqueousueous methylamine were coupled with TBTU. The solid that precipitated from the reaction mixture was washed with water and, after drying, with ethyl acetate to give 51% of N-methyl-3(R)-[3-[(4-(pyridin-4-yl)phenyl]-1H-pyrrol-1-yl]succinamic acid benzyl ester as a yellow solid:

H$_1$NMR (DMSO-d$_6$): δ_8.58 (d, 2H, J=4.4 Hz), 7.84 (br s, 1H), 7.76–7.70 (m, 4H), 7.60 (d, 2H, J=8.5 Hz), 7.29–7.25

(m, 6H), 6.76 (s, 1H), 6.40 (s, 1H), 5.03 (s, 2H), 4.67 (t, 1H, J=6.2 Hz), 3.20 (dd, 1H, J=15.8, 6.2 Hz), 2.86 (dd, 1H, J=16.0, 8.6 Hz), 2.32 (s, 3H); Anal. Calculated for $C_{27}H_{25}N_3O_3 \cdot 1.3\ H_2O$: C, 70.05; H, 6.01; N, 9.08. Found: C, 69.98, 66.97; H, 5.98, 6.00; N, 9.01, 9.00.

Example 8(a)

$N^1$-(1(S)-Benzyl-2-hydroxyethyl)-3(R)-[3-(biphenyl-4-yl)-1H-pyrrol-1-yl)-$N^4$-hydroxysuccinamide To a solution of N-(1(S)-benzyl-2-hydroxyethyl)-3(R)-(3-(biphenyl-4-yl)-1H-pyrrol-1-yl)succinamic acid (prepared as described in Example 1(a); 61 mg, 0.130 mmol) in $CHCl_3$ (2 mL) was added in succession NMM (44 μL, 0.39 mmol), benzotriazole-1-yloxy-tris-1H-pyrrolidino-phosphonium hexafluorophosphate (PyBOP, 203 mg, 0.390 mmol), and hydroxylamine hydrochloride (27 mg, 0.390 mmol). After 20 hours at ambient temperature, 10% aqueous HCl (2 mL) and saturated aqueous $NH_4Cl$ (10 mL) were added, and the resultant mixture extracted with $CHCl_3$ (15 mL) three times. The combined organic layers were washed with saturated aqueous $NH_4Cl$ (10 mL), dried over $Na_2SO_4$, and evaporated to provide a yellow solid, which was purified via flash column chromatography with 1% HOAc/10% MeOH/$CHCl_3$ as eluant. Subsequent radial chromatography with a 1% HOAc/5–10%MeOH/$CH_2Cl_2$ stepwise gradient eluant and azeotropic removal of HOAc with n-heptane gave 9 mg (14%) of $N^1$-(1(S)-benzyl-2-hydroxyethyl)-3(R)-(3-biphenyl-4-yl-1H-pyrrol-1-yl)-$N^4$-hydroxysuccinamide as a yellow solid.

$^1$H NMR ($CD_3OD$): δ6.90–6.79 (m, 1H), 6.58–6.76 (m, 1H), 5.18–5.02 (m, 1H), 4.19–4.01 (m, 1H), 3.00–2.84 (m, 1H), 2.84–270 (m, 3H). IR ($CHCl_3$): 3244, 3018, 1659, 1208, 1201 $cm^{-1}$. HRFABMS: Calculated for $C_{29}H_{30}N_3O_4$ (M+H$^+$): 483.2158. Found: 483.2139. Anal. Calculated for $C_{29}H_{30}N_3O_4 \cdot NH_2OH \cdot 0.2\ CHCl_3 \cdot 0.25\ H_2O$: C, 64.35; H, 6.05; N, 10.28. Found: C, 64.13; H, 5.69; N, 10.56.

The following was made in a similar manner:

Example 8(b)

$N^1$-(1(S)-Benzyl-2-methoxyethyl)-3(R)-[3-(biphenyl-4-yl)-1H-pyrrol-1-yl)-$N^4$-hydroxysuccinamide According to the procedure described in Example 8 (a), N-(1(S)-benzyl-2-methoxyethyl)-3(R)-(3-biphenyl-4-yl-1H-pyrrol-1-yl)succinamic acid (prepared as described in Example 1(f)) and hydroxylamine hydrochloride were coupled with BOP and triturated with MTBE/$CH_2Cl_2$/hex to give in 62% yield $N^1$-(1(S)-Benzyl-2-methoxyethyl)-3(R)-[3-(biphenyl-4-yl)-1H-pyrrol-1-yl)-$N^4$-hydroxysuccinamide as a solid, mp 180–2° C. (d).

$^1$H NMR (DMSO-$d_6$): δ8.80 (s, 1H), 8.26 (d, 1H, J=8.5 Hz), 7.65–7.49 (m, 6H), 7.41 (t, 2h, J=7.4 Hz), 7.31–7.12 (m, 7H), 6.73 (s, 1H), 6.40 (s, 1H), 5.06–5.01 (m, 1H 4.00–3.95 (m, 1H), 3.19 (d, 2H, J=5.2 Hz), 3.14 (s, 3H), 2.81–2.29 (m, 4H). Anal. Calculated for $C_{30}H_{31}N_3O_4$: C, 72.41; H, 6.28; N, 8.44. Found: C, 72.24; H, 6.29; N, 8.39.

Example 8(c)

$N^4$-Hydroxy-$N^1$-(9-oxo-1,8-diaza-tricyclo[10.6.1.0$^{13,18}$]nonadeca-12(19),13,15,17-tetraen-10S-yl)-3(R)-1H-(pyrrol-1-yl)succinamide A mixture of $N^1$-benzyloxy-$N^4$-(9-oxo-1,8-diaza-tricyclo[10.6.1.0$^{13,18}$]nonadeca-12(19),13,15,17-tetraen-10S-yl)-3(R)-1H-pyrrol-1-yl-succindiarnide (180 mg, 0.324 mmol) and 10% Pd/C (40 mg) in THF (250 mL) with a minimal amount of EtOH was stirred under $H_2$ atmosphere. After 3.5 hours, the catalyst was filtered off and rinsed with THF and EtOH. The filtrate was concentrated to about 40 mL, whereupon product precipitated. Filtration provided $N^4$-hydroxy-$N^1$-(9-oxo-1,8-diaza-tricyclo[10.6.1.0$^{13,18}$]nonadeca-12(19),13,15,17-tetraen-10S-yl)-3(R)-1H-(pyrrol-1-yl)

succinamide as a solid, mp 158–65° C. FABMS: 466.1 ($C_{25}H_{32}N_5O_4$; M+H⁺).

Example 9

N¹-[2,2-Dimethyl-1(S)-(hydroxymethyl)propyl]-N⁴-hydroxy-2(R)-[3-[4-(pyridin-4-yl)phenyl]-1H-pyrrol-1-yl]succinamide

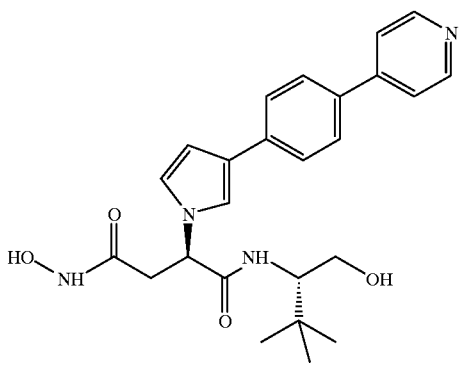

To a solution of N⁴-t-butyldiphenylsiloxy-N¹-[2,2-Dimethyl-1(S)-(hydroxymethyl)propyl]-2(R)-[3-[4-(pyridin-4-yl)phenyl]-1H-pyrrol-1-yl]succinamide (112 mg, 0.160 mmol) in THF (5 mL) was added a solution of tetra-n-butylanimonium fluoride (0.20 mL of 1M in THF). After 1.25 hours at ambient temperature, the mixture was added dropwise to 1M pH7 phosphate buffer (40 mL). The resultant precipitate was collected by filtration and washed with $H_2O$. A solution in $CH_2Cl_2$/MeOH was passed through a 0.45μ syringe filter, and the filtrate was concentrated to give a solid which was triturated with EtOH to yield 30 mg (42%) of N¹-[2,2-Dimethyl-1(S)-(hydroxymethyl)propyl]-N⁴-hydroxy-2(R)-[3-[4-(pyridin-4-yl)phenyl]-1H-pyrrol-1-yl]succinamide as an amorphous solid, which decomposed >200° C.

¹H NMR ($CD_3COOD$): δ8.91 (d, 2H, J=6.6 Hz), 8.23 (d, 2H, J=7.0 Hz), 7.93 (d, 2H, J=8.8 Hz), 7.76 (d, 2H, J=8.5 Hz), 7.42 (s, 1H), 6.95 (s, 1H), 6.60 (s, 1H), 5.44 (t, 1H, J=7.4 Hz), 3.92–3.88 (m, 2H), 3.63–3.55 (m, 1H), 3.21 (dd, 1H, J=6.4, 14.5 Hz), 3.03 (dd, 1H, J=8.1, 15.1 Hz), 0.93 (s, 9H). Anal: Calculated for $C_{25}H_{30}N_4O_4 \cdot 0.4 H_2O$: C, 66.08; H, 6.96; N, 11.95. Found: C, 65.92; H, 6.79; N, 11.86.

The starting material was available as follows:

N⁴-t-butyldiphenylsiloxy-N¹-[2,2-Dimethyl-1(S)-(hydroxymethyl)propyl ]-2(R)-[3-[4-(pyridin-4-yl)phenyl]-1H-pyrrol-1-yl]succinamide

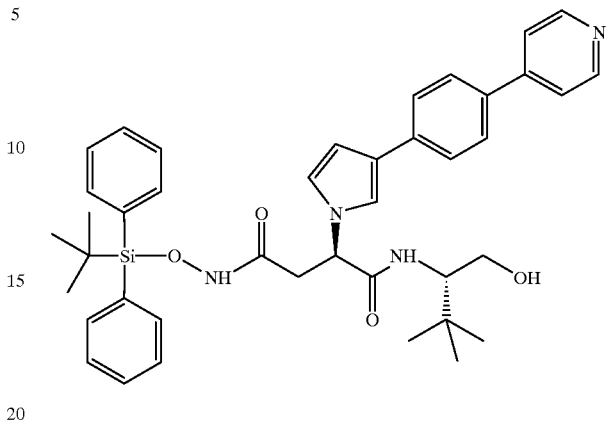

According to the procedure described in Example 1(b) for the preparation of 3(R)-t-butyloxycarbonylamino-N-(2,2-dimethyl-1(S)-(methylcarbamoyl)propyl)succinamic acid benzyl ester, N-(2,2-dimethyl-1(S)-hydroxymethyl-propyl)-3(R)-[3-[4-(pyridin-4-yl)phenyl]-1H-pyrrol-1-yl] succinamic acid (prepared as described in Example 5(a)) and t-butyldiphenylsiloxyamine were coupled with TBTU. Flash column chromatography with 0–5% MeOH/$CH_2Cl_2$ gradient eluant furnished in 43% yield N¹-t-butyldiphenylsiloxy-N⁴-[2,2-Dimethyl-1(S)-(hydroxymethyl)propyl]-2(R)-[3-[4-(pyridin-4-yl)phenyl]-1H-pyrrol-1-yl]succinamide as an amorphous solid.

¹H NMR (DMSO-$d_6$): δ10.73 (s, 1H), 8.59 (d, 2H, J=6.3 Hz), 7.85–7.70 (m, 5H), 7.65–7.56 (m, 6H), 7.45–7.34 (m, 6H), 7.29 (s, 1H), 6.79 (s, 1H), 6.43 (s, 1H), 5.20–5.14 (m, 1H), 4.38–4.36 (m, 1H), 3.54–3.50 (m, 2H), 2.82–2.70 (m, 1H), 0.99 (s, 9H), 0.84 (s, 9H). Anal: Calculated for $C_{41}H_{48}N_4O_4Si \cdot 0.4 H_2O$: C, 70.74; H, 7.07; N, 8.05. Found: C, 70.83; H, 7.04; N, 8.33.

Example 10(a) cl 2S-[1R-(1(S)-Benzyl-2-hydroxyethylcarbamoyl)-(3-biphenyl-4-yl-1H-pyrrol-1-yl)-methyl]-pentanoic Acid

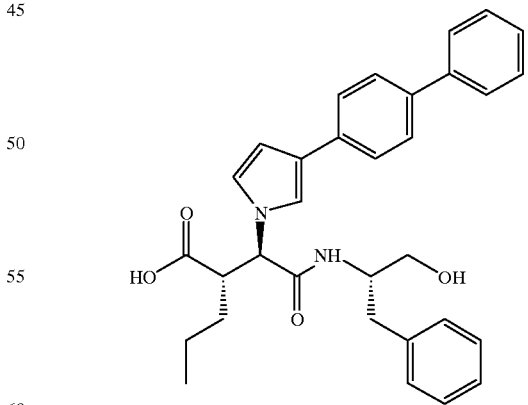

According to the procedure described in Example 1(a), 2S-[1R-(1(S)-benzyl-2-hydroxyethylcarbamoyl)-(3- biphenyl-4-yl-1H-pyrrol-1-yl)-methyl]-pent-4-enoic acid benzyl ester (50 mg, 0.08 mmol) was hydrogenolyzed in EtOAc (1 mL) and MeOH (1 mL). Radial chromatographic purification with 1% HOAc/1–2% MeOH/CH$_2$Cl$_2$ gradient eluant provided 24 mg (55%) of 2S-[1R-(1(S)-benzyl-2-hydroxyethylcarbamoyl)-(3-biphenyl-4-yl-1H-pyrrol -1-yl)-methyl]-pentanoic acid as a slightly pink powder, mp 179–81° C. (d).

$^1$H NMR: ∂7.64–7.54 (m, 5H), 7.47–7.42 (m, 2H), 7.36–7.06 (m, 3H), 6.83 (bs, 1H), 6.54 (bs, 1H), 4.56 (d, 1H, J=8.4 Hz), 4.27–4.10 (bm, 1H), 3.74–3.61 (bm, 1H), 3.50–3.39 (bm, 2H), 2.83 (dd, 1H, J=6.2, 13.4 Hz), 2.70 (dd, 1H, J=8.7, 13.4 Hz), 1.69–1.52 (bm, 1H), 0.87 (t, 3H, J=7.1 H HRLSIMS: Calculated for C$_{33}$H$_{34}$N$_2$O$_4$Cs (M+Cs$^+$): 643.1573. Found: 643.1594. Anal. Calc'd for C$_{32}$H$_{34}$N$_2$O$_4$. 0.5H$_2$O:C, 73.96; H, 6.79; N, 5.39. Found: C, 74.02; H, 6.79; N, 5.41.

The starting materials were made as follows:

Diallyl D-Aspartate p-Toluenesulfonate Salt

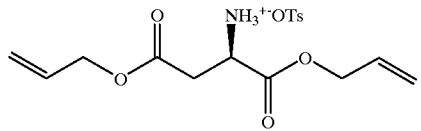

A mixture of D-aspartic acid (4.00 g, 30.1 mmol), allyl alcohol (12.4 mL, 181 mmol), p-toluenesufonic acid hydrate (7.15 g, 37.6 mmol) and benzene (35 mL) was refluxed with removal of water via Dean-Stark trap. After 4 hours, the resultant yellow solution was allowed to cool and then concentrated in vacuo to a yellow solid, which was dissolved in a minimal amount of hot MeOH (~15 mL). The solution was diluted with Et$_2$O (200 mL), and upon gradual addition of hexanes (~100 mL), pale yellow crystals were obtained. Filtration gave 10.00 g (86% yield) of diallyl D-aspartate p-toluenesulfonate salt as analytically pure crystals, mp 60–61° C.

$^1$H NMR: ∂8.40–8.10 (bm, 3H), 7.72 (d, 2H, J=8.1 Hz), 7.12 (d, 2H, J=8.1 Hz), 5.76 (dddd, 2H, J=2.5, 2.5, 8.7, 13.1 Hz), 5.23 (ddd, 2H, J=2.8, 8.7. 13.1 Hz), 5.18 (dd, 2H, J=2.8, 13.1 Hz), 4.58 (ddd, 1H, J=5.6, 13.1, 13.1 Hz), 4.49 (dd, 2H, 1.6, 4.4 Hz), 3.15 (ddd, 2H, J=5.0, 18.1, 18.1 Hz), 3.09 (ddd, 2H, J=5.2, 18.1, 18.1 Hz), 2.17 (s, 3H). IR (KBr): 3436, 2923, 1734, 1215, 1126, 1035, 1011, 685, 569 cm$^{-1}$. Anal. Calculated for C$_{17}$H$_{23}$NO$_7$S .0.5 H$_2$O: C, 51.76; H, 6.13; N, 3.55; S, 8.13. Found: C, 51.61; H, 6.06; N, 3.60; S, 8.04.

Diallyl N-t-Butoxycarbonyl-D-Aspartate

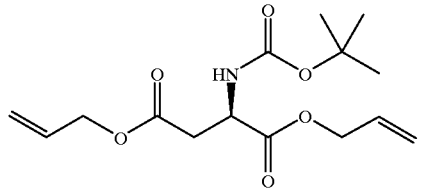

To a solution of diallyl D-aspartate p-toluenesulfonate salt (5.00 g, 13.0 mmol) in CH$_2$Cl$_2$ (50 mL) was added triethylamine (1.99 mL, 14.3 mmol) and di-t-butyl dicarbonate (3.12 g, 14.3 mmol). After 20 hours at ambient temperature, the resultant mixture was stirred with 10% aqueous HCl (5 mL) and H$_2$O (25 mL). The organic layer was separated, washed with saturated aqueous NaHCO$_3$:H$_2$O(2×25:25 mL), dried over Na$_2$SO$_4$, and evaporated to give a yellow oil, which was fractionally distilled under vacuum to remove t-BuOH as a forefraction and gave 3.33 g (82%) of diallyl D-N-t-butoxycarbonyl-aspartate as a colorless oil, bp 160–170° C. (1 mm Hg).

$^1$H NMR: ∂5.90 (dddd, 2H, J=4.7, 10.5, 10.6, 17.1 Hz), 5.51 (bd, 1H, J=8.7 Hz), 5.31 (dddd, 2H, J=1.6, 1.6, 5.9, 17.1 Hz), 5.24, (dd, 2H, J=1.3, 10.3 Hz), 4.68–4.55 (m, 5H), 3.05 (dd, 1H, J=4.7, 17.1 Hz), 2.87 (dd, 1H, J=4.7, 17.1 Hz), 1.45 (s, 9H). IR: 1736, 1719, 1501. 1368, 1166 cm$^{-1}$. Anal. Calculated for C$_{15}$H$_{23}$NO$_6$: C, 57.50; H, 7.40; N, 4.47. Found: C, 57.35; H, 7.39; N, 4.44.

α-Allyl 3(R)-Allyl-N-t-butoxycarbonyl-D-aspartate

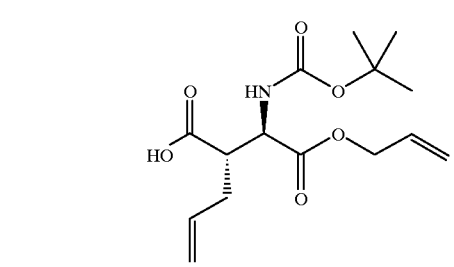

To a solution of diallyl N-t-butoxycarbonyl-D-aspartate (15.00 g, 47.9 mmol) in THF (300 mL) at –78° C. was added a solution of lithium hexamethyldisilazide (96.0 mL of 1.0M in THF) dropwise via addition funnel over 10 minutes. After 30 minutes at –78° C., trimethylsilylchloride (12.2 mL, 96.0 mmol) was added dropwise via addition funnel over 7 minutes, and the resultant gold solution was allowed to warm slowly over 1 hour to ambient temperature. The solution was then heated at 55–65° C. After 1 hour, the mixture was allowed to cool, and MeOH (105 mL) was added, whereupon a yellow suspension resulted. After 5 minutes, the solvent was removed via evaporation at reduced pressure to give a yellow solid, which was stirred with 10% aqueous KHSO$_4$ (100 mL), H$_2$O (100 mL), and extracted with CHCl$_3$ (100 ml) three times. The combined organic layers were washed with saturated aqueous NH$_4$Cl:H$_2$O(100: 100 mL), dried over Na$_2$SO$_4$, and evaporated to give 16.2 g of brown oil, which was purified via flash column chromatography with silica gel. Elution with 1% HOAc/3% MeOH/CH$_2$Cl$_2$ provided 14.94 g (100%) of an (80:20) mixture of epimers by NMR of α-allyl 3(R)-allyl-N-t-butoxycarbonyl-D-aspartate as a light brown oil. This material was routinely used without further purification.

$^1$H NMR: ∂9.00–8.24 (bs, 1H), 5.99–5.72 (m, 2H), 5.53–5.08 (m, 4H), 4.71–4.55(m, 2H), 3.25(ddd, 0.2H, min isomer, J=3.4, 6.2, 7.5 Hz), 2.97 (ddd, 0.8H, major isomer, J=4.7, 7.2, 11.8 Hz), 2.68–2.51 (m, 1H), 2.47–2.30 (m, 1H), 1.42 (s, 9H). IR: 3330, 3082, 2980, 1737, 1715, 1369, 1251, 1163 cm$^{-1}$. Anal. Calculated for C$_{15}$H$_{23}$NO$_6$.0.15 H$_2$O: C, 57.00; H, 7.43; N, 4.43. Found: C, 56.94; H, 7.45; N, 4.31.

123

α-Allyl, β-Benzyl 3(R)-Allyl-t-butoxycarbonyl-D-aspartate

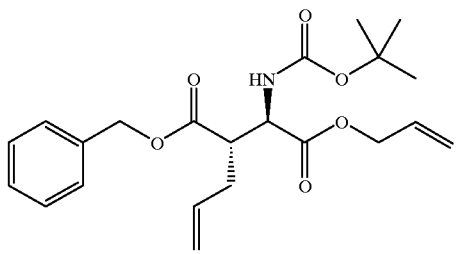

To a solution of α-allyl 3(R)-allyl-N-t-butoxycarbonyl-D-aspartate (213 mg, 0.681 mmol) in $CHCl_3$ (2 mL) was added O-benzyl-N,N'-diisopropylisourea (see Mathias, L. J. Synthesis 1979, 561–576, 165 μL, 1.02 mmol). The resultant solution was heated at reflux for 5.5 hours, allowed to cool, filtered to remove urea byproduct, and evaporated to furnish a suspension, which was purified by passage through a pad of silica gel with 10% EtOAc/hex as eluant to provide 270 mg (100%) of α-allyl, β-benzyl 3(R)-allyl-t-butoxycarbonyl-D-aspartate as a colorless oil.

$^1$H NMR: ∂7.36 (bs, 5H), 5.86 (ddt, 1H, J=5.9, 10.6, 16.2 Hz), 5.76 (ddt, 1H, 6.9, 10.0, 17.1 Hz), 5.30 (ddd, 1H J=1.2, 2.8, 17.1 Hz), 5.31 (bs, 1H), 5.24 (ddd, 1H, J=0.9, 1.2, 10.4 Hz), 5.11 (s, 2H), 5.07 (quintet, 1H, J=1.6 Hz), 5.04 (bs, 1H), 4.66 (dd, 1H, J=4.9, 8.9 Hz), 4.57 (d, 2H, J=5.6 Hz), 3.00(bq, 1H, J=7.5 Hz), 2.59 (ddd, 1H, J=7.5, 8.1, 14.6 Hz) 2.37 (ddd, 1H J=6.9, 13.7, 14.0 Hz), 1.43 (s, 9H). IR: 3374, 2979, 1730, 1504, 1368, 1163, 989 $cm^{-1}$. Anal. Calculated for $C_{22}H_{29}NO_6$: C, 65.49; H, 7.24;N, 3.47 Found: C, 65.46; H, 7.25; N, 3.45.

β-benzyl3(R)-Ally-N-t-butoxycarbonyl-D-aspartate

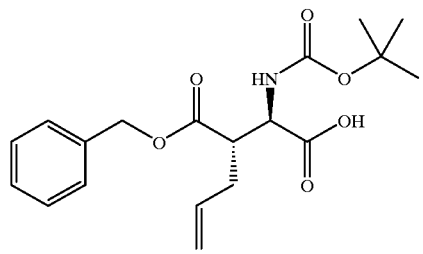

As in example 1(p), α-allyl, β-benzyl 3(R)-allyl-t-butoxycarbonyl-D-aspartate (216 mg, 0.535 mmol) was deprotected. Flash column chromatography with 1% HOAc/30% EtOac/hex as eluant provided 154 mg (79%) of β-benzyl 3(R)-allyl-N-t-butoxycarbonyl-D-aspartate as a yellow oil.

$^1$H NMR ($CDCl_3$): δ7.40–7.20 (m, 5H), 6.75 (bs, 1H), 5.68 (dddd, 1H, J=7.2, 10.0, 10.0, 165 Hz), 598 (d, 1H, J=9.7 Hz), 5.18–4.95 (m, 2H), 4.47(dd, 1H, J=3.4, 10.0 Hz) 3.15 (ddd, 1H, J=3.4, 5.9, 8.4 Hz) 2.45 (ddd, 1H, J=6.3, 7.1, 13.5 Hz), 2.26 (ddd, 1H, J=7.8, 8.7, 13.5 Hz), 1.38 (s, 9H), IR: 3425, 2978, 1722, 1499, 1164 $cm^{-1}$; Anal. Calcd for $C_{19}H_{25}NO_6 \cdot 0.15 \, C_6H_{14}$: C, 63.51; H, 7.26; N, 3.72. Found: C, 63.50; H, 693; N, 3.44.

124

2S-[1R-(1(S)-Benzyl-2-hydroxyethylcarbamoyl)-1-(t-butoxycarbonylamino)methyl]-pent-4-enoic Acid Benzyl Ester

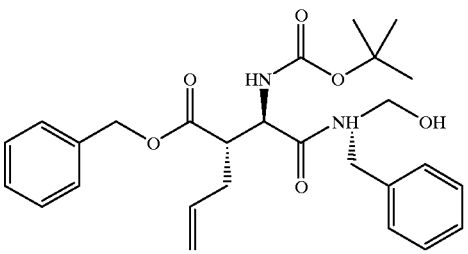

According to the procedure described in Example I(a) for the preparation of N-(1(S)-benzyl-2-hydroxyethyl)-3(R)-t-butoxycarbonyl-amino-succinamic acid benzyl ester, β-benzyl 3(R)-allyl-N-t-butoxycarbonyl-D-aspartate was coupled with EDC to 2S-amino-3-phenyl-1-propanol to give 2.30 g (67%) of 2S-[1R-(1(S)-benzyl-2-hydroxyethylcarbamoyl)-1-(t-butoxycarbonylamino) methyl]-pent-4-enoic acid benzyl ester as white solid.

$^1$H NMR: ∂7.31(m, 5H), 7.20(m, 5H), 6.59(d, 1H, J=8.1 Hz), 5.78 (d, 1H, J=9.0 Hz), 5.71 (ddd, 1H, J=6.9, 9.7, 16.5 Hz), 5.09 (m, 4H), 4.31 (dd, 1H, J=4.2, 9.0 Hz), 4.10(m, 1H), 3.63(d, 1H, J=11.8 Hz), 3.48 (d, 1H, J=11.8 Hz), 3.28 (dd, 1H, J=7.8, 10.9 Hz), 2.83 (ddd, 2H, J=7.3, 13.9, 21.6 Hz), 2.46 (s, 1H), 2.39 (ddd, 1H, J=6.5, 6.9, 13.7 Hz), 2.20 (ddd, 1H, J=7.8, 8.1, 15.0 Hz), 1.44(s, 9H). IR (KBr): 3319, 1735, 1686, 1654, 1560, 1542, 1522, 1297 $cm^{-1}$. HRLSIMS: Calculated for $C_{28}H_{36}N_2O_6Cs$ $(M+Cs^+)$: 629.1628. Found: 629.1603. Anal. Calculated for $C_{28}H_{36}N_2O_6$: C, 67.71; H, 7.32; N, 5.64. Found: C, 67.68; H, 7.37; N, 5.64.

2S-[1R-(1(S)-Benzyl-2-hydroxyethylcarbamoyl)-(3-biphenyl-4-yl-1H-pyrrol-1-y)-methyl]-pent-4-enoic Acid Benzyl Ester

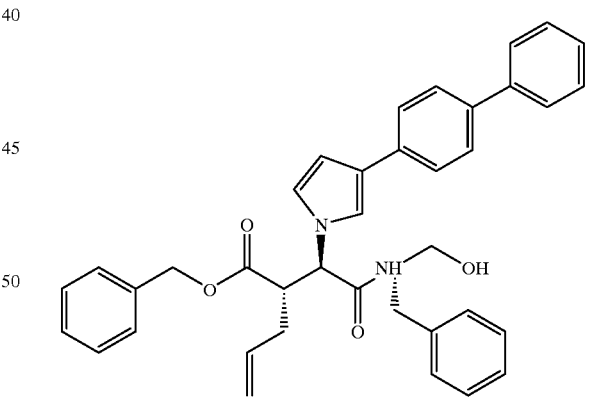

According to the procedure described in Example 1(a) for the preparation of N-(1(S)-benzyl-2-hydroxyethyl)-3(R)-(3-biphenyl-4-yl-1H-pyrrol-1-yl)succinamic acid benzyl ester, 2S-[1R-(1(S)-benzyl-2-hydroxyethylcarbamoyl)-1-(t-butoxycarbonylamino)methyl]-pent-4-enoic acid benzyl ester was deprotected and the crude amine salt condensed with 3-biphenyl-4-yl-2,5-dimethoxy-tetrahydrofuran in HOAc. Radial chromatography with 1% MeOH/$CH_2Cl_2$ as eluant provided 77 mg (30%) of 2S-[1R-(1(S)-benzyl-2-hydroxyethylcarbamoyl)-(3-biphenyl-4-yl-1H-pyrrol-1-yl)-methyl]-pent-4-enoic acid benzyl ester, mp 166–7° C.

¹H NMR: ∂7.68–6.97 (m, 20H), 6.69 (dd, 1H, J=2.5, 2.8 Hz), 6.53 (dd, 1H, J=1.6, 2.8 Hz), 5.79 (d, 1H, J=7.5 Hz), 5.69 (dddd, 1H, J=6.5, 8.2, 10.0, 16.9 Hz), 5.15–4.94 (m, 4H), 4.57 (d, 1 H, J=7.2 Hz), 4.28–4.19(bm, 1H), 3.73–3.63 (bm, 2H 3.50 (ddd, 1H, J=5.3, 5.3, 11.5 Hz), 2.81 (dd, 1H, J=6.2, 13.8 Hz), 2.68 (dd, 1H, J=8.2, 13.8 Hz), 2.59–2.44 (m, 2H), 2.10 (ddd, 1H, J=7.1, 7.1, 14.3 Hz). HRLSIMS: Calculated for $C_{39}H_{38}N_2O_4Cs$ (M+Cs⁺): 731.1886. Found: 731.1853. Anal. Calculated for $C_{39}H_{38}N_2O_4$: C, 78.29; H, 6.42; N, 4.68. Found: C, 78.17, H, 6.43; N, 4.63.

The following compounds were made in a similar manner:

Example 10(b)

2(RS)-{1R-[1(S)-Benzyl-2-hydroxyethylcarbamoyl- [3-(4'-cyano -biphenyl-4-yl)-1H-pyrrol-1-yl]- methyl}-pentanoic Acid

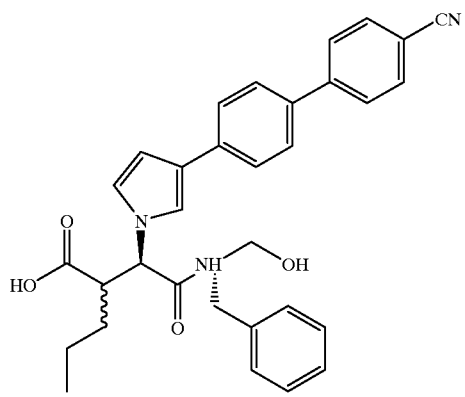

According to the procedure described in Example 1(a), 2(RS)-{1R-[(1(S)-benzyl-2-hydroxyethylcarbamoyl]-[3-(4'-cyano-biphenyl-4-yl)-1H-pyrrol-1-yl]-methyl}-pent-4-enoic acid benzyl ester was hydrogenated in EtOAc and MeOH. Flash column chromatography with 1% HOAc/1% MeOH/CH$_2$Cl$_2$ as eluant gave 29 mg (69%) of 2(RS)-{1R-[1(S)-benzyl -2-hydroxyethylcarbamoyl]-[3-(4'-cyano-biphenyl-4-yl)-1H-pyrrol-1-yl]-methyl}-pentanoic acid as a yellow powder.

¹H NMR: δ7.72 (s, 4H), 7.60 (s, 5H), 7.21–6.99 (bm, 6H), 6.70 (s, 1H), 6.58 (s, 1H), 4.70 (d, 0.67H, major isomer, J=10.3 Hz), 4.62 (d, 0.33H, minor isomer, J=6.5 Hz), 4.19 (bs, 0.33H, minor isomer), 4.02 (bs, 0.67H, major isomer), 3.25–3.14 (bm, 1H), 2.78 (d, 2H, J=7.0 Hz). IR (KBr): 3334, 2226, 1652, 1604, 1558, 1496, 1200, 824 cm⁻¹. HRFABMS: Calculated for $C_{33}H_{34}N_3O_4$(M+H⁺): 536.2549. Found: 536.2555; Anal. Calculated for $C_{33}H_{33}N_3O_4$.0.8 HOAc: C, 71.20; H, 6.25; N7.20. Found: C, 71.21; H, 6.49; N, 7.25.

The starting material was available as follows:

2(RS)-[1(R)-[1(S)-Benzyl-2-(hydroxyethyl) carbamoyl]-1-[3-(4'-cyanobiphenyl-4-yl)-1H-pyrrol- 1-yl]methyl]pent-4-enoic Acid Benzyl Ester

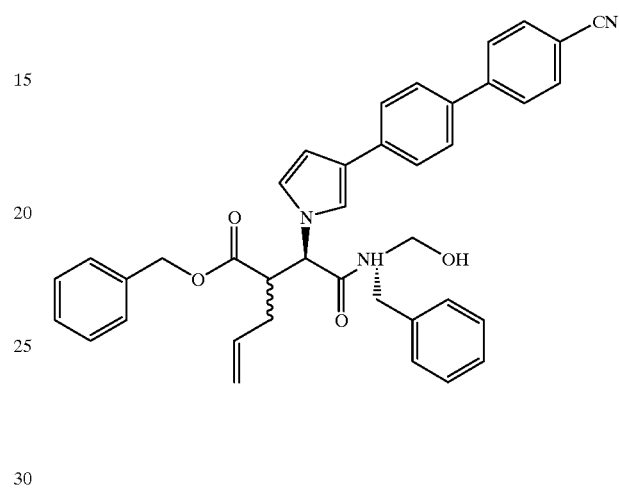

According to the procedure described in Example 1(c) for the preparation of N-(8-oxo-4-oxa-1,7-diaza-tricyclo [9.6.1.0$^{12,17}$]octadeca-11(18),12,14,16-tetraen-9S-yl)-3(R)- (3-phenyl-1H-pyrrol-1-yl) succinamic acid benzyl ester, β-benzyl 3(R)-allyl-N-t -butoxycarbonyl-D-aspartate was deprotected. The corresponding amine salt and 4'-(2,5-dimethoxy-tetrahydrofuran-3-yl)-biphenyl-4-carbonitrile were condensed in 1,2-dichloroethane with trifluoroacetic acid under anhydrous conditions and purified via radial chromatography with 0–20–30–40% EtOAc/hex stepwise gradient to give 168 mg (51%) of 2(RS)-[1(R)-[1(S)-Benzyl-2-(hydroxyethyl)carbamoyl]-1-[3-(4'-cyanobiphenyl-4-yl)-1H -pyrrol-1-yl]methyl]pent-4-enoic acid benzyl ester as a gold powder, mp 84° C., which was used without further purification.

¹H NMR: δ7.72 (d, 2H, J=3.1 Hz), 7.64–7.50 (m, 3H), 7.41–6.96 (m, 4H), 6.72 (t, 0.33H, minor isomer, J=2.5 Hz), 6.68(t, 0.67H, major isomer, J=2.5 Hz), 6.57 (dd, 0.67H, major isomer, J=1.8, 2.8 Hz), 6.52 (dd, 0.33H, minor isomer, J=1.6, 2.8 Hz), 5.83 (d, 1H, J=7.8 Hz), 5.62(dddd, 1H, J=6.5, 7.8, 10.3, 16.8 Hz), 5.18 (d, 2H, J=1.2 Hz), 4.73 (d, 0.67H, major isomer, J=10.6 Hz), 4.57(d, 0.33H, minor isomer, J=7.8 Hz), 4.15 (bm, 1H), 3.99 (dddd, 1H, J=5.0, 7.5, 7.5, 10.9 Hz), 3.75–3.48(m, 2H), 3.38 (dddd, 1H, J=5.3, 5.3, 5.3, 7.8 Hz), 2.93–2.64 (m, 2H). IR: 3406, 2226, 1731, 1660, 1605 cm⁻¹. HRFABMS: Calculated for $C_{40}H_{37}N_3O_4$(M+ H⁺): 624.2862. Found: 624.2875. Anal. Calculated for $C_{40}H_{37}N_3O_4$.0.25 EtOAc.0.5 H$_2$O: C, 75.2 1; H, 6.16; N, 6.42. Found: C, 75.29; H, 5.97; N, 6.42.

Example 10(c)

2S-[1R-(3-(4'-Cyanobiphenyl-4-yl)-1H-pyrrol-1-yl)-1-(2,2-dimethyl -1(S)-(hydroxymethyl) propylcarbamoyl)-methyl]-pentanoic Acid

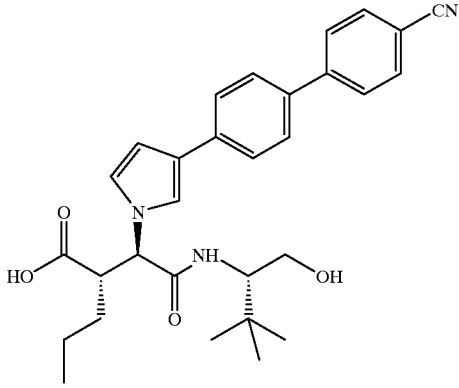

According to the procedure described in Example 1(a), 2S-[1R-(3-(4'-cyano -biphenyl-4-yl)-1H-pyrrol-1-yl)-N-(2, 2-dimethyl-1(S)-hydroxymethylpropyl-carbamoyl) -methyl)]-pentanoic acid benzyl ester was debenzylated in MeOH: EtOAc (2:3) after 18h to provide 30 mg (36%) of 2S-[1 R-(3-(4'-cyanobiphenyl-4-yl)-1H-pyrrol-1-yl)-1-(2,2-dimethyl -1(S)-(hydroxymethyl)propylcarbamoyl)methyl)]- pentanoic acid as a white solid, mp 130–2° C.

$^{1}$H NMR: ∂7.70(m, 4H), 7.60(m, 4H), 7.15(s, 1H), 6.85(s, 1H), 6.75 (s, 1H), 5.72 (d, 1H, J=8.7 Hz), 4.86(d, 1H, J=9.7 Hz), 3.90–3.82(m, 2H), 3.45–3.38(m, 1H), 3.30–3.20 (m, 1H), 1.45–1.10(m, 4H), 0.95(s, 3H), 0.90(s, 9H). IR (KBr): 3406, 2962, 2227, 1719, 1664, 1604, 1560, 1497, 1367, 1200 cm$^{-1}$. FABMS: 502 (M+H$^{+}$). Anal. Calculated for $C_{30}H_{35}N_{3}O_{4}$. 0.15 CHCl$_{3}$: C, 69.70; H, 6.82; N, 8.09. Found: C, 69.71; H, 6.83; N8.01.

The starting material was furnished as follows:

2S-[1R-(t-Butoxycarbonylamino-(2,2-dimethyl-1(S) -(hydroxymethyl)propylcarbamoyl)methyl]-pent-4-enoic Acid Benzyl Ester

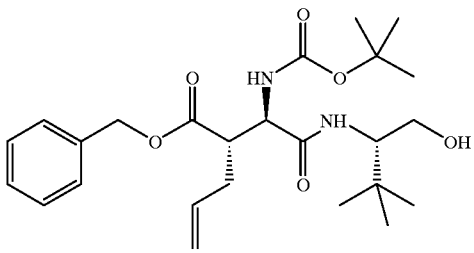

Following the procedure described in Example 1(f) for the preparation of N-(1(S) -benzyl-2-methoxyethyl)-3(R)-t-butoxycarbonylamino-succinamic acid benzyl ester, β-benzyl 3(R)-allyl-N-t-butoxycarbonyl-D-aspartate (154 mg, 0.424 mmol) was coupled with BOP to L-t-leucinol (55 mg, 0.466 mmol). Flash column chromatography with 5% MeOH/CH$_{2}$Cl$_{2}$ as eluant provided 176 mg (90% yield) of 2S-[1R-(t-butoxycarbonylamino-(2,2-dimethyl -1(S)-(hydroxymethyl)propylcarbamoyl)-methyl]-pent-4-enoic acid benzyl ester as waxy plates, mp 75–7° C.

$^{1}$H NMR: ∂7.43–7.20 (bs, 5H), 6.38 (d, 1H, J=9.7 Hz), 5.73 (dddd, 1H, J=7.2, 10.0, 10.3, 16.8 Hz), 5.60 (bm, 1H), 5.20–4.95(m, 4H), 4.40(dd, 1H, J=7.2, 8.4 Hz), 3.78(ddd, 2H, J=3.4, 9.3, 9.3 Hz), 3.50 (ddd, 1H, J=0.9, 8.7, 11.2 Hz), 2.98 (q, 1H, J=6.5 Hz), 2.55(ddd, 2H, J=7.2, 14.6, 14.6 Hz), 2.48 (ddd, 2H, J=7.2, 14.6, 14.6 Hz), 218 (bs, 1H), 1.42 (s, 9H), 0.95 (s, 9H); IR (KBr): 3363, 2996, 1734, 1708, 1654, 1508, 1367, 1253, 1173, 1055 cm$^{-1}$. Anal. Calculated for $C_{25}H_{38}N_{2}O_{6}$: C, 64.91; H, 8.28; N, 6.06. Found: C, 65.02; H, 8.33; N, 6.11.

2S-{1R-[3-(4'-Cyanobiphenyl-4-yl)-1H-pyrrol-1-yl]-(2,2-dimethyl-1(S) -(hydroxymethyl)propyl-carbamoyl)-methyl}-pent-4-enoic Acid Benzyl Ester

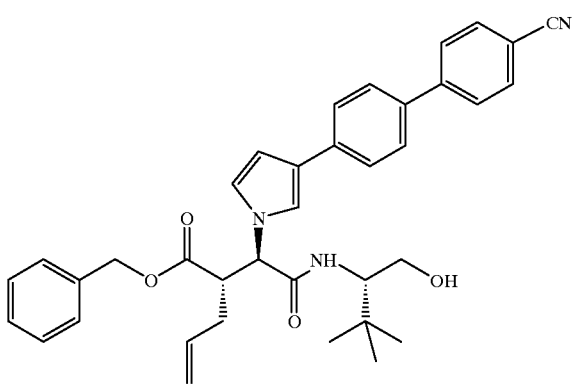

According to the procedure described in Example 4(a) for the preparation of N-(1(S) -benzyl-2-hydroxyethyl)-3(R)-[3-(4'cyano-biphenyl-4-yl)-1H-pyrrol-1-yl]succinamic acid benzyl ester, 2S-[1R-(t-butoxycarbonylamino-(2,2-dimethyl-1(S)-hydroxymethyl -propylcarbamoyl)-methyl]-pent-4-enoic acid benzyl ester was deprotected. The corresponding crude amine salt and 4'-(2,5-dimethoxy-tetrahydro-furan-3-yl)biphenyl-4-carbonitrile were condensed in 1,2-dichloroethane. Flash column chromatography with 1% HOAc/20% EtOAc/hex as eluant afforded 160 mg (63%) of 2S-{1R-[3-(4'-cyanobiphenyl -4-yl)-1H-pyrrol-1-yl]-(2,2-dimethyl-1(S)-(hydroxymethyl)propyl-carbamoyl)-methyl }-pent -4-enoic acid benzyl ester as a yellow foam, mp 74–6° C.

$^{1}$H NMR: δ7.70 (s, 4H), 7.50 (s, 4H), 7.20 (s, 5H), 7.05(s, 1H), 6.80(s, 1H), 6.60 (s, 1H), 5.60 (d, 1H, J=8.1 Hz), 5.20 (d, 2H, J=4.0 Hz), 5.05–4.82 (m, 3H), 3.86–3.68 (m, 2H), 3.30–3.10 (m, 2H), 2.30–2.20 (m, 1H), 1.70–1.50 (m, 2H), 0.90 (s, 9H). IR (KBr): 3358, 3067, 2962, 2226, 1732, 1682, 1604, 1557, 1496, 1360 cm$^{-1}$. Anal. Calculated for $C_{37}H_{39}N_{3}O_{4}$.0.35 CHCl$_{3}$: C, 70.69; H, 6.25; N, 6.62. Found: C, 70.81; H, 6.20; N, 6.70.

Example 11

2S-[1R-(3-(Biphenyl-4-yl)-1H-pyrrol-1-yl)-1-(1(S)-hydroxymethyl-2,2-dimethyl-propylcarbamoyl)-methyl]-5-hydroxypentanoic acid

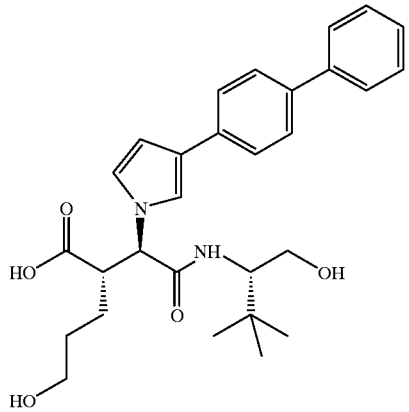

A suspension of palladium (II) hydroxide (20% Pd content on carbon, 30 mg) and 2S -[1R-(3-(biphenyl-4-yl)-1H-pyrrol-1-yl)-1-(1(S)-hydroxymethyl-2,2-dimethyl-propylcarbamoyl)-methyl]-5-hydroxypentanoic acid benzyl ester (120 mg, 0.141 mmol) in MeOH (20 mL) was stirred in an $H_2$ atmosphere for 2 hours. The catalyst was filtered onto Celite and rinsed with MeOH (20 mL). The filtrate was concentrated to afford 70 mg (100%) of 2S-[1R-(3-(biphenyl-4-yl)-1H-pyrrol-1-yl)-1-(1(S)-hydroxymethyl-2,2-dimethyl -propylcarbamoyl)-methyl]-5-hydroxypentanoic acid as white crystals.

$^1$H NMR (CD$_3$OD): δ7.70–7.55 (m, 6H), 7.43 (t, 2H, J=7.4 Hz), 7.38–7.27(m, 2H), 6.93 (dd, 1H, J=2.2,2.2 Hz), 6.53 (bm, 1H), 3.80–3.77 (m, 3H), 2.75–1.23(m, 4H), 0.97 (s, 9H). IR (KBr): 3406 2958, 1719, 1656, 1200, 763 cm$^{-1}$. FABMS: 493(M+H$^+$), 515 (MH+Na$^+$). Anal. Calculated for $C_{29}H_{36}N_2O_5$·0.2CHCl$_3$: C, 67.90; H, 7.06; N, 5.42. Found: C, 67.8; H, 7.11; N, 5.41.

The starting materials were made as follows:

2S-[1R-t-Butoxycarbonylamino-(2,2-dimethyl-1(S)-hydroxymethyl-propylcarbamoyl) -methyl]-5-hydroxy-pent-4-enoic Acid Benzyl Ester

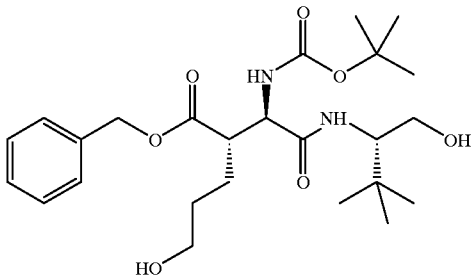

To a solution of BH$_3$. THF (6.93 mL of 1M in THF) at 0° C. was added cyclohexene (1.40 mL, 13.9 mmol) dropwise via syringe. After 5 minutes, the white suspension was diluted with dry THF (5 mL). After 15 minutes at 0° C., the dicyclohexylborane suspension was cautiously added via cannula to a solution of 2S-[1 R-t-butoxycarbonylamino-(2,2-dimethyl-1(S)-hydroxymethyl-propyl-carbamoyl)-methyl]-pent-4-enoic acid benzyl ester (1.07 g, 2.31 mmol) in dry THF (10 mL) at 0° C. and vigorous gas evolution was observed. After 10 minutes at 0° C., the resultant suspension was allowed to warm to ambient temperature. After 90 minutes, the mixture was treated in succession with pH7 phosphate buffer (50 mL), EtOH (20 mL), and 30% aqueous H$_2$O$_2$ (10 mL), and then allowed to stir overnight. After 20 hours at ambient temperature, the mixture was cooled to 0° C. and stirred with fresh 10% aqueous Na$_2$S$_2$O$_3$(100 mL). The mixture was allowed to warm to ambient temperature and extracted with CHCl$_3$(75 mL) three time. The combined organic layers were stirred with p-TsOH.OH$_2$O(100 mg) for 15 minutes, then washed with saturated aqueous NaHCO$_3$:H$_2$O(100: 100 mL), dried over Na$_2$SO$_4$, and evaporated to give 1.96 g of yellow oil, which was purified via flash column chromatography with 5% MeOH/CHCl$_3$ as eluant to afford 500 mg (45%) of 2S-[1R-t-butoxycarbonylamino-(2,2-dimethyl-1(S) -hydroxymethyl-propylcarbamoyl)-methyl]-5-hydroxy-pent-4-enoic acid benzyl ester as a white foam.

$^1$H NMR: δ7.45–7.20 (bs, 5H), 6.56 (d, 1H, J=9.7 Hz), 5.87 (d, 1H, J=7.8 Hz), 5.23–5.05 (m, 2H), 4.56 (dd, 1H, J=5.9, 8.4 Hz), 3.82 (ddd, 2H, J=3.4, 9.3, 11.8 Hz), 3.70–3.39 (m, 4H), 3.06 (ddd, 1H, J=5.9, 10.3, 10.3 Hz), 1.90–1.38(m, 4H), 0.98 (s, 9H), 0.95 (s, 9H). IR: 3342, 2955, 1718, 1696, 1682, 1661, 1522, 1367, 1249, 1166 cm$^{-1}$. Anal. Calculated for $C_{25}H_{40}N_2O_7$·0.4 CHCl$_3$: C, 57.74; H, 7.71; N, 5.30. Found: C, 57.74; H7.85; N, 5.42.

5-Benzyloxy-carboxy-2S-[1R-t-butoxycarbonylamino-(2,2-dimethyl-1(S)-hydroxymethyl -propyl-carbamoyl)-methyl]-pentanoic Acid Benzyl Ester

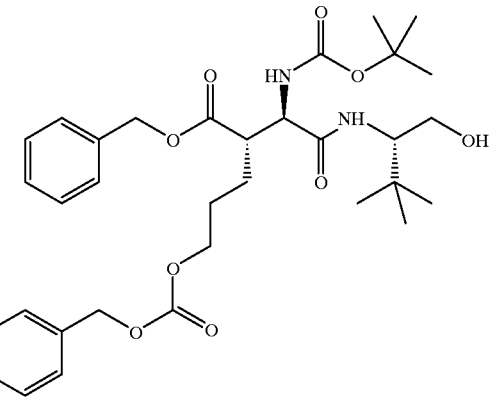

According to the procedure described in Example 5(a) for the preparation of carbonic acid N-(1(S)-benzyloxycarbonyloxymethyl-2,2-dimethyl-propyl)-3(R)-(t-butoxycarbonylamino)succinamic acid benzyl ester, 2S-[1R-t-butoxycarbonylamino-(2,2-dimethyl-1(S)-(hydroxymethyl)propylcarbamoyl)methyl]-5-hydroxy-pent4-enoic acid benzyl ester was initially acylated with benzyl chloroformate to give a yellow oil, which was purified via flash column chromatography with 4% MeOH/CHCl$_3$ as eluant to furnish 172 mg (46%) of 5-benzyloxycarboxy-2S-[1R-t-butoxycarbonylamino-(2,2-dimethyl-1(S) -(hydroxymethyl)propylcarbamoyl)methyl]-pentanoic acid benzyl ester as a colorless oil and 67 mg (17%) of 5-benzyloxycarboxy-2S-[(1(S)-benzyloxycarboxymethyl-2,2-dimethyl -propylcarbamoyl)-t-butoxycarbonyl-amino-methyl]-pentanoic acid benzyl ester.

$^1$H NMR: ∂7.45–7.20 (m, 10H), 6.38 (d, 1H, J=9.7 Hz), 5.48–5.32 (bm, 1H), 5.23–5.05 (m, 4H), 4.45–4.30 (m, 1H), 4.20–3.95 (m, 2H), 3.80–3.72(m, 2H), 3.55–3.40 (m, 1H), 3.00–2.89 (m, 1H), 2.08–1.55 (m, 4H), 1.42 (s, 9H), 0.95 (s, 9H). IR (KBr): 3322, 2964, 1741, 1664, 1264, 1169 cm$^{-1}$. FABMS: (M+Cs$^+$)747.

5-Benzyloxycarboxy-2S-[(1(S)-benzyloxycarboxymethyl-2,2-dimethyl-propylcarbamoyl)-t-butoxycarbonylamino-methyl]-pentanoic Acid Benzyl Ester

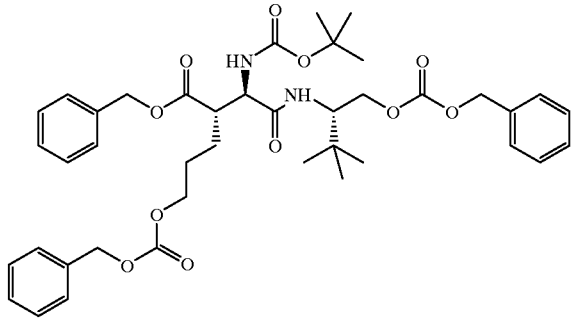

To a solution of 5-benzyloxycarboxy-2S-[1R-t-butoxycarbonylamino-(2,2-dimethyl -1(S)-hydroxymethyl-propylcarbamoyl)methyl]-pentanoic acid benzyl ester (170 mg, 0.277 mmol) in CHCl$_3$(3 mL) was added DMAP (68 mg, 0.692 mmol) and benzyloxychloroformate (100 μL, 0.692 mmol). After 2.5 hours, the mixture was stirred with 10% KHSO$_4$(15 mL) and extracted with CHCl$_3$ (10 mL two times). The CHCl$_3$ layers were washed with 10% aqueous KHSO$_4$(10 mL) and saturated aqueous NaHCO$_3$:H$_2$O (10:10 mL), dried over Na$_2$SO$_4$, and evaporated to provide a yellow oil, which was purified via flash column chromatography with 10–20–30% EtOAc/hex stepwise gradient. In this fashion, 135 mg (65%) of 5-benzyloxycarboxy-2S-[(1 (S)-benzyloxycarboxymethyl-2,2-dimethyl-propylcarbamoyl)-t-butoxycarbonylamino-methyl]-pentanoic acid benzyl ester was isolated as radial plates.

$^1$H NMR: ∂7.35–7.25 (m, 15H), 6.40 (bd, 1H, J=8.4 Hz), 5.22–5.04 (m, 6H), 4.48 (dd, 1H, J=6.9, 8.7 Hz), 4.33 (q, 1H, J=7.3 Hz), 4.16–3.95 (m, 4H), 367 (bm, 1H), 3.51 (dd, 1H, J=4.4, 5.3 Hz), 2.91 (ddd, 1h, J=3.7, 7.2, 10.3 Hz), 1.80–1.50 (m 4H), 1.41 (s, 9H), 0.93 (s, 9H). IR: 3330, 2964, 1743, 1263, 1170 cm$^{-1}$. HRFABMS: Calculated for C$_{41}$H$_{52}$N$_2$O$_{11}$Cs (M+Cs$^+$): 881.2625. Found: 881.2631.

2S-{1R-[(3-Bi-phenyl-4-yl)-1H-pyrrol-1-yl-(1(S)-hydroxymethyl-2,2-dimethyl -propylcarbamoyl)-methyl]}-5-hydroxypentanoic Acid Benzyl Ester

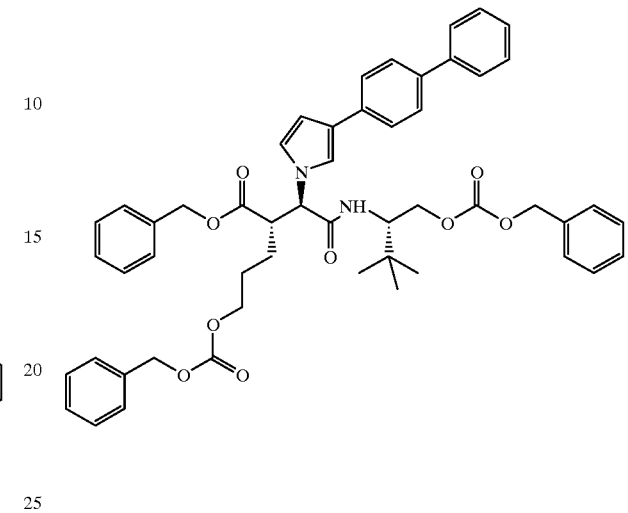

To a solution of 5-benzyloxycarboxy-2S-[(1(S)-benzyloxycarboxymethyl-2,2-dimethyl-propylcarbamoyl)-t-butoxycarbonylamino-methyl]-pentanoic acid benzyl ester (135 mg, 0.180 mmol) in CHCl$_3$(2 mL) was added trifluoroacetic acid (0.5 mL). After 4 hours at ambient temperature, the solvent was removed in vacuo to give a yellow oil that was placed with 3-biphenyl4-yl-2,5-dimethoxytetrahydro furan (66 mg, 0.23 mmol), trifluoroacetic acid (20 μL), and H$_2$O (20 μL) in ClCH$_2$CH$_2$Cl (1 mL). The mixture was heated to 70° C for 90 minutes, allowed to cool, and evaporated to give a brown oil. Flash column chromatography with 1%HOAc/20% EtOAc/hex as eluant and removal of HOAc via n-heptane azeotrope provided 126 mg (82%) of 2S-{1R-[(3-bi-phenyl-4-yl)-1H-pyrrol-1-yl-(1(S)-hydroxymet 2, 2-dimethyl-propylcarbamoyl)-methyl]}-5-hydroxypentanoic acid benzyl ester as a yellow solid.

H$^1$NMR: ∂7.59–7.50 (m, 9H), 7.44 (t, 2H, J=7.4 Hz), 7.38–7.20 (m, 13H), 7.04 (bm, 1H), 6.70 (dd, 1H, J=2.5, 2.5 Hz), 6.49 (bm, 1H), 5.57 (d, 1H, J=9.6 Hz), 5.22 (d, 1H, J=12.1 Hz), 5.14 ( d, 1H, J=12.1 Hz), 5.05(s, 2H), 4.97 (dd, 2H, J=12.1, 15.5 Hz), 4.84(d, 1H, J=10.3 Hz), 4.26 (dd, 1H, J=2.9, 11.0 Hz), 4.10–3.88 (m, 4H), 3.32–3.20 (m, 1H), 1.70–1.15 (m, 4H), 0.87 (s, 9H). IR (KBr): 2961, 1743, 1687, 1453, 1398, 1263, 1167, 763, 697 cm$^{-1}$. HRFABMS: Calculated for C$_{52}$H$_{54}$N$_2$O$_9$Cs (M+Cs$^+$): 983.2884. Found: 983.2861. Anal. Calculated for C$_{52}$H$_{54}$N$_2$O$_9$.0.15 CHCl$_3$: C, 72.02; H, 6.28; N, 3.22. Found: C, 72.03; H, 6.43; N, 3.26.

Example 12. 2S, 2(1S)-[3-(Biphenyl-4-yl)-1H-pyrrol-1R-yl]-[2,2-dimethyl-1(S) -(hydroxymethyl)propylcarbamoyl]methyl]pent4-enoic Acid

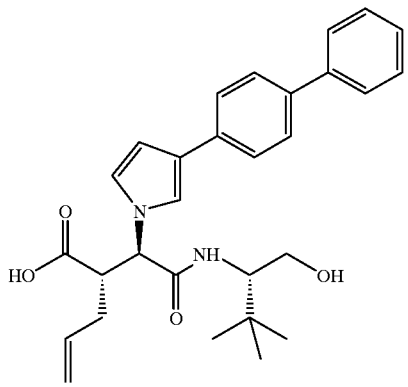

To a solution of 2R-[2(R)-(3-biphenyl4-yl-1H-pyrrol-1-yl)-2-(5R-iodomethyl-2-oxo -tetrahydrofuran-3(S)-yl)acetylamino]-3,3-dimethylbutyl 2,2,2-trichloroethyl carbonate (100 mg, 0.129 mmol) in HOAc (2 mL) was added zinc powder (86 mg, 1.3 mmol). After 24 hours at ambient temperature, the resultant mixture was partitioned with $H_2O$(25 mL) and $CHCl_3$ (15 mL). The aqueousueous layer was adjusted to pH 5 with saturated aqueous $NaHCO_3$ and extracted with $CHCl_3$ (10 mL) two times. The $CHCl_3$ layers were dried over $Na_2SO_4$ and evaporated to give a white solid, which was purified via radial chromatography with a 0.5% HOAc/5–10% MeOH/$CHCl_3$ stepwise gradient to furnish 32 mg (50%) of 2S, 2(1S)-[[3-(iphenyl-4-yl)-1H-pyrrol-1R-yl]-[2,2-dimethyl-1(S) -(hydroxymethyl)propylcarbamoyl]methyl]pent-4-enoic acid as a pale yellow solid.

$^1$H NMR (DMSO-$d_6$): $\partial$7.89 (d, 1H, J=9.3 Hz), 7.80–7.50 (m, 6H), 7.44 (t, 2H, J=7.8 Hz), 7.36–7.23 (m, 2H), 6.88 (bm, 1H), 6.49 (bm, 1H), 5.68 (ddd, 1H, J=7.5, 9.3, 16.8 Hz), 5.03–4.78 (m, 2H), 2.09–1.85 (m, 2H), 0.83 (s, 9H). IR (KBr): 3384, 3240, 2960, 2916, 1743, 1717, 1651, 1562, 1456, 1362, 1240, 1196, 758 $cm^{-1}$. HRFABMS: Calculated for $C_{29}H_{33}N_2O_4Cs$ (M+$Cs^+$): 607.1573. Found: 607.1555. Anal. Calculated for $C_{29}H_{34}N_2O_4 \cdot 0.17\ CHCl_3$: C, 70.80; H, 6.96; N, 5.66. Found: C, 70.76; H, 7.03; N, 5.55.

The starting material was furnished as follows:

2(R)-t-Butoxycarbonylamino-2-(5R-iodomethyl-2-oxo-tetrahydro-furan-3(S)-yl)acetic Acid Allyl Ester

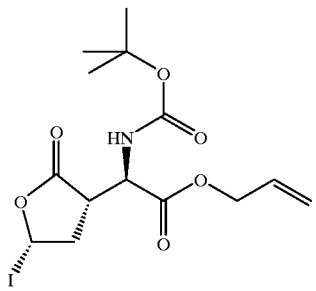

To a solution of 2S-allyl-3(R)-t-butoxycarbonylaminosuccinic acid 4-allyl ester (230 mg, 0.734 mmol) in THF (10 mL) was added saturated aqueous $NaHCO_3$(10 mL). After 20 minutes, the mixture was cooled to 0° C., and iodine (742 mg, 2.94 mmol) was added. The resultant mixture was allowed to slowly warm to ambient temperature overnight. After 20 hours, fresh 10% aqueous $Na_2S_2O_3$(20 mL) was added, and the mixture was extracted with EtOAc (15 mL) three times. The combined organic layers were washed with 10% aqueous $Na_2S_2O_3$(25 mL), dried over $MgSO_4$, and evaporated to give 322 mg (100%) of 2(R)-t-butoxycarbonylamino-2-(5R-iodomethyl-2-oxo-tetrahydro-furan-3(S)-yl)acetic acid allyl ester as a yellow oil, which was used without further purification.

$^1$H NMR: $\partial$5.80 (dddd, 1H, J=6.3, 6.8, 11.1, 12.0 Hz), 5.58 (bs, 1H), 5.27–5.15 (m, 2H), 4.64–4.47(m, 3H), 4.64–4.47 (m, 3H), 4.40 (dddd, 1H, J=5.0, 6.1, 8.6, 10.8 Hz), 3.41–3.04 (m, 3H), 2.65–2.47 (m, 1H), 2.02–1.45 (m, 2H), 1.32 (s, 9H). IR: 3374, 2976, 1774, 1714, 1507, 1367, 1161 $cm^{-1}$. Anal. Calculated for $C_{15}H_{22}NO_6I \cdot 0.25\ EtOAc$: C, 41.66; H, 5.24; N, 3.04; I, 27.51. Found: C, 41.93; H, 5.00; N, 3.04.

2(R)-t-Butoxycarbonylamino-2-(5R-iodomethyl-2-oxo-tetrahydrofuran-3(S)-yl)acetic Acid

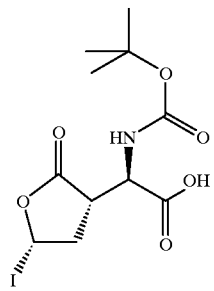

According to the procedure described in Example 10(a) for the preparation of 3(R) -allyl-N-t-butoxycarbonyl-D-aspartate β-benzyl ester, 2(R)-t-butoxycarbonylamino-2-(5R -iodomethyl-2-oxo-tetrahydrofuran-3(S)-yl)acetic acid allyl ester (322 mg, 0.734 mmol) was deprotected to give 293 mg (100%) of 2(R)-t-butoxycarbonylamino-2-(5R-iodomethyl-2-oxo-tetrahydrofuran-3(S)-yl)acetic acid as a yellow oil, which was used without further purification. Analytical sample furnished upon flash column chromatography with 1% HOAc/3–5% MeOH/$CH_2Cl_2$ gradient eluant and azeotrope with n-heptane.

$^1$H NMR: $\partial$9.30 (bs, 1H), 5.40 (d, 1H, J=8.7 Hz), 4.84–4.36 (m, 3H), 3.64(bt, 1H, J=9.5 Hz), 3.56–3.15 (m, 4H), 2.67 (ddd, 1H, J=4.1, 9.0, 13.1 Hz), 1.25 (s, 9H). IR: 3395, 2978, 1772, 1708, 1511, 1366, 1251, 1160 $cm^{-1}$ FABMS: 532(M+$Cs^+$). Anal. Calculated for $C_{12}H_{18}NO_6I \cdot 0.12\ C_7H_{16}$: C, 37.50, H, 4.88, N, 3.41;I30.86. Found: C, 37.51; H, 4.78; N, 3.52I, 30.94.

2(R)-t-Butoxycarbonylamino-N-(3,3-dimethyl-1-hydroxy-but-2(R)-yl)-2-(5R-iodo-methyl-2-oxo-tetrahydrofuran-3(S)-yl)acetamide

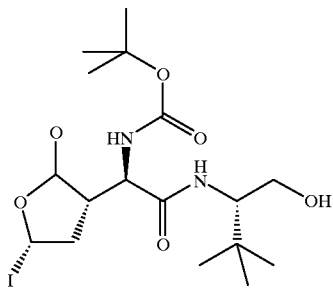

According to the procedure described in Example 1(f) for the preparation of N-(1(S)-benzyl-2-methoxy-ethyl)-3 (R)-t-butoxycarbonylamino-succinamic acid benzyl ester, 2(R)-t-butoxycarbonylamino-2-(5R-iodomethyl-2-oxo-tetrahydro-furan-3(S)-yl)acetic acid (293 mg, 0.734 mmol) was coupled to L-t-leucinol (55 mg, 0.466 mmol) with BOP. After column chromatography with silica gel and 1%/HOAc/5% MeOH/CHCl$_3$ as eluant, azeotropic removal of HOAc with n-heptane, and crystallization from EtOAc/hex, 184 mg (50% yield) of 2(R)-t-butoxycarbonylamino-N-(3,3-dimethyl-1-hydroxy-but-2(R)-yl)-2-(5R-iodo-methyl-2-oxo-tetrahydrofuran-3(S)-yl)acetamide was obtained as a white powder, mp 142–3° C.

$^1$H NMR: ∂6.78 (bd, 1H, J=8.2 Hz), 6.23 (bd, 1H, J=8.2 Hz), 3.88–3.68 (m, 2H), 3.60–3.40 (m, 2H), 3.40–3.25 (m, 2H), 3.15–2.99(bm, 1H), 2.63 (ddd, 1H, J=7.1, 10.5, 13.4 Hz), 2.37 (bs, 2H), 2.00 (q, 1H, J=11.0 Hz), 1.44(s, 9H), 0.94 (s, 9H). IR: 3319, 2965, 1774, 1665, 1530, 1367, 1153, 755 cm$^{-1}$. Anal. Calculated for C$_{18}$H$_{31}$N$_2$O$_6$I; C, 43.38; H, 627 N, 5.62; 1, 25.46. Found: C, 43.13; H, 6.34;N, 5.54; I, 25.31.

2(R)-[2(R)-t-Butoxy-carbonylamino-2-(5R-iodomethyl-2-oxo-tetrahydrofuran-3(S)-yl)acetylamino]-3,3-dimethylbutyl 2,2,2-Trichloroethyl Carbonate

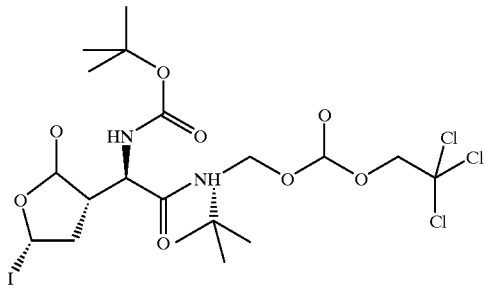

To a solution of 2(R)-t-butoxycarbonylamino-N-(3,3-dimethyl-1-hydroxy-but-2(R)-yl)-2-(5R-iodomethyl-2-oxo-tetrahydrofuran-3(S)-yl)acetamide (155 mg, 0.311 mmol) in CHCl$_3$ (5 mL) was added DMAP (84 mg, 0.68 mmol) and 2,2,2-trichloroethylchloroformate (86 μL, 0.62 mmol). After 2 hours at ambient temperature, the resultant mixture was stirred with 10% aqueous HCl (10 mL). The organic layer was separated, washed with 10% aqueous HCl (10 mL) and saturated aqueous NaHCO$_3$:H$_2$O (10:10 mL), dried over Na$_2$SO$_4$, and evaporated to provide a yellow oil, which was purified via flash column chromatography with 25% EtOAc/hex as eluant to afford 138 mg (66%) of 2(R)-[2(R)-t-butoxy-carbonylamino-2-(5R-iodomethyl-2-oxo-tetrahydrofuran-3(S)-yl)acetylamino]-3,3-dimethylbutyl 2,2,2-trichloroethyl carbonate as a yellow oil.

$^1$H NMR: ∂6.82 (bd, 1H, J=9.0 Hz), 6.17 (bd, 1H, J=7.8 Hz), 4.77 (s, 2H), 4.60 (quintet, 1H), 4.49 (dd, 1H, J=4.7, 87 Hz), 4.42 (dd, 1H, J=3.1, 10.9 Hz), 4.20–4.00 (m, 2H), 3.48 (dd, 1H, J=5.3, 10.0 Hz), 3.33 (q, 1H, J=9.3 Hz), 3.04–2.90 (bm, 1H), 2.64 (ddd, 1H, J=6.5, 10.0, 12.8 Hz), 1.99 (q, 1H, J =12.2 Hz), 1.82–1.72 (bm, 1H), 1.46(s, 9H), 0.97 (s, 9H). IR (KBr): 3386, 2966, 1764, 1703, 1683, 1676, 1521, 1369, 1244, 1165 cm$^{-1}$. Anal. Calculated for C$_{21}$H$_{32}$N$_2$O$_8$Cl$_3$I. 0.25 C$_6$H$_{14}$: C, 38.87; H, 5.15; N, 4.03; Cl, 15.30;I, 18.25. Found: C, 39.04; H, 5.13;N, 4.12; Cl, 15.64; I, 18.65.

2(R)-[2(R)-(3-Biphenyl-4-yl-1H-pyrrol-1-yl)-2-(5R-iodomethyl-2-oxo-tetrahydrofuran-3(S)-yl)acetyl-amino]-3,.3-dimethylbutyl 2, 2.2-Trichloroethyl Carbonate

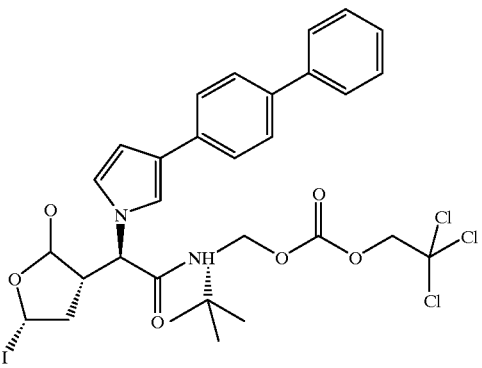

According to the procedure described in Example 1(b) for the preparation of N-(2,2-dimethyl-1(S)-methylcarbamoylpropyl)-3(R)-(3-phenyl-1H-pyrrol-1-yl) succinamic acid benzyl ester, 2(R)-[2(R)-t-butoxycarbonylamino-2-(5R-iodomethyl-2-oxo-tetrahydrofuran -3 (S)-yl)acetylamino]-3,3-dimethylbutyl 2,2,2-trichloroethyl carbonate (105 mg, 0.156 mmol) was deprotected with trifluoroacetic acid and then condensed with 3-biphenyl-4-yl-2,5-dimethoxytetrahydrofuran (prepared as described in Example 1(a)) in 1,2-dichloroethane with H$_2$O and trifluoroacetic acid. Flash column chromatography with 0.5% HOAc/20% EtOAc/hex as eluant furnished 120 mg (99%) of 2(R)-[2(R)-(3-biphenyl-4-yl-1H-pyrrol-1-yl)-2-(5R-iodomethyl-2-oxo-tetrahydrofuran-3(S)-yl)acetyl-amino]-3,3-dimethylbutyl 2,2,2-trichloroethyl carbonate as a yellow solid, which was used in the next reaction.

$^1$H NMR: ∂7.74–7.54 (m, 5H), 7.48–7.19 (m, 4H), 7.16 (dd, 1H, J=1.9, 1.9 Hz), 6.86(dd, 1H, J=2.5, 2.5 Hz), 6.59(dd, 1H, J=1.9, 2.5 Hz), 5.80(d, 1H, J=10.0 Hz), 5.20 (d, 1H, J=3.4 4.63 (dd, 2H, J=12.1, 18.0 Hz), 4.53–4.35 (m, 2H), 4.21(ddd, 1H, J=3.4, 9.0, 9.0 Hz), 4.05 (dd, 1H, J=9.0, 11.2 Hz), 3.73 (ddd, 1H, J=3.1, 9.0, 12.1 Hz), 3.27 (dd, 1H, J=4.7, 10.3 Hz), 3.02(dd, 1H, J=7.5, 9.3 Hz), 2.70(ddd, 1H, J=6.2, 9.3, 12.8 Hz), 1.74(ddd, 1H, J×9.7, 12.1, 12.8 Hz), 0.97 (s, 9H). IR (KBr): 1763, 1686, 1242, 1166, 819, 764 cm$^{-1}$.

Example 13

N-(1(S)-Benzyl-2-hydroxyethyl)-3(S)-[3-(biphenyl-4-yl)-1H-pyrrol-3-yl]succinamic Acid

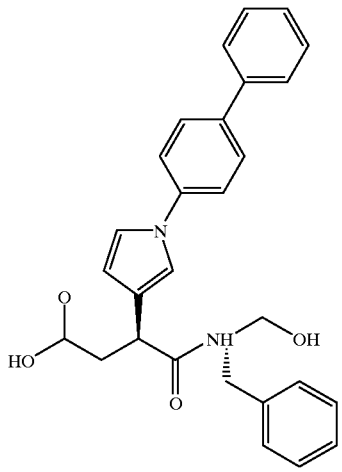

To a solution of N-(4(S)-benzyl-2,2-dimethyl-oxazolidin-3-yl)-3(S)-[3-(biphenyl-4-yl)-1H-pyrrol-3-yl]succinamic acid t-butyl ester (80 mg, 0.14 mmol) in THF (5 mL) was added 2M aqueous LiOH (5 mL). EtOH (few drops) and H$_2$O were added until a homogeneous solution was obtained. The resultant solution was heated at 50° C. After 12 hours, the mixture was acidified with 6N HCl to pH1. After another 5.5 hours at 50° C., the mixture was partitioned between EtOAc and 1 M pH 7 phosphate buffer. The aqueousueous phase was separated and extracted with EtOAc two times. The combined organic layers were washed with brine, dried over Na$_2$SO$_4$, and concentrated to a residue which, upon trituration with CH$_2$Cl$_2$/hex, provided 32 mg (49%) of pure N-(1(S)-benzyl-2-hydroxyethyl)-3(S)-[3-(biphenyl-4-yl)-1H-pyrrol-3-yl]succinamic acid as a white solid, mp 151–4° C.

$^1$H NMR: (DMSO-d$_6$): δ7.83 (d, 1H, J=8.5 Hz), 7.74 (d, 2H, J=8.8 Hz), 7.69 (d, 2H, J=7.4 Hz), 7.59 (d, 2H, J=8.8 Hz), 7.46 (t, 2H, J=7.4 Hz), 7.38–7.31 (m, 2H), 7.28–7.13 (m, 6H), 6.22 (s, 1H), 4.81–4.70 (m, 1H), 3.89–3.78(m, 2H), 2.85–2.69 (m, 2H). Anal. Calculated for C$_{29}$H$_{28}$N$_2$O$_4$.0.4 H$_2$O: C, 73.21; H, 6.10; N, 5.89. Found: C, 73.39; H, 6.09; N, 5.93.

The starting material was furnished as follows:

N-Biphenyl-4-yl-1H-pyrrole

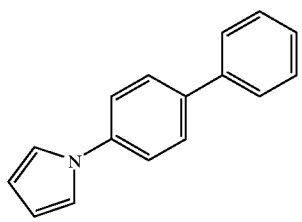

To a solution of 4-aminobiphenyl (1.0 g, 5.9 mmol) in 1,2-dichloroethane (20 mL) was added TFA (0.46 ml, 5.9 mmol). To the resultant suspension of the TFA salt was added 2,5-dimethoxy-tetrahydrofuran (0.92 mL, 7.1 mmol). The suspension was heated at 75° C. for 17 hours. The mixture was allowed to cool, partitioned between EtOAc and 1M pH 7 phosphate buffer, and the aqueousueous layer was extracted again with EtOAc. The combined organic layers were dried over Na$_2$SO$_4$ and concentrated to a crude residue, which was purified via flash column chromatography with 10–25% CH$_2$Cl$_2$/hex gradient eluent. The purified material was triturated with MTBE/hex to give 800 mg (62%) of N-biphenyl-4-yl-1H-pyrrole as an off-white solid, mp190–2° C.

$^1$H NMR: δ7.65 (d, 2H, J=8.5 Hz), 7.61 (d, 2H, J=7.0 Hz), 7.48–7.43 (m, 4H), 7.36 (t, 1H, J=7.0 Hz), 7.14 (t, 2H, J=2.0 Hz), 6.37 (t, 2H, J=2.0 Hz). Anal. Calculated for C$_{16}$H$_{13}$N: C, 87.63; H, 5.98; N, 6.39. Found: C, 87.48; H, 6.01; N, 6.30.

N-(Biphenyl-4-yl)-3-bromo-1H-pyrrole

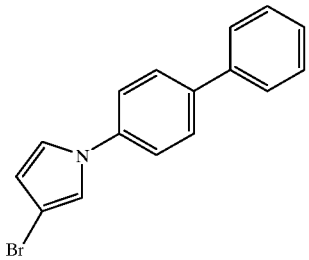

To a mixture of N-biphenyl-4-yl-1H-pyrrole (500 mg, 2.28 mmol), dimethylsulfide (0.25 mL, 3.4 mmol), CH$_2$Cl$_2$ (30 mL), and acetonitrile (10 mL) at −10° C. was added dropwise a solution of bromine in CH$_2$Cl$_2$ (5 mL) over 15 minutes. The mixture was allowed to warm to 10° C. over 2 hours. The resultant mixture was washed with 1M pH 7 phosphate buffer (50 mL) and extracted with CH$_2$Cl$_2$ (25 mL). The combined organic layers were dried over Na$_2$SO$_4$ and concentrated to a crude residue which was purified via flash column chromatography with 0–10% CH$_2$Cl$_2$/hex gradient eluant to furnish 240 mg (40%) of N-(biphenyl-4-yl)-3-bromo-1H-pyrrole as a white solid, mp 141–3° C.

$^1$H NMR: δ7.65 (d, 2H, J=8.5 Hz), 7.59 (d, 2H, J=8.1 Hz), 7.49–7.34 (m, 5H), 7.12 (s, 1H), 7.02 (t, 1H, J=2.6 Hz), 6.36 (dd, 1H, J=3.2, 1.7 Hz). Anal. Calculated for C$_{16}$H$_{12}$NBr: C, 64.45; H, 4.06; N, 4.70; Br, 26.80. Found: C, 64.37; H, 4.10; N, 4.64; Br, 26.69.

N-(4(S)-Benzyl-2,2-dimethyl-oxazolidin-3-yl)-oxamic Acid Ethyl Ester

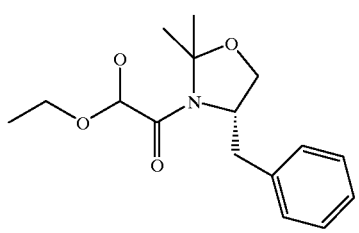

MgSO$_4$ (4 g) was added to a solution of 2S-amino-3-phenyl-1-propanol (2.0 g, 3.12 mmol) in CH$_2$Cl$_2$ (30 mL) and acetone (15 mL). After 17 hours at ambient temperature, triethylamine (2 mL, 14.3 mmol) was added and the mixture cooled to −75° C. Ethyl oxalyl chloride (1.5 mL) was added dropwise via syringe and the mixture was allowed to warm to ambient temperature over 4 hours. The mixture was filtered and the filtrate washed with 1M pH 7 phosphate buffer (50 mL). The aqueousueous layer was extracted with CH₂Cl₂ (25 mL). The combined CH₂Cl₂ layers were washed with brine, dried over Na₂SO₄, and concentrated to a minimal volume, which was diluted with MTBE and filtered. The filtrate was concentrated to an oily residue, which was dissolved in MTBE/ hex/ iso-octane and resulted in a gummy residue that was removed by decanting. The supernatant was concentrated to an oil which was passed through a short column of silica gel with 0–25% EtOAc/ hex gradient eluant to provide 3.1g (83%) of N-(4(S)-benzyl-2,2-dimethyl-oxazolidin-3-yl)-oxamic acid ethyl ester as a colorless oil.

$^1$H NMR: δ7.35–7.22 (m, 3H), 7.19 (d, 2H, J=7.4 Hz), 4.53–4.47 (m, 1H), 4.37–4.25 (m, 2H), 3.89 (m, 2H), 3.00 (dd, 1H, J=4.4, 13.2 Hz), 2.82 (dd, 1H, J=10.5, 13.1 Hz), 1.76 (s, 3H), 1.59 (s 3H), 1.38 (t, 3H, J=7.0 Hz). Anal. Calculated for $C_{16}H_{21}NO_4$: C, 65.96; H, 7.26; N, 4.81. Found: C, 65.96; H, 7.26; N, 4.84.

1(4(S)-Benzyl-2,2-dimethyl-oxazolidin-3-yl)-2-[1-(biphenyl-4-yl)-1H-pyrrol-3-yl]ethane-1,2-dione

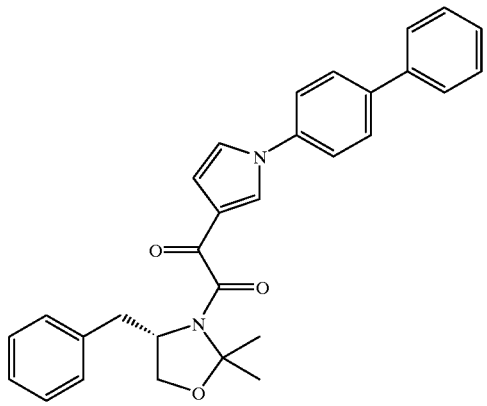

To a solution of N-biphenyl-4-yl-3-bromo-1H-pyrrole (0.45g, 1.5 mmol) in dry THF (10 mL) at −78° C. was added dropwise via syringe n-butyllithium (0.7 mL of 2.5M in hexanes). After 15 minutes at −78° C., the resultant mixture was transferred via cannula to a solution of N-(4(S)-benzyl-2,2-dimethyl-oxazolidin-3-yl)-oxamic acid ethyl ester (714 mg, 2.4 mmol) in dry THF at −90° C. The mixture warmed to −59° C. over 15 minutes and then was cooled at −78° C. for 45 minutes before quenching with saturated aqueous NH₄Cl (25 mL) and allowed to stir at ambient temperature. After 16 hours, the aqueousueous layer was separated and extracted with EtOAc (15 mL). The combined organic layers were washed with brine, dried over Na₂SO₄, and evaporated to give a residue which was purified via flash column chromatography with 0–1% EtOAc/CH₂Cl₂ gradient eluant. The purified product was triturated from MTBE/hex to obtain 300 mg (43%) of 1-(4(S)-benzyl-2,2-dimethyl-oxazolidin-3-yl)-2-[1-(biphenyl-4-yl)-1H-pyrrol-3-yl)ethane-1, 2-dione as an off-white solid, mp 150–2° C.

$^1$H NMR: δ7.86 (s, 1H), 7.70 (d, 2H, J=8.8 Hz), 7.61 (d, 2H, J=7.0 Hz), 7.51–7.45 (m, 4H), 7.39 (t, 1H, J=7.4 Hz), 7.32–7.23 (m, 2H), 7.17–7.13 (m, 3H), 7.10 (dd 1H, J=2.2, 2.9 Hz), 6.91 (dd, 1H, J=1.7, 3.1 Hz), 4.53–4.48 (m, 1H), 3.87 (s, 2H), 3.00 (dd, 1H, J=3.9, 12.7 Hz), 2.76 (dd, 1H, J=10.7, 13.2 Hz), 1.85 (s, 3H), 1.67 (s, 3H). Anal. Calculated for $C_{30}H_{28}N_2O_3$: C, 77.56; H, 6.07; N, 6.03. Found: C, 77.61; H, 6.11; N, 6.05.

1-(4(S)-Benzyl-2,2-dimethyl-oxazolidin-3-yl)-2-[1-(biphenyl-4-yl) 1H-pyrrol-3-yl]-2-hydroxy-ethanone

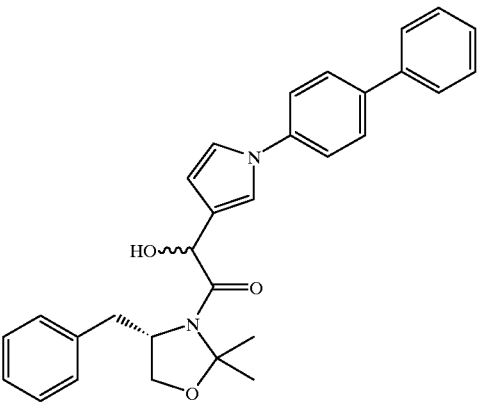

To a solution of 1-(4(S)-benzyl-2,2-dimethyl-oxazolidin-3-yl)-2-[1-(biphenyl-4-yl)-1H-pyrrol-3-yl)ethane-1, 2-dione (250 mg, 0.54 mmol) in EtOAc (6 mL) and MeOH (2 mL) at 0° C. was added NaBH₄ (20 mg, 0.54 mmol). After 2.75 hours at 0° C., more NaBH₄ (20 mg, 0.54 mmol) was added. After 1.25 hours at 0° C., the reaction was quenched with HOAc (few drops) and H₂O (2 mL). The pH was adjusted to 5 (by pH paper) with HOAc and partitioned between H₂O (25 mL) and EtOAc (25 mL). The organic layers were dried over Na₂SO₄ and concentrated to provide 0.25 g (99%) of 1-(4(S)-benzyl-2,2-dimethyl-oxazolidin-3-yl)-2-[1-(biphenyl-4-yl)1H-pyrrol-3-yl]-2-hydroxy-ethanone as a crisp foam.

$^1$H NMR: δ7.65 (d, 2H, J=8.5 Hz), 7.59 (d, 2H, J=7.4 Hz), 7.48–7.19 (m, 10H), 7.14 (t, 1H, J=2.0 Hz), 7.06 (t, 1H, J=2.6 Hz), 6.31 (t, 1H, J=2.4 Hz), 5.11 (d, 1H, J=7.4 Hz), 4.29 (d, 1H, J=6.6 Hz), 3.99–3.95 (m, 1H), 3.76 (d, 1H, J=9.2 Hz), 3.60 (dd, 1H, J=5.0, 8.6 Hz), 3.08–3.02 (m, 1H), 2.90 (dd, 1H, J=10.5, 13.4 Hz), 1.82 (s, 3H), 1.60 (s, s 3H). Anal. Calculated for $C_{30}H_{30}N_2O_3$·0.4 H₂O: C, 76.05; H, 6.55; N, 5.91. Found: C, 76.17; H, 6.66; N, 5.74.

2-Acetoxy-1-(4(S)-benzyl-2,2-dimethyl-oxazolidin-3-yl)-2-[1-(biphenyl-4-yl)-1H-pyrrol-3-yl]-ethanone

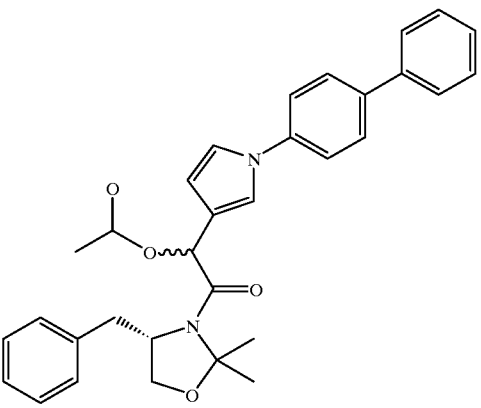

To a solution of 1-(4(S)-benzyl-2,2-dimethyl-oxazolidin-3-yl)-2-[1-(biphenyl-4-yl)1H-pyrrol-3-yl]-2-hydroxy-ethanone (867 mg, 1.86 mmol) in dry pyridine (5 mL) was added acetic anhydride (0.42 mL, 4.5 mmol). After 4.5 hours at ambient temperature, the mixture was partitioned between 1N aqueous NaHSO$_4$ (25 mL) and EtOAc (25 mL). The EtOAc layer was washed with 1N pH7 phosphate buffer (25 mL) two times, H$_2$O (25 mL), and brine (25 mL), dried over Na$_2$SO$_4$, and evaporated to give 0.91 g (100%) of 2-acetoxy-1-(4(S)-benzyl-2,2-dimethyl-oxazolidin-3-yl)-2-[1-(biphenyl-4-yl)-1H-pyrrol-3-yl]-ethanone as an amorphous solid that was used without further purification. An analytical sample was obtained upon flash column chromatography with 0–2% EtOAc/CH$_2$Cl$_2$ gradient eluent.

$^1$H NMR: δ7.65 (d, 2H, J=8.5 Hz), 7.62 (d, 2H, J=7.0 Hz), 7.48–7.24 (m, 1H), 7.10 (t, 1H), J=2.6 Hz), 6.46 (dd, 1H, J=1.7, 2.8 Hz), 6.25 (s, 1H), 3.98–3.93 (m, 1H), 3.81 (d, 1H, J=9.2 Hz), 3.64–3.60 (m, 1H), 3.42 (d, 1H, J=13.6 Hz), 2.96 (dd, 1H, J=11.6, 13.8 Hz), 2.22 (s 3H), 1.78 (s, 3H), 1.55 (s, 3H). Anal. Calculated for C$_{32}$H$_{32}$N$_2$O$_4$: C, 75.57 ; H, 6.34; N, 5.51. Found: C, 75.47; 1H, 6.37; N, 5.45.

1-(4(S)-benzyl-2,2-dimethyl-oxazolidin-3-yl)-2-[1-(biphenyl-4-yl)-1H-pyrrol-3-yl]-ethanone

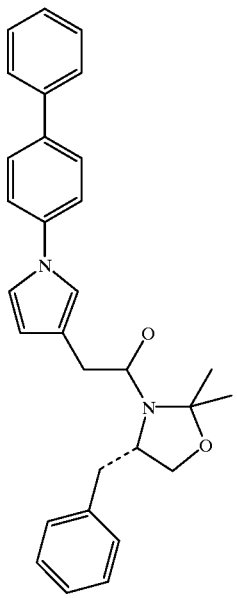

To a mixture of crude 2-acetoxy-1-(4(S)-benzyl-2,2-dimethyl-oxazolidin-3-yl)-2-[1-(biphenyl-4-yl)-1H-pyrrol-3-yl]-ethanone (1.82 mmol) and 10% palladium on carbon (120 mg) in EtOAc (4.5 mL) and EtOH (4.5 mL) was added ammonium formate (0.58 g, 9.2 mmol). After 40 hours at ambient temperature, the resultant mixture was filtered and the filtrate concentrated to a residue which was dissolved in EtOAc, washed with 1M pH7 phosphate buffer, dried over Na$_2$SO$_4$, and evaporated under reduced pressure to give a crude product. Flash column chromatography with 0–4% EtOAc/CH$_2$Cl$_2$ gradient eluant yielded 220 mg (43%) of 1-(4(S)-benzyl-2,2-dimethyl-oxazolidin-3-yl)-2-[1-(biphenyl-4-yl)-1H-pyrrol-3-yl]-ethanone as a pale yellow amorphous solid.

$^1$H NMR: δ7.62 (t, 4H, J=9.4 Hz), 7.47 (d, 2H, J 7.4 Hz), 7.42 (d, 2H, J=8.5 Hz), 7.35 (t, 2H, J=6.6 Hz), 7.30–7.21 (m, 4H), 7.08 (t, 1H, J=2.6 Hz), 7.05 (s, 1H), 6.28 (t, 1H, J=2.21 Hz), 4.16–4.10 (m, 1H), 3.82 (m, 2H), 3.62, 3.54 (AB quartet, 2H, J=15.5 Hz), 3.07 (dd, 1H, J=3.9, 13.8 Hz), 2.91 (dd, 1H, J=9.9, 13.6 Hz), 1.78 (s, 3H), 1.59 (s, 3H). Anal. Calculated for C$_{30}$H$_{30}$N$_2$O$_2$.0.25 H$_2$O: C, 79.18; H, 6.76; N, 6.16. Found: C, 79.24; H, 6.79; N, 6.12.

N-(4(S)-Benzyl-2,2-dimethyl-oxazolidin-3-yl)-2(S)-(biphenyl-4-yl-1H-pyrrol-3-yl)succinamic Acid t-Butyl Ester

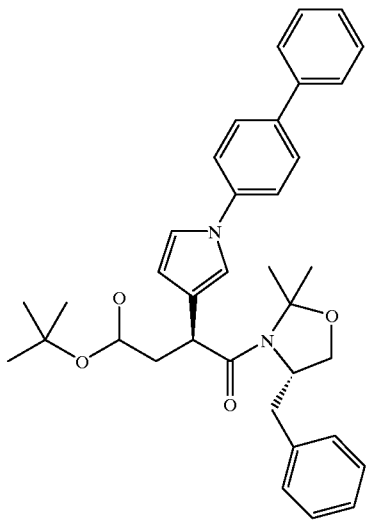

To a solution of 1-(4(S)-benzyl-2,2-dimethyl-oxazolidin-3-yl)-2-(biphenyl-4-yl-1H-pyrrol-3-yl)-ethanone (226 mg, 0.500 mmol) in dry THF (5 mL) at −78° C. was added dropwise via syringe a solution of sodium hexamethyldisilazide (0.60 mL of 1M in THF). After 15 minutes at −78° C., to the resultant dark red mixture was added t-butyl bromoacetate (100 μL, 0.68 mmol). The mixture warmed to −50° C. over 1 hour, then was quenched with 1M pH7 phosphate buffer, and allowed to warm to ambient temperature. The aqueousueous layer was separated and extracted with EtOAc. The combined organic layers were washed with brine, dried over Na$_2$SO$_4$, and concentrated to give a residue which was purified via flash column chromatography with 0–25% EtOAc/hex gradient eluant to afford 108 mg (38%) of N-(4(S)-benzyl-2,2-dimethyl-oxazolidin-3-yl)-2(R)-(biphenyl4-yl-1H-pyrrol-3-yl)succinamic acid t-butyl ester as a colorless amorphous solid.

$^1$H NMR: δ7.60 (t, 4H, J=8.3 Hz), 7.46 (d, 2H, J=7.4 Hz), 7.41 (d, 2H, J=4.8 Hz), 7.36 (d, 2H, J=8.1 Hz), 7.31 (d, 2H, J=7.4 Hz), 7.21 (d, 2H, J=8.1 Hz), 7.11 (t, 1H, J=2.0 Hz), 7.03 (t, 1H, J=2.6 Hz), 6.35 (dd, 1H, J=1.7, 2.8 Hz), 4.56–4.50 (m, 1H), 4.33 (dd, 1H, J=4.0, 10.3 Hz), 3.93–3.88 (m, 1H), 3.82 (d, 1H, J=9.2 Hz), 3.18 (dd, 1H, J=10.5, 16.7 Hz), 2.96 (bd, 1H, J=1H, J=12.5 Hz), 2.73–2.63 (m, 2H), 1.71 (s, 3H), 1.57 (s, 3H), 1.44 (s, 9H). Anal. Calculated for C$_{36}$H$_{40}$N$_2$O$_4$: C, 76.57; H, 7.14; N, 4.96. Found: C, 76.31; H, 7.16; N, 4.93.

Example 14(a)

N-[2,2-Dimethyl-1(S)-(methylcarbamoyl)propyl]-3 (S)-[1-(4-fluorophenyl)-1H-pyrrol-3-yl] succinamic Acid

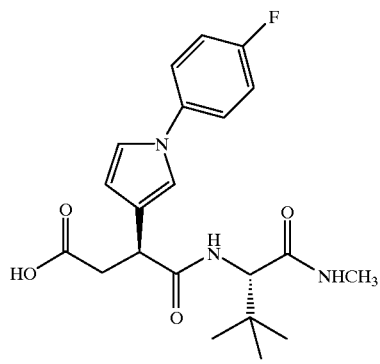

As described in Example 1(a), N-[2,2-dimethyl-1(S)-(methylcarbamoyl)propyl]-3 (S)-[1-(4-fluorophenyl)-1H-pyrrol-3-yl]succinamic acid benzyl ester was hydrogenolyzed in EtOH after 1.5 hours. Trituration with MTBE/hex gave in quantitative yield N-[2,2- dimethyl-1(S)-(methylcarbamoyl)propyl]-3(S)-[1-(4-fluorophenyl)-1H-pyrrol-3-yl]succinamic acid as a colorless amorphous solid. $^1$H NMR: δ7.27–7.23 (m, 2H), 7.07 (t, 2H, J=8.6 Hz), 6.90–6.89 (m, 2H), 6.21 (t, 1H, J=2.2 Hz), 6.13–6.10 (m, 1H), 4.24 (d, 1H, J =9.6 Hz), 4.03 (dd, 1H, J=5.2, 8.5 Hz), 3.14 (dd, 1H, J=8.5, 16.6 Hz), 2.80 (dd, 1H, J=5.7, 16.7 Hz), 2.72 (d, 3H, J=4.8 Hz), 0.94 (s, 9H). Anal. Calculated for $C_{21}H_{26}N_3O_4F$: C, 63.17; H, 6.80; N, 10.09. Found: C, 62.89; H, 6.93; N, 9.81.

The starting material was prepared in the following fashion:

2-(2,5-Dimethoxy-tetrahydrofuran-3-yl-methylidene)-1, 3-dithiane

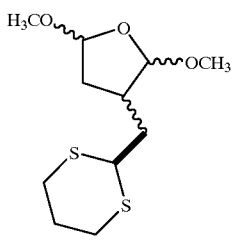

According to a procedure described in Boger, D. L.; Brotherton, C. E. *J Org Chem.* 1984, 49, 4050–4055, to a solution of 2-trimethylsilyl-1, 3-dithiane (1.2 mL, 6.3 mmol) in dry THF (40 mL) at 0° C. was added n-butyllithium (4 mL of 1.6 M in hexanes). After 15 minutes at 0° C. and 20 minutes at 4 mL of 1.6 M ambient temperature, a solution of 2, 5-dimethoxytetrahydrofuran-3-carboxaldehyde (1.00 g, 6.00 mmol) in dry THF (10 mL) was added dropwise. After 17 hours at ambient temperature, the resultant mixture was treated with saturated aqueous NH$_4$Cl (10 mL) and partitioned between EtOAc and H$_2$O. The layers were separated and the aqueousueous phase extracted with EtOAc:hex (1:1) two times. The combined organic layers were washed with brine, dried over Na$_2$SO$_4$, and concentrated to afford a residue which was purified via flash column chromatograpy with 10% EtOAc/hex as eluant to yield 1.06g (70%) of a mixture of diastereomeric 2-(2,5-dimethoxy-tetrahydrofuran-3-yl-methylidene)-1, 3-dithiane as a yellow oil, which was used without any further purification.

$^1$H NMR: δ6.00 (d, 1H, J=9.6 Hz), 5.93 (d, 1H, J=9.6 Hz), 5.77 (d, 1H, J=9.6 Hz). Anal. Calculated for $C_{11}H_{18}O_3S_2$: C, 50.35; H, 6.92; S, 24.44. Found: C, 50.07; H, 7.00; S, 24.33.

Methyl 2-(2,5-Dimethoxy-tetrahydrofuran-3-yl)-acetate

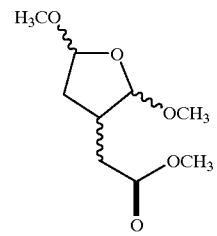

Also according to a procedure from Boger, D. L.; Brotherton, C. E. *J Org. Chem.* 1984, 49, 4050–4055, to a solution of 2-(2,5-dimethoxy-tetrahydrofuran-3-yl-methylidene)-1, 3-dithiane (200 mg, 0.76 mmol) in a mixture of MeOH:THF:H$_2$O (8:1:1; 10 mL) was added mercuric chloride (450 mg, 1.66 mmol). Upon heating at 80° C., a white precipitate formed, and after 5 hours at 80° C., the mixture was filtered through Celite. The collected solid was washed with EtOAc followed by aqueous. NH$_4$Cl. The filtrates were combined, and the biphasic mixture separated. The aqueousueous layer was extracted twice with EtOAc. The combined organic layers were washed with brine, dried over Na$_2$SO$_4$, and concentrated to yield 120 mg (77%) of methyl 2-(2,5-dimethoxy-tetrahydrofuran-3-yl)-acetate as an oil, which was a mixture of diastereomers as evident by NMR, and which was used without further purification. An analytical sample was obtained by flash column chromatography with 0–20% EtOAc/hex as gradient eluant.

$^1$H NMR: δ3.68 (s, 3H), 3.67 (s, 3H). Anal. Calculated for $C_9H_{16}O_5$: C, 53.27; H, 7.90. Found: C, 53.11; H, 7.96.

2-[1-(4-Fluorophenyl)-1H-pyrrol-3-yl]-acetic Acid Methyl Ester

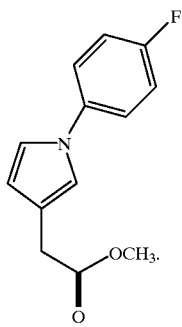

According to the procedure described in Example 1(c) for the preparation of N-(8-oxo-4-oxa-1, 7-diaza-tricyclo[9.6.1.0$^{12,17}$]octadeca-11(18), 12, 14, 16-tetraen-9-yl)-3-(3-phenyl-1H-pyrrol-1-yl)succinamic acid benzyl ester, to a mixture of crude methyl 2-(2,5-dimethoxy-tetrahydrofuran-3-yl)-acetate (120 mg, ~0.58 mmol) and 4-fluoroaniline (50 μL, 0.53 mmol) in 1, 2-dichloroethane (10 mL) was added trifluoroacetic acid (0.2 mL, 0.26 mmol). After 16 hours at 80° C., the resultant mixture was partitioned between EtOAc and 1M pH 7 phosphate buffer. The separated aqueous layer was extracted with EtOAc. The combined organic layers were washed with brine, dried over $Na_2SO_4$, and concentrated to a crude oil, which was purified via flash column chromatography with 0–15% EtOAc/hex gradient eluant to yield 100 mg (77%) of 2-[1-(4-fluorophenyl)-1H-pyrrol-3-yl]-acetic acid methyl ester as an oil.

$^1$H NMR: δ7.34–7.30 (m, 2H), 7.10 (t, 2H, J=8.6 Hz), 6.96–6.94 (m, 2H), 6.28 (t, 1H, J=2.2 Hz), 3.72 (s, 3H), 3.56 (s, 2H). Anal. Calculated for $C_{13}H_{12}NO_2F$ .0.6 $H_2O$: C, 63.98; H 5.45; N, 5.74. Found: C, 64.01; H 5.04; N, 5.65.

2-[1-(4-Fluorophenyl)-1H-pyrrol-3-yl]-acetic Acid

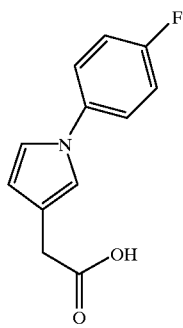

To a solution of 2-[1-(4-fluorophenyl)-1H-pyrrol-3-yl]-acetic acid methyl ester (100 mg, 0.43 mmol) in THF (1 mL) at 0° C. was added dropwise 2N aqueous LiOH (0.5 mL). Afer warming to ambient temperature over 4 hours, the mixture was added dropwise to 0.5N aqueous HCl (10 mL). The resultant light brown solid was collected by filtration, washed with $H_2O$, and dried in vacuo over $P_2O_5$ to yield 700 mg (74%) of analytically pure 2-[1-(4-fluorophenyl)-1H-pyrrol-3-yl]-acetic acid as a solid, mp 100–2° C.

$^1$H NMR: δ7.34–7.30 (m, 2H), 7.10 (t, 2H, J=8.6 Hz), 6.97–6.95 (m, 2H), 6.29 (t, 1H, J=2, 2 Hz), 3.60 (s, 2H). Anal. Calculated for $C_{12}H_{10}NO_2F$.0.15 $H_2O$: C, 64.95; H, 4.68; N, 6.31. Found: C, 65.03; H, 4.71; N, 6.25.

1(4(S)-Benzyl-oxazolidin-2-on-3-yl)-2-[1-(4-fluorophenyl)-1H-pyrrol-3-yl]-ethanone

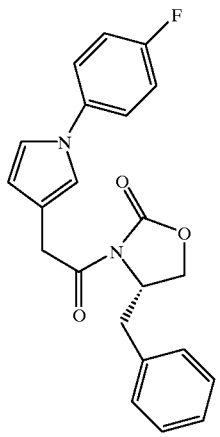

To a solution of (S)-(-)-4-benzyl-2-oxazolidinone (710 mg, 4 mmol) in dry THF (10 mL) at −78° C. was added n-butyllithium (2.5 mL of 1.6 M in hexanes). In a separate reaction vessel, to a solution of 2-[1-(4-fluorophenyl)-1H-pyrrol-3-yl]-acetic acid (920 mg, 4.2 mmol) and triethylamine (0.7 mL, 5 mmol) in dry THF (20 mL) at −78° C. was added dropwise pivaloyl chloride (0.5 mL, 4 mmol). After stirring at −78° to 0° C. over 1 hour, then recooling to −78° C., the above solution was added via cannula. The resultant mixture was allowed to warm to ambient temperature over 17 hours, then partitioned with EtOAc and aqueous $NH_4Cl$. The separated aqueousueous phase was extracted with EtOAc. The combined organic layers were washed with brine, dried over $Na_2SO_4$, and concentrated to an oil, which was purified via flash column chromatography with 15–20% EtOAc/hex gradient eluant. The oily product crystallized from benzene to give 1.04 g (69%) of 1-(4(S)-benzyl-oxazolidin-2-on-3-yl)-2-[1-(4-fluorophenyl)-1H-pyrrol-3-yl]-ethanone as a solid, mp 106–8° C.

$^1$H NMR:δ7.36–7.25 (m, 5H), 7.17–7.07 (m, 4H), 7.04 (s, 1H), 6.98 (t, 1H, J=2.6 Hz), 6.35 (dd, 1H, J =1.8, 2.6 Hz), 4.72–4.67 (m, 1H), 4.28–4.14 (m, 4H), 3.28 (dd, 1H, J=3.3, 3.6 Hz), 2.79 (dd, 1H, J=9.4, 13.4 Hz). Anal. Calculated for $C_{22}H_{19}N_2O_3F$: C, 69.83; H, 5.06; N, 7.40. Found: C, 69.80; H, 5.07; N, 7.30.

1-(4(S)-Benzyl-oxazolidin-2-on-3-yl)-3(S)-[1-(4-fluorophenyl)-1H-pyrrol-3-yl]succinamic Acid Benzyl Ester

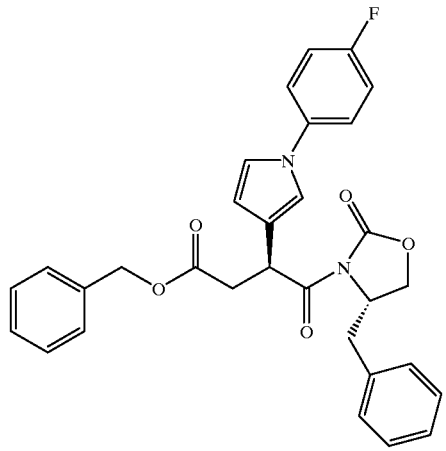

According to the procedure described in Example 13 for the preparation of 1-(4(S)-benzyl-2, 2-dimethyl-oxazolidin-3-yl)-3(S)-(1-biphenyl-4-yl-1H-pyrrol-3-yl)succinamic t-butyl ester, 1-(4(S)-benzyl-oxazolidin-2-on-3-yl)-2-[1-(4-fluoro-phenyl)-1H-pyrrol-3-yl ]-ethanone was alkylated with benzyl bromoacetate to give 550 mg (50%) of 1-(4(S)-benzyl-oxazolidin-2-on-3-yl)-3(S)-[1-(4-fluorophenyl)-1H-pyrrol-3-yl]succinamic acid benzyl ester as an amorphous solid.

$^1$H NMR: δ7.35–7.20 (m, 12H), 7.09 (t, 2H4, J=8.6 Hz), 7.02 (t, 1H, J=2.0 Hz), 6.91 (t, 1H, J=2.6 Hz), 6.30 (dd, 1H, J=1.8, 2.9 Hz), 5.54 (dd, 1H, J=4.0, 11.4 Hz), 5.13 (s, 2H), 4.59–4.53 (m, 1H), 4.06 (d, 2H, J=4.8 Hz), 3.49 (dd, 1H, J=11.4, 17.3 Hz), 3.25 (dd, 1H, J=2.8, 13.1 Hz), 2.79 (dd, 1H, J=4.1, 17.3 Hz), 2.51 (dd, 1H, J=10.1, 13.4 Hz). Anal. Calculated for $C_{31}H_{27}N_2O_5F$: C, 70.71; H, 5.17; N, 5.32. Found: C, 70.83; H, 5.27; N, 5.30.

2(S)-[1-(4-Fluorophenyl)-1H-pyrrol-3-yl]-succinic Acid 4-Benzyl Ester

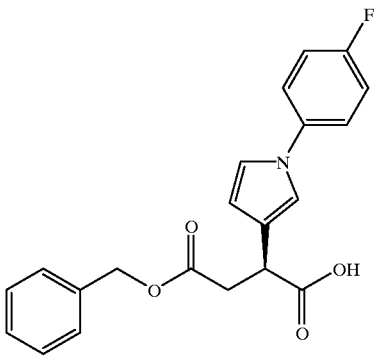

To solution of 1-(4(S)-benzyl-oxazolidin-2-on-3-yl)-3(S)-[1-(4-fluorophenyl)-1H-pyrrol-3-yl]succinamic acid benzyl ester (900 mg, 1.7 mmol) in THF (15 mL) at 0° C. was added 30% aqueous $H_2O_2$ (0.8 mL, 6.8 mmol), followed by dropwise addition of 2N aqueous LiOH (1.7 mL). After stirring at 0° C. for 1 hour, more 30% aqueous $H_2O_2$ (0.04 mL) and 2N aqueous LiOH (0.08 mL) were added. After 45 minutes at 0° C., the mixture was treated with a mixture of saturated aqueous $NaHCO_3$ (10 mL) and 2N aqueous $Na_2SO_3$ (5 mL). After 10 minutes at 0° C., the mixture was partitioned with EtOAc and 1M pH7 phosphate buffer. The aqueousueous phase was separated and extracted twice with EtOAc. The combined organic layers were washed with brine, dried over $Na_2SO_4$, and concentrated to an oil which was purified via flash column chromatography with a 0–5% $MeOH/CH_2Cl_2$ gradient eluant to yield 320 mg (51%) of 2(S)-[1-(4-fluorophenyl)-1H-pyrrol-3-yl]succinic acid 4-benzyl ester as an oil.

$^1$H NMR: δ7.36–7.26 (m, 7H), 7.10 (t, 2H, J=8.6 Hz), 6.93–6.92 (m, 2H), 6.27 (t, 1H, J=2.4 Hz), 5.14 (s, 2H), 4.14 (dd, 1H, J=5.7, 9.4 Hz), 3.19 (dd, 1H, J=9.6, 16.9 Hz), 2.81 (dd, 1H, J=5.9, 16.9 Hz). Anal. Calculated for $C_{21}H_{18}NO_4F \cdot 0.5\ H_2O$: C, 67.01; H, 5.09; N, 3.72. Found: C, 66.96; H, 4.95; N, 3.63.

N-[2,2-Dimethyl-1(S)-(methylcarbamoyl)propyl]-3(S)-[1-(4-fluorophenyl)-1H-pyrrol-3-yl]succinamic Acid Benzyl Ester

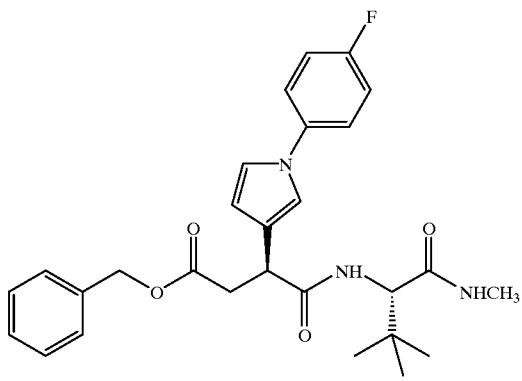

According to the procedure described in Example 1(b) for the preparation of 3(R)-t-butoxycarbonylamino-N-(2,2-dimethyl-1(S)-(methylcarbamoyl)propyl)succinamic acid benzyl ester, 2(S)-[1-(4-fluorophenyl)-1H-pyrrol-3-yl]-succinic acid 4-benzyl ester and L-t-leucine N-methylamide (see Malon, P.; Pancoska, P.; Budesinsky, M.; Hlavacek, J.; Pospisek, J.; Blaha, K. Coll. Czech. Chem Commun. 1983, 48, 2844–2861) were coupled with TBTU. Flash column chromatography with 0–5% $MeOH/CH_2Cl_2$ as gradient eluant provided in 82% yield N-(2,2-dimethyl-1(S)-(methylcarbamoyl)propyl)-3(S)-[1-(4-fluorophenyl)-1H-pyrrol-3-yl]succinamic acid benzyl ester as a crisp foam.

$^1$H NMR: δ7.34–7.26 (m, 7H), 7.10 (t, 2H, J=8.6 Hz), 6.95 (t, 1H, J=2.4 Hz), 6.89 (t, 1H, J=2.0 Hz), 6.49 (d, 1H, J=8.8 Hz), 6.23 (dd, 1H, J=1.8, 3.0 Hz), 5.76–5.74 (m, 1H), 5.11 (s, 2H), 4.12 (d, 1H, J=9.2 Hz), 4.00 (t, 1H, J=7.2 Hz), 3.20 (dd, 1H, J=7.7, 16.5 Hz), 2.84 (dd, 1H, J=6.6, 16.6 Hz), 2.75 (d, 3H, J=4.8 Hz), 0.95 (s, 9H). Anal. Calculated for $C_{28}H_{32}N_3O_4F$: C, 67.89; H, 6.55; N, 8.48. Found: C, 67.78; H, 6.52; N, 8.50.

The following compound was made in similar fashion:

Example 14(b)

3(S)-[1-(4'-Cyanobiphenyl-4-yl)-1H-pyrrol-3-yl]-N-[2,2-dimethyl-1(S)-(methylcarbamoyl)propyl] succinamic Acid

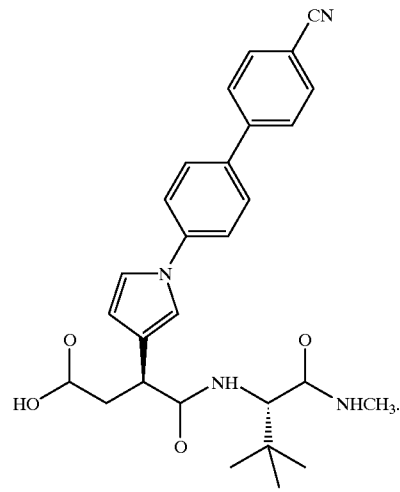

According to the procedure described in Example 1(a), 3(S)-[1-(4'-cyanobiphenyl-4-yl)-1H-pyrrol-3-yl]-N-[2,2-dimethyl-1(S)-(methylcarbamoyl)propyl]succinamic acid benzyl ester was hydrogenolyzed in EtOH/EtOAc after 6 hours to give in 87% yield 3(S)-[1-(4'-cyanobiphenyl-4-yl)-1H-pyrrol-3-yl]-N-[2,2-dimethyl-1(S)-(methylcarbamoyl) propyl]succinamic acid as a colorless amorphous solid.

$^1$H NMR: δ7.74 (d, 2H, 8.5 Hz), 7.68 (d, 2H, 8.5 Hz), 7.63 (d, 2H, J=8.5 Hz), 7.45 (d, 2H, J=8.5 Hz), 7.08 (t, 1H, J=2.4 Hz), 6.89–6.83 (m, 1H), 6.29 (t, 1H, J=1.8 Hz), 5.77–5.71 (m, 1 H), 4.17 (d, 1H, J=9.2 Hz), 4.06–4.01 (m, 1H), 3.19 (dd, 1 H, J=8.6, 16.4 Hz), 2.85 (dd, 1H, J=4.6, 16.4 Hz), 2.78 (d, 3H, J=4.8 Hz), 0.96 (s, 9H). Anal. Calculated for $C_{28}H_{30}N_4O_4 \cdot 0.25$ EtOAc·0.2 $C_6H_{14}$: C, 68.98; H, 6.67; N, 10.66. Found: C, 68.91; H, 6.79; N, 10.64.

The starting material was furnished in the following fashion:

149

2-[1-(4'-Cyanobiphenyl-4-yl)-1H-pyrrol-3-yl]-acetic Acid Methyl Ester

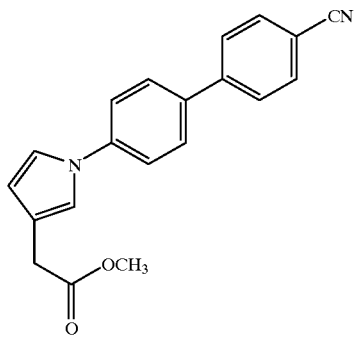

According to the procedure described in Example 14(a) for the preparation of 2-[1-(4-fluorophenyl)-1H-pyrrol-3-yl]-acetic acid methyl ester, 4-amino-4-cyano-biphenyl (commercially available from TCI) and methyl 2-(2,5-dimethoxy-tetrahydrofuran-3-yl)acetate were condensed in 6 hours at 80° C. to give a crude product. Successive flash column chromatography with EtOAc/CH$_2$Cl$_2$/hex gave in 60% yield 2-[1-(4'-cyanobiphenyl-4-yl)-1H-pyrrol-3-yl]-acetic acid methyl ester as an amorphous solid.

$^1$H NMR: δ7.75 (d, 2H, J=8.8 Hz), 7.69 (d, 2H, J=8.8 Hz), 7.64 (d, 2H, J=8.5 Hz), 7.48 (d, 2H, J=8.8 Hz), 7.10–7.09 (m, 2H), 6.33 (t, 1H, J=2.2 Hz), 3.73 (s, 3H), 3.58 (s, 2H). Anal. Calculated for C$_{20}$H$_{16}$N$_2$O$_2$: C, 75.93; H, 5.10; N, 8.86. Found: C, 75.86; H, 5.14; N, 8.90.

2-[1-(4'-Cyanobiphenyl-4-yl)-1H-pyrrol-3-yl]-acetic Acid

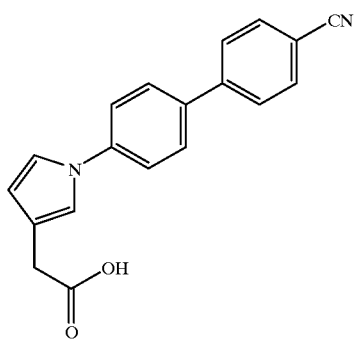

According to the procedure described in Example 14(a) for the preparation of 2-[1-(4-fluorophenyl)-1H-pyrrol-3-yl]-acetic acid, 2-[1-(4'-cyanobiphenyl-4-yl)-1H-pyrrol-3-yl]-acetic acid methyl ester was hydrolyzed in 86% yield to 2-[1-(4'-cyanobiphenyl-4-yl)-1H-pyrrol-3-yl]-acetic acid as a solid, mp 201–4° C. (d).

$^1$H NMR (DMSO-d$_6$): δ12, 20 (bs, 1H), 7.92 (s, 4H), 7.84 (d, 2H, J=8.8 Hz), 7.68 (d, 2H, J=8.5 Hz), 7.40 (s, 1H), 7.35 (s, 1H), 6.22 (s, 1H), 3.41 (s, 2H). Anal. Calculated for C$_{19}$H$_{14}$N$_2$O$_2$: C, 74.81; H, 4.73; N, 9.18. Found: C, 74.90; H 4.92; N, 9.12.

150

1-(4(S)-Benzyl-oxazolidin-2-on-3-yl)-2-[1-(4'-cyanobiphenyl-4-yl)-1H-Pyrrol-3-yl]-ethanone

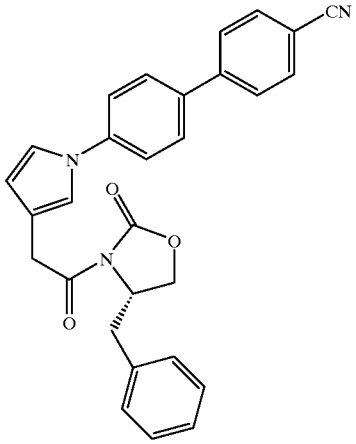

As in Example 14(a) for 1-(4(S)-benzyl-oxazolidin-2-on-3-yl)-2-[1-(4-fluorophenyl)-1H-pyrrol-3-yl]-ethanone 2-[1-(4'-cyanobiphenyl-4-yl)-1H-pyrrol-3-yl]-acetic acid and 4(S)-benzyl-2-oxazolidinone were coupled. Flash column chromatography with 10–25% EtOAc/hex to CH$_2$Cl$_2$ stepwise gradient eluant and subsequent trituration with EtOAc/MTBE/hex provided in 59% yield 1-(4(S)-benzyl-oxazolidin-2-on-3-yl)-2-[1-(4'-cyanobiphenyl4-yl)-1H-pyrrol-3-yl]-ethanone as a pale yellow amorphous solid.

$^1$H NMR: δ7.75 (d, 2H, J=8.8 Hz), 7.70 (d, 2H, J=8.5 Hz), 7.65 (d, 2H, J=8.8 Hz), 7.49 (d, 2H, J=8.8 Hz), 7.32–7.25 (m, 3H), 7.17–7.15 (m, 3H), 7.12 (t, 1H, J=2.8 Hz), 6.40 (dd, 1H, J=1.7, 2.8 Hz), 4.74–4.68 (m, 1H), 4.31–4.16 (m, 4H), 3.29 (dd, 1H, J=2.9, 13.6 Hz), 2.80 (dd, 1H J =9.4, 13.4 Hz). Anal. Calculated for C$_{29}$H$_{23}$N$_3$O$_3$: C, 75.47; H, 5.02; N, 9.11. Found: C, 75.36; H 5.08; N, 9.15.

1-(4(S)-Benzyl-oxazolidin-2-on-3-yl)-3(S)-[1-(4'-cyanobiphenyl-4-yl)-1H-pyrrol-3-yl]succinamic Acid Benzyl Ester

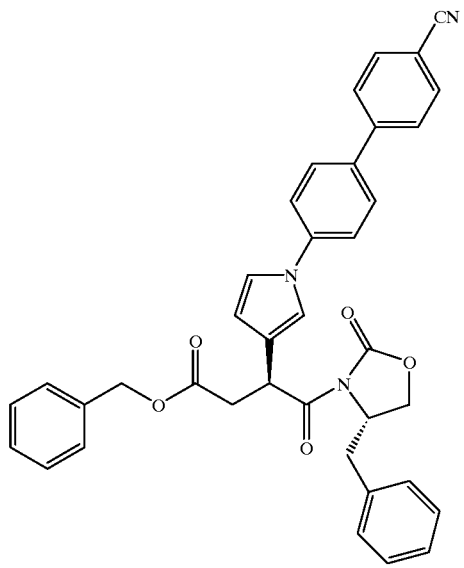

According to the procedure described in Example 14(a) for the preparation of 1-(4(S)-benzyl-oxazolidin-2-on-3- yl)-3 (S)-[1-(4-fluorophenyl)-1H-pyrrol-3-yl]succinarnic acid benzyl ester, 1-(4(S)-benzyl-oxazolidin-2-on-3-yl)-2-[1-(4'-cyanobiphenyl-4-yl)-1H-pyrrol-3-yl]-ethanone was alkylated with benzyl bromoacetate. Flash column chromatography with 25% EtOAc/hex and $CH_2Cl_2$ as stepwise gradient eluant gave in 60% yield 1-(4(S)-benzyl-oxazolidin-2-on-3-yl)-3(S)-[1-(4'-cyanobiphenyl-4-yl) 1H-pyrrol-3-yl]succinarnic acid benzyl ester as an amorphous solid.

$^1$H NMR: δ7.74 (d, 2H, J=8.5 Hz), 7.68 (d, 2H, J=8.8 Hz), 7.63 (d, 2H, J=8.8 Hz), 7.45 (d, 2H, J=8.5 Hz), 7.35–7.21 (m, 10H), 7.16 (t, 1H, J =2.2 Hz), 7.05 (t, 1H, J=2.8 Hz), 6.35 (dd, 1H, J=1.8, 2.9 Hz), 5.57 (dd, 1H, J=4.2, 11.2 Hz), 5.14 (s, 2H), 4.61–4.56 (m, 1H), 4.07 (d, 2H, J=5.2 Hz), 3.51 (dd, 1H, J=11.4, 17.3 Hz), 3.26 (dd, 1H, J=2.9, 13.6 Hz), 2.81 (dd, 1H, J=4.2, 17.1 Hz), 2.53 (dd, 1H, J=10.1, 13.4 Hz). Anal. Calculated for $C_{38}H_{31}N_3O_5 \cdot 0.4 H_2O$: C, 73.98; H, 5.20; N, 6.81. Found: C, 73.87; H, 5.53; N, 6.63.

2(S)-[1-(4'-Cyanobiphenyl-4-yl)-1H-pyrrol-3-yl] succinic Acid 4-Benzyl Ester

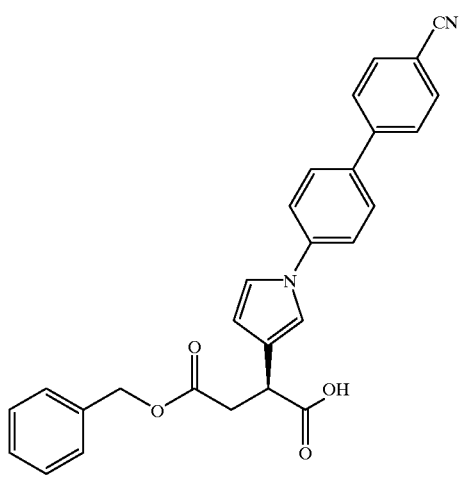

According to the procedure described in Example 14(a) for the preparation of 2(S)-[1-(4-fluorophenyl)-1H-pyrrol-3-yl]succinic acid 4-benzyl ester, 1-(4(S)-benzyl oxazolidin-2-on-3-yl)-3(S)-[1-(4'-cyanobiphenyl-4-yl)-1H-pyrrol-3-yl]succinamic acid benzyl ester was hydrolyzed and purified via flash column chromatography with a 25–75% EtOAc/hex to 5% MeOH/$CH_2Cl_2$ gradient eluant to yield in 55% 2(S)-[1-(4'-cyanobiphenyl-4-yl)-1H-pyrrol-3-yl]succinic acid 4-benzyl ester as an oil, which had some residual 4(S)-benzyl-2-oxazolidinone by NMR, and which was used without further purification. Analyses were performed on pure chromatography fractions.

$^1$H NMR: δ7.74 (d, 2H, J=8.5 Hz), 7.68 (d, 2H, J=8.8 Hz), 7.63 (d, 2H, J=8.5 Hz), 7.43 (d, 2H, J=8.8 Hz), 7.32 (s, 5H), 7.07 (s, 1H), 7.06 (s, 1H), 6.33 (t, 1H, J=2.4 Hz), 5.14 (s, 2H), 4.16 (dd, 1H, J=5.7, 9.4 Hz), 3.21 (dd, 1H, J=9.6, 16.9 Hz), 2.83 (dd, 1H, J=5.9, 16.9 Hz). Anal. Calculated for $C_{28}H_{22}N_2O_4 \cdot 0.4 H_2O$: C, 73.48; H, 5.02; N, 6.12. Found: C, 73.38; H, 5.17; N, 6.00.

3(S)-[1-(4'-Cyanobiphenyl-4-yl)-1H-pyrrol-3-yl]-N-(2, 2-dimethyl-1(S)-(methylcarbamoyl)propyl) succinamic Acid Benzyl Ester

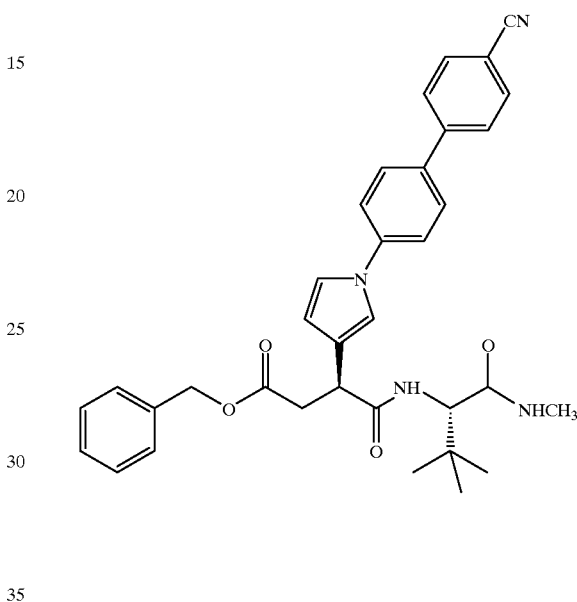

According to the procedure described in Example 1(b) for the preparation of 3(R)-t-butoxycarbonylamino-N-(2, 2-dimethyl-1(S)-(methylcarbamoyl)propyl)succinamic acid benzyl ester, 2(S)-[1-(4'-cyanobiphenyl-4-yl)-1H-pyrrol-3-yl]succinic acid 4-benzyl ester and L-t-leucine N-methylamide (see Malon, P.; Pancoska, P.; Budesinsky, M.; Hlavacek, J.; Pospisek, J.; Blaha, K. *Coll. Czech. Chem Commun.* 1983, 48, 2844–2861) were coupled with TBTU. Successive flash column chromatography with 0–30% EtOAc/$CH_2Cl_2$ and 2–5% MeOH/$CH_2Cl_2$ gradient eluants, respectively, and radial chromatography with 0–40% EtOAc/hex gradient eluant furnished in 66% yield 3(S)-[1-(4'-cyanobiphenyl-4-yl)-1H-pyrrol-3-yl]-N-(2,2-dimethyl-1 (S)-(methylcarbamoyl)propyl)succinamic acid benzyl ester as a crisp foam.

$^1$H NMR: δ7.75 (d, 2H, J=8.5 Hz), 7.69 (d, 2H, J=8.5 Hz), 7.64 (d, 2H, J=8.8 Hz), 7.44 (d, 2H, J=8.5 Hz), 7.31 (s, 5H), 7.09 (t, 1H, J=2.6 Hz), 7.04 (t, 1H, J=1.8 Hz), 6.50 (bd, 1H, J=9.6 Hz), 6.28 (dd, 1H, J=1.7, 2.8 Hz), 5.70–5.67 (m, 1H), 5.12 (s, 2H), 4.13 (d, 1H, J=9.2 Hz), 4.02 (t, 1H, J=7.4 Hz), 3.23 (dd, 1H, J=7.5, 16.7 Hz), 2.85 (dd, 1H, J=6.8, 16.7 Hz), 2.76 (d, 3H, J=4.8 Hz), 0.96 (s, 9H). Anal. Calculated for $C_{35}H_{36}N_4O_4 \cdot 0.5 H_2O$: C, 71.77; H, 6.37; N, 9.57. Found: C, 71.73; H, 6.35; N, 9.54.

Example 14(c)

3(S)-1-(4'-Cyanobiphenyl-4-yl)-1H-pyrrol-3-yl]-N-[1()-(1H-imidazol-2-yl)-3-methylbutyl]succinamic Acid

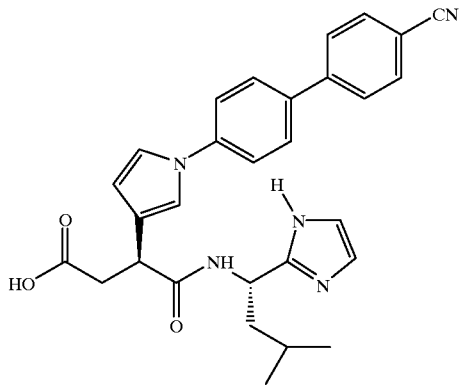

According to the procedure described in Example 1(a), 3(S)-[1-(4'-cyanobiphenyl-4-yl)-1H-pyrrol-3-yl]-N-[1(S)-(1H-imidazol-2-yl)-3-methylbutyl]succinamic acid benzyl ester was hydrogenolyzed in EtOH/THF for 3h to give a 54% yield of 3(S)-[1-(4'-cyanobiphenyl-4-yl)-1H-pyrrol-3-yl]-N-[1(S)-(1H-imidazol-2-yl)-3-methylbutyl]succinamic acid: mp 206–210° C. (dec);

$^1$HNMR (DMSO-$d_6$): δ_12.0 (bs, 1 H), 8.31 (d, 1H, J=8.45 Hz), 7.93 (s, 4H), 7.86 (d, 2H, J=8.5 Hz), 7.63 (d, 2H, J=8.8 Hz), 7.33–7.30 (m, 2H), 6.81 (s, 2H), 6.18 (s, 1H), 5.02 (dd, 1H, J=15.8, 8.8 Hz), 3.86 (dd, 1H, J=9.6, 4.8 Hz), 2.87 (dd, 1H, J=16.9, 10.3 Hz), 2.60 (dd, 1H, J=16.5, 4.8 Hz), 1.7–1.5 (m, 3H), 0.87 (d, 3H, J=6.6 Hz), 0.84 (d, 3H, J=5.9 Hz); HRFABMS Calculated for $C_{29}H_{29}N_5O_3Cs$ (M+Cs): 628.1325 Found: 628.1335

The starting material was furnished in the following fashion:

3(S)-1-(4'-Cyanobiphenyl-4-yl)-1H-pyrrol-3-yl]-N-[1(S)-(1H-imidazol-2-yl)-3-methylbutyl]succinamic Acid Benzyl Ester

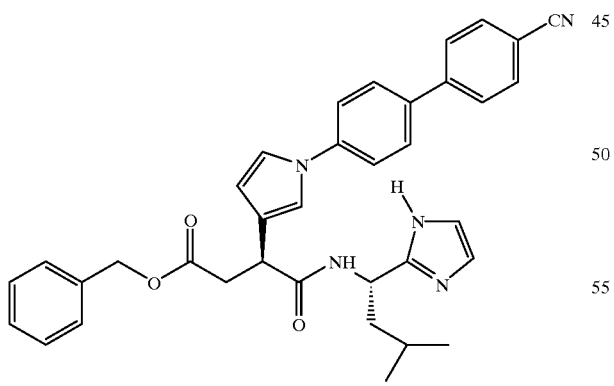

According to the procedure described in Example 1(b) for the preparation of 3(R)-t-butoxycarbonylamino-N-(2, 2-dimethyl-1(S)-(methylcarbamoyl)propyl)succinamic acid benzyl ester, 2(S)-[1-(4'-cyanobiphenyl-4-yl)-1H-pyrrol-3-yl]succinic acid 4-benzyl ester (prepared as described in Example 14(b)) and 2-(1(S)-amino-3-methyl-butyl)-imidazole (see Chen, J. J.; Zhang, Y.; Hammond, S.; Dewdney, N.; Ho, T.; Browner, M. F.; Castelhano, A. L., submitted for publication; and Abel-Meguid, S. S.; Metcalf B. W.; Caw, T. J.; DeMarsh, P.; Des Jarlais, R. L.; Fisher, S.; Green, D. W.; et al. *Biochemistry*, 1994, 33, 11671–11677) were coupled with TBTU to provide a 49% yield of 3(S)-[1-(4'-cyanobiphenyl-4-yl)-1H-pyrrol-3-yl]-N-[1(S)-(1H-imidazol-2-yl)-3-methylbutyl]succinamic acid benzyl ester: mp 186–188° C. (dec);

$^1$HNMR (DMSO-$d_6$) δ11.79 (s, 1H), 8.40 (d, 1H, J=8.5 Hz), 7.92 (s, 4H), 7.85 (d, 2H, J=8.5 Hz), 7.62 (d, 2H, J=8.8 Hz), 7.34 (s, 5 H), 6.97 (s, 1H), 6.84 (s, 1H), 6.20 (s, 1H), 5.13–5.00 (m, 3H), 3.96 (dd, 1H, J=9.9, 5.5 Hz), 2.99 (dd, 1H, J=16.4, 10.8 Hz), 2.78 (dd, 1H, J=16.4, 5.0 Hz), 1.67–1.60 (m, 2H), 1.55–1.45 (m, 1H), 0.85 (d, 3H, J=6.6 Hz), 0.81 (d, 3H, J=6.3 Hz); Anal. Calculated for $C_{36}H_{35}N_5O_3 \cdot H_2O$: C, 71.62; H, 6.18; N, 11.60. Found: C, 71.50, 71.45; H, 5.97, 6.01; N, 11.51, 11.48.

Example 14(d)

3(S)-[1-(4'-Cyanobiphenyl-4-yl)-1H-pyrrol-3-yl]-N-(4, 4-dimethyl-2-oxo-tetrahydrofuran-3(S)-yl) succinamic Acid

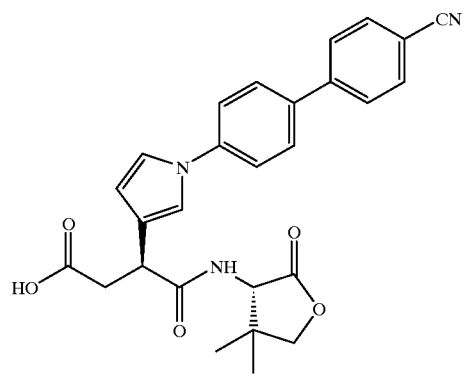

According to the procedure described in Example 1(a), 3(S)-[1-(4'-cyanobiphenyl-4-yl)-1H-pyrrol-3-yl]-N-(4, 4-dimethyl-2-oxo-tetrahydrofuran-3 (S)-yl)succinamic acid benzyl ester was hydrogenolyzed in EtOH/EtOAc for 3h to give a 81% yield of 3(S)-[1-(4'-cyanobiphenyl-4-yl)-1H-pyrrol-3-yl]-N-(4, 4-dimethyl-2-oxo-tetrahydrofuran-3(S)-yl)succinamic acid:

$^1$HNMR (DMSO-$d_6$): δ12.2 (bs, 1H), 8.48 (d, 1H, J=8.8 Hz), 7.92 (s, 4H), 7.86 (d, 2H, J=8.5 Hz), 7.67 (d, 2H, J=8.5 Hz), 7.40 (s, 1H), 7.37 (s, 1H), 6.33 (s, 1H), 4.75 (d, 1H, J=8.8 Hz), 4.08, 4.00 (AB quartet, 2H, J=8.6 Hz), 3.97–3.92 (m, 1H), 3.01–2.92 (m, 1H), 2.64 (dd, 1H, J=16.54, 4.0 Hz), 1.05 (s, 3H), 0.97 (s, 3H); Anal. Calculated for $C_{27}H_{25}N_3O_5 \cdot C_5H_{12}O$ (MTBE): C, 68.67; H, 6.66; N, 7.51. Found: 69.00, 68.91; H, 6.37, 6.42; N, 7.60, 7.52.

The starting material was furnished in the following fashion:

155

3(S)-[1-(4'-Cyanobiphenyl-4-yl)-1H-pyrrol-3-yl]-N-(4, 4-dimethyl-2-oxo-tetrahydrofuran-3(S)-yl) succinamic Acid Benzyl Ester

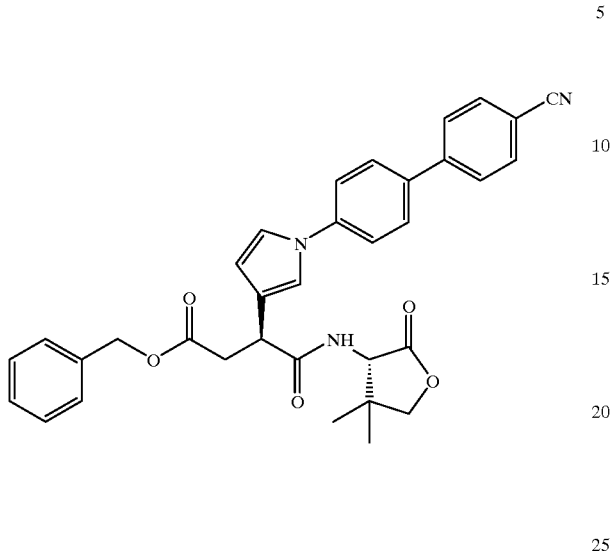

According to the procedure described in Example 1(b) for the preparation 3(R)-t-butoxycarbonylamino-N-(2, 2-dimethyl-1(S)-(methylcarbamoyl)propyl)succinamic acid benzyl ester, 2(S)-[1-4'-cyanobiphenyl-4-yl)-1H-pyrrol-3-yl]succinic acid 4-benzyl ester (prepared as described in Example 14(b)) and 3(R)-amino-4, 4-dimethyl-2-oxo-tetrahydrofuran (see Freskos, J. N. *Syn Commun.* 1994, 24, 557–563) were coupled using TBTU with N-methylmorpholine as the base to provide a mixture of diastereomers which were separated using chromatography on silica gel column with 0 to 5% MeOH gradient in $CH_2Cl_2$. Mixed fraction was repurified on a chromatotron using 0–2.5% MeOH/$CH_2Cl_2$ then 0–1.25% MeOH/$CH_2Cl_2$ as eluent to obtain 3(S)-[1-(4'-cyanobiphenyl-4-yl)-1H-pyrrol-3-yl]-N-(4, 4-dimethyl-2-oxo-tetrahydrofuran-3(S)-yl)succinamic acid benzyl ester in 29% yield as an amorphous solid:

$^1$H NMR (CDCl$_3$): δ7.75 (d, 2H, 8.1 Hz), 7.69 (d, 2H, J=8.5 Hz), 7.64 (d, 2H, J=8.5 Hz), 7.46 (d, 2H, J=8.5 Hz), 7.32 (s, 5H), 7.13 (s, 1H), 7.09 (t, 1H, J=2.2 Hz), 6.32 (s, 1H), 6.06 (d, 1H, J=7.7 Hz), 5.13 (s, 2H), 4.67 (d, 1H, J=7.7 Hz), 4.08–4.01 (m, 3H), 3.31 (dd, 1H, J=16.9, 8.5 Hz), 2.82 (dd, 1H, J=16.7, 6.1 Hz), 1.23 (s, 3H), 0.98 (s, 3H); Anal. Calculated for $C_{34}H_{31}N_3O_5$·0.2 $H_2O$: C, 72, 25; H, 5.60; N, 7.43. Found: 72.32, 72, 26; H, 5.88, 5.91; N, 7.07, 7.02.

156

Example 15(a)
N-(1(S)-Benzyl-2-hydroxyethyl)-3(S)-(2-(biphenyl-4-yl)furan-5-yl)succinamic Acid

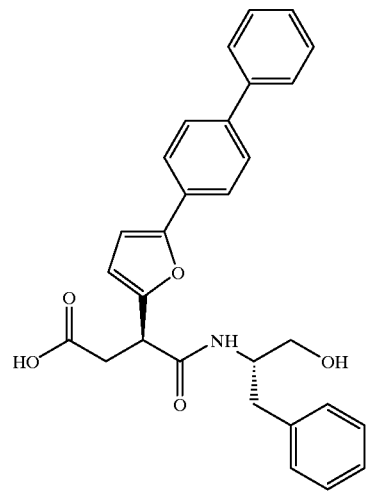

To a solution of N-(4(S)-benzyl-2,2-dimethyl-oxazolidin-3-yl)-3(S)-(2-biphenyl-4-yl-furan-5-yl)succinamic acid t-butyl ester (240 mg, 0.42 mmol) in $CH_2Cl_2$ (6 mL) was added trifluoroacetic acid (3 mL). After 30 minuntes at ambient temperature, the mixure was partitioned between $CH_2Cl_2$/pH7 phosphate buffer. The organic layer was washed with pH7 phosphate buffer and brine, dried over $Na_2SO_4$, and evaporated to give a residue which was purified via flash column chromatography with 0–1%HOAc/10%MeOH/$CH_2Cl_2$ gradient eluant. The purified product was triturated with $CH_2Cl_2$/hex to obtain 40 mg (20%) of N-(1(S)-benzyl-2-hydroxyethyl)-3(S)-(2-(biphenyl-4-yl)furan-5-yl)succinamic acid as a pale yellow solid.

$^1$H NMR (DMSO-d$_6$): δ8.12 (bm, 1H), 7.74–7.68 (m, 6H), 7.46 (t, 2H, J=7.5 Hz), 7.35 (t, 1H, J=7.4 Hz), 7.25–7.12 (m, 5H), 6.86 (d, 1H, J=3.3 Hz), 6.26 (d, 1H, J=3.0 Hz), 4.04 (t, 1H, J=7.5 Hz), 3.89–3.84 (m, 1H), 2.83 (dd, 1H, J=5.7, 13.8 Hz), 2.71–2.59 (m, 3H). Anal. Calculated for $C_{29}H_{27}NO_5$·$H_2O$: C, 71.44; H, 6.00; N, 2.87. Found: C, 71.51; H, 5.78; N, 2.92.

The starting material was furnished in the following fashion:

2-Biphenyl-4-yl-furan

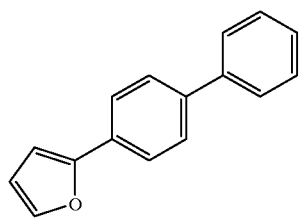

To a mixture of 4-bromobiphenyl (1.00 g, 4.80 mmol) and bis(triphenylphosphine) palladium(II) chloride (0.3 g, 0.4 mmol) in THF (10 mL) was added 2-tributylstannylfuran (1.6 mL, 5.0 mmol). After heating at reflux for 1h, the resultant mixture was concentrated to a residue which was dissolved in minimal $CH_2Cl_2$ and applied to a flash chromatography column. Elution with 10% $CH_2Cl_2$/hex led to isolation of a mixture, which upon successive triturations with hexanes or pentane gave pure product. The mother liquor was partitioned with acetonitrile and hexanes. The separated acetonitrile layer was evaporated to obtain more pure product. A total of 0.55 g (58%) of pure 2-biphenyl-4-yl-furan as pale yellow solid, mp 155–7° C. (d), was made.

$^1$H NMR: δ7.75 (d, 2H, J=8.1 Hz), 7.63 (d, 4H, J=8.5 Hz), 7.49–7.43 (m, 3H), 7.35 (t, 1H, J=7.0 Hz), 6.69 (d, 1H, J=3.3 Hz), 6.50 (dd, 1H, J=1.5, 3.3 Hz). Anal. Calculated for $C_{16}H_{12}O$: C, 87.25; H, 5.49. Found: C, 87.16; H, 5.49.

1-(4(S)-Benzyl-2,2-dimethyl-oxazolidin-3-yl)-2-(2-biphenyl-4-yl-furan-5-yl)ethane-1, 2-dione

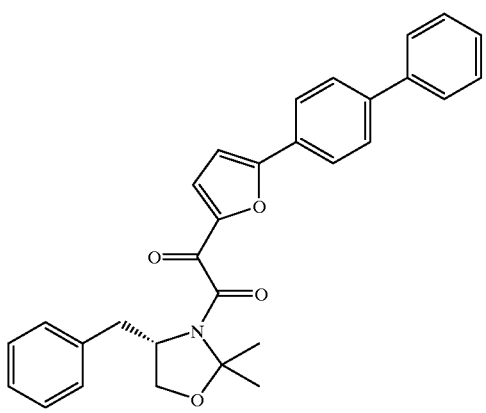

According to the procedure described in Example 13 for the preparation of 1-(4(S)-benzyl-2, 2-dimethyl-oxazolidin-3-yl)-2-(biphenyl-4-yl-1H-pyrrol-3-yl)ethane-1, 2-dione, 2-biphenyl-4-yl-furan was deprotonated and alkylated with N-(4(S)-benzyl-2,2-dimethyl-oxazolidin-3-yl)-oxamic acid ethyl ester to give in 57% yield 1-(4(S)-benzyl-2,2-dimethyl-oxazolidin-3-yl)-2-(2-biphenyl-4-yl-furan-5-yl) ethane-1, 2-dione as a pale yellow amorphous solid.

$^1$H NMR: δ7.91 (d, 2H, J=8.1 Hz), 7.69 (d, 2H, J=8.1 Hz), 7.64 (d, 2H, J=8.1 Hz), 7.49–7.36 (m, 4H), 7.25–7.10 (m, 5H), 6.85 (d, 1H, J=4.0 Hz), 4.62–4.57 (m, 1H), 3.91 (m, 2H), 3.00 (dd, 1H, J=5.0, 13.0 Hz), 3.82 (dd, 1H, J=10.1, 13.2 Hz), 1.86 (s, 3H), 1.68 (s, 3H). Anal. Calculated for $C_{30}H_{27}NO_4$: C, 77.40; H, 5.85; N, 3.01. Found: C, 77.43; H, 5.88; N, 3.06.

1-(4(S)-Benzyl-2,2-dimethyl-oxazolidin-3-yl)-2-(2-biphenyl-4-yl-furan-5-yl)-2-hydroxy-ethanone

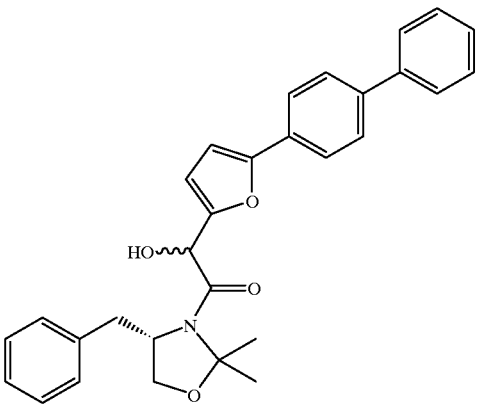

According to the procdure described in Example 13 for the preparation of 1-(4(S)-benzyl-2, 2-dimethyl-oxazolidin-3-yl)-2-(biphenyl-4-yl-1H-pyrrol-3-yl)-2-hydroxy-ethanone, 1-(4(S)-benzyl-2,2-dimethyl-oxazolidin-3-yl)-2-(2-biphenyl-4-y-furan-5-yl)ethane-1, 2-dione was reduced with $NaBH_4$ to give in quantitative yield 1-(4(S)-benzyl-2, 2-dimethyl-oxazolidin-3-yl)-2-(2-biphenyl-4-yl-furan-5-yl)-2-hydroxy-ethanone.

$^1$H NMR: δ7.70 (d, 2H, J=7.7 Hz), 7.61 (d, 4H, J=8.5 Hz), 7.45 (t, 2H, J=7.4 Hz), 7.38–7.19(m, 6H), 6.64 (d, 1H, J=2.9 Hz), 6.43 (d, 1H, J=3.3 Hz), 5.08 (d, 1H, J=6.6 Hz), 4.45 (d, 1H, J=7.0 Hz), 3.88–3.85 (m, 1H), 3.78 (d, 1H, J=8.8 Hz), 3.63 (dd, 1H, J=5.2, 8.8 Hz), 3.03 (dd, 1H, J=4.2, 13.1 Hz), 2.89 (dd, 1H, J=9.8, 13.4 Hz), 1.83 (s, 3H), 1.58 (s, 3H). Anal. Calculated for $C_{30}H_{29}NO_4 \cdot 0.5\ H_2O$: C, 75.61; H, 6.34; N, 2.94. Found: C, 75.62; H, 6.32; N, 2.88.

2-Acetoxy-1-(4(S)-beml-2,2-dimethyl-oxazolidin-3-yl)-2-(2-biphenyl-4-yl-furan-5-yl-ethanone

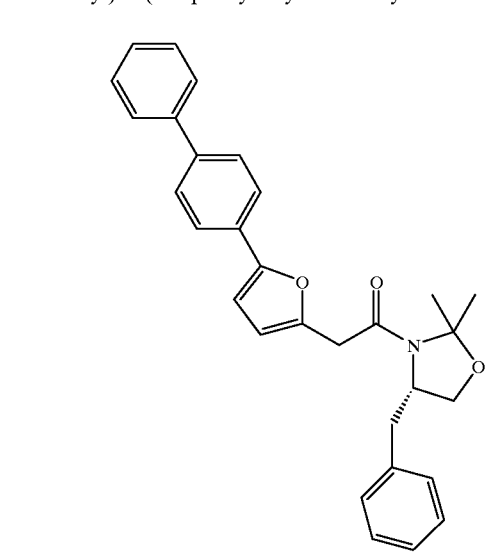

According to the procedure described in Example 13 for the preparation of 2-acetoxy-1-(4(S)-benzyl-2,2-dimethyl-oxazolidin-3-yl)-2-(biphenyl-4-yl-1H-pyrrol-3-yl)-ethanone, 1-(4(S)-benzyl-2,2-dimethyl-oxazolidin-3-yl)-2-(2-biphenyl-4-yl-furan-5-yl)-2-hydroxy-ethanone was acylated to furnish in quantitative yield 2-acetoxy-1-(4(S)-benzyl-2,2-dimethyl-oxazolidin-3-yl)-2-(2-biphenyl-4-yl-furan-5-yl)-ethanone as an off white solid, mp 120–8° C., which was used without further purification.

$^1$H NMR; δ7.75 (d, 2H, J=8.5 Hz), 7.66–7.62 (m, 4H), 7.46 (t, 2H, J=7.4 Hz), 7.39–7.22 (m, 6H), 6.70 (d, 1H, J=3.7 Hz), 6.62 (d, 1H, J=3.3 Hz), 6.39 (s, 1H), 3.86–3.79 (m, 2H), 3.64–3.60 (m, 1H), 3.39 (d, 1H, J=14.0 Hz), 2.96 (dd, 1H, J=11.4, 14.0 Hz), 2.25 (s, 3H), 1.78 (s, 3H). Anal. Calculated for $C_{32}H_{31}NO_5$: C, 75.42; H, 6.13; N, 2.75. Found: C, 75.27; H, 6.22; N, 2.65.

1-(4(S)-Benzyl-2,2-dimethyl-oxazolidin-3-yl)-2-(2-biphenyl-4-yl-furan-5-yl)-ethanone

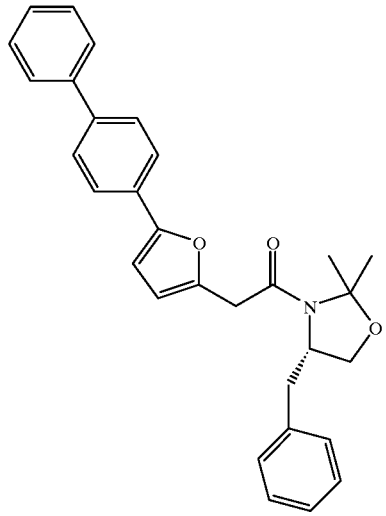

According to the procedure described in Example 13 for the preparation of 1-(4(S)-benzyl-2,2-dimethyl-oxazolidin-3-yl)-2-(biphenyl-4-yl-1H-pyrrol-3-yl)-ethanone, 2-acetoxy-1-(4(S)-benzyl-2,2-dimethyl-oxazolidin-3-yl)-2-(2-biphenyl-4-yl-furan-5-yl)-ethanone was hydrogenolyzed to provide in 42% yield 1-(4(S)-benzyl-2,2-dimethyl-oxazolidin-3-yl)-2-(2-biphenyl-4-yl-furan-5-yl)-ethanone as an amorphous solid.

$^1$H NMR: δ 7.68 (d, 2H, J=8.1 Hz), 7.62–7.58 (m, 4H), 7.44 (t, 2H, J=7.5 Hz), 7.37–7.25 (m, 6H), 6.64 (d, 1H, J=3.3 HZ 6.32 (d, 1H, J=2.9 Hz), 4.17–4.14 (m, 1H), 3.87 (m, 2H), 3.77, 3.65 (AB quartet, 2H, J=15.8 Hz), 3.09 (dd, 1H, J=4.8, 13.6 Hz), 2.94 (dd, 1H, J=9.6, 13.6 Hz), 1.78 (s, 3H), 159 (s, 3H). Anal. Calculated for $C_{30}H_{29}NO_3$: C, 79.80; H, 6.47; N, 3.10. Found: C, 79.72; H, 6.49; N, 3.03.

N-(4(S)-Benzyl-2,2-dimethyl-oxazolidin-3-yl)-3(R)-(2-biphenyl-4-yl-furan-5-yl)succinamic Acid t-Butyl Ester

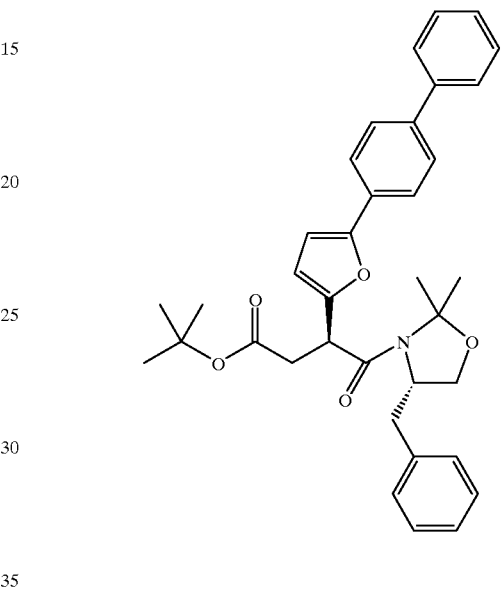

According to the procedure described in Example 13 for the preparation of N-(4(S)-benzyl-2,2-dimethyl-oxazolidin-3-yl)-3(R)-(1-biphenyl-4-yl-1H-pyrrol-3-yl)succinamic acid t-butyl ester, 1-(4(S)-benzyl-2,2-dimethyl-oxazolidin-3-yl)-2-(2-biphenyl4-yl-furan-5-yl)-ethanone was deprotonated with sodium hexamethyldisilazide and alkylated to furnish in 74% yield N-(4(S)-benzyl-2,2-dimethyl-oxazolidin-3-yl)-3(R)-(2-biphenyl-4-yl-furan-4-yl)succinamic acid t-butyl ester.

$^1$H NMR: δ 7.65 (d, 2H, J=8.5 Hz), 7.57 (t, 4H, J=8.3 Hz), 7.43 (t, 2H, J=7.4 Hz), 7.35–7.22 (m, 6H), 6.63 (d, 1H, J=3.3 Hz), 6.36 (d, 1H, J=3.3 Hz), 4.88–4.52 (m, 2H), 3.96–3.87 (m, 2H), 3.24 (dd, 1H, J=10.9, 17.1 Hz), 3.04 (d, 1H, J=11.4 Hz), 2.88–2.81 (m, 2H), 1.72 (s, 3H), 1.44 (s, 3H). Anal. Calculated for $C_{36}H_{39}NO_5 \cdot 0.25\ H_2O$: C, 75.83; H, 6.98; N, 2.46. Found: C, 75.83; H, 6.97; N, 2.46.

Example 15(b)

N-[2,2-Dimethyl-1(S)-(methylcarbamoyl)propyl]-3-(2-(biphenyl-4-yl)-furan-5-yl)succinamic Acid

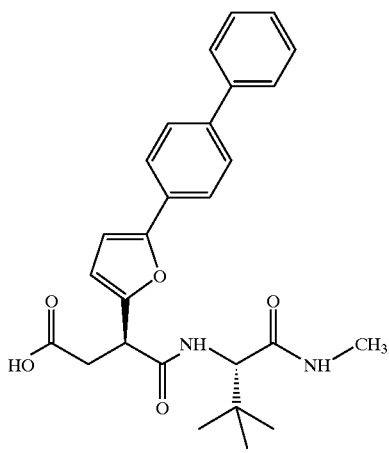

According to the procedure described in Example 15(a) for the preparation of N-(1(S)-benzyl-2-hydroxyethyl)-3(S)-(2-biphenyl-4-yl-furan-5-yl)succinamic acid, N-[2,2-dimethyl-1(S)-(methylcarbamoyl)propy]-3-(2-(biphenyl-4-yl)-furan-5-yl)succinamic acid t-butyl ester was deprotected with trifluoroacetic acid in $CH_2Cl_2$ after 1 hour. Trituration of crude with MTBE/hex provided in 48% yield N-[2,2-dimethyl-1(S)-(methylcarbamoyl)propyl]-3-(2-(biphenyl-4-yl)-furan-5-yl)succinamic acid as a rust-colored amorphous solid.

$^1$H NMR ($CD_3CN$): δ 7.75 (d, 2H, J=8.5 Hz), 7.69–7.66 (m, 4H), 7.47 (t, 2H, J=7.2 Hz), 7.37 (t, 1H, J=7.2 Hz), 6.91 (d, 1H, J=7.7 Hz), 6.77 (d, 1H, J=3.3 Hz), 6.56 (bs, 1H), 6.39 (d, 1H, J=3.3 Hz), 4.24–4.19 (m, 1H), 4.12 (d, 1H, J=9.2 Hz), 3.17–3.08 (m, 1H), 2.82 (dd, 1H, J=5.0, 17.1 Hz), 2.67 (d, 3H, J=4.8 Hz), 0.86 (s, 9H). HRFABMS: Calculated for $C_{27}H_{31}N_2O_5$ (M+H$^+$) 463.2233. Found: 463.2236.

The starting material was furnished in the following fashion:

2-(2-Biphenyl-4-yl-furan-5-yl)-2-oxoacetic Acid Ethyl Ester

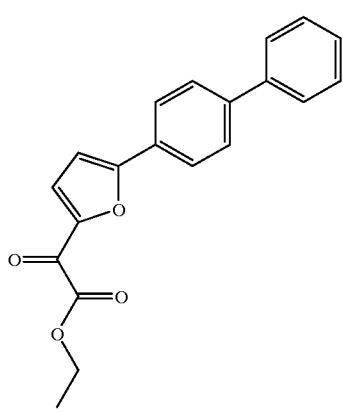

According to the procedure described in Example 13 for the preparation of 1-(4(S)-benzyl-2,2-dimethyl-oxazolidin-3-yl)-2-(biphenyl-4-yl-1H-pyrrol-3-yl)ethane-1,2-dione, 2-biphenyl-4-yl-furan was deprotonated and alkylated with diethyl oxalate to give in 74% yield 2-(2-biphenyl-4-yl-furan-5-yl)-2-oxoacetic acid ethyl ester as a yellow solid, mp 91–94° C.

$^1$H NMR: δ 7.94 (d, 2H, J=8.5 Hz), 7.83 (d, 1H, J=4.1 Hz), 7.69 (d, 2H, J=8.1 Hz), 7.64 (d, 2H, J=7.7 Hz), 7.47 (t, 2H, J=7.4 Hz), 7.39 (t,1H, J=7.2 Hz), 6.90 (d, 1H, J=4.2 Hz), 4.44 (q, 2H, J=7.0 Hz), 1.45 (t, 3H, J=7.2 Hz). Anal. Calculated for $C_{20}H_{16}O_4$: C, 74.99; H, 5.03. Found: C, 75.11; H, 5.07.

2-(2-Biphenyl-4-yl-furan-5-yl)-2-hydroxy-acetic Acid Ethyl Ester

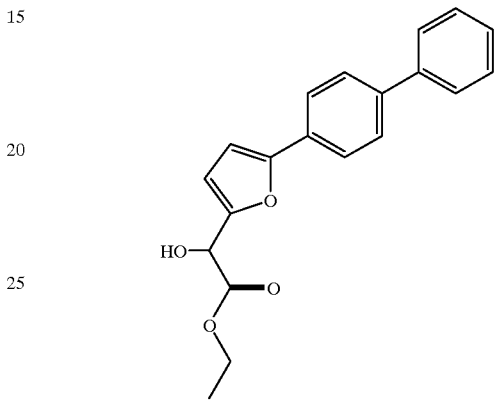

According to the procedure described in Example 13 for the preparation of 1-(4(S)-benzyl-2,2-dimethyl-oxazolidin-3-yl)-2-(biphenyl-4-yl-1H-pyrrol-3-yl)-2-hydroxy-ethanone, 2-(2-biphenyl-4-yl-furan-5-yl)-2-oxoacetic acid ethyl ester was reduced with $NaBH_4$ to give in quantitative yield 2-(2-biphenyl-4-yl-furan-5-yl)-2-hydroxy-acetic acid ethyl ester as a yellow solid, mp 75–80° C. (d), which was used crude without purification.

$^1$H NMR: δ 8 7.73 (d, 2H, J=8.5 Hz), 7.62 (d, 4H, J=8.1 Hz), 7.45 (t, 2H, J=7.4 Hz), 7.35 (t, 1H, J=7.4 Hz), 6.66 (d, 1H, J=3.3 Hz), 6.48 (d, 1H, J=3.3 Hz), 5.24 (d, 1H, J=5.9 Hz), 4.36–4.28 (m, 2H), 3.42 (d, 1H, J=6.3 Hz), 1.30 (t, 3H, J=7.2 Hz).

2-Acetoxy-2-(2-biphenyl-4-yl-furan-5-yl)-acetic Acid Ethyl Ester

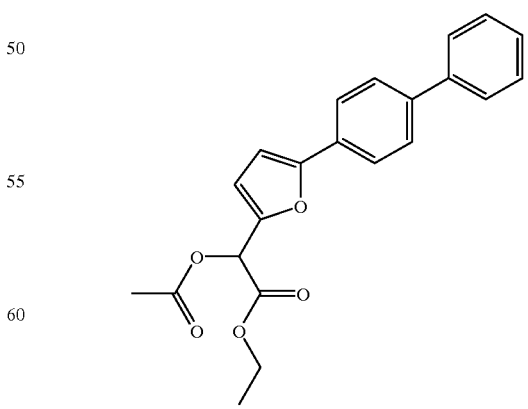

According to the procedure described in Example 13 for the preparation of 2-acetoxy-1-(4(S)-benzyl-2,2-dimethyloxazolidin-3-yl)-2-(biphenyl-4-yl-1H-pyrrol-3-yl)-ethanone, 2-(2-biphenyl-4-yl-furan-5-yl)-2-hydroxy-acetic acid ethyl ester was acylated to furnish in 83% yield 2-acetoxy-2-(2-biphenyl-4-yl-furan-5-yl)-acetic acid ethyl ester which was used without purification. Flash column chromatography with 0–20% EtOAc/hex as eluant gave an analytically pure pink solid, mp 136–140° C.

$^1$H NMR: δ 7.74 (d, 2H, J=8.5 Hz), 7.63 (d, 4H, J=8.5 Hz), 7.46 (t, 2H, =7.4 Hz), 7.36 (t, 1H, J=7.2 Hz), 6.68 (d, 1H, J=3.7 Hz), 6.58 (d, 1H, J=3.3 Hz), 6.57 (s, 1H), 4.29 (q, 2H, J=7.0 Hz), 2.21 (s, 3H), 1.29 (t, 3H, J=7.2 Hz). Anal. Calculated for $C_{22}H_{20}O_5$: C, 72.51;H, 5.53. Found: C, 72.61; H, 5.63.

2-(2-Biphenyl-4-yl-furan-5-yl)-acetic Acid Ethyl Ester

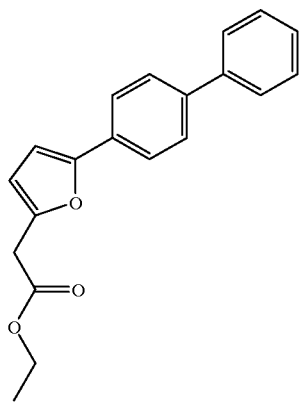

According to the procedure described in Example 13 for the preparation of (4(S)-benzyl-2,2-dimethyl-oxazolidin-3-yl)-2-(biphenyl-4-yl-1H-pyrrol-3-yl)-ethanone, 2-acetoxy-2-(2-biphenyl-4-yl-furan-5-yl)-acetic acid ethyl ester was hydrogenolyzed to provide in 61% yield 2-(2-biphenyl-4-yl-furan-5-yl)-acetic acid ethyl ester as a white solid, mp 77–78° C.

$^1$H NMR: δ 7.71 (d, 2H, J=8.5 Hz), 7.63–7.59 (m, 4H), 7.45 (t, 2H, J=7.4 Hz), 7.35 (t, 1H, J=7.4 Hz), 6.64 (d, 1H, J=2.9 Hz), 6.34 (d, 1H, J=3.3 Hz), 4.22 (q, 2H, J=7.2 Hz), 3.76 (s, 2H), 1.30 (t, 3H, J=7.2 Hz). Anal. Calculated for $C_{20}H_{18}O_3$: C, 78.41; H, 5.92. Found: C, 78.16; H, 5.92.

2-(2-Biphenyl-4-yl-furan-5-yl)-acetic Acid

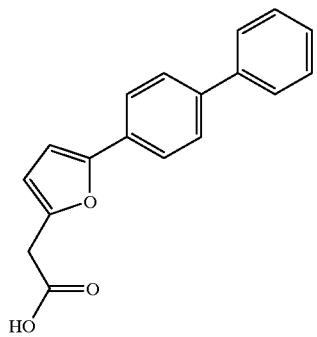

To a solution of 2-(2-biphenyl-4-yl-furan-5-yl)-acetic acid ethyl ester (0.465 g, 1.44 mmol) in THF (10 mL) at 0° C. was added 2M aqueous LiOH (2 mL). The mixture was allowed to warm over 4 hours to ambient temperature and then poured into 0.5M aqueous HCl (50 mL). The resultant pale orange precipitate was filtered off, rinsed with water, and dried under vacuum over $P_2O_5$ to provide 400 mg (100%) of 2-(2-biphenyl-4-yl-furan-5-yl)-acetic acid as a light orange solid, mp 196–210° C., used without further purification.

$^1$H NMR (acetone-$d_6$): δ 7.78 (d, 2H, J=8.1 Hz), 7.72–7.67 (m, 4H), 7.46 (t, 2H, J=7.4 Hz), 7.35 (t, 1H, J=7.4 Hz), 6.84 (d, 1H, J=3.3 Hz), 6.41 (d, 1H, J=3.3 Hz), 3.81 (s, 2H). Anal. Calculated for $C_{18}H_{14}O_3$: C, 77.68; H, 5.07. Found: C, 77.44; H, 5.16.

N-[2,2-Dimethyl-1(S)-(N-methyl-carbamoyl)-propyl]-2-(2-biphenyl-4-yl-furan-5-yl)-acetamide

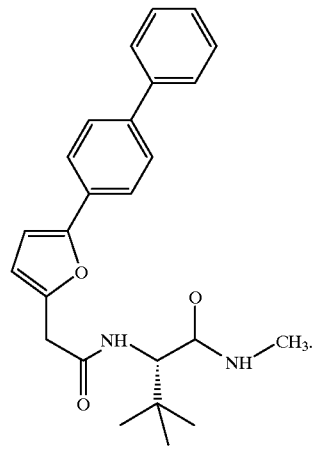

According to the procedure described in Example 1(f) for the preparation of N-(1(S)-benzyl-2-methoxy-ethyl)-3(R)-t-butoxycarbonyl-amino-succinamic acid benzyl ester, 2-(2-biphenyl-4-yl-furan-5-yl)-acetic acid was coupled to L-t-leucine N-methylamide trifluoroacetic acid salt with BOP. Flash column chromatography with 0–5% MeOH/$CH_2Cl_2$ gradient eluant provided in 58% yield N-[2,2-dimethyl-1 (S)-(N-methyl-carbamoyl)-propyl]-2-(2-biphenyl-4-yl-furan-5-yl)-acetamide as an orange foam, which decomposed >75° C. and was used without further purification.

$^1$H NMR (acetone-$d_6$): δ 7.72 (d, 2H, J=8.5 Hz), 7.61 (d, 4H, J=7.7 Hz), 7.45 (t, 2H, J=7.5 Hz),7.35 (t, 1H, J=7.4 Hz), 6.65 (d, 1H, J=3.3 Hz), 6.56 (d, 1H, J=9.2 Hz), 6.36 (d, 1H, J=3.3 Hz), 5.93 (bs, 1H), 4.22 (d, 1H, J=9.2 Hz), 3.71 (s, 2H), 2.79 (d, 3H, J=4.5 Hz), 0.94 (s, 9H). Anal. Calculated for $C_{25}H_{28}N_2O_3 \cdot 0.6\ H_2O \cdot 0.1$ MTBE: C, 72.21; H, 7.23; N, 6.61. Found: C, 72.10; H, 6.97; N, 6.39.

N-[2,2-Dimethyl-1(S)-(methylcarbamoyl)propyl]-3-(2-(biphenyl-4-yl)-furan-5-yl)succinamic Acid t-Butyl Ester

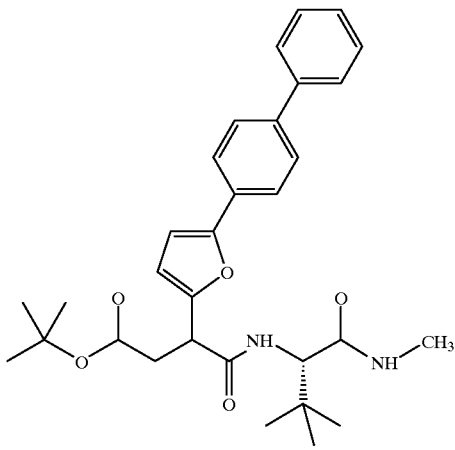

According to the procedure described in Example 13 for the preparation of N-(4(S)-benzyl-2,2-dimethyl-oxazolidin-3-yl)-2(R)-(biphenyl-4-yl-1H-pyrrol-3-yl)succinamic acid t-butyl ester, but N-(2,2-dimethyl-1(S)-(N-methylcarbamoyl)-propyl)-2-(2-biphenyl-4-yl-furan-5-yl)-acetamide was instead deprotonated with n-butyllithium (3.1 equiv) and alkylated to furnish 17 mg (7%) of N-[2,2-dimethyl-1(S)-(methylcarbamoyl)propyl]-3-(2-(biphenyl-4-yl)-furan-5-yl)succinamic acid t-butyl ester as an amorphous solid.

$^1$H NMR: δ 7.70 (d, 2H, J=8.1 Hz), 7.62–7.59 (m, 4H), 7.45 (t, 2H, J=7.5 Hz), 7.35 (t, 1H, J=7.4 Hz), 6.63 (d, 1H, J=3.3 Hz), 6.50 (d, 1H, J=9.6 Hz), 6.33 (d, 1H, J=3.3 Hz), 5.09 (bm, 1H), 4.19–4.10 (m, 2H), 3.15 (dd, 1H, J=8.5, 16.6 Hz), 2.86–2.73 (m, 4H), 1.41 (s, 9H), 0.89 (s, 9H). HRMS: Calculated for $C_{31}H_{39}N_2O_5$ (M+H$^+$): 519.2859. Found: 519.2865.

Example 16

N-(1(S)-Benzyl-2-hydroxyethyl)-3(R)-[4-(biphenyl-4-yl)-pyrazol-1-yl]succinamic Acid

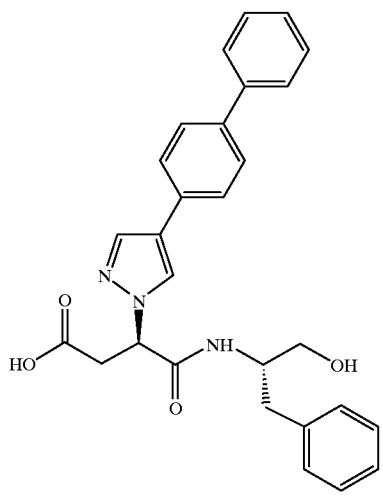

According to the procedure described in Example 1(a), N-(1(S)-benzyl-2-hydroxyethyl)-3(R)-[4-(biphenyl-4-yl)pyrazol-1-yl]succinamic acid benzyl ester was hydrogenolyzed to obtain in 74% yield N-(1(S)-benzyl-2-hydroxyethyl)-3(R)-[4-(biphenyl-4-yl)pyrazol-1-yl]succinamic acid as a white solid, mp 154–9° C.

$^1$H NMR (D$_3$COOD): δ 8.17 (s, 1H), 8.06 (s, 1H), 7.64–7.67 (m, 6H), 7.49 (t, 2H, J=7.5 Hz), 7.38 (t, 1H, J=7.0 Hz), 7.29–7.16 (m, 5H), 5.60 (t, 1H, J=7.2 Hz), 4.32–4.28 (m, 1H), 3.79–3.65 (m, 2H), 3.35 (d, 2H, J=6.6 Hz), 2.96–2.83 (m, 2H). Anal. Calculated for $C_{28}H_{27}N_3O_4$·0.25 $H_2O$·0.25 $C_6H_{14}$: C, 71.49; H, 6.31; N, 8.48. Found: C, 71.54; H, 6.30; N, 8.40.

The starting material was furnished in the following fashion:

2-Bromo-N-(1(S)-hydroxymethyl-2-phenylethyl)acetamide

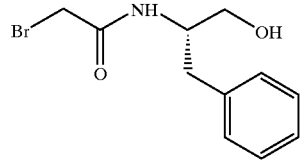

To a solution of (S)-2-amino-3-phenyl-1-propanol (1.00 g, 6.61 mmol) and triethylamine (1 mL, 7.17 mmol) in THF (70 mL) at −78° C. was added dropwise bromoactyl bromide (0.60 mL, 6.9 mmol). After 1.25 hours at −78° C., the resultant mixture was partitioned between 1M pH7 phosphate buffer (100 mL) and hexanes (100 mL). The aqueous layer was extracted with EtOAc:hex (2:1, 50 mL). The combined organic layers were washed with brine, dried over Na$_2$SO$_4$, and concentrated to give 1.59 g (85%) of 2-bromo-N-(1(S)-hydroxymethyl-2-phenylethyl)acetamide as a solid, mp 83–5° C.

$^1$H NMR (DMSO-d$_6$): δ 8.15 (d, 1H, J=8.1 Hz), 7.32–7.11 (m, 5H), 4.82 (t, 1H, J=5.3 Hz), 3.83–3.74 (m, 3H), 2.80 (dd, 1H, J=5.9, 13.6 Hz), 2.59 (dd, 1H, J=8.9, 13.6 Hz). Anal. Calculated for $C_{11}H_{14}NO_2Br$: C, 48.55; H, 5.19; N, 5.15; Br, 29.36. Found: C, 48.69; H, 5.13; N, 5.13; Br, 29.30.

3-(2-Bromoacetyl)-2,2-dimethyl-4(S)-phenylmethyl-oxazolidine

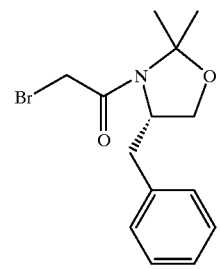

To a mixture of 2-bromo-N-(1(S)-hydroxymethyl-2-phenylethyl)acetamide (1.55 g, 5.45 mmol) and p-toluenesulfonic acid monohydrate (100 mg) in CH$_2$Cl$_2$ (50 mL) was added 2-methoxypropene (1.50 mL, 15.7 mmol) dropwise via syringe. After 15 minutes at ambient temperature, the resultant mixture was washed with 1M pH7 phosphate buffer (25 mL) and brine (25 mL), dried over Na$_2$SO$_4$, and concentrated to give a dark solid, which was triturated with MTBE/hex to provide 1.46 g (86%) of 3-(2-bromoacetyl)-2,2-dimethyl-4(S)-phenylmethyl-oxazolidine as a pale yellow solid.

¹H NMR (DMSO-d₆): δ 7.33–7.17 (m, 5H), 4.21–4.15 (m, 1H), 4.04, 3.86 (AB quartet, 2H, J=12.1 Hz), 3.79 (dd, 1H, J=4.8, 9.2 Hz), 3.71 (d, 1H, J=9.2 Hz), 2.99 (dd, 1H, J=5.0, 13.4 Hz), 2.70 (dd, 1H, J=9.2, 13.2 Hz), 1.55 (s, 3H), 1.38 (s, 3H). Anal. Calculated for $C_{14}H_{18}NO_2Br$: C, 53.86; H, 5.81; N, 4.49; Br, 25.59. Found: C, 53.91; H, 5.82; N, 4.47; Br, 25.58.

1-(4(S)-Benzyl-2,2-dimethyl-oxazolidinyl)-2-(4-iodopyrazol-1-yl)-ethanone

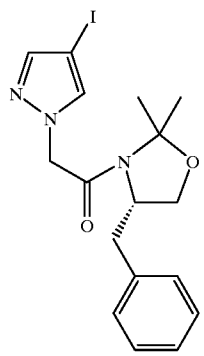

To a suspension of hexane-washed sodium hydride (from 15 mg of 60% dispersion in oil, 0.38 mmol) in THF (2 mL) at 0° C. was added a solution of pyrazole (62 mg, 0.32 mmol) in THF (1 mL) dropwise via cannula. After 15 minutes at 0° C., a solution of 3-(2-bromoacetyl)-2,2-dimethyl-4(S)-phenylmethyl-oxazolidine (100 mg, 0.320 mmol) in THF (1 mL) was added via cannula. After 5 minutes at 0° C., the mixture was allowed to stir at ambient temperature for 30 minutes. The resultant mixture was partitioned between EtOAc and pH7 phosphate buffer. The aqueousueous layer was extracted with more EtOAc. The combined organic layers, were dried over $Na_2SO_4$ and concentrated to an oily residue, which spontaneously crystallized. The crystals were triturated with MTBE/hex to obtain a white solid. The filtrate yielded another crop and in total 100 mg (75%) of 1-(4(S)-benzyl-2,2-dimethyl-oxazolidinyl)-2-(4-iodopyrazol-1-yl)-ethanone as white crystals, mp 117–20° C., were obtained.

¹H NMR (DMSO-d₆): δ 7.76 (s, 1H), 7.51 (s, 1H), 7.37–7.24 (m, 5H), 5.25, 4.87 (AB quartet, 2H, J=16.6 Hz), 4.35–4.30 (m, 1H), 3.86–3.81 (m, 1H), 3.76 (d, 1H, J=8.8 Hz), 3.06 (dd, 1H, J=4.0, 13.6 Hz), 2.80 (dd, 1H, J=9.9, 13.6 Hz), 1.55 (s, 3H), 1.41 (s, 3H). Anal. Calculated for $C_{17}H_{20}N_3O_2I$: C, 48.01; H, 4.74; N, 9.88. Found: C, 48.28; H 4.78; N, 9.79.

1-(4(S)-Benzyl-2,2-dimethyl-oxazolidinyl)-2-(4-biphenyl-4-yl-pyrazol-1-yl)-ethanone

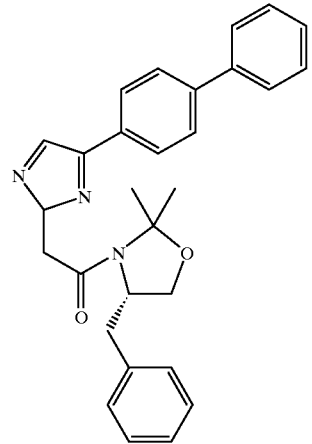

According to the procedure described in Example 1(a) for the preparation of 3-biphenyl-4-yl-furan, 1-(4(S)-benzyl-2,2-dimethyl-oxazolidinyl)-2-(4-iodopyrazol-1-yl)-ethanone was coupled to 4-biphenylboronic acid to provide in 39% yield 1-(4(S)-benzyl-2,2-dimethyl-oxazolidinyl)-2-(4-biphenyl-4-yl-pyrazol-1-yl)-ethanone as a white solid, mp 150–1° C.

¹H NMR: δ 7.83 (s, 1H), 7.68 (s, 1H), 7.62–7.52 (m, 6H), 7.47–7.28 (m, 8H), 483, 4.38 (AB quartet, 2H, J=15.6 Hz), 4.22–4.18 (m, 1H), 3.94 (m, 2H), 3.09 (dd, 1H, J=6.4, 13.0 Hz), 2.97 (dd, 1H, J=8.5, 13.2 Hz), 1.79 (s, 3H), 1.55 (s, 3H). Anal. Calculated for $C_{29}H_{29}N_3O_2$: C, 77.14; H, 6.47; N, 9.31. Found: C, 77.04; H, 6.52; N, 9.37.

4-(4(S)-Benzyl-2,2-dimethyl-oxazolidin-3-yl)-3(R)-(4-biphenyl-4-yl-pyrazol-1-yl)succinamic Acid Benzyl Ester

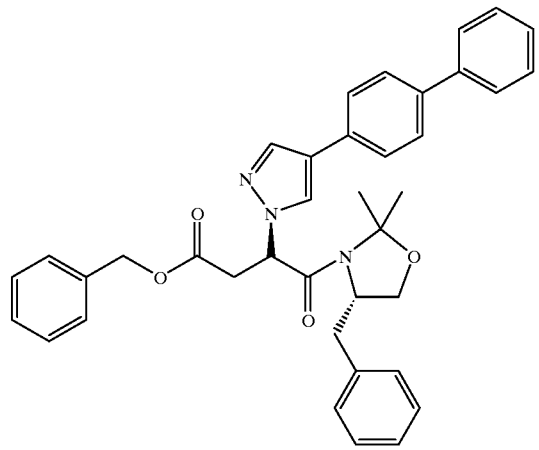

To a solution of diisopropylamine (0.10 mL, 0.76 mmol) in THF (2 mL) at 0° C. was added n-butyllithium (0.4 mL of 2.5M in hexanes). After 30 minutes at 0° C., the solution was added dropwise to a solution of 1-(4(S)-benzyl-2,2-dimethyl-oxazolidinyl)-2-(4-biphenyl-4-yl-pyrazol-1-yl)-ethanone (325 mg, 0.720 mmol) in THF (8 mL) at −78° C. After 15 minutes at −78° C., the bright yellow solution was cooled to −100° C. and benzyl 2-bromoacetate (freshly passed through Al₂O₃; 0.16 mL, 1.0 mmol) was added. After 1 hour at −100 to −70° C., the mixture was partitioned between EtOAc and water and the aqueousueous layer was extracted with more EtOAc. The combined organic layers were dried over Na₂SO₄ and concentrated to furnish a crude oil which was purified via flash column chromatography with 0–5% EtOAc/CH₂Cl₂ gradient eluant to give 150 mg (35%) of 4-(4(S)-benzyl-2,2-dimethyl-oxazolidin-3-yl)-3 (R)-(4-biphenyl-4-yl-pyrazol-1-yl)succinamic acid benzyl ester as an oil, which was used without further purification. An analytical sample was obtained after trituration with MTBE/hex and drying to an amorphous solid.

¹H NMR: δ 8.01 (s, 1H), 7.82 (s, 1H), 7.62–7.53 (m, 7H), 7.44 (t, 2H, J=7.7 Hz), 7.36–7.30 (m, 10H), 5.83 (dd, 1H, J=4.2, 10.5 Hz), 5.14 (s, 2H), 4.44–4.39 (m, 1H), 3.85 (d, 1H, J=9.2 Hz), 3.79–3.74 (m, 1H), 3.57 (dd, 1H, J=10.3, 16.9 Hz), 3.08 (dd, 1H, J=3.1, 15.6 Hz), 2.79–2.64 (m, 2H), 1.67 (s, 3H), 1.50 (s, 3H). Anal. Calculated for C₃₈H₃₇N₃O₄·0.2 H₂O: C, 75.65; H, 6.25; N, 6.97. Found: C, 75.74; H, 6.56; N, 6.90.

N-(1(S)-Benzyl-2-hydroxyethyl)-3(R)-(4-biphenyl-4-yl-pyrazol-1-yl)succinamic Acid Benzyl Ester

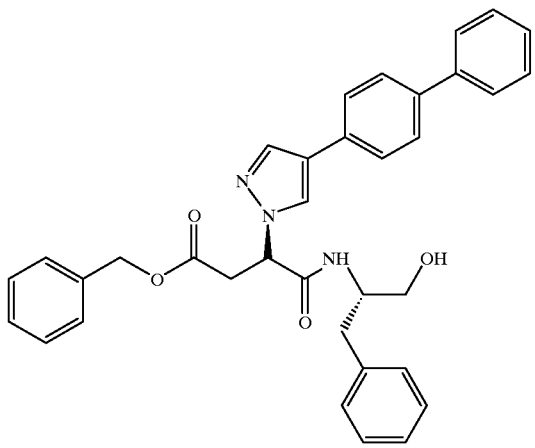

To a solution of 4-(4(S)-benzyl-2,2-dimethyl-oxazolidin-3-yl)-3(R)-(4-biphenyl-4-yl-pyrazol-1-yl)succinamic acid benzyl ester (174 mg, 0.290 mmol) in THF (3 mL) was added 0.5M aqueous HCl (1 mL). After 1 hour at ambient temperature with no apparent reaction, 6N HCl (4 drops) was added and the mixture was warmed to 45° C. After 17 hours, the mixture was partitioned between EtOAc and saturated aqueous NaHCO₃ and the aqueousueous layer was extracted with CH₂Cl₂. The combined organic layers were washed with water, dried over Na₂SO₄, and concentrated to provide 70 mg (43%) of N-(1(S)-benzyl-2-hydroxyethyl)-3(R)-[4(biphenyl-4-yl)pyrazol-1-yl[succinamic acid benzyl ester as colorless crystals, mp 116–7° C.

¹H NMR: δ 7.88 (s, 1H), 7.65 (d, 5H, J=8.1 Hz), 7.53 (d, 2H, J=8.1 Hz), 7.47 (t, 2H, J=7.5 Hz), 7.37 (t, 1H, J=7.5 Hz), 7.34–7.23 (m, 5H), 7.19–7.13 (m, 3H), 7.01 (d, 2H, J=7.7 Hz), 6.54 (d, 1H, J=6.6 Hz), 5.22 (t, 1H, J=6.8 Hz), 5.11, 5.06 (AB quartet, 2H, J=12.1 Hz), 4.20–4.10 (m, 1H), 3.72 (dd, 1H, J=3.7, 11.0 Hz), 3.56 (dd, 1H, J=5.2, 11.4 Hz), 3.34–3.31 (m, 2H), 2.82 (dd, 1H, J=6.6, 13.6 Hz), 2.70 (dd, 1H, J=8.3, 13.8 Hz). Anal. Calculated for C₃₅H₃₃N₃O₄·0.3 H₂O: C, 74.39; H, 5.99; N, 7.44. Found: C, 74.49; H, 6.02; N, 7.44.

Example 17(a)

4-[2(S)-(2(R)-Carboxymethyl-2-(thien-2-yl)acetylaminol-4-methyl-valeroyl]-aminobenzoic Acid Methyl Ester

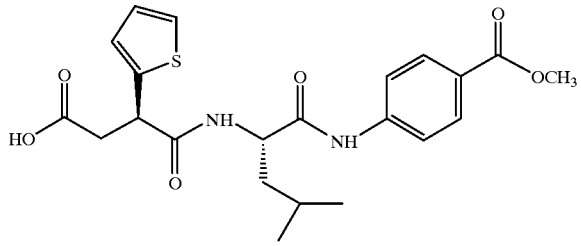

According to the procedure described in Example 15(a), 4-[2S-(2(R)-t-butoxycarbonylmethyl-2-thien-2-ylacetylamino)-4-methyl-valeroyl]-aminobenzoic acid methyl ester was hydrolyzed with trifluoroacetic acid, except in CH₂Cl₂:anisole (1:1) as solvent, to give in 88% yield 4-[2S-(2(R)-carboxymethyl-2-thien-2-ylacetylamino)-4-methyl-valeroyl]-aminobenzoic acid methyl ester as a white solid, mp 197–200° C.

¹H NMR (DMSO-d₆): δ 12.25 (s, 1H), 10.32 (s, 1H), 8.52 (d, 1H, J=7.7 Hz), 7.88 (d, 2H, J=8.7 Hz), 7.68 (d, 2H, J=8.7 Hz), 7.33 (d, 1H, J=5.0 Hz), 6.96–6.90 (m, 2H), 4.49–4.45 (m, 1H), 4.31 (dd, 1H, J=5.4, 9.8 Hz), 3.80 (s, 3H), 2.92 (dd, 1H, J=9.8, 16.5 Hz), 2.61 (dd, 1H, J=5.4, 16.6 Hz), 1.74–1.46 (m 3H), 0.90 (d, 3H, J=6.6 Hz), 0.86 (d, 3H, J=6.5 Hz). Anal. Calculated for C₂₂H₂₆N₂O₆S: C, 59.18; H, 5.87; N, 6.27; S, 7.18. Found: C, 59.28; H, 5.92; N, 6.29; S, 7.27.

The starting materials were available as follows:

4(S)-Benzyl-3-(2-thien-2-yl-acetyl)-2-oxazolidinone

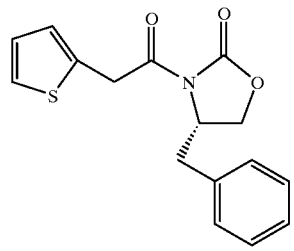

To a solution of (S)-(−)-4-benzyl-2-oxazolidinone (350 mg, 2.00 mmol) in dry THF (10 mL) at −30° C. was added dropwise n-butyllithium (2.59 M in hexanes, 0.8 mL). The mixture was cooled to −78° C. and treated with 2-thiopheneacetyl chloride (0.25 mL, 2 mmol). After stirring at −78° C. for 45 minutes, the mixture was allowed to warm to ambient temperature and stir for 1 hour. The mixture was diluted with hexanes (10 mL), quenched with 1M pH7 phosphate buffer, and stirred for 45 minutes. The layers of the resultant biphasic mixture were separated and the aqueousueous phase extracted with EtOAc. The combined organic layers were washed with 0.5N aqueous HCl two times, saturated aqueous NaHCO₃ two times, and brine, dried over Na₂SO₄, and concentrated to provide a crude residue which was purified via flash column chromatography with 20% EtOAc/hex as eluant to yield 319 mg (53%) of 4(S)-benzyl-3-(2-thien-2-yl-acetyl)-2-oxazolidinone as a tan solid, mp 56–9° C.

¹H NMR: δ 7.34–7.26 (m, 5H), 7.17–7.14 (m, 2H), 7.02–6.98 (m, 1H), 4.72–4.67 (m, 1H), 4.57, 4.48 (AB quartet, 2H, J=16.8 Hz), 4.26–4.17 (m, 2H), 3.29 (dd, 1H, J=3.2, 13.4 Hz), 2.78 (dd, 1H, J=9.5, 13.4 Hz). Anal. Calculated for $C_{16}H_{15}NO_3S$: C, 63.77; H, 5.02; N, 4.65; S, 10.64. Found: C, 63.87; H, 5.04; N, 4.71; S, 10.74.

4-(4(S)-Benzyloxazolidin-2-on-3-yl)-3(R)-thien-2-yl-succinamic Acid t-Butyl Ester

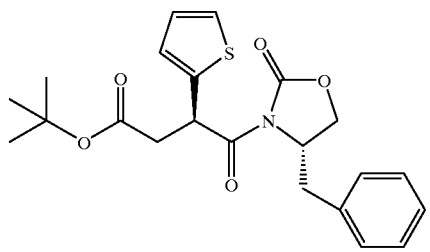

According to the procedure described in Example 13 for the preparation of N-(4(S)-benzyl-2,2-dimethyl-oxazolidin-3-yl)-3(R)-(biphenyl-4-yl-1H-pyrrol-3-yl)succinamic acid t-butyl ester, the corresponding anion of 4(S)-benzyl-3-(2-thien-2-yl-acetyl)-2-oxazolidinone was alkylated with t-butyl 2-bromoacetate. Flash column chromatography with 10% EtOAc/hex as eluant provided in 65% yield 4-(4(S)-benzyloxazolidin-2-on-3-yl)-3(R)-thien-2-yl-succinamic acid t-butyl ester as a white solid, mp 109–11° C.

¹H NMR: δ 7.36–7.26 (m, 5H), 7.22 (d, 1H, J=5.0 Hz), 7.06 (d, 1H, J=3.5 Hz), 6.93 (dd, 1H, J=3.9, 5.2 Hz), 5.85 (dd, 1H, J=4.2, 11.4 Hz), 4.62–4.57 (m, 1H), 4.14–4.09 (m, 2H), 3.42–3.33 (m, 2H), 2.82 –2.70 (m, 2H), 1.43 (s, 9H). Anal. Calculated for $C_{22}H_{25}NO_5S$: C, 63.60; H, 6.06; N, 3.37; S, 7.72. Found: C, 63.37; H, 6.07; N, 3.31; S, 7.69.

2(R)-Thien-2-yl-succinic Acid 4-t-Butyl Ester

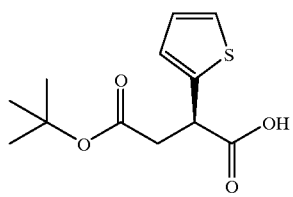

To a solution of 4-(4(S)-benzyloxazolidin-2-on-3-yl)-3 (R)-thien-2-yl-succinamic acid t-butyl ester (630 mg, 1.52 mmol) in THF (15 mL) at 0° C. was added 2N aqueous LiOH (1.14 mL). $H_2O$ was added periodically to maintain homogeneity. After 5.75 hours at 0° C., saturated aqueous $NaHCO_3$ (5 mL) was added. THF was removed under reduced pressure, and the mixture extracted with $CH_2Cl_2$ (5 mL) three times. The combined organic layers were extracted with saturated aqueous $NaHCO_3$. The combined aqueous layers were acidified to~pH2 using 2N aqueous HCl and extracted with $CH_2Cl_2$ (5 mL) three times. These extracts were dried over $Na_2SO_4$ and concentrated to yield 350 mg (90%) of 2(R)-thien-2-yl-succinic acid 4-t-butyl ester as an oil, which was pure and used without further purification.

¹H NMR: δ 7.22 (d, 1H, J=5.1 Hz), 6.99 (m, 2H), 4.33 (dd, 1H, J=5.4, 9.9Hz), 3.11 (dd, 1H, J=9.9, 16.7 Hz), 2.74 (dd, 1H, J=5.4, 16.7 Hz), 1.41 (s, 9H). IR: 2980, 2934, 1732, 1715, 1370, 1285, 1256, 1152, 843, 702 $cm^{-1}$. Anal. Calculated for $C_{12}H_{16}NO_4S$: C, 56.23; H, 6.29; S, 12.51. Found: C, 56.24; H, 6.35; S, 12.45.

4-[2S-(2(R)-t-Butoxycarbonylmethyl-2-thien-2-ylacetylamino)-4-methyivaleroyl]-aminobenzoic Acid Methyl Ester

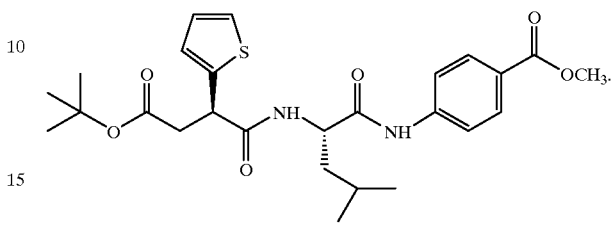

According to the procedure described in Example 1(f) for the preparation of N-(1(S)-benzyl-2-methoxy-ethyl)-3(R)-t-butoxycarbonyl-amino-succinarnic acid benzyl ester, 2(R)-thien-2-yl-succinarnic acid 4-t-butyl ester and 4-(2S-amino-4-methyl-pentanoylamino)benzoic acid methyl ester (see Castelhano, A. L.; Yuan, Z.; Horne, S.; Liak, T. J. W095/12603-AI, May 11, 1995) were coupled with BOP to give a mixture of diastereomers which were separated via flash column chromatography with a 10–25% EtOAc/hex gradient eluant. Mixed fractions were purified via radial chromatography with MTBE/$CH_2Cl_2$/hex (1:5:5) as eluant. In this manner a total yield of 51% of 4-[2S-(2(R)-t-butoxyaarbonymethyl-2-thien-2-yaacetylamino)-4-methylvaleroyl]-aminobenzoic acid methyl ester as a white solid, mp 80–1° C. was obtained.

¹H NMR: δ 8.72 (s, 1H), 7.95 (d, 2H, J=8.6 Hz), 7.61 (d, 2H, J=8.6 Hz), 6.99–6.96 (m, 2H), 6.02 (d, 1H, J=8.0 Hz), 4.64–4.56 (m, 1H), 4.20 (t, 1H, J=6.2 Hz), 3.89 (s, 3H), 3.04 (d, 2H, J=6.2 Hz), 1.89–1.83 (m, 1H), 1.44 (s, 9H), 0.91 (t, 6H, J=6.2 Hz). Anal. Calculated for $C_{26}H_{34}N_2O_6S$: C, 62.13; H, 6.82; N, 5.57; S, 6.38. Found: C, 62.13; H, 6.83; N, 5.54; S, 6.46.

Example 17(b)

4-[2(S)-[2(R)-Carboxymethyl-2-(thien-3-yl)acetylamino]-4-methyl-valeroyl]-aminobenzoic Acid Methyl Ester

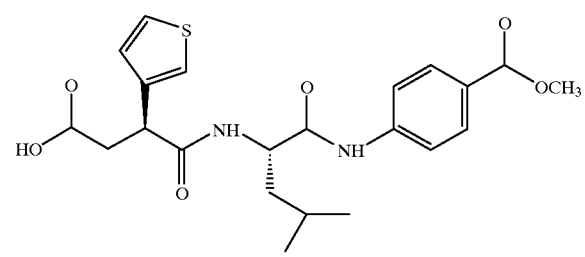

According to the procedure described in Example 17(a), 4-[2S-(2(R)-t-butoxycarbonylmethyl-2-thien-3-ylacetylamino)-4-methyl-valeroyl]-aminobenzoic acid methyl ester was hydrolyzed with trifluoroacetic acid in $CH_2Cl_2$:anisole (1:1) to give in 88% yield 4-[2S-(2(R)-carboxymethyl-2-thien-2-ylacetylamino)-4-methyl-valeroyl]-aminobenzoic acid methyl ester as a white solid, mp 199–201° C.

¹H NMR (DMSO-d₆): δ 12.15 (s, 1H), 10.31 (s, 1H), 8.43 (d, 1H, J=7.5 Hz), 7.89 (d, 2H, J=8.6 Hz), 7.68 (d, 2H, J=8.7 Hz), 7.44–7.41 (m, 1H), 7.25 (d, 1H, J=2.5 Hz), 7.09 (d, 1H, J=4.1 Hz), 4.48–4.45 (m, 1H), 4.08 (dd, 1H, J=4.8, 10.2 Hz), 3.80 (s, 3H), 2.89 (dd, 1H, J=10.3, 16.5 Hz), 2.61 (dd, 1H, J=5.0, 16.6 Hz), 1.75–1.44 (m, 3H), 0.90 (d, 3H, J=6.6 Hz), 0.86 (d, 3H, J=6.5 Hz). Anal. Calculated for $C_{22}H_{26}N_2O_6S$: C, 59.18; H, 5.87; N, 6.27; S, 7.18. Found: C, 59.21; H, 5.92; N, 6.21; S, 7.25.

The starting materials were available as follows:

4(S)-Benzyl-3-(2-thien-3-yl-acetyl)-2-oxazolidinone

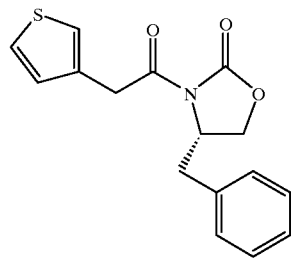

According to the procedure described in Example 17(a) for the preparation of 4(S)-benzyl-3-(2-thien-2-yl-acetyl)-2-oxazolidinone, 3-thiopheneacetyl chloride and (S)-(–)-4-benzyl-2-oxazolidinone furnished in 68% yield 4(S)-benzyl-3-(2-thien-3-yl-acetyl)-2-oxazolidinone as a solid, mp 80–1° C.

¹H NMR: δ 7.33–7.24 (m, 5H), 7.15–7.09 (m, 3H), 4.72–4.65 (m, 1H), 4.39, 4.28 (AB quartet, 2H, J=15.9 Hz), 4.22–4.15 (m, 2H), 3.26 (dd, 1H, J=3.2, 13.4 Hz), 2.77 (dd, 1H, J=9.4, 13.4 Hz). Anal. Calculated for $C_{16}H_{15}NO_3S$: C, 63.77; H, 5.02; N, 4.65; S, 10.64. Found: C, 63.80; H, 5.04; N, 4.69; S, 10.70.

4-(4(S)-Benzyloxazolidin-2-on-3-yl)-3(R)-thien-3-yl-succinamic Acid t-Butyl Ester

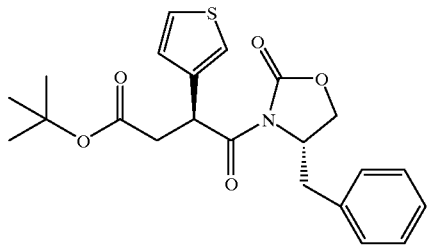

According to the procedure described in Example 13 for the preparation of N-(4(S)-benzyl-2,2-dimethyl-oxazoeldin-3-yl)-3(R)-(biphenyl-4-yl-1H-pyrrol-3-yl)succinamic acid t-butyl ester, the corresponding anion of 4(S)-benzyl-3-(2-thien-3)-yl-acetyl)-2-oxazolidinone was alkylated with t-butyl 2-bromnoacetate. Flash column chromatography with 10% EtOAc/hex as eluant afforded in 77% yield 4-(4(S)-benzyloxazolidin-2-on-3-yl)-3 (R)-thien-2-yl-succinamic acid t-butyl ester as a white solid, mp 103–4° C.

¹H NMR: δ 7.36–7.25 (m, 7H), 7.10 (t, 1H, J=3.2 Hz), 5.64 (dd, 1H, J=4.4, 11.2 Hz), 4.62–4.57 (m, 1H), 4.14–4.04 (m, 2H), 3.39–3.27 (m, 2H), 2.78 (dd, 1H, J=10.0, 13.4 Hz), 2.63 (dd, 1H, J=4.4, 17.1 Hz), 1.43 (s, 9H). Anal. Calculated for $C_{22}H_{24}NO_5S$: C, 63.60; H, 6.06; N, 3.37; S, 7.72. Found : C, 63.44; H, 6.09; N, 3.33; S, 7.78.

2(R)-Thien-3-yl-succinic Acid 4-t-Butyl Ester

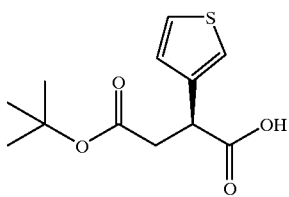

According to the procedure described in Example 17(a) for the preparation of 2(R)-thien-2-yl-succinic acid 4-t-butyl ester, 4-(4(S)-benzyloxazoldin-2-on-3-yl)-3(R)-thien-3-yl-succinamic acid t-butyl ester was hydrolyzed in 70% yield to 2(R)-thien-3-yl-succinic acid 4-t-butyl ester as an oil, which was used without further purification.

¹H NMR: δ 7.29 (dd, 1H, J=3.0,4.9 Hz), 7.17 (d, 1H, J=2.7 Hz), 7.05 (d, 1H, J=5.0 Hz), 4.18 (dd, 1H, J=5.5, 9.8 Hz), 3.06 (dd, 1H, J=9.9, 16.7 Hz), 2.66 (dd, 1H, J=5.6, 16.7 Hz), 1.40 (s 9H). IR: 3104, 2978, 2934, 1728, 1715, 1370, 1258, 1154, 855, 774 cm⁻¹. Anal. Calculated for $C_{12}H_{16}NO_4S$: C, 56.23; H, 6.29; S, 12.51. Found: C, 56.29; H, 6.35; S, 12.42.

4-[2S-(2(R)-t-Butoxycarbonylmethyl-2-thien-3-ylacetylamino)-4-methylvaleroyl]-aminobenzoic Acid Methyl Ester

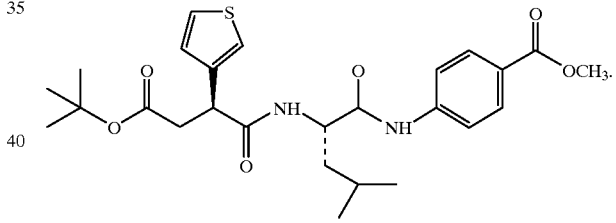

According to the procedure described in Example 1(f) for the preparation of N-(1(S)-benzyl-2-methoxy-ethyl)-3(R)-t-butoxycarbonyl-amino-succinamic acid benzyl ester, 2(R)-thien-3-yl-succinamic acid 4-t-butyl ester and 4-(2S-amino-4-methyl-pentanoylamino)benzoic acid methyl ester (see Castellano, A. L.; Yuan, Z; Horne, S.; Liak, T. J. WO95/12603-A1, May 11, 1995) were coupled with BOP. Precipitation with H₂O and recrystallization from toluene gave in 55% yield 4-[2S-(2(R)-t-butoxy-carbonylmethyl-2-thien-3-ylacetylamino)-4-methylvaleroyl]-aminobenzoic acid methyl ester as a white solid, mp 168–70° C.

¹H NMR: δ8.62 (s, 1H), 7.96 (d, 2H, J=8.6 Hz), 7.56 (d, 2H, J=8.8 Hz), 7.33 (dd, 1H, J=3.0, 4.8 Hz), 7.19 (s, 1H), 7.02 (d, 1H, J=5.1 Hz), 5.86 (bd, 1H, J=6.7 Hz), 4.57–4.51 (m, 1H), 4.04 (t, 1H, J=6.6 Hz), 3.89 (s, 3H), 3.04 (dd, 1H, J=7.4, 16.9 Hz), 2.88 (dd, 1H, J=5.6, 16.9 Hz), 1.88–1.81 (m, 1H), 1.42 (s, 9H), 0.92 (t, 6H, J=6.5 Hz). Anal. Calculated for $C_{26}H_{34}N_2O_6S$: C, 62.13; H, 6.82; N, 5.57; S, 6.38. Found: C, 62.08; H, 6.79; N, 5.64; S, 6.46.

Example 17(c)

N-[2,2-Dimethyl-1(S)-(pyridin4-ylcarbamoyl)-propyl]-3(R)-thien-3-yl-succinamic Acid

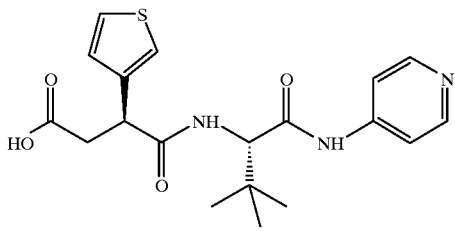

According to the procedure described in Example 17(a), N-[2,2-dimethyl-1(S)-(pyridin-4-ylcarbamoyl)-propyl]-3(RS)-thien-3-yl-succinamic acid t-butyl ester was deprotected. Flash column chromatography with 1% HOAc/5% MeOH/CH$_2$Cl$_2$ as eluant led to isolation of the major isomer; 15 mg (21%) of N-[2,2-dimethyl-1(S)-(pyridin-4-ylcarbamoyl)-propyl]-3(R)-thien-3-yl-succinamic acid as a white solid, mp 205° C. (d).

$^1$H NMR (DMSO-d$_6$): δ8.30 (d, 2H, J=6.0 Hz), 7.45 (dd, 2H, J=1.5, 6.0 Hz), 7.26 (dd, 1H, J=3.0, 5.0 Hz), 7.21–7.18 (m, 1H), 7.04 (dd, 1H, J=1.0, 5.0 Hz), 4.38 (s, 1H), 4.26 (dd, 1H, J=5.0, 10.0 Hz), 3.04 (dd, 1H, J=10.0, 16.5 Hz), 2.65 (dd, 1H, J=5.0, 16.5 Hz), 1.01 (s, 9H). Anal. Calculated for C$_{19}$H$_{23}$N$_3$O$_4$S.0.6 HOAc: C, 57.02; H, 6.02; N, 9.88; S, 7.54. Found: C, 56.99; H, 6.06; N, 9.88; S, 7.55.

The starting material was made as follows:

N-[2,2-Dimethyl-1(S)-(pyridin-4-ylcarbamoyl)-propyl]-3(RS)-thien-3-yl-succinamic Acid t-Butyl Ester

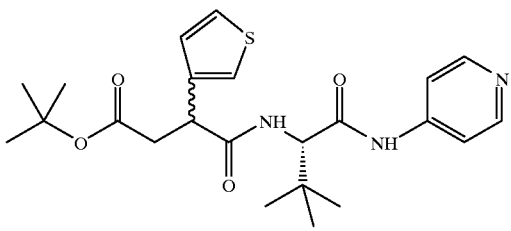

According to the procedure described in Example 1(f) for the preparation of N-(1(S)-benzyl-2-methoxy-ethyl)-3(R)-t-butoxycarbonylamino-succinamic acid benzyl ester, 2(R)-thien-3-yl-succinamic acid 4-t-butyl ester (prepared as described in Example 17(b)) and 2S-amino-3,3-dimethyl-N-4-pyridinyl-butanamide (prepared as described in Example 5(d)) were coupled with BOP in 48 h at ambient temeprature. Flash column chromatography with 10% MeOH in CH$_2$Cl$_2$ gave 718 mg (39%) of N-[2,2-dimethyl-1(S)-(pyridin-4-ylcarbamoyl)-propyl]-3(RS)-thien-3-yl-succinamic acid t-butyl ester as a white solid, mp 205° C. (d), which was an inseparable mixture of isomers by NMR (3(R):S; 87:13, respectively) and used without further purification.

$^1$H NMR (DMSO-d$_6$): δ8.48 (d, 1.74H, J=5.5 Hz, major isomer), 8.38 (d, 0.87H, J=9.0 Hz, major isomer), 7.65 (d, 1.74H, J=5.5 Hz, major isomer), 7.59 (d, 0.26H, J=5.0 Hz, minor isomer), 7.49 (dd, 0.87H, J=3.0, 4.0 Hz, major isomer), 7.43 (m, 0.87H, major isomer), 7.30 (m, 0.13H, minor isomer), 7.23 (d, 0.87H, J=5.0 Hz, major isomer), 7.12 (d, 0.13H, J=5.0 Hz, minor isomer), 4.52 (d, 0.87H, J=9.0 Hz, major isomer), 4.37 ( dd, 0.87H, J=5.0, 10.0 Hz, major isomer), 4.08 ( dd, 0.13H, J=7.0, 15.5 Hz, minor isomer), 3.00 (dd, 0.87H, J=10.0, 16.0 Hz, major isomer), 1.40 (s, 1.17H, minor isomer), 1.29 (s, 7.83H, major isomer), 1.03 (s, 0.13H, minor isomer), 0.84 (s, 7.83H, major isomer).

Example 18(a)

3(RS)-(3-Biphenyl-4-yl-1H-imidazol-1-yl)-N-(hexahydroazepin-2-on-3(S)-yl)succinamic Acid

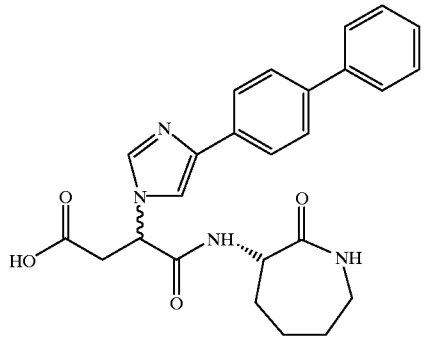

According to the procedure described in Example 1(a), a suspension of 3(RS)-(3-biphenyl-4-yl-1H-imidazol-1-yl)-N-(hexahydroazepin-2-on-3(S)-yl)succinamic acid benzyl ester in EtOH was hydrogenolyzed after 90 minutes to provide 779 mg (94%) of 3(RS)-(3-biphenyl-4-yl-1H-imidazol-1-yl)-N-(hexahydroazepin-2-on-3(S)-yl) succinamic acid as a solid.

FABMS: 447 (C$_{25}$H$_{27}$N$_4$O$_4$; M +H$^+$).

The starting materials were prepared as follows:

2(RS)-(3-Biphenyl-4-yl-1H-imidazol-1-yl)-succinic Acid Dibenzyl Ester

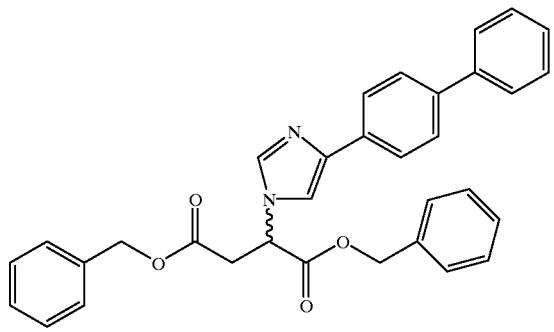

A mixture of dibenzyl fumarate (5.30 g, 18.0 mmol) and 4-biphenyl-4-yl-1H-imidazole (see Ellis, et al. *J Pharm. Pharmacol.* 1964, 400–3; 3.94 g, 18.0 mmol) was heated at 110–5° C. After 4 hours, the mixture was allowed to cool, diluted with ether, washed with 0.05% aqueous HCl, 0.01N aqueous NaOH, and brine, dried over Na$_2$SO$_4$, and concentrated under reduced pressure to give 5.75 g (62%) of 2(RS)-(3-biphenyl-4-yl-1H-imidazol-1-yl)-succinic acid dibenzyl ester.

FABMS: 517.3 (C$_{33}$H$_{29}$N$_2$O$_4$; M+H$^+$).

177

2(RS)-(3-Biphenyl-4-yl-1H-imidazol-1-yl)-succinic Acid 4-Benzyl Ester

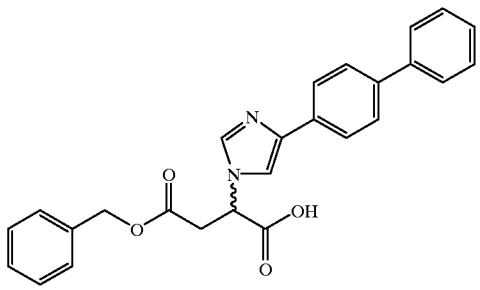

A suspension of 2(RS)-(3-biphenyl-4-yl-1H-imidazol-1-yl)-succinic acid dibenzyl ester (551 mg, 1.07 mmol) in H$_2$O (0.5 mL) was refluxed overnight. Once allowed to cool to ambient temperature, the resultant precipitate was collected and dried in vacuo to provide 436 mg (96%) of 2(RS)-(3-biphenyl-4-yl-1H-imidazol-1-yl)-succinic acid 4-benzyl ester.

FABMS: 427 (C$_{26}$H$_{23}$N$_2$O$_4$; M+H$^+$).

3(RS)-(3-Biphenyl-4-yl-1H-imidazol-1-yl)-N-(hexahydroazepin-2-on-3(S)-yl)succinamic Acid Benzyl Ester

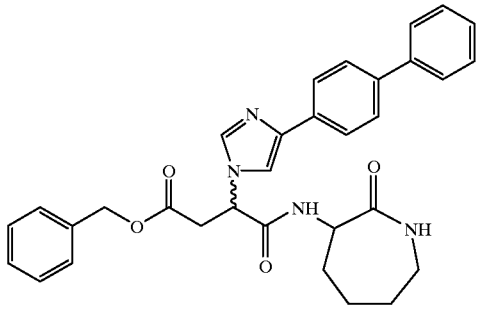

According to the procedure described in Example 8(a), 2(RS)-(3-biphenyl4-yl-1H-imidazol-1-yl)-succinic acid 4-benzyl ester (1.20 g, 2.82 mmol) and L-α-amino-ε-caprolactam (469 mg, 3.67 mmol) was coupled in DMF with pyBOP to furnish 1.02 g (67%) of 3(RS)-(3-biphenyl-4-yl-1H-imidazol-1-yl)-N-(hexahydroazepin-2-on-3(S)-yl)succinamic acid benzyl ester.

FABMS: 537.5 (C$_{32}$H$_{33}$N$_4$O$_4$; M+H$^+$).

The following were made in a similar manner:

178

Example 18(b)

3(RS)-(3-Biphenyl-4-yl-1H-imidazol-1-yl)-N-(2,2-dimethyl-1(S)-hydroxymethylpropyl)succinamic Acid

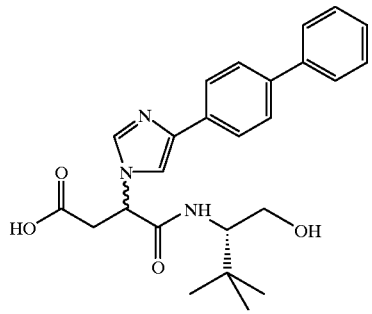

According to the procedure described in Example 1(a), a suspension of 3(RS)-(3-biphenyl-4-yl-1H-imidazol-1-yl)-N-(2,2-dimethyl-1(S)-hydroxymethylpropyl)succinamic acid benzyl ester in EtOH was hydrogenated to provide 3(RS)-(3-biphenyl-4-yl-1H-imidazol-1-yl)-N-(2,2-dimethyl-1(S)-hydroxymethylpropyl)succinamic acid as a solid, mp 145–50° C.

FABMS: 436.1 (C$_{25}$H$_{30}$N$_3$O$_4$; M+H$^+$).

Example 18(c)

3(RS)-(3-Biphenyl-4-yl-1H-imidazol-1-yl)-N-(2,2-dimethyl-1(S)-methylcarbamoylpropyl)succinamic Acid

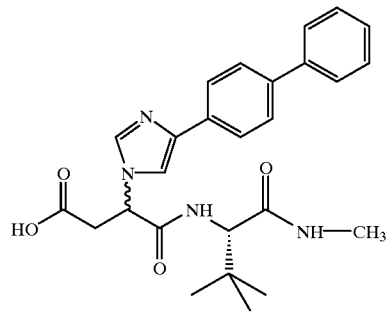

According to the procedure described in Example 1(a), a suspension of 3(RS)-(3-biphenyl-4-yl-1H-imidazol-1-yl)-N-(2,2-dimethyl-1(S)-methylcarbamoylpropyl)succinamic acid benzyl ester in EtOH was hydrogenated to provide 3(RS)-(3-biphenyl-4-yl-1H-imidazol-1-yl)-N-(2,2-dimethyl-1(S)-methylcarbamoylpropyl)succinamic acid as a solid, mp 187.0–8.2° C.

FABMS: 463.2 (C$_{26}$H$_{31}$N$_4$O$_4$; M+H$^+$).

Example 19(a)

3(RS)-(3-Biphenyl-4-yl-1H-imidazol-1-yl)-N$^4$-(2,2-dimethyl-1(S)-hydroxymethylpropyl)-N$^1$-hydroxy-succindiamide

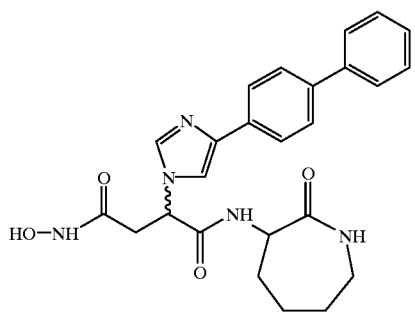

A suspension of crude N¹-benzyloxy-3(RS)-(3-biphenyl-4-yl-1H-imidazol-1-yl)-N⁴-(hexahydroazepin-2-on-3(S)-yl)-succindiamide (800 mg, 1.45 mmol) and 10% Pd/C (800 mg) in EtOH (100 mL) was stirred under H₂ atmosphere. After 6 hours, more catalyst (300 mg) was added. After 2 hours, the catalyst was filtered onto Celite and rinsed. The filtrate was concentrated to provide 301 mg (45%) of 3(RS)-(3-biphenyl-4-yl-1H-imidazol-1-yl)-N-(hexahydroazepin-2-on-3(S)-yl)-N¹-hydroxy-succindiamide as a solid, which effervesced at 180.5° C.

FABMS: 462.2 ($C_{25}H_{28}N_5O_4$; M+H⁺).

The starting materials were furnished as follows:

N¹-Benzyloxy-3(RS)-(3-biphenyl-4-yl-1H-imidazol-1-yl)-N⁴-(hexahydroazepin-2-on-3(S-yl)-succindiamide

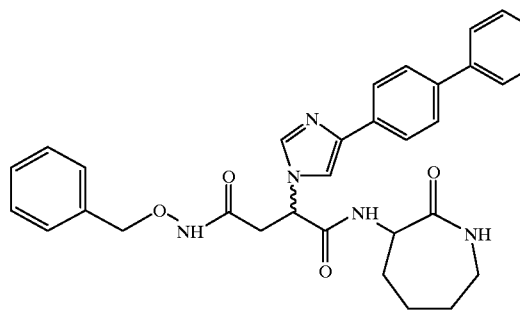

According to the procedures described in Example 8(a), 3(RS)-(3-biphenyl-4-yl-1H-imidazol-1-yl)-N-(hexahydroazepin-2-on-3(S)-yl)succinamic acid (prepared as described in Example 18(a); 779 mg, 1.74 mmol) and benzyloxyamine hydrochloride (334 mg, 2.09 mmol) were coupled with pyBOP to afford 800 mg (83%) of N¹-benzyloxy-3(RS)-(3-biphenyl-4-yl-1H-imidazol-1-yl)-N⁴-(hexahydroazepin-2-on-3(S)-yl)-succindiamide.

FABMS: 552.2 ($C_{32}H_{34}N_5O_4$; M+H⁺).

The following were made in a similar manner:

Example 19(b)

3(RS)-(3-Biphenyl-4-yl-1H-imidazol-1-yl)-N⁴-(2,2-dimethyl-1(S)-hydroxymethylpropyl)-N¹-hydroxy-succindiamide

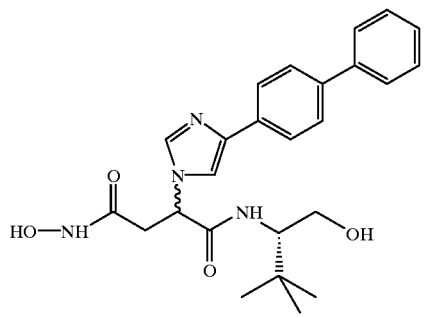

According to the procedure described in Example 19(a), N¹-benzyloxy-3(RS)-(3-biphenyl-4-yl-1H-imidazol-1-yl)-N⁴(2,2-dimmethyl-1(S)-hydroxymethylpropyl)-succindiamide was selectively hydrogenated to provide 3(RS)-(3-biphenyl4-yl-1H-imidazol- 1-yl)-N⁴-(2,2-dimethyl-1(S)-hydroxymethylpropyl)-N¹-hydroxy-succindiamide.

FABMS: 451.3 ($C_{25}H_{31}N_4O_4$; M+H⁺).

Example 19(c)

3(R)-(3-Biphenyl-4-yl-1H-imidazol-1-yl)-N⁴-(2,2-dimethyl-1(S)-hydroxymethylpropyl)-N¹-hydroxy-succindiamide

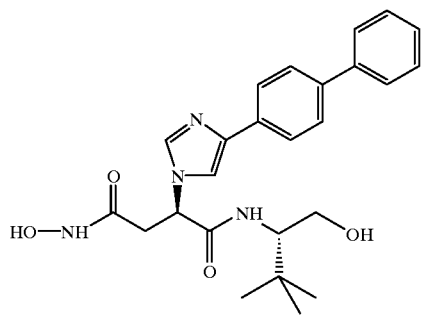

The diastereomeric mixture N¹-benzyloxy-3(RS)-(3-biphenyl-4yl-1H-imidazol-1-yl)-N⁴-(2,2-dimethyl-1(S)-hydroxymethylpropyl)-succindiamide (Example 19(b)) was purified via preparative RPHPLC (C18) to provide 3(R)-(3-biphenyl-4-yl-1H-imidazol-1-yl)-N-(2,2-dimethyl-1(S)-hydroxymethylpropyl)-N¹-hydroxy-succindiamide as a solid, mp 157.5–60.° C.

FABMS: 451.2 ($C_{25}H_{31}N_4O_4$; M+H⁺).

Example 19(d)

3(S)-(3-Biphenyl-4-yl-1H-imidazol-1-yl)-$N^4$-(2,2-dimethyl-1(S)-hydroxymethylpropyl)-$N^1$-hydroxy-succindiamide

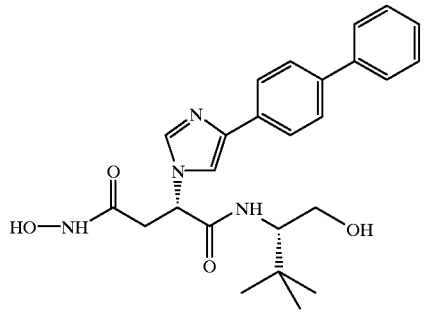

The separation of Example 19(b) described in Example 19(c) also furnished 3(S)-(3-biphenyl-4-yl-1H-imidazol-1yl)-N-(2,2-dimethyl-1(S)-hydroxymethylpropyl)-$N^1$-hydroxy-succindiamide as a solid, mp 134.5–6.5° C.

FABMS: 451.1 ($C_{25}H_{31}N_4O_4$; M+H$^+$).

Example 19(e)

3(RS)-(3-Biphenyl-4-yl-1H-imidazol-1-yl)-$N^4$-(2,2-dimethyl-1(S)-methylcarbamoylpropyl)-$N^1$-hydroxy succindiamide

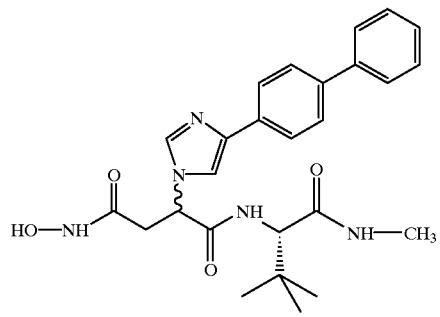

According to the procedure described in Example 19(a), $N^1$-benzyloxy-3(RS)-(3-biphenyl-4-yl-1H-imidazol-1-yl)-$N^4$-(2,2-dimethyl-1(S)-methylcarbarnoylpropyl)-succindiarnide was selectively hydrogenated to provide 3(RS)-(3-biphenyl4-yl-1H-imidazol-1-yl)-$N^4$-(2,2-dimethyl-1(S)-methylcarbamoylpropyl)-$N^1$-hydroxy-succindiamide as a solid, which effervesced at 169° C.

FABMS: 478.2 ($C_{26}H_{32}N_5O_4$; M+H$^+$).

The results obtained during biological testing of some preferred embodiments of the inventive compounds are described below.

Biological Data

Isolation of MMP's for Assays

The catalytic domain of human collagenase-1 was expressed as a fusion protein with ubiquitin in *E. coli* (see Gehring, E. R., *J Biol. Chem.*, 1995, 270, 22507). After purification of the fusion protein, the fibroblast collagenase-1 catalytic domain (HFC) was released either by treatment with purified, active stromelysin-1 (1:50 w/w ratio), which generated nearly 100% N-terminal Phe1, or by autoprocessing the concentrated collagenase-1 fusion and then incubating at 37° C. for 1 hour. Final purification was completed using zinc chelate chromatography.

The propeptide and catalytic domain of human collagenase-3 (Coll3) was expressed in *E coli* as an N-terminal fusion protein with ubiquitin. After purification of the fusion from inclusion bodies, the catalytic domain was liberated by treatment with 2 mM APMA at room temperature overnight. Final purification was completed using copper chelate chromatography.

The catalytic domain of human stromelysin (Hsln) was obtained by expression and purification of a C-terminally truncated prostromelysin-1 from *E. coli* host BL21 (see Marcy et al. *Biochem.*, 1991, 30, 6476). The subsequent activation of the mature form (Hsln) was completed with 2 mM APMA for 1 hour at 37° C., followed by separation using a sizing column.

Human matrilysin (Matr) was expressed in *E. coli* as a fusion protein with ubiquitin. After purification of the matrilysin/ubiquitin fusion from inclusion bodies, the catalytic domain was liberated by treatment with 2 mM APMA at 37° C. for 2 hours. Final purification was complete using copper chelate chromatography.

The catalytic and fibronectin-like portion of human progelatinase A (GelA) was expressed as a fusion protein with ubiquitin in *E. Coli*. Assays were carried out on autocatalytically activated material.

Compounds of Formula I exhibited the ability to inhibit MMPs when tested in the following assay.

In Vitro Assay Procedure

Assays were performed in assay buffer (50 mM Tricine pH 7.5, 200 mM sodium chloride, 10 mM calcium chloride, 0.5 mM zinc acetate containing 2% dimethyl sulfoxide (DMSO)) once the substrate and inhibitor were diluted into it. Stock solutions of inhibitors were prepared in 100% DMSO. Stock solutions of the substrate were prepared in 100% DMSO at a concentration of 6 mM.

The assay method was based on the hydrolysis of MCA-Pro-Leu-Gly-Leu-DPA-Ala-Arg-$NH_2$ (American Peptide Co.) at 37° C. (see Knight, C. G. et al., *FEBS*, 1992, 296, 263–266). The fluorescence changes were monitored with a Perkin-Elmer LS-50B fluorimeter using an excitation wavelength of 328 nm and an emission wavelength of 393 nm. The substrate concentration used in the assays was 10 μM. The inhibitor was diluted into the assays from a solution in 100% DMSO, and controls substituted an equal volume of DMSO so that the final DMSO concentration from inhibitor and substrate dilution in all assays was 2%. The concentration of enzyme in the assay ranged from 60 pM for gelatinase A to 1.5 nM for stromelysin and is a function of the enzymes respective $k_{cat}/K_m$ for the MCA peptide substrate. Proper determination of steady-state rates of substrate cleavage required assay lengths of 60 minutes to allow for complete equilibration of the enzyme-inhibitor complex.

The $K_m$ for the MCA peptide substrate with the matrix metalloproteinases is quite high and exceeds its solubility under assay conditions. Consequently, the apparent $K_i$ (Ki, $_{app}$) was determined to describe the strength of inhibition. However, in this case, $K_{i,app}$ would be essentially equal to $K_i$ since [S]<<$K_m$. For the determination of $K_{i,app}$, the concentration of the inhibitor was varied at a constant and low concentration of substrate and the steady-state rates of fluorescence change determined. In most cases absorptive quench due to the presence of ligand was not observed. For slow-binding inhibitors, onset of inhibition curves were collected for at least 45 minutes so that equilibrium was established. Steady-state rates of fluorescence change were obtained by fitting a curve to an equation for a single exponential decay containing a linear phase. The fitted value of the linear phase was taken as the steady-state rate. The steady-state rates were fitted to the Michaelis equation describing competitive inhibition by non-linear methods. Data resulting from tight-binding inhibition was analyzed, and $K_{i,app}$ determined by fitting the data to the tight-binding equation of Morrison (*Biochem. Biophys. Acta,* vol. 185, pp. 269–286 (1969)) by non-linear methods.

The results of the above-described tests are presented below in Table 1.

TABLE 1

| Example | Hsln (Ki, app) | Matr (Ki, app) | HFC (Ki, app) | GelA (Ki,app) | Coll3 (Ki, app) | LogP |
|---|---|---|---|---|---|---|
| 1 (a) | 65.0 | 1000 | | 5.40 | 30.0 | |
| 1 (b) | 2000 | | | 5.91 | 18.3 | −0.83 |
| 1 (c) | 486 | 16900 | | 2.00 | 0.868 | −0.97 |
| 1 (d) | 1220 | | 4500 | 3.90 | 24.0 | |
| 1 (e) | 3.10 | 500 | | 0.108 | 0.900 | 1.19 |
| 1 (f) | 331 | 1000 | | 93.0 | 542 | |
| 1 (g) | 58.0 | | | 8.50 | 58.5 | |
| 1 (h) | 822 | | | 58.0 | 3000 | |
| 1 (i) | 113 | | | 8.00 | 89.6 | |
| 1 (j) | 133 | | | 1.43 | 9.43 | |
| 1 (k) | 0.150 | 11.0 | | 1.90 | 40 | |
| 1 (l) | 317 | | | 54 | 227 | |
| 1 (m) | 50 | | 997 | 0.410 | 1.00 | |
| 1 (n) | 2000 | >10000 | 1900 | | 8500 | |
| 1 (o) | >10000 | 15000 | 51500 | | | |
| 1 (p) | 55000 | | | 1230 | | |
| 2 | 89 | 400 | | 6.20 | 123 | |
| 3 | 150 | 1250 | | 58 | 180 | |
| 4 (a) | 30 | 5200 | | 1.30 | 2.70 | |
| 4 (b) | 23 | 1520 | | 1.11 | 2.13 | |
| 4 (c) | 64 | 2530 | | 7.20 | | |
| 5 (a) | 84 | | | 1.60 | 1.80 | 0.11 |
| 5 (b) | 30 | 5200 | >12000 | 1.04 | 9.10 | |
| 5 (c) | 1.50 | 305 | 1500 | 0.041 | 0.049 | 3.41 |
| 5 (d) | 1.60 | 4.50 | >2000 | 0.028 | 0.23 | |
| 5 (e) | 1.70 | 182 | 530 | 0.109 | 0.076 | 1.71 |
| 5 (f) | 0.460 | 2.10 | 818 | 0.023 | 0.012 | 2.56 |
| 5 (g) | 57 | | | 2.20 | 14.5 | |
| 5 (h) | 650 | | | 17.4 | 43.0 | |
| 6 (a) | 15.0 | 1500 | 8860 | 6.62 | 15.6 | |
| 6 (b) | 3.60 | | 2900 | 0.066 | 0.210 | |
| 6 (c) | 54 | 5000 | | 0.806 | 7.60 | |
| 7 (a) | 2.00 | 640 | 333 | 0.015 | 0.013 | |
| 7 (b) | 0.290 | 5.00 | 453 | 0.0070 | 0.010 | |
| 7 (c) | 26 | 5326 | | 0.055 | 1.30 | |
| 7 (d) | 1580 | | | 121 | 284 | |
| 8 (a) | 0.690 | 36 | | 0.027 | | |
| 8 (b) | 0.390 | 71 | | 0.330 | 0.450 | |
| 9 | 0.200 | | | 0.011 | 0.018 | |
| 10 (a) | 1.50 | 617 | | 3.30 | 50 | |
| 10 (b) | 16 | 510 | | 9.60 | 23.5 | |
| 10 (c) | 40 | 2185 | | 22 | 50 | |
| 11 | 62 | | | 60 | >750 | |
| 12 | >500 | | | >500 | | |
| 13 | 35 | 16900 | 72000 | 1.70 | 21 | |
| 14 (a) | 558 | | | 4.30 | 7.20 | |
| 14 (b) | 130 | | | 0.012 | 0.028 | |
| 14 (c) | 17.7 | | | 0.044 | | |
| 14 (d) | 19 | | | 0.900 | | |
| 15 (a) | 92 | | | 72 | 300 | |
| 15 (b) | 122 | | | 91 | 1025 | |
| 16 | 1500 | 63000 | | 81 | | |
| 17 (a) | 965 | 454 | 32000 | | | |
| 17 (b) | 720 | 309 | 20000 | | | |
| 17 (c) | 935 | 156 | | 157 | | |
| 18 (b) | 3000 | >100000 | | | 490 | |
| 18 (c) | 180 | | 24000 | | 31 | |
| 19 (a) | 31 | | 57000 | | 43 | |
| 19 (b) | 17 | | 66000 | | 9.7 | |
| 19 (c) | 17 | | 45000 | | 6.5 | |
| 19 (d) | 120 | | >100000 | | 43 | |
| 19 (e) | 2.3 | | 310 | | 0.13 | |

Determination of Inhibitor Concentration in Plasma after Oral Dosing

The dosing solution consisted of the inhibitor dissolved in either a molar equivalent of HCl in water (vehicle A), in 60% aq. propylene glycol (vehicle B), or in 2.8 mg/mL sodium bicarbonate in 60% aqueous propylene glycol (vehicle C), yielding a final concentration that ranged from 10–15 mg/ml. Sprague Dawley rats (Hilltop Lab Animals, Scottsdale, Pa.) were dosed as a function of drug weight per body weight, usually 50 mg per kg. Blood was taken from the rats and centrifuged, and the plasma was stored in the freezer. Drug was extracted from a 50 μl plasma aliquot by adding 1 ml of acetonitrile, shaking for 2 minutes, centrifuging for 15 minutes at 4000 rpm, collecting the supernatant, and then evaporating it to dryness under a stream of nitrogen. The samples were reconstituted with 130 μl of mobile phase, shook for 2 minutes, and centrifuged for 15 minutes at 4000 rpm. The supernatant was collected and the samples were analyzed by injecting 100 μl of supernatant onto HPLC.

Quantitation of drug levels was accomplished by generating a standard curve of known drug amounts that were extracted from added plasma. Drug levels were plotted as a function of time and analyzed to provide area under the curve (AUC) and maximum concentration (Cmax) values. The results are shown in Table 2.

TABLE 2

| Example | dose (mg/kg) | Vehicle | AUC (μg/min*mL) | Cmax (μg/mL) |
|---|---|---|---|---|
| 7 (b) | 50 | B | 24 | 0.21 |
| 5 (c) | 50 | B | 73 | 0.41 |
| 6 (b)* | 50 | B | 37 | 0.30 |
| 1 (m) | 50 | B | 58 | 0.59 |
| 6 (c) | 25 | A | 56 | 0.45 |
| 6 (c)* | 50 | A | 265 | 1.14 |
| 5 (a) | 50 | A | 211 | 1.6 |
| 14 (a) | 50 | B | 94 | 0.82 |
| 14 (d) | 25 | C | 349 | 1.37 |

*dosed as the benzyl ester prodrug

We claim:

1. A compound of the formula I:

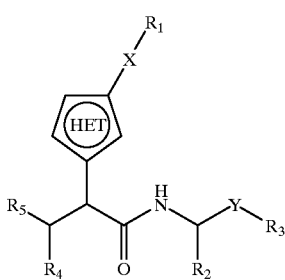

(I)

wherein
X is a single bond or a straight or branched, saturated or unsaturated chain containing 1 to 6 carbon atoms, wherein one or more of the carbon atoms are optionally independently replaced with O or S, and wherein one or more of the hydrogen atoms are optionally replaced with F;
Y is a single bond, —CH(OH)—, or —C(O)—;
$R_1$ is an aryl group, a heteroaryl group, a cycloalkyl group, or a heterocycloalkyl group;
$R_2$ is H, an alkyl group, an aryl group, a heteroaryl group, a cycloalkyl group, a heterocycloalkyl group, or $C(O)R_{10}$,
wherein $R_{10}$ is H, an alkyl group, an aryl group, a heteroaryl group, a cycloalkyl group, a heterocycloalkyl group, an O-aryl group, an O-alkyl group, or $NR_{11}R_{12}$;
wherein $R_{11}$ is H, an alkyl group, an O-alkyl group, an aryl group, a heteroaryl group, a cycloalkyl group, or a heterocycloalkyl group, and
wherein $R_{12}$ is H, an alkyl group, an aryl group, a heteroaryl group, a cycloalkyl group, or a heterocycloalkyl group,
or wherein $R_{11}$ and $R_{12}$ form, together with the nitrogen to which they are attached, a heteroaryl group or a heterocycloalkyl group, and
$R_3$ is H, an alkyl group, an aryl group, a heteroaryl group, a cycloalkyl group, a heterocycloalkyl group, $NR_{11}R_{12}$, or $OR_{11}$ wherein $R_{11}$ and $R_{12}$ are as defined above,
or $R_2$ and $R_3$, together with the atom(s) to which they are attached, form a cycloalkyl group or a heterocycloalkyl group;
R4 is H or any suitable organic moiety;
$R_5$ is $C(O)NHOH$, $C(O)OR_{13}$, SH, $N(OH)CHO$, $SC(O)R_{14}$, $P(O)(OH)R_{15}$ or $P(O)(OH)OR_{13}$,
$R_{13}$ is H, an alkyl group, or an aryl group,
$R_{14}$ is an alkyl group or an aryl group, and
$R_{15}$ is an alkyl group; and

is a heteroaryl group having five ring atoms, including 1, 2 or 3 S heteroatoms;
or a pharmaceutically acceptable salt or solvate thereof, or a pharmaceutically acceptable prodrug thereof, said prodrug being different from a compound of the formula (I).

2. A compound of claim 1, wherein X is a single bond; or a pharmaceutically acceptable salt or solvate thereof, or a pharmaceutically acceptable prodrug thereof, said prodrug being different from a compound of the formula (I).

3. A compound of claim 1, wherein Y is —CH(OH)— or —C(O)—; or a pharmaceutically acceptable salt or solvate thereof, or a pharmaceutically acceptable prodrug thereof, said prodrug being different from a compound of the formula (I).

4. A compound of claim 3, wherein Y is —CH(OH)— and $R_3$ is H or an alkyl group or together with $R_2$ and the atom(s) to which $R_2$ and $R_3$ are attached forms a cycloalkyl group or heterocycloalkyl group; or a pharmaceutically acceptable salt or solvate thereof, or a pharmaceutically acceptable prodrug thereof, said prodrug being different from a compound of the formula (I).

5. A compound of claim 4, wherein Y is —CH(OH)— and $R_3$ is H; or a pharmaceutically acceptable salt or solvate thereof, or a pharmaceutically acceptable prodrug thereof, said prodrug being different from a compound of the formula (I).

6. A compound of claim 3, wherein Y is —C(O)— and $R_3$ is an alkyl group, $NR_{11}R_{12}$, or $OR_{11}$, wherein $R_{11}$ is H, an alkyl group, an O-alkyl group, an aryl group, a heteroaryl group, a cycloalkyl group, or a heterocycloalkyl group, and wherein $R_{12}$ is H, an alkyl group, an aryl group, a heteroaryl group, a cycloalkyl group, or a heterocycloalkyl group, or wherein $R_{11}$ and $R_{12}$ form, together with the nitrogen to which they are attached, a heteroaryl group or a heterocycloalkyl group; or wherein Y is —C(O)— and R2 and $R_3$, together with the atoms to which they are attached, form a cycloalkyl group or a heterocycloalkyl group; or a pharmaceutically acceptable salt or solvate thereof, or a pharmaceutically acceptable prodrug thereof, said prodrug being different from a compound of the formula (I).

7. A compound of claim 1, wherein $R_1$ is an aryl group of the formula:

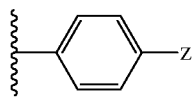

wherein Z is H, halogen, an alkyl group, an O-alkyl group, a cyano group, a hydroxy group, an aryl group, a heteroaryl group, or a heterocycloalkyl group; or a pharmaceutically acceptable salt or solvate thereof, or a pharmaceutically acceptable prodrug thereof, said prodrug being different from a compound of the formula (I).

8. A compound of claim 1, wherein $R_2$ is an aryl group or an alkyl group; or a pharmaceutically acceptable salt or solvate thereof, or a pharmaceutically acceptable prodrug thereof, said prodrug being different from a compound of the formula (I).

9. A compound of claim 1, wherein $R_4$ is H, an alkyl group, OH, O-alkyl, $NH_2$, NH-alkyl, or a cycloalkyl group; or a pharmaceutically acceptable salt or solvate thereof, or a pharmaceutically acceptable prodrug thereof, said prodrug being different from a compound of the formula (I).

10. A compound of claim 9, wherein $R_4$ is an alkyl group selected from $CHR_{16}OH$ and $CH(NHR_{17})R_{16}$, wherein $R_{16}$ is H, an alkyl group, an aryl group, a heteroaryl group, a cycloalkyl group, or a heterocycloalkyl group, and $R_{17}$ is $C(O)R_{18}$, $SO_2R_{18}$, H, an alkyl group, an aryl group, a heteroaryl group, a cycloalkyl group, or a heterocycloalkyl group, or $R_{16}$ and $R_{17}$, together with the atoms to which they are attached, form a heterocycloalkyl group; wherein $R_{18}$ is H, an alkyl group, an aryl group, a heteroaryl group, a cycloalkyl group, a heterocycloalkyl group, an O-aryl group, an O-alkyl group, or $NR_{19}R_{20}$; wherein $R_{19}$ and $R_{20}$ independently are H, an alkyl group, an aryl group, a heteroaryl group, a cycloalkyl group, or a heterocycloalkyl group, or $R_{19}$ and $R_{20}$, together with the nitrogen atom to which they are attached, form a heterocycloalkyl group; or a pharmaceutically acceptable salt or solvate thereof, or a pharmaceutically acceptable prodrug thereof, said prodrug being different from a compound of the formula (I).

11. A compound of claim 1, wherein

is thienyl; or a pharmaceutically acceptable salt or solvate thereof, or a pharmaceutically acceptable prodrug thereof, said prodrug being different from a compound of the formula (I).

12. A compound of claim 1 where $R_5$ is C(O)NHOH or $C(O)OR_{13}$, wherein $R_{13}$ is hydrogen; or a pharmaceutically acceptable salt or solvate thereof, or a pharmaceutically acceptable prodrug thereof, said prodrug being different from a compound of the formula (I).

13. A compound of claim 1, wherein Y is a single bond and $R_3$ is a heteroaryl group.

14. A compound of claim 13, wherein $R_3$ is the heteroaryl group:

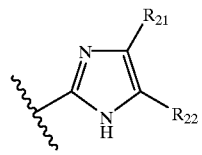

wherein $R_{21}$ and $R_{22}$ are independently any suitable organic moiety or together with the carbon atoms to which they are attached form an aryl group, a heteroaryl group, a cycloalkyl group, or a heterocycloalkyl group; or a pharmaceutically acceptable prodrug thereof, said prodrug being different from a compound of the formula (I).

15. A compound according to claim 14, wherein $R_{21}$ and $R_{22}$ are independently selected from hydrogen, an alkyl group, an aryl group, a heteroaryl group, a halo group, a C(O)O-alkyl group, a carbamoyl group, a cycloalkyl group, or a heterocycloalkyl group; or a pharmaceutically acceptable salt or solvate thereof, or a pharmaceutically acceptable prodrug thereof, said prodrug being different from a compound of the formula (I).

16. A compound of the formula 1:

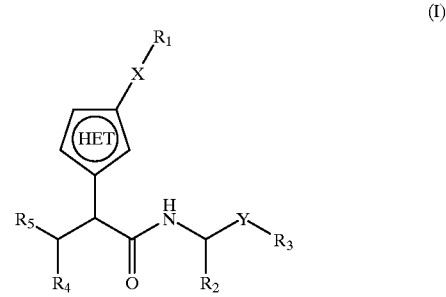

(I)

wherein
X is a single bond;
Y is a single bond, —CH(OH)— or —C(O)—;
$R_1$ is an aryl group or a heteroaryl group;
$R_2$ is H, an alkyl group, an aryl group, a heteroaryl group, a cycloalkyl group, a heterocycloalkyl group, or $C(O)R_{10}$,
wherein $R_{10}$ is H, an alkyl group, an aryl group, a heteroaryl group, a cycloalkyl group, a heterocycloalkyl group, an O-aryl group, an O-alkyl group, or $NR_{11} R_{12}$;
wherein $R_{11}$ is H, an alkyl group, an O-alkyl group, an aryl group, a heteroaryl group, a cycloalkyl group, or a heterocycloalkyl group, and wherein $R_{12}$ is H, an alkyl group, an aryl group, a heteroaryl group, a cycloalkyl group, or a heterocycloalkyl group,
or wherein $R_{11}$ and $R_{12}$ form, together with the nitrogen to which they are attached, a heteroaryl group or a heterocycloalkyl group, and
$R_3$ is H, an alkyl group, a heteroaryl group, $NR_{11}R_{12}$, or $OR_{11}$
wherein $R_{11}$ and $R_{12}$ are as defined above,
or $R_2$ and $R_3$, together with the atoms to which they are attached, form a cycloalkyl group or heterocycloalkyl group;

$R_4$ is H, an alkyl group, or OH;

$R_5$ is C(O)NHOH, C(O)OR$_{13}$, SH, or SC(O)R$_{14}$, wherein $R_{13}$ is H, an alkyl group, or an aryl group, and $R_{14}$ s an alkyl group or an aryl group; and

is thienyl;

or a pharmaceutically acceptable salt or solvate thereof, or a pharmaceutically acceptable prodrug thereof, said prodrug being different from a compound of the formula (I).

17. A pharmaceutical composition comprising:
(a) a therapeutically effective amount of a compound as defined in claim 1 or a pharmaceutically acceptable salt or solvate thereof, or a pharmaceutically acceptable prodrug thereof, said prodrug being different from a compound of the formula (I); and
(b) a pharmaceutically acceptable carrier, diluent, vehicle, or excipient.

18. A method of treating a mammalian disease condition mediated by metalloproteinase activity that comprises administering to a mammal in need thereof a therapeutically effective amount of a compound as defined in claim 1 or a pharmaceutically acceptable salt or solvate thereof, or a pharmaceutically acceptable prodrug thereof, said prodrug being different from a compound of the formula (I).

19. A method according to claim 18 wherein the mammalian disease condition is tumor growth, invasion or metastasis.

20. A method of inhibiting the in vivo activity of a metalloproteinase that comprises contacting the metalloproteinase with an effective amount of a compound as defined in claim 1 or a pharmaceutically acceptable salt or solvate thereof, or a pharmaceutically acceptable prodrug thereof, said prodrug being different from a compound of the formula (I).

* * * * *

UNITED STATES PATENT AND TRADEMARK OFFICE
CERTIFICATE OF CORRECTION

PATENT NO.   : 6,306,892 B1
DATED        : October 23, 2001
INVENTOR(S)  : Steven L. Bender et al.

It is certified that error appears in the above-identified patent and that said Letters Patent is hereby corrected as shown below:

Column 2,
Line 38, "*J Cereb.*" should read -- *J. Cereb.* --; and
Line 41, "*J Respir.*" should read -- *J. Respir.* --.

Column 3,
Line 8, "*J Enzyme*" should read -- *J. Enzyme* --; and
Line 58, "on e" should read -- one --.

Column 6,
Line 32, "$CH_2O$," should read -- $CH_2$, O, --.

Column 7,
Line 63, "$R_{18}$, is H," should read -- $R_{18}$ is H, --.

Column 8,
Line 12, "fuyl" should read -- furyl --.

Column 9,
Line 27, "succinarnic" should read -- succinamic --.

Column 11,

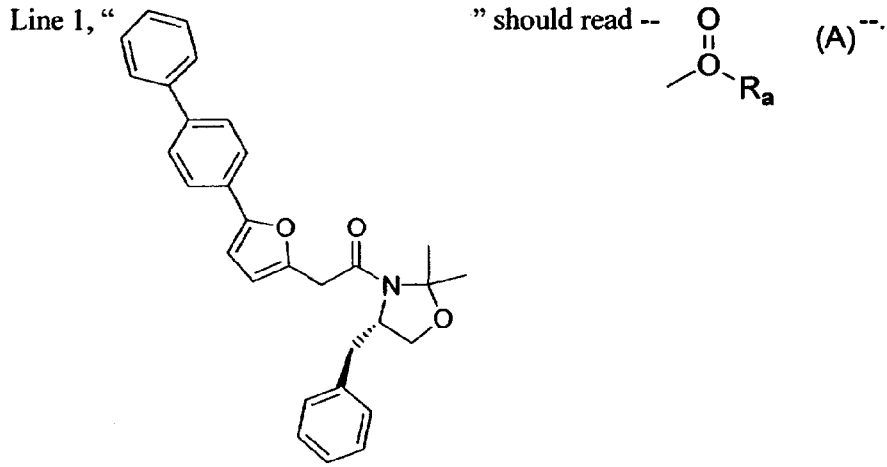

UNITED STATES PATENT AND TRADEMARK OFFICE
CERTIFICATE OF CORRECTION

PATENT NO.     : 6,306,892 B1
DATED          : October 23, 2001
INVENTOR(S)    : Steven L. Bender et al.

It is certified that error appears in the above-identified patent and that said Letters Patent is hereby corrected as shown below:

Column 14,
Line 25, "a" should read -- as --; and
Line 34, "arnmonia" should read -- ammonia --.

Column 16,
Line 15, "rhematoid" should read -- rheumatoid --.

Column 20,
Line 10, "hydroxarnates" should read -- hydroxamates --.

Column 23,
Line 23, "a" should be deleted.

Column 30,
Line 13, "tetrahydrofairan" should read -- tetrahydrofuran --.

Column 36,
Line 64, "a-haloacetic" should read -- α-haloacetic --.

Column 37,
Line 30, "α-halo acetic" should read -- α-haloacetic --.

Column 43,
Line 60, "67 7.66" should read -- δ7.66 --.

Column 46,
Line 58, "biphenyl4" should read -- biphenyl-4 --.

Column 48,
Line 37, "(M+Cs$^{+):}$" should read -- (M+CS$^+$): --.

Column 49,
Line 2, "*Coll*" should read -- *Coll.* --.

UNITED STATES PATENT AND TRADEMARK OFFICE
CERTIFICATE OF CORRECTION

PATENT NO. : 6,306,892 B1
DATED : October 23, 2001
INVENTOR(S) : Steven L. Bender et al.

It is certified that error appears in the above-identified patent and that said Letters Patent is hereby corrected as shown below:

Column 50,
Line 35, "–(3-phenyl1H–pyrrol–l–yl" should read -- –(3–phenyl–1H–pyrrol–1–yl --;
Line 52, "3)R)–amino" should read -- 3(R)–amino --; and
Line 56, "(50 µL, 2.8 =mol" should read -- (50 µL, 2.8 mmol) --.

Column 51,
Line 4, "($M^+Cs+$):" should read -- M+$Cs^+$): --; and
Line 9, "diazatricyclo" should read -- diaza-tricyclo --.

Column 52,
Line 1, "3(R–"should read -- 3(R)– --;
Line 35, "3(7)" should read -- 3(R) --.

Column 53,
Line 51, "(CDC13):" should read -- ($CDCl_3$): --; and
Line 57, "H2O:" should read -- $H_2O$ --.

Column 54,
Line 35, "1337." should read -- 13.37. --.

Column 55,
Line 62, "(CDC13)" should read -- ($CDCl_3$) --.

Column 56,
Line 2, "4–yl[–lH–pyrrol–" should read -- 4–y1–1H–pyrrol– --;
Line 27, "MeOH/$CH_2Cl$," should read -- MeOH/$CH_2Cl_2$ --; and
Line 28, "methylcarbarnoylpropyl" should read -- methylcarbamoylpropyl) --.

Column 57,
Line 46, "–4oxa" should read -- 4–oxa --; and
Line 59, "(CDC13)" should read -- ($CDC_{l3}$) --.

Column 58,
Line 3, "3–(biphenyl–" should read -- 3–[3–(biphenyl– --;
Line 29, "(CDCl3):" should read --($CDCl_3$): --; and
Line 30, "725-" should read -- 7.25- --.

UNITED STATES PATENT AND TRADEMARK OFFICE
CERTIFICATE OF CORRECTION

PATENT NO.   : 6,306,892 B1
DATED        : October 23, 2001
INVENTOR(S)  : Steven L. Bender et al.

It is certified that error appears in the above-identified patent and that said Letters Patent is hereby corrected as shown below:

Column 59,
Line 9, "(CDCl3):" should read -- (CDCl$_3$): --;
Line 21, "(biphenyl4–yl)" should read -- (biphenyl–4-yl) --;
Line 58, "(CDCl3):" should read -- (CDCl$_3$): --; and
Line 62, "4.2-4.16" should read -- 4.20-4.16 --.

Column 60,
Line 23, "provedure" should read -- procedure --.

Column 61,
Line 33, "11(18),12,14,1 6-tetraen–9S–yl" should read
-- 11(18),12,14,16-tetraen–9S–yl) --;
Line 36, "imidazol4–yl)" should read -- imidazol–4–yl) --; and
Line 48, "(CDC13):" should read -- (CDCl$_3$): --.

Column 62,
Line 26, "(bipheny14–yl)" should read -- (biphenyl–4–yl) --.

Column 63,
Line 59, "(CDC13):" should read -- (CDC1$_3$): --.

Column 64,
Line 3, "(Bipheny14–yl)" should read -- Biphenyl–4–yl) --; and
Line 42, "dimethyl4R" should read -- dimethyl–4R --.

Column 65,
Line 1, "cried" should read -- dried --;
Line 39, "dimethyl4R" should read -- dimethyl-4R --;
Line 45, "butoxycarbonylamido" should read -- butoxycarbonylamino --; and
Line 59, "(m 1H)," should read -- (m, 1H), --.

UNITED STATES PATENT AND TRADEMARK OFFICE
CERTIFICATE OF CORRECTION

PATENT NO. : 6,306,892 B1
DATED : October 23, 2001
INVENTOR(S) : Steven L. Bender et al.

It is certified that error appears in the above-identified patent and that said Letters Patent is hereby corrected as shown below:

Column 66,
Line 2, "hydroxyl(S)" should read -- hydroxy-1(S) --.

Column 67,
Line 10, "2.6-2.50" should read -- 2.60-2.50 --;
Line 36, "(CDCl3):" should read -- (CDCl$_3$): --;
Line 55, "3-biphenyl4–yl" should read -- 3–biphenyl–4–yl --; and
Line 61, "(CDCl3):" should read -- (CDCl$_3$): --.

Column 68,
Line 19, "(CDCl3):" should read -- (CDCl$_3$): --;
Line 43, "pyridin4–yl" should read -- pyridin–4–yl --;
Line 56, "(CDCl3):" should read -- (CDCl$_3$): --; and
Line 66, "C$_3$" should read -- C$_{31}$ --.

Column 69,
Line 1, "(Biphenyl4–yl)" should read -- (Biphenyl–4–yl) --;
Line 31, "4–methyl–" should read -- –4–methyl– --; and
Line 42, "Benzyloxycarbony12(R)–t–" should read -- Benzyloxycarbony1–2(R)–t– --.

Column 70,
Line 5, "(CDCl3):" should read -- (CDCl$_3$): --; and
Line 62, "(CDCl3):" should read -- (CDCl$_3$): --.

Column 71,
Line 32, "(CDCl3):" should read -- (CDCl$_3$): --; and
Line 33, "(m, 1H)," should read -- (m, 1H), 7.10 (s, 1H), --.

Column 72,
Line 10, "(CDCl3):" should read -- (CDCl$_3$): --;
Line 19, -N-methylcarbamnoyl)" should read -- N-methylcarbamoyl) --; and
Line 34, "(CDCl3):" should read -- (CDCl$_3$): --.

Column 73,
Line 65, "(CDCl3):" should read -- (CDCl$_3$): --; and
Line 67, "796cm$^-$" should read -- 796cm$^{-1}$ --.

UNITED STATES PATENT AND TRADEMARK OFFICE
CERTIFICATE OF CORRECTION

PATENT NO. : 6,306,892 B1
DATED : October 23, 2001
INVENTOR(S) : Steven L. Bender et al.

It is certified that error appears in the above-identified patent and that said Letters Patent is hereby corrected as shown below:

Column 74,
Line 31, "(CDCl3):" should read -- (CDCl$_3$): --;
Line 34, "28322," should read -- 2832, --; and
Line 65, "(CDCl3):" should read -- (CDCl$_3$): --.

Column 75,
Line 33, "(CDCl3):" should read -- (CDCl$_3$): and --.

Column 79,
Line 23, "N–methylarnide" should read -- N–methylamide --; and
Line 32, "1H NMR (CDCl3):" should read -- $^1$H NMR (CDCl$_3$): --.

Column 80,
Line 22, "tetrahydrofaran" should read -- tetrahydrofuran --.

Column 81,
Line 15, "tetrahydrofaran" should read -- tetrahydrofuran --;
Line 24, "(CDCl3):" should read -- (CDCl$_3$): --; and
Line 66, "(CDCl3):" should read -- (CDCl$_3$): --.

Column 82,
Line 7, "(CDCl3):" should read -- (CDCl$_3$): --; and
Line 59, "(CDCl3):" should read -- (CDCl$_3$): --.

Column 83,
Line 49, "(CDCl3):" should read -- (CDCl$_3$): --.

Column 85,
Line 3, "*Org*" should read -- *Org.* --;
Line 24, "3–fuiranboronic acid" should read -- 3–furanboronic acid --;
Line 31, "(CDCl3):" should read -- (CDCl$_3$): --; and
Line 60, "(CDCl3):" should read -- (CDCl$_3$): --.

Column 86,
Line 22, "H1 NMR (CDCl3):" should read -- $^1$H NMR (CDCl$_3$):--;
Line 30, "1H" should read -- $^1$H --;
Line 63, "cyanobiphenyl4–yl)–" should read -- cyanobiphenyl–4–yl) --; and
Line 65, "(CDCl3):" should read -- (CDCl$_3$): --.

UNITED STATES PATENT AND TRADEMARK OFFICE
CERTIFICATE OF CORRECTION

PATENT NO. : 6,306,892 B1
DATED : October 23, 2001
INVENTOR(S) : Steven L. Bender et al.

It is certified that error appears in the above-identified patent and that said Letters Patent is hereby corrected as shown below:

<u>Column 87,</u>
Line 52, "1H" should read -- $^1$H --.

<u>Column 88,</u>
Line 26, "1H NMR (CDCl3):" should read -- $^1$H NMR (CDCl$_3$): --.

<u>Column 89,</u>
Line 7, "1H NMR" should read -- $^1$H NMR --;
Line 22, "Carbamoylbiphenyl4–yl)" should read -- Carbamoylbipheny1–4–yl) --; and
Line 48, "carbamnoylbiphenyl–4–yl)" should read -- carbamoylbiphenyl–4–yl) --.

<u>Column 90,</u>
Line 21, "3.40 mrnol)" should read -- -3.40 mmol) --;
Line 26, "(CDCl3):" should read -- (CDCl$_3$): --;
Line 35, "Carbarnoylbiphenyl–4–yl)" should read -- Carbamoylbiphenyl–4–yl) --;
Line 37, "propyl" should read -- propyl) --;
Line 54, "biphenyl4–yl)" should read -- biphenyl–4–yl) --; and
Line 62, "CDCl3):" should read -- (CDCl$_3$): --.

<u>Column 92,</u>
Line 6, "498cm$^{31\ 1}$" should read -- 498 cm$^{-1}$. --;
Line 29, "3-(4'–pyridylphenyl4–yl)" should read -- 3–(4'–pyridylphenyl–4–yl) --;
Line 31, "(CDCl3):" should read -- (CDCl$_3$): --;
Line 37, "(pyridin4–yl)" should read -- pyridin–4–yl) --; and
Line 59, "(CDCl3):" should read -- (CDCl$_3$): --.

<u>Column 93,</u>
Line 24, "(CDCl3):" should read -- (CDCl$_3$): --;
Line 56, "aqueousueous" should read -- aqueous --; and
Line 65, "(CDCl3):" should read -- (CDCl$_3$): --.

<u>Column 94,</u>
Line 52, "(CDCl3):" should read -- (CDCl$_3$): --.

<u>Column 96,</u>
Line 1, "(CDCl3):" should read -- (CDCl$_3$): --; and
Line 38, "(CDCl3):" should read -- (CDCl$_3$): --.

UNITED STATES PATENT AND TRADEMARK OFFICE
CERTIFICATE OF CORRECTION

PATENT NO. : 6,306,892 B1
DATED : October 23, 2001
INVENTOR(S) : Steven L. Bender et al.

It is certified that error appears in the above-identified patent and that said Letters Patent is hereby corrected as shown below:

Column 97,
Line 13, "(CDCl3):" should read -- (CDCl$_3$): --; and
Line 56, "(CDCl3):" should read -- (CDCl$_3$): --.

Column 98,
Line 27, "biphenyl4–" should read -- biphenyl–4– --; and
Line 32, "(CDCl3):" should read -- (CDCl$_3$): --.

Column 99,
Line 4, "(pyridin4–" should read -- (pyridin–4– --; and
Line 9, "(DMSO–d6):" should read -- (DMSO–d$_6$): --.

Column 101,
Line 11, "1H–pyrro–yl]" should read -- 1H–pyrrol–1–yl] --.

Column 107,
Line 47, "butoxycarbonylarnino" should read -- butoxycarbonylamino --.

Column 108,
Line 46, "(pyridin4–yl)" should read -- pyridin–4–yl) --;
Line 47, "Berzyl" should read -- Benzyl --; and
Line 66, "(methylcarbarnoyl)" should read -- (methylcarbamoyl) --.

Column 111,
Line 34, "1  6" should read -- 16 --.

Column 112,
Line 37, "butoxycarbonylarnino" should read -- butoxycarbonylamino --.

Column 115,
Line 44, "Metcalf B.W.;" should read -- Metcalf, B.W.; --.

UNITED STATES PATENT AND TRADEMARK OFFICE
CERTIFICATE OF CORRECTION

PATENT NO. : 6,306,892 B1
DATED : October 23, 2001
INVENTOR(S) : Steven L. Bender et al.

It is certified that error appears in the above-identified patent and that said Letters Patent is hereby corrected as shown below:

Column 116,
Line 24, "(pyridin4–" should read -- (pyridin–4– --;
Line 31, ".10H$_2$O." should read -- •1.0H$_2$O• --;
Line 55, "butyloxycarbonylarnino–" should read -- butyloxycarbonylamino --; and
Line 66, "H$_1$NMR" should read -- $^1$HNMR --, and "δ_8.58" should read -- δ8.58 --.

Column 117,
Line 5, "66.97;" should read -- 69.97; --.

Column 118,
Line 60, "succindiarnide" should read -- succindiamide --.

Column 119,
Line 38, "tetra–n–butylanimonium" should read -- tetra–n–butylammonium --.

Column 120,
Line 29, "yield N$_1$" should read -- yield N$^4$ --;
Line 30, "N$^4$" should read -- N$^1$ --;
Line 37, "Anal:" should read -- Anal. --; and
Line 40, "Example 10(a) c1" should read -- Example 10(a) ¶ --.

Column 121,
Line 45, "1.6," should read -- J=1.6, --.

Column 122,
Line 61, "min" should read -- minor --.

Column 123,
Line 65, "Calcd" should read -- Calculated --.

Column 127,
Line 39, "N8.01." should read -- N, 8.01. --.

Column 128,
Line 12, "218" should read -- 2.18 --.

UNITED STATES PATENT AND TRADEMARK OFFICE
CERTIFICATE OF CORRECTION

PATENT NO.    : 6,306,892 B1
DATED         : October 23, 2001
INVENTOR(S)   : Steven L. Bender et al.

It is certified that error appears in the above-identified patent and that said Letters Patent is hereby corrected as shown below:

<u>Column 129,</u>
Line 38, "3406" should read -- 3406, --; and
Line 41, "C, 67.8;" should read -- C, 67.85; --.

<u>Column 130,</u>
Line 11, ".OH$_2$O" should read -- •H$_2$O --;
Line 27, "H7.85;" should read -- H, 7.85; --; and
Line 57, "pent4–enoic" should read -- pent–4–enoic --.

<u>Column 132,</u>
Line 33, "3–biphenyl4" should read -- 3-biphenyl–4– --; and
Line 47, "H$^1$NMR:" should read --$^1$H NMR --.

<u>Column 133,</u>
Line 1, "Example 12." should read -- Example 12 ¶ --;
Line 22, "biphenyl4–" should read -- biphenyl–4– --; and
Line 28, "aqueousueous" should read -- aqueous --.

<u>Column 135,</u>
Line 36, "627" should read -- 6.27 --.

<u>Column 136,</u>
Line 20, "–3, .3–" should read -- –3,3– --;
Line 60, "J=3.4" should read -- J=3.4 Hz), --; and
Line 64, "JX9.7," should read -- J=9.7, --.

<u>Column 137,</u>
Line 34, "aqueousueous" should read -- aqueous --.

<u>Column 138,</u>
Line 2, "aqueousueous" should read -- aqueous --.

<u>Column 139,</u>
Line 3, "aqueousueous" should read -- aqueous --; and
Line 50, "aqueousueous" should read -- aqueous --.

UNITED STATES PATENT AND TRADEMARK OFFICE
CERTIFICATE OF CORRECTION

PATENT NO. : 6,306,892 B1
DATED : October 23, 2001
INVENTOR(S) : Steven L. Bender et al.

It is certified that error appears in the above-identified patent and that said Letters Patent is hereby corrected as shown below:

Column 141,
Line 59, "J 7.4 Hz)," should read -- J=7.4 Hz), --.

Column 142,
Line 43, "aqueousueous" should read -- aqueous --; and
Line 49, "biphenyl4–" should read -- biphenyl–4– --.

Column 143,
Line 29, "$^1$H NMR:" should read -- ¶ $^1$H NMR --; and
Line 64, "aqueousueous" should read -- aqueous --.

Column 144,
Line 33, "aqueousueous" should read -- aqueous --; and
Line 42, "$C_9 1H_{16}O_5$:" should read -- $C_9H_{16}O_5$: --.

Column 145,
Line 45, "1(4(S)–" should read -- 1–(4(S)– --.

Column 146,
Line 10, "aqueousueous" should read -- aqueous --; and
Line 59, "(t, 2H4," should read -- (t, 2H, --.

Column 147,
Line 30, "aqueousueous" should read -- aqueous --.

Column 150,
Line 29, "(4'–cyanobiphenyl4–yl)" should read -- 4'–cyanobiphenyl–4–yl) --.

Column 153,
Line 2, "[ 1( )–" should read -- [ 1(S)– --; and
Line 38, "fuimished" should read -- furnished --.

UNITED STATES PATENT AND TRADEMARK OFFICE
CERTIFICATE OF CORRECTION

PATENT NO. : 6,306,892 B1
DATED : October 23, 2001
INVENTOR(S) : Steven L. Bender et al.

It is certified that error appears in the above-identified patent and that said Letters Patent is hereby corrected as shown below:

Column 158,
Line 21, "procdure" should read -- procedure --;
Line 25, "–4–y" should read -- –4–yl --;
Line 38, "beml" should read -- benzyl --; and
Line 41, " 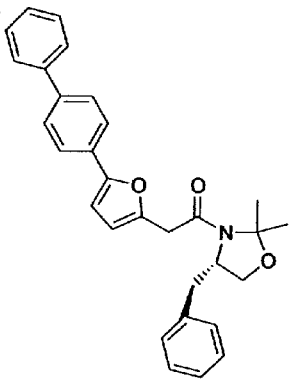 " should read -- 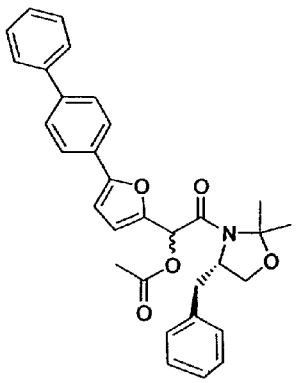 --.

Column 159,
Line 56, "HZ" should read -- Hz), --.

Column 160,
Line 2, "159" should read -- 1.59 --;
Line 42, "-bipheny14-" should read -- -biphenyl-4– --; and
Line 56, "$C_{36}H_{39}NO_5 0.25H_2O$:" should read -- $C_{36}H_{39}NO_5 \cdot 0.25H_2O$: --.

Column 167,
Line 49, "aqueousueous" should read -- aqueous --.

Column 169,
Line 57, "aqueousueous" should read -- aqueous --.

Column 170,
Line 4, "acetylaminol" should read -- acetylamino] --.

UNITED STATES PATENT AND TRADEMARK OFFICE
CERTIFICATE OF CORRECTION

PATENT NO. : 6,306,892 B1
DATED : October 23, 2001
INVENTOR(S) : Steven L. Bender et al.

It is certified that error appears in the above-identified patent and that said Letters Patent is hereby corrected as shown below:

<u>Column 172,</u>
Line 21, "succinarnic" should read -- succinamic --;
Line 22, "succinarnic" should read -- succinamic --; and
Line 31, "butoxyaarbonymethyl" should read -- butoxycarbonymethyl --, and "yaacetylamino" should read -- ylacetylamino --.

<u>Column 173,</u>
Line 57, "2–bromnoacetate." should read -- 2–bromoacetate. --.

<u>Column 175,</u>
Line 1, "pyridin4–" should read -- pyridin–4– --; and
Line 55, "temepra-" should read -- tempera- --.

<u>Column 177,</u>
Line 54, "(3-biphenyl4–" should read -- (3-biphenyl–4– --.

<u>Column 181,</u>
Line 23, "lyl)–" should read -- 1–yl)– --;
Line 49, "methylcarbarnoylpropyl)–" should read -- methylcarbamoylpropyl)– --; and
Line 50, "succindiarnide" should read -- succindiamide --.

<u>Column 186,</u>
Line 23, "R4" should read -- $R_4$ --.

<u>Column 189,</u>
Line 3, "R2" should read -- $R_2$ --.

Signed and Sealed this

Thirteenth Day of August, 2002

*Attest:*

*Attesting Officer*

JAMES E. ROGAN
*Director of the United States Patent and Trademark Office*